(12) United States Patent
Nicolau et al.

(10) Patent No.: US 12,016,885 B2
(45) Date of Patent: Jun. 25, 2024

(54) METHOD OF SOLUBILIZING TDP-43 PROTEIN AGGREGATES IN AMYOTROPHIC LATERAL SCLEROSIS USING A MICROVASCULAR ENDOTHELIAL CELL EXPRESSING AN ANTI-TDP-43 FAB

(71) Applicant: ALSaTECH, Inc., Boston, MA (US)

(72) Inventors: Claude Nicolau, Boston, MA (US); Claudine Kieda, Boston, MA (US); Reynald Thinard, Boston, MA (US); Ruth Greferath, Boston, MA (US); Melanie Chevalier, Boston, MA (US)

(73) Assignee: ALSaTECH, Inc., Boston, MA (US)

( * ) Notice: Subject to any disclaimer, the term of this patent is extended or adjusted under 35 U.S.C. 154(b) by 0 days.

(21) Appl. No.: 17/290,608

(22) PCT Filed: Nov. 6, 2019

(86) PCT No.: PCT/US2019/059989
§ 371 (c)(1),
(2) Date: Apr. 30, 2021

(87) PCT Pub. No.: WO2020/097155
PCT Pub. Date: May 14, 2020

(65) Prior Publication Data
US 2022/0000935 A1 Jan. 6, 2022

Related U.S. Application Data

(60) Provisional application No. 62/896,627, filed on Sep. 6, 2019, provisional application No. 62/847,586, filed on May 14, 2019, provisional application No. 62/843,755, filed on May 6, 2019, provisional application No. 62/773,659, filed on Nov. 30, 2018, provisional application No. 62/756,417, filed on Nov. 6, 2018.

(51) Int. Cl.
| | |
|---|---|
| *A61K 35/12* | (2015.01) |
| *A61K 35/44* | (2015.01) |
| *A61K 39/00* | (2006.01) |
| *A61K 39/395* | (2006.01) |
| *A61P 25/00* | (2006.01) |
| *A61P 25/28* | (2006.01) |
| *C07K 16/00* | (2006.01) |
| *C07K 16/18* | (2006.01) |
| *C12N 5/00* | (2006.01) |
| *C12N 5/07* | (2010.01) |
| *C12N 5/071* | (2010.01) |
| *C12N 15/00* | (2006.01) |
| *C12N 15/09* | (2006.01) |
| *C12N 15/85* | (2006.01) |

(52) U.S. Cl.
CPC ............. *A61K 35/44* (2013.01); *C07K 16/18* (2013.01); *C12N 5/0691* (2013.01); *C12N 15/85* (2013.01); *C07K 2317/50* (2013.01); *C07K 2317/54* (2013.01); *C07K 2317/55* (2013.01); *C07K 2317/565* (2013.01); *C07K 2317/76* (2013.01); *C07K 2319/01* (2013.01); *C07K 2319/02* (2013.01)

(58) Field of Classification Search
CPC ........ A61K 48/00; A61K 35/28; A61K 35/44; A61K 2039/5156; C12N 5/0623; C12N 15/85; C12N 2502/28; C12N 5/069; C12N 5/0602; C12N 15/86; C07K 16/18; A61P 25/00; A61P 25/28; A61P 25/14
See application file for complete search history.

(56) References Cited

U.S. PATENT DOCUMENTS

| | | | |
|---|---|---|---|
| 5,273,743 | A | 12/1993 | Ahlem et al. |
| 5,527,814 | A | 6/1996 | Louvel |
| 5,837,242 | A | 11/1998 | Holliger et al. |
| 5,837,821 | A | 11/1998 | Wu |
| 6,294,654 | B1 | 9/2001 | Bogen et al. |
| 6,303,341 | B1 | 10/2001 | Hiatt et al. |
| 6,432,992 | B1 | 8/2002 | Aubourg et al. |
| 6,551,592 | B2 | 4/2003 | Lindhofer et al. |
| 6,838,254 | B1 | 1/2005 | Hamers et al. |
| 7,087,411 | B2 | 8/2006 | Daly et al. |
| 7,150,872 | B2 | 12/2006 | Whitlow et al. |
| 7,235,641 | B2 | 6/2007 | Kufer et al. |
| 7,772,375 | B2 | 8/2010 | Greferath et al. |
| 7,807,171 | B2 | 10/2010 | Tosi et al. |
| 7,807,175 | B2 | 10/2010 | Pfeifer et al. |

(Continued)

FOREIGN PATENT DOCUMENTS

| | | |
|---|---|---|
| EP | 2152872 B1 | 9/2010 |
| EP | 1763364 B1 | 4/2012 |

(Continued)

OTHER PUBLICATIONS

Morrice et al., Neural Regen. Res. 2018; 13:2050-2054. doi:10.4103/1673-5374.241445.*
Henstridge et al., Nat. Rev. Neurosci. 2019; 20: 94-107.*
Tayebati, Mech. Ageing Dev. 2006. 127: 100-8.*
Sarter, Neurosci. and Biobehav. Rev. 2004. 28: 645-650.*
Garbuzova-Davis et al., Front. Cell. Neurosci. 2014; doi:103389/fncel.2014.00021.*
Korbelin et al., EMBO Mol. Med., 2016; 8:609-625.*
Biemans et al., J. Neurosci. Res. 2017; 95:1513-1522.*

(Continued)

*Primary Examiner* — Chang-Yu Wang
(74) *Attorney, Agent, or Firm* — Morgan, Lewis & Bockius LLP

(57) ABSTRACT

The present invention relates, in part, to cell-based gene therapies, including those targeting, by way of non-limiting example, TDP43 and Aβ aggregates, for the use in neurodegenerative disorders, including without limitation Amyotrophic Lateral Sclerosis (ALS) and Alzheimer's Disease, respectively.

9 Claims, 26 Drawing Sheets

Specification includes a Sequence Listing.

(56) References Cited

U.S. PATENT DOCUMENTS

| | | | |
|---|---|---|---|
| 7,892,544 | B2 | 2/2011 | Pfeifer et al. |
| 8,048,420 | B2 | 11/2011 | Pfeifer et al. |
| 8,124,353 | B2 | 2/2012 | Pfeifer et al. |
| 8,246,954 | B2 | 8/2012 | Pfeifer et al. |
| 8,409,580 | B2 | 4/2013 | Tosi et al. |
| 8,603,487 | B2 | 12/2013 | Pfeifer et al. |
| 8,613,923 | B2 | 12/2013 | Pfeifer et al. |
| 8,647,631 | B2 | 2/2014 | Pfeifer et al. |
| 8,663,650 | B2 | 3/2014 | Nicolau et al. |
| 8,673,940 | B2 | 3/2014 | Froestl et al. |
| 8,796,439 | B2 | 8/2014 | Pfeifer et al. |
| 8,916,590 | B2 | 12/2014 | Kroth et al. |
| 8,926,983 | B2 | 1/2015 | Nicolau et al. |
| 9,146,244 | B2 | 9/2015 | Pfeifer et al. |
| 9,175,094 | B2 | 11/2015 | Pfeifer et al. |
| 9,221,812 | B2 | 12/2015 | Kroth et al. |
| 9,221,900 | B2 | 12/2015 | Pfeifer et al. |
| 9,228,173 | B2 | 1/2016 | Kieda et al. |
| 9,241,988 | B2 | 1/2016 | Shaw et al. |
| 9,289,488 | B2 | 3/2016 | Hickman et al. |
| 9,304,138 | B2 | 4/2016 | Pfeifer et al. |
| 9,314,486 | B2 * | 4/2016 | Guha .................. A61K 35/407 |
| 9,403,902 | B2 | 8/2016 | Pfeifer et al. |
| 9,518,078 | B2 | 12/2016 | Shaw et al. |
| 9,540,434 | B2 | 1/2017 | Pfeifer et al. |
| 9,585,956 | B2 | 3/2017 | Pfeifer et al. |
| 9,598,485 | B2 | 3/2017 | Ayalon et al. |
| 9,631,117 | B2 | 4/2017 | Sommer et al. |
| 9,631,178 | B2 | 4/2017 | Kieda et al. |
| 9,657,091 | B2 | 5/2017 | Pfeifer et al. |
| 9,687,447 | B2 | 6/2017 | Reis et al. |
| 9,701,660 | B2 | 7/2017 | Kroth et al. |
| 9,902,940 | B2 * | 2/2018 | Shusta .................. C12N 5/069 |
| 9,975,946 | B2 | 5/2018 | Nicolau et al. |
| 9,993,564 | B2 * | 6/2018 | Freskgard .............. C07K 5/081 |
| 10,066,010 | B2 | 9/2018 | Pfeifer et al. |
| 10,100,104 | B2 | 10/2018 | Pfeifer et al. |
| 10,112,990 | B2 | 10/2018 | Adolfsson et al. |
| 10,143,744 | B2 | 12/2018 | Shaw et al. |
| 2003/0088074 | A1 | 5/2003 | Hamers et al. |
| 2004/0101905 | A1 | 5/2004 | Brekke et al. |
| 2004/0146505 | A1 | 7/2004 | Durrant et al. |
| 2004/0253238 | A1 | 12/2004 | Bogen et al. |
| 2005/0033031 | A1 | 2/2005 | Couto |
| 2005/0043519 | A1 | 2/2005 | Dooley et al. |
| 2005/0079170 | A1 | 4/2005 | Le Gall et al. |
| 2005/0089519 | A1 | 4/2005 | Kipriyanov et al. |
| 2006/0280734 | A1 | 12/2006 | Winter et al. |
| 2007/0004909 | A1 | 1/2007 | Johnson et al. |
| 2008/0095767 | A1 | 4/2008 | Jennings et al. |
| 2008/0181890 | A1 | 7/2008 | Lazar et al. |
| 2008/0227958 | A1 | 9/2008 | Thompson et al. |
| 2009/0148438 | A1 | 6/2009 | Nuttal et al. |
| 2009/0298195 | A1 | 12/2009 | Rüker et al. |
| 2010/0105874 | A1 | 4/2010 | Schuurman et al. |
| 2010/0316602 | A1 | 12/2010 | Zardi et al. |
| 2017/0035938 | A1 | 2/2017 | Guha et al. |
| 2017/0065638 | A1 * | 3/2017 | Fraser ..................... A61P 25/00 |
| 2017/0128581 | A1 * | 5/2017 | Freskgard .............. A61K 38/10 |
| 2019/0153471 | A1 * | 5/2019 | Paul ........................ C07K 16/18 |
| 2019/0225699 | A1 * | 7/2019 | Lannfelt ................ C07K 16/18 |

FOREIGN PATENT DOCUMENTS

| | | | |
|---|---|---|---|
| EP | | 1959991 B1 | 3/2013 |
| EP | | 2046833 B1 | 8/2013 |
| EP | | 2238166 B1 | 11/2013 |
| EP | | 2361638 B1 | 1/2014 |
| EP | | 2170389 B1 | 10/2014 |
| EP | | 2465533 B1 | 3/2015 |
| EP | | 2170953 B1 | 7/2015 |
| EP | | 2625198 B1 | 7/2015 |
| EP | | 2380588 B1 | 8/2015 |
| EP | | 1651257 B1 | 2/2016 |
| EP | | 2108644 B1 | 7/2016 |
| EP | | 2413957 B1 | 7/2016 |
| EP | | 2764022 B1 | 8/2016 |
| EP | | 2205631 B1 | 11/2016 |
| EP | | 2205632 B1 | 11/2016 |
| EP | | 2316478 B1 | 4/2017 |
| EP | | 2598882 B1 | 7/2017 |
| EP | | 2074145 B1 | 8/2017 |
| EP | | 2527366 B1 | 8/2017 |
| EP | | 2468770 B1 | 12/2017 |
| EP | | 2488513 B1 | 12/2017 |
| EP | | 2586795 B1 | 5/2018 |
| EP | | 2808032 B1 | 8/2018 |
| EP | | 2758071 B1 | 11/2018 |
| EP | | 3135689 B1 | 12/2018 |
| WO | WO 2005/081872 A2 | | 9/2005 |
| WO | WO 2009/117531 A1 | | 9/2009 |
| WO | WO 2010/063785 A2 | | 6/2010 |
| WO | WO 2017/079831 A1 | | 5/2017 |

OTHER PUBLICATIONS

Burgess et al. J of Cell Bio. 111:2129-2138, 1990.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
MacCallum et al., J. Mol. Biol., 1996; 262: 732-745.*
Pascalis et al., The Journal of Immunology, 2002; 169: 3076-3084.*
Casset et al., BBRC, 2003; 307: 198-205.*
Vajdos et al., J. Mol. Biol. 2002; 320: 415-428.*
Holm et al., Mol. Immunol., 2007; 44: 1075-1084.*
Chen et al., J. Mol. Bio., 1999; 293: 865-881.*
Wu et al., J. Mol. Biol., 1999; 294:151-162.*
Rudikoff et al.Proc. Natl. Acad. Sci. USA 1982 vol. 79: p. 1979.*
Garbuzova-Davis et al., Stem Cells, 2017; 35:1246-1258.*
Suzuki et al., Mol. Thera. 2008; 16:2002-2010.*
Klein et al., Hum. Gene Thera. 2005; 16:509-521.*
Assmann et al. Biochem. Biophy. Acta 2016; 1862:381-394.*
Swerdlow, Clin. Interv. Ageing 2007; 2:347-359.*
Atwood et al., J. Alzheimer's Disease; 2015; 47:33-47.*
Anger. Neurotoxicology 1991. 12: 403-13.*
Riku et al., Intl. J. Mol. Sci. 2021; 22:3843. doi.org/10.3390/ijms22083843.*
Jo et al., Exp. Mol. Med. 2020; 52:1652-1662.*
Bernas, et al., "Establishment of primary cultures of human brain microvascular endothelial cells to provide an in vitro cellular model of the blood-brain barrier," Natural Protocols, vol. 5, No. 7, pp. 1265-1272, 2010.
International Search Report & Written Opinion, PCT Application No. PCT/US19/59989, dated Mar. 10, 2020, 17 pages.
Kaiser, et al., "Liposome-Mediated High-Efficiency Transfection of Human Endothelial Cells," J Vasc Res, vol. 38, pp. 133-143, 2001.
Rafii, et al., "Isolation and Characterization of Human Bone Marrow Microvascular Endothelial Cells: Hemapoietic Progenitor Cell Adhesion," Blood, vol. 84, No. 1, pp. 10-19, Jul. 1, 1994.
Yockell-Lelièvre, et al., "Efficient Transfection of Endothelial Cells by a Double-Pulse Electroporation Method," DNA and Cell Biology, vol. 28, No. 11, pp. 561-566, 2009.
Alving, et al., "Liposomes containing lipid A: an effective, safe, generic adjuvant system for synthetic vaccines," Expert Review of Vaccines, vol. 11, No. 6, pp. 733-744, Jun. 2012.
Arai, et al., "TDP-43 is a component of ubiquitin-positive tau-negative inclusions in frontotemporal lobar degeneration and amyotrophic lateral sclerosis," Biochem. Biophys. Comm. vol. 351, pp. 602-611, 2006.
Bosco, et al., "Wild-type and mutant SOD1 share an aberrant conformation and a common pathogenic pathway in ALS," Nat Neurosci, vol. 13, No. 11, pp. 1396-1403, Nov. 2010.
Chandra, et al., "A Broken α-Helix in Folded α-Synuclein," The Journal of Biological Chemistry, vol. 278, No. 17, pp. 15313-15318, Apr. 25, 2003.
Chia, et al., "Superoxide Dismutase 1 and tgSOD1$^{G93A}$ Mouse Spinal Cord Seed Fibrils, Suggesting a Propagative Cell Death Mechanism in Amyotrophic Lateral Sclerosis," PLOS One, vol. 5, No. 5, pp. e10627, May 2010.

(56) References Cited

OTHER PUBLICATIONS

Collet, et al., "Hypoxia-shaped vascular niche for cancer stem cells," Contemp. Oncol. (Pozn.). 19(1A): A39-A43, 2015.
Deffar, et al., "Nanobodies—the new concept in antibody engineering," African Journal of Biotechnology, vol. 8, No. 12, pp. 2645-2652, Jun. 17, 2009.
Gatouillat, et al., "Immunization with liposome-anchored pegylated peptides modulates doxorubicin sensitivity in P-glycoprotein-expressing P388 cells," Cancer Letters, vol. 257, pp. 165-171, 2007.
Gilks, et al., "Stress Granule Assembly Is Mediated by Prion-like Aggregation of TIA-1," Molecular Biology of the Cell, vol. 15, pp. 5383-5398, Dec. 2004.
Grad, et al., "Intermolecular transmission of superoxide dismutase 1 misfolding in living cells," PNAS, vol. 108, No. 39, pp. 16398-16403, Sep. 27, 2011.
Guilliams, et al., "Nanobodies Raised against Monomeric α-Synuclein Distinguish between Fibrils at Different Maturation Stages," J. Mol. Biol., vol. 425, pp. 2397-2411, 2013.
Harmsen, et al., "Properties, production, and applications of camelid single-domain antibody fragments," Appl. Microbiol Biotechnol, vol. 77, pp. 13-22, 2007.
Hickman, et al., "Sequence-independent Control of Peptide Conformation in Liposomal Vaccines for Targeting Protein Misfolding Diseases," The Journal of Biological Chemistry, vol. 286, No. 16, pp. 13966-13976, Apr. 22, 2011.
Higham, et al., "Processing of synthetic pro-islet amyloid polypeptide (proIAPP) 'amylin' by recombinant prohormone convertase enzymes, PC2 and PC3, in vitro," Eur. J. Biochem., vol. 267, pp. 4998-5004, 2000.
Ilieva, et al., "Non-cell autonomous toxicity in neurodegenerative disorders: ALS and beyond," J. Cell. Biol., vol. 187, No. 6, pp. 761-772, 2009.
Jaikaran, et al., "Islet amyloid and type 2 diabetes; from molecular misfolding to islet pathophysiology," Biochimica et Biophysica Acta, vol. 1537, pp. 179-203, 2001.
Kabashi, et al., "TARDBP mutations in individuals with sporadic and familial amyotrophic lateral sclerosis," Nature Genetics, vol. 40, pp. 572-574, 2008.
Kerman, et al., "Amyotrophic lateral sclerosis is a non-amyloid disease in which extensive misfolding of $SOD_1$ is unique to the familial form," Acta Neuropathologica, vol. 119, pp. 335-344, 2010.
Klimkiewicz, et al., "A 3D model of tumour angiogenic microenvironment to monitor hypoxia effects on cell interactions and cancer stem cell selection," Cancer Letters, vol. 396, pp. 10-20, 2017.
Laiger-Tourenne, et al., "TDP-43 and FUS/TLS: emerging roles in RNA processing and neurodegeneration," Human Molecular Genetics, vol. 19, No. R1, pp. R46-R64, 2010.
Lim, et al., "ALS-Causing Mutations Significantly Perturb the Self-Assembly and Interaction with Nucleic Acid of the Intrinsically Disordered Prion-Like Domain of TDP-43," PLOS Biology, Jan. 6, 2016.
Mandelkow, et al., "Biochemistry and Cell Biology of Tau Protein in Neurofibrillary Degeneration," Cold Spring Harb Perspect Med, 2012, 2:006247, 25 pages.
Marzban, et al., "Islet amyloid polypeptide and type 2 diabetes," Experimental Gerontology, vol. 38, No. 4, pp. 347-351, Apr. 2003.
Münch, et al., "Prion-like propagation of mutant superoxide dismutase-1 misfolding in neuronal cells," PNAS, vol. 108, No. 9, pp. 3548-3553, Mar. 1, 2011.
Muhs, et al., "Liposomal vaccines with conformation-specific amyloid peptide antigens define immune response and efficacy in APP transgenic mice," PNAS, vol. 104, No. 23, pp. 9810-9815, Jun. 5, 2007.
Neumann, et al., "Ubiquitinated TDP-43 in Frontotemporal Lobar Degeneration and Amyotrophic Lateral Sclerosis,".
Nicolau, et al., "A liposome-based therapeutic vaccine against β-amyloid plaques on the pancreas of transgenic NORBA mice," PNAS, vol. 99, No. 4, pp. 2332-2337, Feb. 19, 2002.
Pawlak-Robin, et al., "Inhibition of multidrug resistance by immunization with synthetic P-glycoprotein-derived peptides," European Journal of Cancer, vol. 40, No. 4, pp. 606-613, Mar. 2004.
Perrin, et al., "Induction of autoantibodies to murine P-glycoprotein: Consequences on drug sensitivity in MDR cancer cells and on the expression of mdr genes in organs," Biochemical and Biophysical Research Communications, vol. 358, No. 1, pp. 325-330, Jun. 22, 2007.
Polymenidou, et al., "The Seeds of Neurodegeneration: Prion-like Spreading in ALS," Cell, vol. 143, No. 3, pp. 498-508, Oct. 28, 2011.
Polymenidou, et al., "Prion-like spread of protein aggregates in neurodegeneration," J. Exp. Med, vol. 209, No. 5, pp. 889-893, 2012.
Prudencio, et al., "Variation in aggregation propensities among ALS-associated variants of SOD1: Correlation to human disease," Human Molecular Genetics, vol. 18, No. 17, pp. 3217-3226, 2009.
Rosen, et al., "Mutations in Cu/Zn superoxide dismutase gene are associated with familial amyotrophic lateral sclerosis," Nature, vol. 362, pp. 59-62, 1993.
Sreedharan, et al., "TDP-43 Mutations in Familial and Sporadic Amyotrophic Lateral Sclerosis," Science, vol. 319, No. 5870, pp. 1668-1672, Mar. 21, 2008.
Stefanis, "α-Synuclein in Parkinson's Disease," Cold Spring Harb Perspect Med, 2012, 4:a009399, 23 pages.
Tosi, et al., "Immune Response against the Murine MDRI Protein Induced by Vaccination with Synthetic Lipopeptides in Liposomes," Biochemical and Biophysical Research Communications, vol. 212, No. 2, pp. 494-500, Jul. 17, 1995.
Vance, et al., "Mutations in FUS, an RNA Processing Protein, Cause Familial Amyotrophic Lateral Sclerosis Type 6," Science, vol. 323, No. 5918, pp. 1208-1211, Feb. 27, 2009.
Watson, et al., "Role of lipid structure in the humoral immune response in mice to covalent lipid-peptides from the membrane proximal region of HIV-1 gp41," Vaccine, vol. 27, No. 34, pp. 4672-4683, Jul. 23, 2009.
Weksler, et al., "The hCMEC/D3 cell line as a model of the human blood brain barrier," Fluids and Barriers of the CNS, 10:16, 10 pages, 2013.
Wegorzewska and Baloh, "TDP-43-based animal models of neurodegeneration: new insights into ALS pathology and pathophysiology." *Neurodegener Dis.* vol. 8, No. 4, 2011: pp. 262-274.

\* cited by examiner

A)

B)

C)

A)

B)

A)

B)

Dual CAG Hyro with cAb2508 heavy and light Fab
11,147 bp

METHOD OF SOLUBILIZING TDP-43 PROTEIN AGGREGATES IN AMYOTROPHIC LATERAL SCLEROSIS USING A MICROVASCULAR ENDOTHELIAL CELL EXPRESSING AN ANTI-TDP-43 FAB

CROSS-REFERENCE TO RELATED APPLICATIONS

This application is a national stage entry of International Application No. PCT/US19/59989, filed Nov. 6, 2019, which claims priority to and the benefit of U.S. Provisional Patent Application Nos. 62/756,417, filed on Nov. 6, 2018; 62/773,659, filed on Nov. 30, 2018; 62/843,755, filed on May 6, 2019; 62/847,586, filed on May 14, 2019; and 62/896,627, filed on Sep. 6, 2019, the entire contents of which are herein incorporated by reference.

FIELD

The present invention relates to, in part, cell-based gene therapies for various disorders, including neurodegenerative disorders, including, without limitation, Amyotrophic Lateral Sclerosis (ALS) and Alzheimer's disease.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ALS-007PC_ST25; date recorded: Nov. 6, 2019; file size: 163,000 bytes).

BACKGROUND

Diseases of the brain and central nervous system (CNS) can have permanent and devastating consequences on the physical and social well-being of the affected individual. In some cases, highly invasive surgery is required to correct the source of the problem or improve the symptoms of disease. Alternatively, or in addition, medication may be used to treat the cause or symptoms of disease.

Methods for effective administration of medicines to and/or past the blood brain barrier (BBB) and often onwards into the brain, are needed. To date, the focus has been on receptor-mediated ligand targeting; however, this is hindered by a lack of receptors which are exclusively expressed at the BBB. Delivery of biologic agents, e.g., antibodies, across the BBB continues to be a challenge. For instance, the humanized anti-VEGF monoclonal antibody bevacizumab (AVASTIN) has also been developed as a targeted treatment of brain cancer. However, a randomized, double-blind, placebo-controlled clinical trials showed no overall improvement to patient survival rates following this treatment regime (Gilbert, et al. 'A Randomized Trial of Bevacizumab for Newly Diagnosed Glioblastoma' N. Engl. J. Med. 2014, 699-708), perhaps due to poor penetration of the antibody across the BBB. Accordingly, there is a need for improved delivery of agents, especially biologic agents, across and/or past the BBB.

Protein aggregations that result from abnormal protein folding form different deposits called amyloid which is associated with different diseases including but not limited to neurodegenerative disorders and Type II diabetes mellitus.

Neurodegenerative disorders, such as Parkinson's, Huntington's and Alzheimer's diseases, fronto-temporal lobar degeneration (FTLD) and Amyotrophic Lateral Sclerosis (ALS) are associated with the accumulation of misfolded proteins both inside and outside of neuronal and glial cells in the central nervous system. These misfolded protein aggregates are pathological hallmarks of these diseases. The major component of these aggregates is characteristic for each neurodegenerative disease, e.g. α-synuclein for Parkinson, Huntingtin for Huntington, Aβ for Alzheimer disease. Although the major protein component of the pathological aggregation may be unique for each of the diseases, several proteins misfold and accumulate in multiple diseases. The most glaring example is TDP43, which aggregates in ALS, FTLD and many other conditions. Another example is Tau proteins which stabilize microtubules in the neurons. Defective Tau proteins are discovered and associated with Alzheimer's and Parkinson's diseases. Further, beta amyloid is associated with Alzheimer's disease.

Type II diabetes mellitus is associated with a decrease in insulin secretion as a result of β-cells failure. Islet amyloid polypeptide (IAPP) is co-localized with insulin in the islet β-cells to play a role in regulating glucose levels by suppressing food intake and gastric emptying. In Type II diabetes, IAPP aggregates to form amyloid fibrils which are toxic to β-cells.

While there is some understanding in the field of therapeutics antibodies about the role of aggregation in disease progression, there is a paucity of safe and effective therapies for various neurodegenerative disorders and type II diabetes mellitus.

SUMMARY

Accordingly, the present invention relates to, in some aspects, therapies involving cell-based gene agents which effectively deliver therapeutic agents across the BBB. In some aspects, the present invention relates to therapies involving cell-based gene agents which effectively deliver therapeutic agents to and/or past the BBB, for example to the brain parenchyma and/or microvasculature. The present invention relates to, in some aspects, therapies involving cell-based gene therapies comprising nucleic acid vectors encoding antibodies against components of the aggregates. For example, the present invention contemplates a cell (e.g., a microvascular endothelial cell), or precursor thereof, engineered to release a therapeutic protein or peptide (e.g, a soluble protein or peptide), including, without limitation, an antibody or antibody fragment, at a site of therapeutic action.

Such therapies may solubilize the intra- or extra-cellular protein aggregates and inhibit the spreading of the disease. In some aspects, the present invention provides for a method for treating or preventing a neurodegenerative disease (e.g., Parkinson's disease, Huntington's disease, Alzheimer's disease, fronto-temporal lobar degeneration (FTLD) and Amyotrophic Lateral Sclerosis (ALS)), comprising administering to a subject a cell, or precursor thereof, engineered to release a therapeutic protein or peptide, including, without limitation, an antibody or antibody fragment, at a site of therapeutic action. In some embodiments, the microvascular endothelial cell is derived from bone marrow of the patient or subject. In some embodiments, the microvascular endothelial cell is from the central nervous system (CNS), optionally the brain. In further embodiments, the site of therapeutic action is selected from, but not limited to, the brain, the CNS, the heart, the liver, and the pancreas. In some embodiments, the microvascular endothelial cell is derived from the subject having the neurodegenerative disorder in need of treatment.

In some aspects, the present invention relates to compositions and methods involving cell-based gene therapies comprising nucleic acid vectors encoding antibodies against components of disease-related aggregates. Such compositions and methods may solubilize the intra- or extra-cellular protein aggregates and inhibit the spreading of the disease once released at the therapeutic site of action. Such compositions and methods cross the BBB (e.g. better BBB crossing than antibodies delivered via standard methods, e.g., intravenously). Compositions of the present invention may also be delivered to and/or past the BBB.

In some aspects, the present invention provides delivery (e.g., to, across, and/or past the BBB) of a protein or peptide, including, without limitation, an antibody or antibody fragment, including, but not limited to, a conformation-sensitive antibody or antibody fragment that is directed against one or more of mutated TDP43, beta-amyloid (Aβ), SOD-1, FUS/TLS, α-synuclein, Tau protein, and IAPP, including peptide fragments thereof. In various embodiments, the agent of the invention targets protein aggregates that comprise one or more of mutated and/or misfolded TDP43 and beta-amyloid (Aβ) proteins. In some embodiments, the agents of the invention are conformation-sensitive antibodies directed against the mutated TDP43 and beta-amyloid (Aβ) protein aggregates. In some embodiments, the agents of the invention are conformation-sensitive antibodies directed against the mutated TDP43, beta-amyloid (Aβ), SOD-1, FUS/TLS, α-synuclein, Tau protein, and IAPP protein aggregates, including peptide fragments thereof.

In some aspects, the present invention provides a method of constructing an expression vector encoding said sequences. In some embodiments, the vector is based on the pUC high copy derived from pBR322. In further embodiments, the vector comprises a Synapsin promoter that promotes expression in neurons. In still further embodiments, the vector comprises a CAG promoter that promotes expression in endothelial cells. In some embodiments, the vector comprises a peptide used for neuronal targeting (e.g., directed against ApoE4). In further embodiments, the expression vectors of the present invention comprise an amino acid sequence that expresses insulin. In some embodiments, the insulin sequence promotes the export of the expressed antibodies.

In some aspects, the present invention provides for transfection of the autologous microvascular endothelial cells (e.g., autologous brain microvascular endothelial cells or microvascular endothelial cells derived from bone marrow, or precursors thereof) with any one of the aforementioned nucleic acid expression vectors that encode the therapeutic protein or peptide, including, without limitation, an antibody or antibody fragment. In some embodiments, the transfection is performed via electroporation. In some embodiments, transfection involves the use of a cationic lipid, including but not limited to, lipofectine and lipofectamine.

In some embodiments, the present invention provides for making a microvascular endothelial cell that is suitable for delivery of protein or peptide or antibody or antibody fragment agents across the BBB. In some embodiments, the present invention provides for making a microvascular endothelial cell that is suitable for delivery of protein or peptide or antibody or antibody fragment agents to and/or past the BBB.

In some aspects, the present invention relates to a method for delivering a protein or peptide, including, without limitation, an antibody or antibody fragment, across the BBB. In further aspects, the present invention relates to a method for delivering a protein or peptide, including, without limitation, an antibody or antibody fragment, to and/or past the BBB. In some aspects, the present invention relates to a method for delivering a protein or peptide, including, without limitation, an antibody or antibody fragment, across the BBB (or to and/or past the BBB) and cause an about 2-fold, or about a 3-fold, or about a 4-fold, or about a 5-fold, or about a 10-fold, or about a 30-fold, or about a 100-fold, or about a 300-fold, or about a 500-fold, or about a 1,000-fold increase in crossing the BBB, relative to a protein or peptide, including, without limitation, an antibody or antibody fragment, not delivered using the present methods (e.g., without a endothelial cell delivery, e.g. upon administration of a "naked" antibody or antibody fragment). In embodiments, the protein or peptide, including, without limitation, the antibody or antibody fragment, crosses the BBB by either a paracellular pathway or a transcellular pathway.

In some aspects, the present invention relates to a method delivering a protein or peptide, including, without limitation, an antibody or antibody fragment, e.g. across one or more brain microvascular endothelial cells, pericytes, astrocytes, tight junctions, neurons, and basal membrane.

In some aspects, the present invention relates to a method of treating a neurodegenerative disorder and/or Type 2 diabetes mellitus by administering a therapeutically effective amount of an agent of the invention, e.g. the autologous transfected cells, to a patient in need thereof. Such administration may be one or more of the agents of the invention targeting mutated TDP43, beta-amyloid (Aβ), SOD-1, FUS/TLS, α-synuclein, Tau protein, and IAPP (e.g. a cocktail of antibodies). In some embodiments, such administration comprises autologous microvascular endothelial cells that are transfected with a nucleic acid vector encoding one or more antibodies directed against TDP43, beta-amyloid (Aβ), SOD-1, FUS/TLS, α-synuclein, Tau protein, and IAPP. In other embodiments, the invention includes vectors that encode one or more antibodies directed against TDP43, beta-amyloid (Aβ), SOD-1, FUS/TLS, α-synuclein, Tau protein, and IAPP.

In some aspects, the invention provides for pharmaceutical compositions comprising cell-based gene therapies comprising autologous cells transfected with nucleic acid vectors encoding conformation-sensitive antibodies directed against the mutated TDP43, beta-amyloid (Aβ), SOD-1, FUS/TLS, α-synuclein, Tau protein, and IAPP protein aggregates, in a pharmaceutically or physiologically accepted carrier.

In some aspects, the present invention relates to a method of treating a neurodegenerative disorder by administering an effective amount of an agent (e.g., autologous transfected cells comprising nucleic acid vectors encoding conformation-sensitive antibodies directed against the mutated TDP43, beta-amyloid (Aβ), SOD-1, FUS/TLS, α-synuclein, Tau protein, and IAPP protein aggregates) of the invention to a patient in need thereof by using his own endothelial cells. Indeed, the present invention contemplates, in some embodiments, the use of autologous transfected microvascular endothelial cells for the treatment of a neurodegenerative disorder by reintroduction at the BBB via IA or IV injection.

In some embodiments, the agent of the invention is administered to the patient via inferior alveolar injection or intravenous injection. In some embodiments, the transfected cells are delivered to and/or past the blood brain barrier (BBB) of said patients in need thereof. In further embodiments, the transfected cells are early precursors such that they exhibit homing to and/or past the BBB. In some embodiments, the cells are administered so that they are allowed to cross the BBB. In further embodiments, the transfected cells insert into the apical surface of the BBB and release proteins, peptides, antibodies, and/or antigen presenting fragments to the basolateral side of the BBB. In such embodiments, the proteins, peptides, antibodies, and/or antigen presenting fragments are delivered to the brain parenchyma and/or microvasculature. In some embodiments, the present invention provides for the use of organ-specific and/or early progenitors of endothelial cells in order to transport cells comprising vectors encoding therapeutic proteins or peptides, including, without limitation, antibodies or antibody fragments into the brain. In further embodiments, the present invention provides for the use of homing properties of endothelial cells (e.g., precursors) to transfer agents of the invention in an organo-specific manner.

In specific embodiments, the present methods of making or treatment relate to the transfection of microvascular endothelial cells with nucleic acids (optionally codon optimized) encoding antibodies (or Fab fragments) directed against TDP43 and beta-amyloid (Aβ), e.g. as defined by SEQ ID NOs: 13 and 14 or SEQ ID Nos: 94 and 31.

In specific embodiments, the present invention provides for treatment of ALS by delivering to a subject a microvascular endothelial cell having a nucleic acid (optionally codon optimized) encoding an antibody (or Fab fragment) directed against TDP43, e.g. as defined by SEQ ID NOs: 13 and 14.

In specific embodiments, the present invention provides for treatment of Alzheimer's disease by delivering to a subject a microvascular endothelial cell having a nucleic acid (optionally codon optimized) encoding an antibody (or Fab fragment) directed against Aβ, e.g. as defined by SEQ ID Nos: 94 and 31.

In some embodiments, the present invention can be used to repair the BBB, e.g., in diseases like Alzheimer Disease (AD) and Amyotrophic Lateral Sclerosis (ALS). In other embodiments, the present invention allows for the repair of BBB as well as release of antibodies or antibody fragments by the BBB without damaging the BBB and its functions.

In some embodiments, the present invention relates to the repair of cellular damage in tumors, diabetes II, heart attack, myocardial infarction, stroke, respiratory insufficiency, etc.

In some embodiments, the present invention is used for repair of angiogenesis in retina, repair of wounds caused by a deficient blood supply (diabetes foot), repair of myocardial tissue after heart attack, vessel normalization in case of pathological tumor angiogenesis, skin diseases, etc.

Other aspects and embodiments of the invention will be apparent from the following detailed description.

DESCRIPTION OF THE DRAWINGS

FIG. 4A depicts fluorescence imaging at 5 hours, and FIG. 4B depicts fluorescence imaging at 12 hours.

FIG. 1a shows TDP43 and FIG. 1b shows Aβ.

FIG. 9A shows shows the solubilization of TDP-43 aggregates with anti-TDP-43 antigen-binding fragments (Fab) expressed by vector in human cells (HEK293 cell line), as compared to a control group where no Fab was administered and a control group where an irrelevant antibody was administered. FIG. 9B shows the solubilization of β-Amyloid aggregates with anti-β-Amyloid antigen-binding fragments (Fab) expressed by vector in human cells (HEK293 cell line), as compared to a control group where no Fab was administered and a control group where an irrelevant antibody was administered.

DETAILED DESCRIPTION

Figure 1:
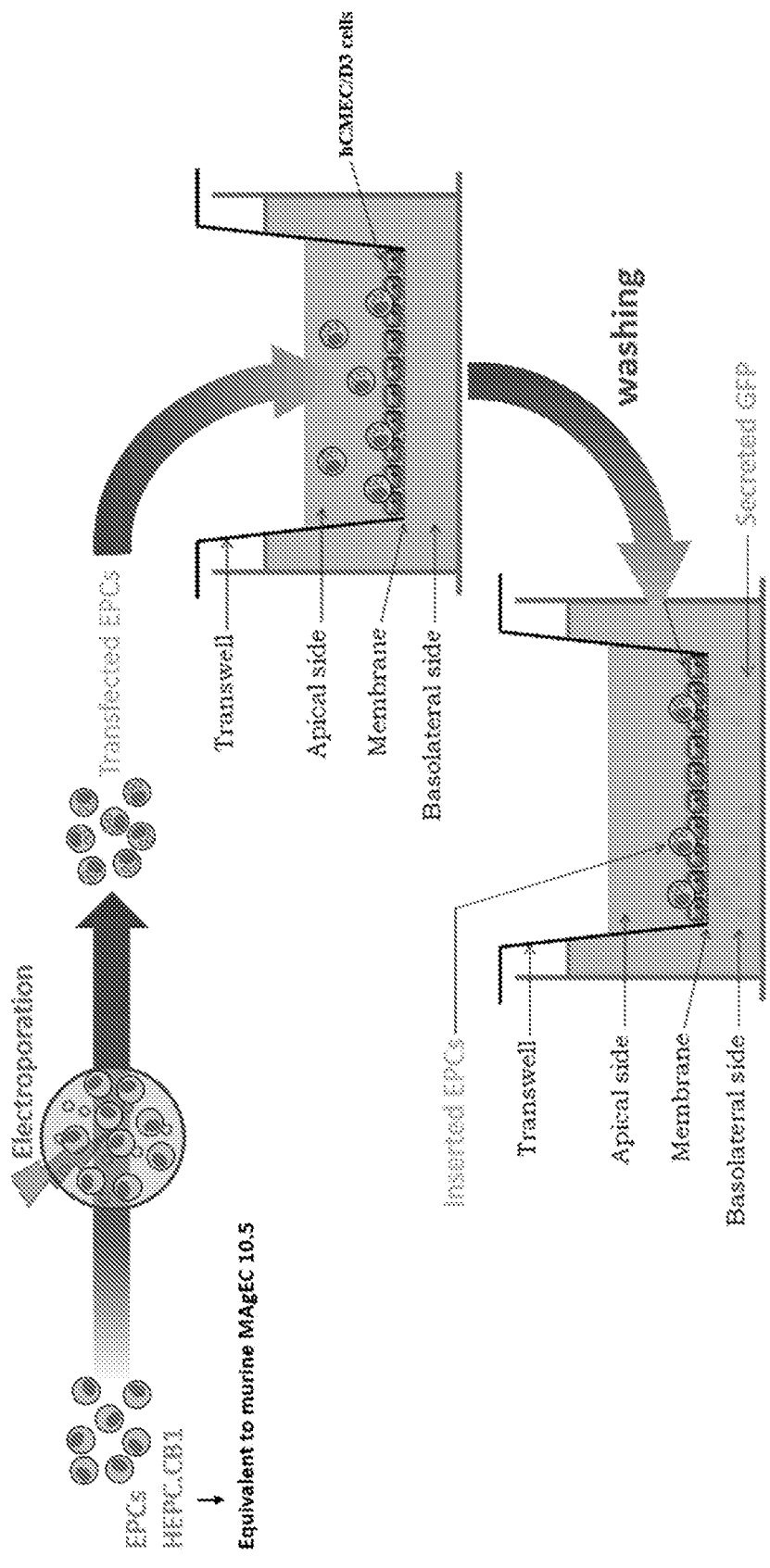
FIG. 1 depicts a schematic of the insertion of transfected cells in an in vitro model of the human Blood Brain Barrier (BBB) and export of GFP by the transfected cells.

The present invention is based, in part, on the discovery that proteins or peptides, including, without limitation, antibodies directed against one or more of mutated protein aggregates associated with various neurodegenerative diseases can be delivered to the brain via microvascular endothelial cells (e.g., from the CNS) comprising nucleic acid vectors encoding such proteins or antibodies. In some embodiments, the microvascular endothelial cell, or precursor thereof, is engineered to release a therapeutic protein or peptide, including, without limitation, an antibody or antibody fragment, at a site of therapeutic action (e.g., a neuron, the CNS, or the brain).

In certain aspects, the present invention provides for the use of microvascular endothelial cells (e.g., from the CNS or the brain) to deliver therapeutic proteins or peptides, including, without limitation, antibodies, or fragments thereof, to therapeutic sites of action (e.g., the blood brain barrier and neurons). Microvascular endothelial cells transfected ex vivo with nucleic acid vectors encoding such proteins, including therapeutic antibodies, can be delivered to and/or past the blood brain barrier (BBB), which acts as a highly specialized structural and biochemical barrier that regulates the entry of blood-borne molecules into brain, and preserves ionic homeostasis within the brain microenvironment. Indeed, BBB properties are primarily determined by junctional complexes between the cerebral endothelial cells. In some embodiments, the endothelial cells, transfected ex vivo are collected from the patient's blood.

In addition, the present invention provides for neuronal targeting via a targeting element, including, but not limited to, an additional peptide directed against ApoE4. The present invention further contemplates the use of homing properties of microvascular endothelial cells (or precursors thereof) to transfer molecules in an organospecific manner. In further embodiments, the expression vectors of the present invention comprise an amino acid sequence that expresses insulin. In such embodiments, the insulin sequence promotes the export of the expressed antibodies. In some embodiments, administration of the aforementioned cell-based therapies occurs via inferior alveolar (IA) and/or intravenous (IV) injection in order to allow the cells to cross the BBB.

In some aspects, the present invention provides for antibodies directed against one or more of mutated SOD-1, TDP43 and FUS/TLS protein aggregates are useful in treating ALS by, for example, solubilizing the protein aggregates and preventing their spreading to motor neurons. In some aspects, the present invention provides for antibodies directed against mutated beta-amyloid (Aβ) protein aggregates are useful in treating Alzheimer's disease by, for example, solubilizing the protein aggregates and interaction with amyloid oligomers.

The present invention is also based, in part, on the discovery that antibodies directed against one or more of the amyloid protein of TDP43, beta-amyloid (Aβ), SOD-1, FUS/TLS, α-synuclein, Tau protein, and IAPP, protein aggregates are useful in treating ALS by, for example, solubilizing the protein aggregates and preventing their spreading to motor neurons. Similarly, antibodies directed against one or more of the amyloid protein of IAPP protein aggregates is useful in treating type II diabetes mellitus.

In various aspects, the present agent of the invention is a cell, for example a microvascular endothelial cell, or precursor thereof, engineered to release a therapeutic protein or peptide, including, without limitation, an antibody or antibody fragment, at a site of therapeutic action. In various embodiments, the therapeutic protein or peptide, including, without limitation, the antibody or antibody fragment, is directed against one or more mutated protein selected from TDP43, beta-amyloid (Aβ), SOD-1, FUS/TLS, α-synuclein, Tau protein, and IAPP. Accordingly, the present invention provides for methods of treating and/or preventing one or more neurodegenerative disorders selected from Parkinson's disease, Huntington's disease, Alzheimer's disease, frontotemporal lobar degeneration (FTLD) and Amyotrophic Lateral Sclerosis (ALS).

Microvascular Endothelial Cells

The present invention provides for the use of microvascular endothelial cells (or progenitors/precursors thereof) as vehicles for transporting and delivering therapeutic proteins or peptides, including, without limitation, antibodies, to sites of action, such as, but not limited to, the brain, the neuron, and the CNS. The microvascular endothelial cells can be derived from the bone marrow, brain, the CNS, the heart, the liver, the pancreas, etc. Certain properties of such microvascular endothelial cells allow for organospecific delivery of the molecules of the present invention.

Brain microvascular endothelial cells (BMEC), the major component of the blood-brain barrier, limit the passage of soluble and cellular substances from the blood into the brain. BMEC have unique features to distinguish themselves from those of peripheral endothelial cells, such as 1) intercellular tight junctions that display high electrical resistance and slow paracellular flux, 2) the absence of fenestrae and a reduced level of pinocytic activity, and 3) asymmetrically-localized enzymes and carrier-mediated transport systems. Similar to peripheral endothelial cells, BMEC express, or can be induced to express, cell adhesion molecules on their surface that regulate the extravasation of leukocytes into the brain. BMEC have been widely used for studying the molecular and cellular properties of blood-brain barrier because of their unique functions.

The present invention also includes cells that are precursors of endothelial cells, and in some embodiments, does not include embryonic stem cells, as described in U.S. Pat. No. 9,631,117, which is hereby incorporated by reference in its entirety. In some embodiments, the cells of the present invention include lines of isolated human cells that are precursors of endothelial cells and established cell lines of isolated cells that are precursors of endothelial cells. These cells include isolated human endothelial cell precursor cells, and murine endothelial cell precursor cells. In some embodiments, the cells are immortalized cells or established cell lines, i.e. immortalized, stable, nontumorigenic cell lines whose characteristics are identical from one generation to another. The present invention also relates to an isolated human endothelial cell precursor cell, other than embryonic stem cells, comprising the clusters of differentiation (CD) 133, 13, 271, 90 202b, 309, 146, 105 and 143; and not comprising the clusters of differentiation CD31 and CD45.

In some embodiments, the cells include cells deposited under the Budapest Treaty at the National Collection of Cultures of Microorganisms (Collection Nationale de Cultures de Microorganismes, CNCM), Institut Pasteur, 25 rue du Docteur Roux, 75724 Paris cedex 15, France. These are, for example, isolated human cells that are endothelial cell precursors other than embryonic stem cells deposited at the Collection Nationale de Cultures de Microorganismes (CNCM), Institut Pasteur, 25 rue du Docteur Roux, 75724 Paris cedex 15, France on Aug. 18, 2009 under CNCM numbers No. 1-4220 (HucPEC 55.1) and No. 1-4221 (HucPEC 55.2).

In some embodiments, the cells include isolated human cells that are endothelial cell precursors isolated from cord blood. The endothelial cell precursors are selected from HEPC.CB1 and HEPC.CB2. See Paprocka, et al. "CD133 positive progenitor endothelial cell lines from human cord blood," *Cytometry A.* 2011 August; 79(8):594-602. doi: 10.1002/cyto.a.21092., the entire contents of which are hereby incorporated in their entirety.

In other embodiments, the cells of the present invention include isolated murine cells that are endothelial cell precursors. In particular, the cells can be isolated murine cell that is a precursor of endothelial cells, other than embryonic stem cells, deposited at the Collection Nationale de Cultures de Microorganismes (CNCM), Institut Pasteur, 25 rue du Docteur Roux, 75724 Paris cedex 15, France on Aug. 18, 2009 under CNCM numbers No. I-4222 (MAgEC 10.5) and No. 1-4223 (MagEC 11.5).

The present invention includes isolated cells that are capable of targeting pathological sites as well as regenerating new endothelial tissues at the targeted sites. In some embodiments, the cells according to the invention, are capable of specifically targeting tumors and/or injured tissues. Thus, in some embodiments, the cells of the invention can supply therapeutic molecules and/or genes at pathological sites.

In some aspects, the present agent of the invention is a cell, for example, a microvascular endothelial cell, or precursor thereof, engineered to release a therapeutic protein or peptide, including, without limitation, an antibody or antibody fragment, at a site of therapeutic action. In some aspects, the present agent of the invention is a cell, for example, a microvascular endothelial cell, or precursor thereof, engineered to release a therapeutic protein or peptide, including, without limitation, an antibody or antibody fragment in spinal cord motor neurons or glial cells.

In various embodiments, the site of therapeutic action is one or more of the CNS, brain, spinal cord, glial cells, neurons in the hippocampus and habenular nuclei, and astrocytes. In various embodiments, the pathological site is one or more of the CNS, brain, spinal cord, glial cells, neurons in the hippocampus and habenular nuclei, and astrocytes.

The engineered cell comprises, in some embodiments, a nucleic acid expression vector having one or more nucleic acid sequences selected from SEQ ID Nos: 1-12 or a variant thereof (e.g. one or more nucleic acid sequences having about 90%, or about 93%, or about 95%, or about 97%, or about 98%, or about 99% sequence identity with one of SEQ ID Nos: 1-6). In various embodiments, the DNA sequences encode variable heavy and variable light chain domains. For example, the DNA sequences can encode, for each chain, a variable domain, a signal peptide, and/or a constant domain.

The engineered cell comprises, in some embodiments, a nucleic acid expression vector having one or more amino acid sequences selected from SEQ ID NOs: 13 and 14.

The engineered cell comprises, in some embodiments, a nucleic acid expression vector having one or more amino acid sequences selected from SEQ ID NOs: 94 and 31.

The engineered cell comprises, in some embodiments, a nucleic acid expression vector of any one of SEQ ID Nos: 83-93 or a variant thereof (e.g. one or more nucleic acid sequences having about 90%, or about 93%, or about 95%, or about 97%, or about 98%, or about 99% sequence identity with one of SEQ ID NOs: 83-93). In some embodiments, the cell comprises a vector of any one of FIGS. 10-23.

In some embodiments, the DNA sequence encoding a variable heavy chain of the anti-TDP43 antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 1:

(SEQ ID NO: 1)
CAGGTTCAGCTGCAGCAGTCTGGAGCTGAGCTGGCGAGGCCTGGGGC

TTCAGTGAAGCTGTCCTGCAAGGCTTCTGGCTACACCTTCACAAGCTAT

GGTATAAGCTGGGTGAGGCAGAGAACTGGACAGGGCCTTGAGTGGATT

GGAGAGATTTATCCTAGACGTGGTAATACTTACTACAATGAGAAGTTCA

AGGGCAAGGCCACACTGACTGCATACAAATCCTCCGGCACAGCGTACA

TGGAGCTCCGCAGCCTGACATCTGAGGACTCTGCGGTCTTTTTCTGTG

CAAGAGGGGGTATCTACTATGGTAACTTATTTGACTACTGGGGCCAAGG

CACCACTCTCACAGTCTCCTCA.

In some embodiments, the DNA sequence encoding a signal peptide of the variable heavy chain of the anti-TDP43 antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 2:

(SEQ ID NO: 2)
ATGGAATGGATCTGGATCTTTCTCTTCATCCTGTCAGGAACTGCAGGTG

TCCAATCC.

In some embodiments, the DNA sequence encoding a constant domain of the variable heavy chain of the anti-TDP43 antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 3:

(SEQ ID NO: 3)
GCCAAAACAACACCCCCATCAGTCTATCCACTGGCCCCTGGGTGTGGA

GATACAACTGGTTCCTCTGTGACTCTGGGATGCCTGGTCAAGGGCTAC

TTCCCTGAGTCAGTGACTGTGACTTGGAACTCTGGATCCCTGTCCAGCA

GTGTGCACACCTTCCCAGCTCTCCTGCAGTCTGGACTCTACACTATGAG

CAGCTCAGTGACTGTCCCCTCCAGCACCTGGCCAAGTCAGACCGTCAC

CTGCAGCGTTGCTCACCCAGCCAGCAGCACCACGGTGGACAAAAAACT

TGAGCCCAGCGGGCCCATTTCAACAATCAACCCCTGTCCTCCATGCAA

GGAGTGTCACAAATGCCCAGCTCCTAACCTCGAGGGTGGACCATCCGT

CTTCATCTTCCCTCCAAATATCAAGGATGTACTCATGATCTCCCTGACA

CCCAAGGTCACGTGTGTGGTGGTGGATGTGAGCGAGGATGACCCAGAC

GTCCGGATCAGCTGGTTTGTGAACAACGTGGAAGTACACACAGCTCAG

ACACAAACCCATAGAGAGGATTACAACAGTACTATCCGGGTGGTCAGT

GCCCTCCCCATCCAGCACCAGGACTGGATGAGTGGCAAGGAGTTCAAA

TGCAAGGTCAACAACAAAGACCTCCCATCACCCATCGAGAGAACCATCT

CAAAAATTAAAGGGCTAGTCAGAGCTCCACAAGTATACATCTTGCCGCC

ACCAGCAGAGCAGTTGTCCAGGAAAGATGTCAGTCTCACTTGCCTGGT

CGTGGGCTTCAACCCTGGAGACATCAGTGTGGAGTGGACCAGCAATGG

GCATACAGAGGAGAACTACAAGGACACCGCACCAGTCCTGGACTCTGA

CGGTTCTTACTTCATATACAGCAAGCTCGATATAAAAACAAGCAAGTGG

GAGAAAACAGATTCCTTCTCATGCAACGTGAGACACGAGGGTCTGAAAA

ATTACTACCTGAAGAAGACCATCTCCCGGTCTCCGGGTAAA.

In some embodiments, the DNA sequence encoding a variable light chain of the anti-TDP43 antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 4:

(SEQ ID NO: 4)
CAGGCTGTTGTGACTCAGGAATCTGCACTCACCACATCACCTGGTGAAA

CAGTCACACTCACTTGTCGCTCAAGTACTGGGGCTGTTACAACTAGTAA

CTATGCCAACTGGGTCCAAGAAAAACCAGATCATTTATTCACTGGTCTA

ATAGGTGGTACCAACAACCGAGCTCCAGGTGTTCCTGCCAGATTCTCA

GGCTCCCTGATTGGAGACAAGGCTGCCCTCACCATCACAGGGGCACAG

ACTGAGGATGAGGCAATATATTTCTGTGCTCTATGGTTCAGCAACCACT

GGGTGTTCGGTGGAGGAACCAAACTGACTGTCCTAGGC.

In some embodiments, the DNA sequence encoding a signal peptide of the variable light chain of the anti-TDP43 antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 5:

(SEQ ID NO: 5)
ATGGCCTGGATTTCACTTATACTCTCTCTCCTGGCTCTCAGCTCAGGGG

CCATTTCC.

In some embodiments, the DNA sequence encoding a constant domain of the variable light chain of the anti-TDP43 antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 6:

(SEQ ID NO: 6)
CAGCCCAAGTCTTCGCCATCAGTCACCCTGTTTCCACCTTCCTCTGAAG

AGCTCGAGACTAACAAGGCCACACTGGTGTGTACGATCACTGATTTCTA

CCCAGGTGTGGTGACAGTGGACTGGAAGGTAGATGGTACCCCTGTCAC

TCAGGGTATGGAGACAACCCAGCCTTCCAAACAGAGCAACAACAAGTA

CATGGCTAGCAGCTACCTGACCCTGACAGCAAGAGCATGGGAAAGGCA

TAGCAGTTACAGCTGCCAGGTCACTCATGAAGGTCACACTGTGGAGAA

GAGTTTGTCCCGTGCTGACTGTTCC.

In some embodiments, the DNA sequence encoding a variable heavy chain of the beta-amyloid antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 7:

(SEQ ID NO: 7)
CAGGTTCAGCTGCAGCAGTCTGGGGCTGAGCTGGTGAAGCCTGGGGC

CTCAGTGAAGATTTCCTGCAAAGCTTCTGGCTACGCATTCAGTAACTAC

TGGATGAACTGGGTGAAGCAGAGGCCTGGAAAGGGTCTTGAGTGGATT

GGACAGATTTATCCTGGAGATGGTGATACTAACTACAACGGAAAGTTCA

AGGGCAAGGCCACACTGACTGCAGACAAATCCTCCAGCACAGCCTACA

TGCAGCTCAGCAGCCTGACCTCTGAGGACTCTGCGGTCTATTTCTGTG

CAAGAGGTGACTACTGGGGCCAAGGCACCACTCTCACAGTCTCCTCA.

In some embodiments, the DNA sequence encoding a variable light chain of the beta-amyloid antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 8:

(SEQ ID NO: 8)
GACATTGTGATGACACAGTCTCCATCCTCCCTGGCTATGTCAGTAGGA

CAGAAGGTCACTATGAGCTGCAAGTCCAGTCAGAGCCTTTTAAATAGTA

GCAATCAAAAGAACTATTTGGCCTGGTACCAGCAGAAACCAGGACAGT

CTCCTAAACTTCTGGTATACTTTGCATCCACTAGGGAATCTGGGGTCCC

TGATCGCTTCATAGGCAGTGGATCTGGGACAGATTTCACTCTTACCATC

AGCAGTGTGCAGGCTGAAGACCTGGCAGATTACTTCTGTCAGCAACAT

TATAACACTCCGCTCACGTTCGGTGCTGGGACCAAGCTGGAGCTGAAA.

In some embodiments, the DNA sequence encoding a constant heavy chain of the beta-amyloid antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 9:

(SEQ ID NO: 9)
GAGAGTCAGTCCTTCCCAAATGTCTTCCCCCTCGTCTCCTGCGAGAGC

CCCCTGTCTGATAAGAATCTGGTGGCCATGGGCTGCCTGGCCCGGGAC

TTCCTGCCCAGCACCATTTCCTTCACCTGGAACTACCAGAACAACACT

-continued
GAAGTCATCCAGGGTATCAGAACCTTCCCAACACTGAGGACAGGGGGC

AAGTACCTAGCCACCTCGCAGGTGTTGCTGTCTCCCAAGAGCATCCTT

GAAGGTTCAGATGAATACCTGGTATGCAAAATCCACTACGGAGGCAAA

AACAAAGATCTGCATGTGCCCATTCCAGCTGTCGCAGAGATGAACCCC

AATGTAAATGTGTTCGTCCCACCACGGGATGGCTTCTCTGGCCCTGCA

CCACGCAAGTCTAAACTCATCTGCGAGGCCACGAACTTCACTCCAAAA

CCGATCACAGTATCCTGGCTAAAGGATGGGAAGCTCGTGGAATCTGGC

TTCACCACAGATCCGGTGACCATCGAGAACAAAGGATCCACACCCCAA

ACCTACAAGGTCATAAGCACACTTACCATCTCTGAAATCGACTGGCTGA

ACCTGAATGTGTACACCTGCCGTGTGGATCACAGGGGTCTCACCTTCT

TGAAGAACGTGTCCTCCACATGTGCTGCCAGTCCCTCCACAGACATCC

TAACCTTCACCATCCCCCCCTCCTTTGCCGACATCTTCCTCAGCAAGTC

CGCTAACCTGACCTGTCTGGTCTCAAACCTGGCAACCTATGAAACCCT

GAATATCTCCTGGGCTTCTCAAAGTGGTGAACCACTGGAAACCAAAATT

AAAATCATGGAAAGCCATCCCAATGGCACCTTCAGTGCTAAGGGTGTG

GCTAGTGTTTGTGTGGAAGACTGGAATAACAGGAAGGAATTTGTGTGTA

CTGTGACTCACAGGGATCTGCCTTCACCACAGAAGAAATTCATCTCAAA

ACCCAATGAGGTGCACAAACATCCACCTGCTGTGTACCTGCTGCCACC

AGCTCGTGAGCAACTGAACCTGAGGGAGTCAGCCACAGTCACCTGCCT

GGTGAAGGGCTTCTCTCCTGCAGACATCAGTGTGCAGTGGCTTCAGAG

AGGGCAACTCTTGCCCCAAGAGAAGTATGTGACCAGTGCCCCGATGCC

AGAGCCTGGGCCCCAGGCTTCTACTTTACCCACAGCATCCTGACTGT

GACAGAGGAGGAATGGAACTCCGGAGAGACCTATACCTGTGTTGTAGG

CCACGAGGCCCTGCCACACCTGGTGACCGAGAGGACCGTGGACAAGT

CCACTGGTAAACCCACACTGTACAATGTCTCCCTGATCATGTCTGACAC

AGGCGGCACCTGCTAT.

In some embodiments, the DNA sequence encoding a constant light chain the beta-amyloid antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 10:

(SEQ ID NO: 10)
CGGGCTGATGCTGCACCAACTGTATCCATCTTCCCACCATCCAGTGAG

CAGTTAACATCTGGAGGTGCCTCAGTCGTGTGCTTCTTGAACAACTTCT

ACCCCAAAGACATCAATGTCAAGTGGAAGATTGATGGCAGTGAACGAC

AAAATGGCGTCCTGAACAGTTGGACTGATCAGGACAGCAAAGACAGCA

CCTACAGCATGAGCAGCACCCTCACGTTGACCAAGGACGAGTATGAAC

GACATAACAGCTATACCTGTGAGGCCACTCACAAGACATCAACTTCACC

CATTGTCAAGAGCTTCAACAGGAATGAGTGT.

In some embodiments, the DNA sequence encoding a signal peptide of the heavy chain of the beta-amyloid antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 11:

(SEQ ID NO: 11)
ATGGAATGGCCTTTGATCTTTCTCTTCCTCCTGTCAGGAACTGCAGGTG

TCCAATCC.

In some embodiments, the DNA sequence encoding a signal peptide of the light chain of the beta-amyloid antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 12:

(SEQ ID NO: 12)
ATGGAATCACAGACCCAGGTCCTCATGTTTCTTCTGCTCTGGGTATCTG

GTGCCTGTGCA.

Therapeutic Proteins or Peptides, Including Antibodies or Fragments Thereof

In embodiments, the therapeutic proteins or peptides find use in a gene replacement therapy, e.g. delivery of a wild type protein or peptide to a subject bearing a mutant form of the protein or peptide, which is associated with a disease. For instance, the present endothelial cells can be transfected or transformed with a vector, e.g. those described herein, being a wild type or otherwise non-defective protein or peptide and such cell can be delivered to a subject bearing a mutant form of the protein or peptide, which is associated with a disease. In embodiments, the therapeutic protein or peptide is selected from nerve growth factor (NGF, e.g. without limitation for use in treating Alzheimer's), apolipoprotein E (ApoE, e.g. ApoE1, ApoE2, ApoE3, and ApoE4, e.g. without limitation for use in treating Alzheimer's), survival motor neuron 1 (SMN1, e.g. without limitation for use in treating SMA), almitoyl-protein thioesterase 1 (PPT1 e.g., without limitation for use in treating CLN1 disease), CLN3/battenin (e.g., without limitation for use in treating CLN3 disease), CLN6 (e.g., without limitation for use in treating CLN6 disease), CLN8 (e.g., without limitation for use in treating CLN8 disease), huntingtin (e.g., without limitation for use in treating Huntington's Disease), ASAP (e.g., without limitation for use in treating Canavan disease), neurturin, GDNF, BDNF, CDNF, VEGF-A (e.g., without limitation for use in treating Parkinson's), MECP2 (e.g., without limitation for use in treating Rett Syndrome), beta-galactosidase (β-galactosidase, e.g., without limitation for use in treating GM-1 gangliosidoses), aromatic L-amino acid decarboxylase (AADC, e.g., without limitation for use in treating Parkinson's Disease), SOD-1 (e.g., without limitation for use in treating ALS), TDP43 (e.g., without limitation for use in treating ALS), beta-amyloid (Aβ, e.g. without limitation for use in treating Alzheimer's disease), FUS/TLS (e.g., without limitation for use in treating ALS), α-synuclein (e.g., without limitation for use in treating Parkinson's), Tau protein (e.g. without limitation for use in treating Alzheimer's disease), and IAPP (e.g. without limitation for use in treating Alzheimer's disease).

In some aspects, the present agent of the invention is a protein or peptide, including, without limitation, an antibody, or fragment thereof (e.g., Fab fragment), that is directed against one or more of mutated TDP43, beta-amyloid (Aβ), SOD-1, FUS/TLS, α-synuclein, Tau protein, and IAPP, optionally in the context of protein aggregates. In various embodiments, the agent of the invention targets protein aggregates that comprise one or more of mutated TDP43, beta-amyloid (Aβ), SOD-1, FUS/TLS, α-synuclein, Tau protein, and IAPP proteins. In some embodiments, the agents of the invention are conformation-sensitive antibodies directed against the mutated TDP43, beta-amyloid (Aβ), SOD-1, FUS/TLS, α-synuclein, Tau protein, and IAPP protein aggregates. In various embodiments the present antibodies solubilize the intra- or extra-cellular protein aggregates and therefore prevent or reduce their spreading.

In some aspects, the present invention agent of the invention is an antibody, or fragment thereof (e.g., Fab fragment), that is directed against one or more of mutated TDP43, beta-amyloid (Aβ), SOD-1, FUS/TLS, α-synuclein, Tau protein, and IAPP, optionally in the context of protein aggregates. In various embodiments, the agent of the invention targets protein aggregates that comprise one or more of mutated TDP43, beta-amyloid (Aβ), SOD-1, FUS/TLS, α-synuclein, Tau protein, and IAPP. In some embodiments, the agents of the invention are conformation-sensitive antibodies directed against the mutated TDP43, beta-amyloid (Aβ), SOD-1, FUS/TLS, α-synuclein, Tau protein, and IAPP protein aggregates.

In some embodiments, the present invention provides for an antibody, or Fab, directed against wild type or mutant TDP43, or peptide fragment. In various embodiments, the antibody, or Fab, comprises a heavy chain and/or a light chain, which are identified based on the sequence of the constant domain (e.g., mouse IgG1, rat kappa, etc.). The antibody, or Fab, can comprise, for each chain, a variable domain, a signal peptide, and/or a constant domain. In some embodiments, the antibody, or Fab, of the present invention comprises a variable heavy domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 13:

```
                                       (SEQ ID NO: 13)
QVQLQQSGAELARPGASVKLSCKASGYTFTSYGISWVRQRTGQGLEWIG

EIYPRRGNTYYNEKFKGKATLTAYKSSGTAYMELRSLTSEDSAVFFCAR

GGIYYGNLFDYWGQGTTLTVSS.
```

In some embodiments, the antibody, or Fab, of the present invention comprises a variable light domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 14:

```
                                       (SEQ ID NO: 14)
QAVVTQESALTTSPGETVTLTCRSSTGAVTTSNYANWVQEKPDHLFTGL

IGGTNNRAPGVPARFSGSLIGDKAALTITGAQTEDEAIYFCALWFSNHW

VFGGGTKLTVLG.
```

In various embodiments, the antibody, or Fab, of the present invention comprises a constant domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 15 and/or SEQ ID NO: 16:

```
                                       SEQ ID NO: 15
AKTTPPSVYPLAPGCGDTTGSSVTLGCLVKGYFPESVTVTWNSGSLSSSV

HTFPALLQSGLYTMSSSVTVPSSTWPSQTVTCSVAHPASSTTVDKKLEPS

GPISTINPCPPCKECHKCPAPNLEGGPSVFIFPPNIKDVLMISLTPKVTC

VVVDVSEDDPDVRISWFVNNVEVHTAQTQTHREDYNSTIRVVSALPIQHQ

DWMSGKEFKCKVNNKDLPSPIERTISKIKGLVRAPQVYILPPPAEQLSRK

DVSLTCLVVGFNPGDISVEWTSNGHTEENYKDTAPVLDSDGSYFIYSKLD

IKTSKWEKTDSFSCNVRHEGLKNYYLKKTISRSPGK;
and/or

SEQ ID NO: 16
QPKSSPSVTLFPPSSEELETNKATLVCTITDFYPGVVTVDWKVDGTPVTQ

GMETTQPSKQSNNKYMASSYLTLTARAWERHSSYSCQVTHEGHTVEKSLS

RADCS.
```

In some embodiments, the antibody, or Fab, of the present invention comprises a signal peptide comprising a peptide having amino acid sequence identity to SEQ ID NO: 17 and/or SEQ ID NO: 18: MEWIWIFLFILSGTAGVQS (SEQ ID NO: 17), and/or MAWISLILSLLALSSGAIS (SEQ ID NO: 18). In various embodiments, the signal peptide comprises an amino acid sequence having one or more amino acid mutations. In various embodiments, the signal peptide comprises an amino acid sequence having one, or two, or three, or four, or five, or six, or seven, or eight, or nine, or ten amino acid mutations. In some embodiments, the one or more amino acid mutations may be independently selected from substitutions, insertions, deletions, and truncations. In some embodiments, the amino acid mutations are amino acid substitutions, and may include conservative and/or non-conservative substitutions.

In further embodiments, the present invention contemplates an antibody, or Fab, comprising one or more complementarity-determining regions (CDR) for the variable heavy and/or variable light domains. In some embodiments, the CDRs are presented in Kabat definition. In various embodiments, the CDR comprises an amino acid sequence having one or more amino acid mutations. In various embodiments, the CDR comprises an amino acid sequence having one, or two, or three, or four, or five, or six, or seven, or eight, or nine, or ten amino acid mutations. In some embodiments, the one or more amino acid mutations may be independently selected from substitutions, insertions, deletions, and truncations. In some embodiments, the amino acid mutations are amino acid substitutions, and may include conservative and/or non-conservative substitutions. In further embodiments, the variable heavy domain comprises a CDR1 having an amino acid sequence of SEQ ID NO: 19. In further embodiments, the variable heavy domain comprises a CDR2 having an amino acid sequence of SEQ ID NO: 20. In still further embodiments, the variable heavy domain comprises a CDR3 having an amino acid sequence of SEQ ID NO: 21. In some embodiments, the antibody, or Fab, of the present invention comprises CDR1: SYGIS (SEQ ID NO: 19); CDR2: EIYPRRGNTYYNEKFKG (SEQ ID NO: 20); and/or CDR3: GGIYYGNLFDY (SEQ ID NO: 21). In some embodiments, the variable light domain comprises a CDR1 having an amino acid sequence of SEQ ID NO: 22. In further embodiments, the variable heavy domain comprises a CDR2 having an amino acid sequence of SEQ ID NO: 23. In still further embodiments, the variable heavy domain comprises a CDR3 having an amino acid sequence of SEQ ID NO: 24. In some embodiments, the antibody, or Fab, of the present invention comprises CDR1: RSSTGAVTTSNYAN (SEQ ID NO: 22); CDR2: GTNNRAP (SEQ ID NO: 23); and/or CDR3: ALWFSNHWV (SEQ ID NO: 24).

Amyotrophic Lateral Sclerosis (ALS)

ALS is a neurodegenerative condition that targets primarily motor neurons, resulting in progressive paralysis and death within a few years from onset. Just like Alzheimer's, Parkinson's and other neurodegenerative disease, a proportion (~10%) of ALS is dominantly inherited, with the remaining 90% (referred to as sporadic) of unknown origin. The identification in 1993 of mutation in the gene encoding superoxide dismutase 1 (SOD-1) as the first or second most common form of inherited ALS, and subsequent generation of transgenic mice expressing ALS-causing mutants in SOD1, initiated the molecular era of deciphering disease mechanism. A flurry of approaches established that non-cell autonomous disease depends on one or more toxic properties of mutant SOD-1. The latter drives disease initiation when synthesized within motor neurons while its synthesis by glial neighbors provokes rapid disease advance. Along with prion-infected mice, the ALS-linked mutant SOD-1 mice are among the most faithful model of neuro-degeneration, recapitulating the selective progressive loss of motor neurons that leads to the paralysis characteristic of human ALS.

In both inherited and sporadic ALS, affected neurons and glial cells contain abnormal proteinaceous accumulations, often labeled by anti-ubiquitin antibodies. The major protein component of these accumulations in familial cases with SOD-1 mutations, and in mutant sporadic disease has recently been challenged. This controversy notwithstanding, over the past five years it has been established that a main component of proteinaceous cytoplasmic inclusions in essentially all sporadic ALS cases is the RNA/DNA-binding protein TDP43, accompanied by its nuclear depletion. Moreover, mutations in TDP43 are causes of inherited ALS and rare instances of FTLD.

Affected neurons of patients with TDP43 mutations also develop cytoplasmic TDP43-positive inclusions and nuclear loss, implying that abnormal localization and aggregation of TDP43 could represent a first mechanistic link between sporadic ALS and an inherited form caused by a known mutation. Furthermore, ALS-causing mutations were identified in a gene encoding another RNA/DNA-binding protein, called FUS/TLS for fused in sarcoma or translocated in liposarcoma. FUS-mutant mediated disease is also accompanied by FUS/TLS-containing cytoplasmic inclusions and disturbed subcellular localization. Unresolved is whether pathogenesis in TDP43- or FUS/TLS-mediated disease results from a loss of nuclear function of either protein, from a gain of toxic property(ies) associated (or not) with the cytoplasmic inclusions, or—perhaps most likely, from a combination of all possibilities.

SOD-1 is a small 153-amino acid protein, which in its native state occurs as a remarkably stable dimmer that is highly resistant to proteolytic degradation. ALS-associated point mutations occur in almost every position (>140 mutations are known) with each leading to destabilization and eventually accumulation of misfolded species within affected cells of the nervous system. In vitro studies with purified SOD-1 have shown that both the wild-type and several mutant versions of the protein spontaneously fibrillize under denaturing conditions with propensity to aggregate that is enhanced in the mutants.

In various embodiments, present agents are raised against and/or target a peptide. In various embodiments, peptide refers to a series of residues, typically L-amino acids, connected one to the other typically by peptide bonds between the α-amino and carboxyl groups of adjacent amino acids. The term includes modified peptides and synthetic peptide analogues. In various embodiments, the peptide epitope of the invention comprises a sequence as set out in any of the preceding statements of the invention and consists of 6 to 18 amino acids. In various embodiments, the peptide consists of 8, 9, 10, 11, 12, 13, 14, 15, 16, 17 or 18 amino acids. For example, the peptide epitope may comprise a sequence of 8 to 12 amino acids or 8 to 10 amino acids. It is understood by those in the art that other fragments of proteins and peptides disclosed herein, such as amino-truncated, carboxy-truncated, or internal deletions, or any combination of these, as well as conservative variants of these peptides, may be employed in this invention.

In various embodiments, the present agents target a mutated protein comprising one or more mutations of Table 1, optionally in the context of a protein aggregate. For instance, the present agents may be an antibody targeting a protein bearing one or more mutations of Table 1, optionally in the context of a protein aggregate.

In various embodiments, the present agents target a mutated protein comprising one or more mutations of Table 1, optionally in the context of a protein aggregate. For instance, the present agents may be conformation-specific antibodies targeting a protein bearing one or more mutations of Table 1, optionally in the context of a protein aggregate.

In various embodiments, the present agents target mutated SOD-1, optionally in the context of a protein aggregate. In some embodiments, the mutated SOD-1 comprises the A4V mutation. In some embodiments, the mutated SOD-1 comprises an SOD-1 mutation of Table 1.

Mutations of TAR DNA binding protein 43 (TDP43) cause a dominant form of ALS. The normal role of the TDP43 protein includes binding to RNA, the genetic messenger molecule. Mutations in the TDP43 gene cause the TDP43 protein to mislocalize in motor neurons, away from the nucleus where it is normally found, and into the cytoplasm, where it aggregates into clumps that can be seen under the microscope. Even in ALS not caused by TDP43 mutations, the protein is found in these aggregates, suggesting it may play a pivotal role in many forms of ALS.

In various embodiments, the present agents target mutated TDP43, optionally in the context of a protein aggregate. In various embodiments, the present agents target mutated ALS10 (TARDBP). Mutations of TARDBP include: p.Gly298Ser, p.Ala315Thr, p.Ala382Thr, p.Met337Val, p.Gly348Cys, p.Gly287Ser, p.Gly294Val, and p.Ala382Thr.

The human TDP43 protein is made of 414 amino acids and is encoded by the TARDBP gene. The amino acid sequence of human TDP43 is shown by SEQ ID NO: 25.

SEQ ID NO.: 25

MSEYIRVTEDENDEPIEIPSEDDGTVLLSTVTAQFPGACGLRYRNPVSQC

MRGVRLVEGILHAPDAGWGNLMNNYPKDNKRKMDETDASSAVKVKRAVQK

TSDLIVLGLPWKTTEQDLKEYFSTFGEVLMVQVKKDLKTGHSKGFGFVRF

TEYETQVKVMSQRHMIDGRWCDCKLPNSKQSQDEPLRSRKVFVGRCTEDM

TEDELREFFSQYGDVMDVFIPKPFRAFAFVTFADDQIAQSLCGEDLIIKG

ISVHISNAEPKHNSNRQLERSGRFGGNPGGFGNQGGFGNSRGGGAGLGNN

QGSNMGGGMNFGAFSINPAMMAAAQAALQSSWGMMGMLASQQNQSGPSGN

-continued

NQNQGNMQREPNQAFGSGNNSYSGSNSGAAIGWGSASNAGSGSGFNGGFG
SSMDSKSSGWGM

In various embodiments, the present antibodies are directed to/or raised against a peptide comprising part of wild type or mutant TDP43, including stretches of amino acids of SEQ ID NO: 25.

In various embodiments, the present agents of conformation-sensitive antibodies target the following peptide sequences of amyloid TDP43, including but not limited to SEQ ID NOs: 26-28.

```
(311-344)
                                          SEQ ID NO: 26
MNFGAFSINPAMMAAAQAALQSSWGMMGMLASQQ (311-320)
                                          SEQ ID NO: 27
MNFGAFSINP (246-25)
                                          SEQ ID NO: 28
EDLIIKGISV
```

In various embodiments, the present antibodies are directed to/or raised against a peptide comprising part or all of the amino acids of SEQ ID Nos: 26-28.

In some embodiments, the present invention provides for an antibody, or Fab, directed against wild type or mutant TDP43, or peptide fragment. In various embodiments, the antibody, or Fab, comprises a heavy chain and/or a light chain, which are identified based on the sequence of the constant domain (e.g., mouse IgG1, rat kappa, etc.). The antibody, or Fab, can comprise, for each chain, a variable domain, a signal peptide, and/or a constant domain. In some embodiments, the antibody, or Fab, of the present invention comprises a variable heavy domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 13.

In some embodiments, the antibody, or Fab, of the present invention comprises a variable light domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 14.

In various embodiments, the antibody, or Fab, of the present invention comprises a constant domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 15 and/or SEQ ID NO: 16.

In some embodiments, the antibody, or Fab, of the present invention comprises a signal peptide comprising a peptide having amino acid sequence identity to SEQ ID NO: 17 and/or SEQ ID NO: 18: MEWIWIFLFILSGTAGVQS (SEQ ID NO: 17), and/or MAWISLILSLLALSSGAIS (SEQ ID NO: 18). In various embodiments, the signal peptide comprises an amino acid sequence having one or more amino acid mutations. In various embodiments, the signal peptide comprises an amino acid sequence having one, or two, or three, or four, or five, or six, or seven, or eight, or nine, or ten amino acid mutations. In some embodiments, the one or more amino acid mutations may be independently selected from substitutions, insertions, deletions, and truncations. In some embodiments, the amino acid mutations are amino acid substitutions, and may include conservative and/or non-conservative substitutions.

In further embodiments, the present invention contemplates an antibody, or Fab, comprising one or more complementarity-determining regions (CDR) for the variable heavy and/or variable light domains. In some embodiments, the CDRs are presented in Kabat definition. In various embodiments, the CDR comprises an amino acid sequence having one or more amino acid mutations. In various embodiments, the CDR comprises an amino acid sequence having one, or two, or three, or four, or five, or six, or seven, or eight, or nine, or ten amino acid mutations. In some embodiments, the one or more amino acid mutations may be independently selected from substitutions, insertions, deletions, and truncations. In some embodiments, the amino acid mutations are amino acid substitutions, and may include conservative and/or non-conservative substitutions. In further embodiments, the variable heavy domain comprises a CDR1 having an amino acid sequence of SEQ ID NO: 19. In further embodiments, the variable heavy domain comprises a CDR2 having an amino acid sequence of SEQ ID NO: 20. In still further embodiments, the variable heavy domain comprises a CDR3 having an amino acid sequence of SEQ ID NO: 21. In some embodiments, the antibody, or Fab, of the present invention comprises CDR1: SYGIS (SEQ ID NO: 19); CDR2: EIYPRRGNTYYNEKFKG (SEQ ID NO: 20); and/or CDR3: GGIYYGNLFDY (SEQ ID NO: 21). In some embodiments, the variable light domain comprises a CDR1 having an amino acid sequence of SEQ ID NO: 22. In further embodiments, the variable heavy domain comprises a CDR2 having an amino acid sequence of SEQ ID NO: 23. In still further embodiments, the variable heavy domain comprises a CDR3 having an amino acid sequence of SEQ ID NO: 24. In some embodiments, the antibody, or Fab, of the present invention comprises CDR1: RSSTGAVTTSNYAN (SEQ ID NO: 22); CDR2: GTNNRAP (SEQ ID NO: 23); and/or CDR3: ALWFSNHWV (SEQ ID NO: 24). Fused in sarcoma/Translocated in sarcoma (FUS/TLS) is inherited in a dominant manner. It is also an RNA binding protein, and may play a similar normal role in the cell as TDP43. FUS and TDP43 may in fact interact as part of their normal function.

In various embodiments, any FUS/TLS mutations described in Science 27 Feb. 2009: vol. 323 no. 5918 1205-1208, the entire contents of which are hereby incorporated by reference, may be targeted by the present agents.

In various embodiments, the following mutations in the fused in sarcoma/translated in liposarcoma (FUS/TLS) gene on chromosome 16 may be present (base numbering begins with the start codon; amino acid numbering begins with the methionine start codon):

| ID | Mutation | | |
|---|---|---|---|
| | Amino acid | Base pair | Exon |
| F577 | H517Q | C1551G* | 15 |
| F55 | R521G | C1561G | 15 |
| F213 | insGG | insGAGGTG523 | 5 |
| MTL 10 | delGG | delGAGGTG523 | 5 |
| MTL 7 | R244C | C730T | 6 |
| F360 | R514S, G515C | G1542T, G1543T | 15 |
| NUFMS9900 | R518K | G1553A | 15 |
| F072 | R521C | C1561T | 15 |
| F080 | R521C | C1561T | 15 |

-continued

| | Mutation | | |
|---|---|---|---|
| ID | Amino acid | Base pair | Exon |
| F085 | R521C | C1561T | 15 |
| F002 | R521G | C1561G | 15 |
| F136 | R521G | C1561G | 15 |
| F067 | R521H | G1562A | 15 |
| F287 | R522G | A1564G | 15 |
| F597 | R524T | G1571C | 15 |
| F346 | R524S | G1572C | 15 |
| F568 | P525L | C1574T | 15 |

In various embodiments, the present agents target mutated FUS/TLS, optionally in the context of a protein aggregate. In various embodiments, the present antibodies are directed to/or raised against a peptide comprising part of wild type or mutant FUS/TLS.

In various embodiments, the present agents target Ubiquilin-2, including mutants thereof. Ubiquilin-2 resides on the X chromosome. The normal function of the protein is to help degrade damaged or defective proteins in the cell. It is likely that mutations in the gene interfere with this function, and may lead to accumulation of harmful material within the cell. In various embodiments, the present antibodies are directed to/or raised against a peptide comprising part of wild type or mutant ubiquilin-2.

In various embodiments, the present agents are directed to/or raised against a protein bearing mutations in one or more of the following illustrative ALS-related mutations, including peptide fragments thereof:

| Locus Name (Gene) | Protein Name |
|---|---|
| ALS1 (SOD7) | Superoxide dismutase (Cu—Zn) |
| ALS3 (18q21) | |
| ALS4 (SETX) | Probable helicase senataxin |
| ALS6 (FUS/TLS) | RNA-binding protein FUS |
| ALS7 (20p13) | |
| ALS8 (VAPB) | Vesicle-associated membrane protein-associated protein B/C |
| ALS9 (ANG) | Angiogenin |
| ALS10 (TARDBP) | TAR DNA-binding protein 43 |
| ALS11 (FIG4) | Polyphosphoinositide phosphatase |
| ALS/FTD (C9orf72) | Uncharacterized protein C9orf72 |
| ALS/FTD (CHCHD10) | Coiled-coil-helix-coiled-coil-helix domain-containing protein 10, mitochondrial |
| ALS-FTD (17q) | Unknown |
| ALS14 (VCP) | Transitional endoplasmic reticulum ATPase |

BBB Delivery

In some aspects, therapies involving cell-based gene agents which effectively deliver therapeutic agents across the BBB are provided. In some aspects, therapies involving cell-based gene agents which effectively deliver therapeutic agents to and/or past the BBB are provided.

In some aspects, the present invention relates to a method of delivering an antibody or antibody fragment across the BBB. In some aspects, the present invention relates to a method delivering an antibody or antibody fragment across the BBB and cause an about 2-fold, or about a 3-fold, or about a 4-fold, or about a 5-fold, or about a 10-fold, or about a 30-fold, or about a 100-fold, or about a 300-fold, or about a 500-fold, or about a 1,000-fold increase in crossing the BBB, relative to an antibody or antibody fragment not delivered using the present methods (e.g. without a endothelial cell delivery, e.g. upon administration of a "naked" antibody or antibody fragment). In embodiments, the antibody or antibody fragment crosses the BBB by either a paracellular pathway or a transcellular pathway.

In some aspects, the present invention relates to a method delivering an antibody or antibody fragment, e.g. across one or more brain microvascular endothelial cells, pericytes, astrocytes, tight junctions, neurons, and basal membrane.

In embodiments, the present invention provides delivery of an antibody or antibody fragment, e.g. across the BBB, including, but not limited to, an antibody or antibody fragment that is directed against one or more of mutated TDP43, beta-amyloid (Aβ), SOD-1, FUS/TLS, α-synuclein, Tau protein, and IAPP, including peptide fragments thereof, inclusive of a Fab having SEQ ID Nos: 13 and 14 and/or CDRs of SEQ ID Nos: 19-24 and/or SEQ ID Nos: 94 and 31 and/or CDRs of SEQ ID Nos: 36-38 and 39-41.

In some embodiments, the use of autologous transfected microvascular endothelial cells for the treatment of a neurodegenerative disorder by reintroduction at and/or past the BBB via IA or IV injection.

In some embodiments, the agent of the invention is administered to the patient via inferior alveolar injection or intravenous injection. In some embodiments, the transfected cells are delivered to the blood brain barrier (BBB) of said patients in need thereof. In further embodiments, the transfected cells are early precursors such that they exhibit homing to and/or past the BBB. In some embodiments, the cells are administered so that they are allowed to cross the BBB. In some embodiments, the present invention provides for the use of organ-specific and/or early progenitors of endothelial cells in order to transport cells comprising vectors encoding therapeutic antibodies or antibody fragments into the brain. In further embodiments, the present invention provides for the use of homing properties of endothelial cells (e.g., precursors) to transfer agents of the invention in an organo-specific manner.

In such embodiments, the insulin sequence promotes the export of the expressed antibodies. In some embodiments, administration of the aforementioned cell-based therapies occurs via inferior alveolar (IA) and/or intravenous (IV) injection in order to allow the cells to cross the BBB.

In various embodiments, the present cells, administered peripherally, cross the blood brain barrier and cause substantial release of therapeutic antibodies or antibody fragments. In embodiments, this effect is obtained without the need of using blood-brain barrier disrupting agents. Hyperthermia, mannitol, bradykinin and NS1619 are illustrative blood-brain barrier disrupting agents.

Accordingly, in a particular embodiment, the invention relates to use or method as described herein, comprising peripheral administration of the present cells, wherein no blood-brain barrier disrupting agent is implemented. Furthermore, the invention relates to a use or method as described herein, wherein no mannitol is injected to the subject.

Alternatively, in embodiments, the invention relates to a use or method as described herein, further comprising disruption of the blood-brain barrier with a blood-brain barrier disrupting agent or process, to further increase the crossing of the cells or therapeutic antibodies implemented in the present invention through the blood-brain barrier.

Alzheimer's Disease

Proteinaceous deposits (called amyloid) appear as neurofibrillary tangles, amyloid plaque cores, and amyloid of the congophilic angiopathy in Alzheimer's disease. Beta-amyloid (Aβ) peptide naturally occurs as a series of peptides which are 39 to 43 amino acids long, with the shorter, more soluble forms being present in cerebrovascular deposits and the longer forms being found primarily in senile plaques. F. Prelli, et al. Journal of Neurochemistry, 51:648-651 (1988). Indeed, beta-amyloid is a small piece of a larger protein called "amyloid precursor protein" (APP). When APP is activated to do its normal job, it is cut by other proteins into separate, smaller sections that stay inside and outside of cells. In some circumstances, APP is cut in such a way to produce beta-amyloid.

In turn, beta-amyloid can accumulate in stages into microscopic amyloid plaques that are considered a hallmark of a brain affected by Alzheimer's disease. The pieces first form small oligomer clusters, then fibril chains of clusters, followed by beta-sheet mats of fibrils. The final stage is plaques, which contain clumps of beta-sheets and other substances. Without wishing to be bound by any one theory, it is believed that these stages of beta-amyloid aggregation disrupt cell-to-cell communication and activate immune cells, which trigger inflammation and ultimately destroy the brain cells.

The primary structure of the 42 amino acid residue long, beta-amyloid peptide is SEQ ID NO: 29:

```
                                        (SEQ ID NO: 29)
DAEFRHDSGYEVHHQKLVFFAEDVGSNKGAIIGLMVGGVVIA.
```

In various embodiments, the present agents of conformation-sensitive antibodies target beta-amyloid, optionally in the context of a protein aggregate. In various embodiments, the present antibodies are directed to/or raised against a peptide comprising part of wild type or mutant beta-amyloid, including stretches of amino acids of SEQ ID NO: 29. In further embodiments, the antibody or antibody fragment is directed to/or raised against a peptide comprising amino acids 1-16 of SEQ ID NO: 29.

In various embodiments, the present agents of conformation-sensitive antibodies target the following peptide sequence of beta-amyloid (Aβ) peptide, including but not limited to SEQ ID NO: 30.

SEQ ID NO: 30 (1-16):
DAEFRHDSGYEVHHQK

In various embodiments, the present antibodies are directed to/or raised against a peptide comprising part or all of the amino acids of SEQ ID NO: 30. In some embodiments, the present antibodies are directed to/or raised against an epitope present in SEQ ID NO: 30.

In some embodiments, the present invention provides for an antibody, or Fab, directed against wild type or mutant beta-amyloid (Aβ) peptide, or peptide fragment. In various embodiments, the antibody, or Fab, comprises a heavy chain and/or a light chain, which are identified based on the sequence of the constant domain (e.g., mouse IgG1, rat kappa, etc.). The antibody, or Fab, can comprise, for each chain, a variable domain, a signal peptide, and/or a constant domain. In some embodiments, the antibody, or Fab, of the present invention comprises a variable heavy domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 94:

```
                                        (SEQ ID NO: 94)
QVQLQQSGAELVKPGASVKISCKASGYAFSNYWMNWVKQRPGKGLEWIGQ

IYPGDGDTNYNGKFKGKATLTADKSSSTAYMQLSSLTSEDSAVYFCARGD

YWGQGTTLTVSS.
```

In some embodiments, the antibody, or Fab, of the present invention comprises a variable light domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 31:

```
                                        (SEQ ID NO: 31)
DIVMTQSPSSLAMSVGQKVTMSCKSSQSLLNSSNQKNYLAINYQQKPGQS

PKLLVYFASTRESGVPDRFIGSGSGTDFTLTISSVQAEDLADYFCQQHYN

TPLTFGAGTKLELK.
```

In various embodiments, the antibody, or Fab, of the present invention comprises a constant domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 32 and/or SEQ ID NO: 33:

```
(Heavy Chain)
                                          SEQ ID NO: 32
ESQSFPNVFPLVSCESPLSDKNLVAMGCLARDFLPSTISFTWNYQNNTEV

IQGIRTFPTLRTGGKYLATSQVLLSPKSILEGSDEYLVCKIHYGGKNKDL

HVPIPAVAEMNPNVNVFVPPRDGFSGPAPRKSKLICEATNFTPKPITVSW

LKDGKLVESGFTTDPVTIENKGSTPQTYKVISTLTISEIDWLNLNVYTCR

VDHRGLTFLKNVSSTCAASPSTDILTFTIPPSFADIFLSKSANLTCLVSN

LATYETLNISWASQSGEPLETKIKIMESHPNGTFSAKGVASVCVEDWNNR

KEFVCTVTHRDLPSPQKKFISKPNEVHKHPPAVYLLPPAREQLNLRESAT

VTCLVKGFSPADISVQWLQRGQLLPQEKYVTSAPMPEPGAPGFYFTHSIL

TVTEEEWNSGETYTCVVGHEALPHLVTERTVDKSTGKPTLYNVSLIMSDT

GGTCY;
and/or (Light Chain)
                                          SEQ ID NO: 33
RADAAPTVSIFPPSSEQLTSGGASVVCFLNNFYPKDINVKWKIDGSERQN

GVLNSWTDQDSKDSTYSMSSTLTLTKDEYERHNSYTCEATHKTSTSPIVK

SFNRNEC.
```

In some embodiments, the antibody, or Fab, of the present invention comprises a signal peptide comprising a peptide having amino acid sequence identity to SEQ ID NO: 34 and/or SEQ ID NO: 35: MEWPLIFLFLLSGTAGVQS (SEQ ID NO: 34), and/or MESQTQVLMFLLLWVSGACA (SEQ ID NO: 35). In various embodiments, the signal peptide comprises an amino acid sequence having one or more amino acid mutations. In various embodiments, the signal peptide comprises an amino acid sequence having one, or two, or three, or four, or five, or six, or seven, or eight, or nine, or ten amino acid mutations. In some embodiments, the one or more amino acid mutations may be independently selected from substitutions, insertions, deletions, and truncations. In some embodiments, the amino acid mutations are amino acid substitutions, and may include conservative and/or non-conservative substitutions.

In further embodiments, the present invention contemplates an antibody, or Fab, comprising one or more complementarity-determining regions (CDR) for the variable heavy and/or variable light domains. In some embodiments, the CDRs are presented in Kabat definition. In various embodiments, the CDR comprises an amino acid sequence having one or more amino acid mutations. In various embodiments, the CDR comprises an amino acid sequence having one, or two, or three, or four, or five, or six, or seven, or eight, or nine, or ten amino acid mutations. In some embodiments, the one or more amino acid mutations may be independently selected from substitutions, insertions, deletions, and truncations. In some embodiments, the amino acid mutations are amino acid substitutions, and may include conservative and/or non-conservative substitutions.

In further embodiments, the variable heavy domain comprises a CDR1 having an amino acid sequence of SEQ ID NO: 36. In further embodiments, the variable heavy domain comprises a CDR2 having an amino acid sequence of SEQ ID NO: 37. In still further embodiments, the variable heavy domain comprises a CDR3 having an amino acid sequence of SEQ ID NO: 38. In some embodiments, the antibody, or Fab, of the present invention comprises CDR1: NYWMN (SEQ ID NO: 36); CDR2: QIYPGDGDTNYNGKFKG (SEQ ID NO: 37); and/or CDR3: GDY (SEQ ID NO: 38).

In some embodiments, the variable light domain comprises a CDR1 having an amino acid sequence of SEQ ID NO: 39. In further embodiments, the variable heavy domain comprises a CDR2 having an amino acid sequence of SEQ ID NO: 40. In still further embodiments, the variable heavy domain comprises a CDR3 having an amino acid sequence of SEQ ID NO: 41. In some embodiments, the antibody, or Fab, of the present invention comprises CDR1: KSSQSLLNSSNQKNYLA (SEQ ID NO: 39); CDR2: FASTRES (SEQ ID NO: 40); and/or CDR3: QQHYNTPLT (SEQ ID NO: 41).

In some embodiments, the antibody, or Fab, of the present invention comprises a variable heavy domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 42:

(SEQ ID NO: 42)
QVQLQQSGAELARPGASVKLSCKASGYTFTSYGIRWVKQRTGQGLEWIGE

IXPRSGNTYYNEKFKGKATVTADKSSSTAYMELRSLTSEDSAVYFCARSI

YYGRPYYFDYWGQGTTLTVSS.

In some embodiments, the antibody, or Fab, of the present invention comprises a variable light domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 43:

(SEQ ID NO: 43)
DIVMTQSQLFMSTSDRVSVTCKASQNVAVGTNVAWYQQKPGQSPKALIYS

ASYRYSGVPDRFTGSGSGTDFTLTISNVQSEDLAEYFCQQYNSYPLTFGA

GTKLELK.

In further embodiments, the variable heavy domain comprises a CDR1 having an amino acid sequence of GYTFTSYGIR (SEQ ID NO: 44). In further embodiments, the variable heavy domain comprises a CDR2 having an amino acid sequence of EIXPRSGNTYYNEKFK (SEQ ID NO: 45). In still further embodiments, the variable heavy domain comprises a CDR3 having an amino acid sequence of SIYYGRPYYFDY (SEQ ID NO: 46).

In some embodiments, the variable light domain comprises a CDR1 having an amino acid sequence of KASQNVATNVA (SEQ ID NO: 47). In further embodiments, the variable light domain comprises a CDR2 having an amino acid sequence of SASYRYS (SEQ ID NO: 48). In still further embodiments, the variable light domain comprises a CDR3 having an amino acid sequence of QQYNSYPLT (SEQ ID NO: 49).

In some embodiments, the antibody, or Fab, of the present invention comprises a variable heavy domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 50:

(SEQ ID NO: 50)
QVQLQQSDAELVKPGASVKISCKVSGYTFTDHTIHWMKQRPEQGLEWIGY

IYPRDGSTKYNEKFKGKATLTADKSSSTAYMQLNSLTSEDSAVYFCARDY

GYAFDYWGQGTTLTVSS.

In some embodiments, the antibody, or Fab, of the present invention comprises a variable heavy domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 51:

(SEQ ID NO: 51)
QVQLQQSDAELVKPGASVKISCKVSGYTFTDHTIHWMKQRPEQGLEWIGY

IYPRDGSTKYNEKFKGKATLTADKSSSTAYMQLNSLTSEDSAVYFCARDY

GYAFDYWGQGTTLTVSS.

In some embodiments, the antibody, or Fab, of the present invention comprises a variable light domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 52:

(SEQ ID NO: 52)
QAVVTQESALTTSPGGTVILTCRSSTGAVTTSNYANWVQEKPDHLFTGLI

GGTSNRAPGVPVRFSGSLIGDKAALTITGAQTEDDAMYFCALWYSTHYVF

GGGTKVTVL.

In some embodiments, the antibody, or Fab, of the present invention comprises a variable light domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 53:

(SEQ ID NO: 53)
QAVVTQESALTTSPGGTVILTCRSSTGAVTTSNYANWVQEKPDHLFTGLI

GGTSNRAPGVPVRFSGSLIGDKAALTITGAQTEDDAMYFCALWYSTHYVF

GGGTKVTVL.

In some embodiments, the variable heavy domain comprises a CDR1 having an amino acid sequence of GYTFTDHTIH (SEQ ID NO: 54). In further embodiments, the variable heavy domain comprises a CDR2 having an amino acid sequence of YIYPRDGSTKYNEKFK (SEQ ID NO: 55). In still further embodiments, the variable heavy domain comprises a CDR3 having an amino acid sequence of DYGYAFDY (SEQ ID NO: 56).

In further embodiments, the variable light domain comprises a CDR1 having an amino acid sequence of RSSTGAVTTSNYAN (SEQ ID NO: 57). In further embodiments, the variable light domain comprises a CDR2 having an amino acid sequence of GTSNRAP (SEQ ID NO: 58). In still further embodiments, the variable light domain comprises a CDR3 having an amino acid sequence of ALWYSTHYV (SEQ ID NO: 59).

In some embodiments, the antibody, or Fab, of the present invention comprises a variable heavy domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 60:

(SEQ ID NO: 60)
QVQLQQSGAELARPGASVKLSCKASGYTFTSYGIRWVKQRTGQGLEWIGE

IXPRSGNTYYNEKFKGKATVTADKSSSTAYMELRSLTSEDSAVYFCARSI

YYGRPYYFDYWGQGTTLTVSS.

In some embodiments, the antibody, or Fab, of the present invention comprises a variable light domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 61:

(SEQ ID NO: 61)
DIVMTQSQLFMSTSVGDRVSVTCKASQNVATNVAWYQQKPGQSPKALIYS

ASYRYSGVPDRFTGSGSGTDFTLTISNVQSEDLAEYFCQQYNSYPLTFGA

GTKLELK.

In some embodiments, the antibody, or Fab, of the present invention comprises a variable heavy domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 62:

(SEQ ID NO: 62)
QVQLQQSDAELVKPGASVKISCKVSGYTFTDHTIHWMKQRPEQGLEWIGY

IYPRDGSTKYNEKFKGKATLTADKSSSTAYMQLNSLTSEDSAVYFCARDY

GYAFDYWGQGTTTVSS.

In some embodiments, the antibody, or Fab, of the present invention comprises a variable light domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 63:

(SEQ ID NO: 63)
QAVVTQESALTTSPGGTVILTCRSSTGAVTTSNYANWVQEKPDHLFTGLI

GGTSNRAPGVPVRFSGSLIGDKAALTITGAQTEDDAMYFCALWYSTHYVF

GGGTKVTVL.

In some embodiments, the antibody, or Fab, of the present invention comprises a variable heavy domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 64:

(SEQ ID NO: 64)
QVQLQQSDAELVKPGASVKISCKVSGYTFTDHTIHWMKQRPEQGLEWIGY

IYPRDGSTKYNEKFKGKATLTADKSSSTAYMQLNSLTSEDSAVYFCARDY

GYAFDYWGQGTTLTVSS

In some embodiments, the antibody, or Fab, of the present invention comprises a variable light domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 65:

(SEQ ID NO: 65)
QAVVTQESALTTSPGGTVILTCRSSTGAVTTSNYANWVQEKPDHLFTGLI

GGTSNRAPGVPVRFSGSLIGDKAALTITGAQTEDDAMYFCALWYSTHYVF

GGGTKVTVL

In some embodiments, the antibody, or Fab, of the present invention comprises a variable heavy domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 66:

(SEQ ID NO: 66)
EVQLVESGGGLVQPGGSLRLSCAASGFTFSSYGMSWVRQAPGKGLELVAS

INSNGGSTYYPDSVKGRFTISRDNAKNSLYLQMNSLRAEDTAVYYCASGD

YWGQGTTVTVSS

In some embodiments, the antibody, or Fab, of the present invention comprises a variable light domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 67:

(SEQ ID NO: 67)
DIVMTQSPLSLPVTPGEPASISCRSSQSLVYSNGDTYLHWYLQKPGQSPQ

LLIYKVSNRFSGVPDRFSGSGSGTDFTLKISRVEAEDVGVYYCSQSTHVP

WTFGQGTKVEIK.

In some embodiments, the variable heavy domain comprises a CDR1 having an amino acid sequence of GFTFSSYGMS (SEQ ID NO: 68). In further embodiments, the variable heavy domain comprises a CDR2 having an amino acid sequence of SINSNGGSTYYPDSVK (SEQ ID NO: 69). In still further embodiments, the variable heavy domain comprises a CDR3 having an amino acid sequence of GDY (SEQ ID NO: 70).

In further embodiments, the variable light domain comprises a CDR1 having an amino acid sequence of RSSQSLVYSNGDTYLH (SEQ ID NO: 71). In further embodiments, the variable light domain comprises a CDR2 having an amino acid sequence of KVSNRFS (SEQ ID NO: 72). In still further embodiments, the variable light domain comprises a CDR3 having an amino acid sequence of SQSTHVPWT (SEQ ID NO: 73). In still further embodiments, the variable light domain comprises a CDR having an amino acid sequence of RVSNRFS (SEQ ID NO: 74) or KVSSRFS (SEQ ID NO: 75).

Parkinson's Disease

Lewy bodies are the hallmark of Parkinson's disease which is mainly composed of alpha-synuclein. Alpha-synuclein plays a role in the development of rare familial and more common sporadic cases of Parkinson's disease. In familial Parkinson's disease, the expression levels of alpha-synuclein gene is increased or an abnormal form of the protein is found which are toxic to brain cells and result in neuron dysfunction. Alpha-synuclein is the primary structural component of Lewy bodies, suggesting that protein aggregation plays a role in sporadic Parkinson's disease. To treat Parkinson's disease, therapies that reduce alpha-synuclein gene expression or block its aggregation should be developed.

Alpha-synuclein is abundant in the human brain at the neurons tips in specialized structures called presynaptic terminals. Presynaptic terminals release chemical messengers, neurotransmitters, from synaptic vesicles. The release of neurotransmitters relays signals between neurons and is critical for normal brain function. So, alpha-Synuclein is a presynaptic neuronal protein that is thought that its abnormal soluble oligomeric conformations, i.e. protofibrils, are the toxic species that mediate disruption of cellular homeostasis and neuronal death, through effects on various intracellular targets, including synaptic function. Furthermore, secreted Alpha-synuclein may exert deleterious effects on neighboring cells, including seeding of aggregation, thus possibly contributing to disease propagation.

The human alpha-synuclein protein is made of 140 amino acids and is encoded by the SNCA gene. The amino acid sequence of human alpha-synuclein is shown by SEQ ID NO: 76.

SEQ ID NO: 76
SNCAMDVFMKGLSKAKEGVVAAAEKTKQGVAEAAGKTKEGVLYVGSKTKE

GVVHGVATVAEKTKEQVTNVGGAVVTGVTAVAQKTVEGAGSIAAATGFVK

KDQLGKEGYQDYEPEA

In various embodiments, the present antibodies are directed to/or raised against a peptide comprising part of wild type or mutant SCNA, including stretches of amino acids of SEQ ID NO: 76.

In various embodiments, the present agents of conformation-sensitive antibodies target mutated alpha-synuclein, optionally in the context of a protein aggregate. In various embodiments, the present agents of conformation-sensitive antibodies target the following peptide sequences of alpha-synuclein, including but not limited to SEQ ID NO.: 77.

SEQ ID NO: 77 (60-95)
KEQVTNVGGAVVTGVTAVAQKTVEGAGSIAAATGFV

In various embodiments, the present antibodies are directed to/or raised against a peptide comprising part or all of amino acids of SEQ ID NO: 77.

Tau proteins (Tubulin-binding protein) are proteins that function in stabilizing microtubules. Tau proteins are abundant in nerve cells and when become defective or fail to stabilize microtubules, pathologies of the nervous system can develop such as Alzheimer's disease or Parkinson's disease. Tau proteins are mainly active in the distal portions of axons where they stabilize microtubules as well as providing flexibility. Together with tubulin, Tau proteins stabilize microtubules and aid the assembly of tubulin in the microtubules. Hyper-phosphorylation of tau proteins can cause the helical and straight filaments to tangle (referred to as neurofibrillary tangles) which contribute to the pathology of Alzheimer's disease or Parkinson's disease.

Human Tau is encoded on chromosome 17q21 and the protein occurs mainly in the axons of the CNS and consists largely of six isoforms generated by alternative splicing (27). In various embodiments, any mutations of different Tau isoforms described in Cold Spring Harbor Perspectives in Medicine 2012; 2:a006247, the entire contents of which are hereby incorporated by reference, may be targeted by the present agents of conformation-sensitive antibodies.

The human Tau protein is made of 863 amino acids and is encoded by the MAPT gene. The amino acid sequence of human Tau protein is shown by SEQ ID NO: 78.

SEQ ID NO: 78
MAEPRQEFEVMEDHAGTYGLGDRKDQGGYTMHQDQEGDTDAGLKESPLQT

PTEDGSEEPGSETSDAKSTPTAEDVTAPLVDEGAPGKQAAAQPHTEIPEG

TTAEEAGIGDTPSLEDEAAGHVTQEPESGKVVQEGFLREPGPPGLSHQLM

SGMPGAPLLPEGPREATRQPSGTGPEDTEGGRHAPELLKHQLLGDLHQEG

PPLKGAGGKERPGSKEEVDEDRDVDESSPQDSPPSKASPAQDGRPPQTAA

REATSIPGFPAEGAIPLPVDFLSKVSTEIPASEPDGPSVGRAKGQDAPLE

FTFHVEITPNVQKEQAHSEEHLGRAAFPGAPGEGPEARGPSLGEDTKEAD

LPEPSEKQPAAAPRGKPVSRVPQLKARMVSKSKDGTGSDDKKAKTSTRSS

AKTLKNRPCLSPKHPTPGSSDPLIQPSSPAVCPEPPSSPKYVSSVTSRTG

SSGAKEMKLKGADGKTKIATPRGAAPPGQKGQANATRIPAKTPPAPKTPP

SSGEPPKSGDRSGYSSPGSPGTPGSRSRTPSLPTPPTREPKKVAVVRTPP

KSPSSAKSRLQTAPVPMPDLKNVKSKIGSTENLKHQPGGGKVQIINKKLD

-continued

LSNVQSKCGSKDNIKHVPGGGSVQIVYKPVDLSKVTSKCGSLGNIHHKPG

GGQVEVKSEKLDFKDRVQSKIGSLDNITHVPGGGNKKIETHKLTFRENAK

AKTDHGAEIVYKSPVVSGDTSPRHLSNVSSTGSIDMVDSPQLATLADEVS

ASLAKQGL

In various embodiments, the present agents of conformation-sensitive antibodies target mutated Tau protein, optionally in the context of a protein aggregate. In various embodiments, the present antibodies are directed to/or raised against a peptide comprising part of wild type or mutant tau, including stretches of amino acids of SEQ ID NO: 78.

In various embodiments, the present agents of conformation-sensitive antibodies target the following peptide sequences of Tau protein, including but not limited to SEQ ID NOs: 79-80.

SEQ ID NO: 79 (275-305)
VSTEIPASEPDGPSVGRAKGQDAPLEFTFHV

SEQ ID NO: 80 (306-336)
EITPNVQKEQAHSEEHLGRAAFPGAPGEGPE

In various embodiments, the present antibodies are directed to/or raised against a peptide comprising part or all of amino acids of SEQ ID NO: 79 or 80.

Type II Diabetes

There are two major types of diabetes in man, both of which result in a disturbance of the normally tight control of glucose homeostasis affected by insulin secreted from pancreatic islets. Insulin-dependent (Type 1) diabetes is an autoimmune disease resulting in destruction of insulin-secreting cells and the requirement for insulin replacement therapy. Type 2 diabetes is a multifactorial disease with genetic and environmental components; it is characterized by a progressive decrease in the regulation of blood glucose levels. Amyloid is formed only in type 2 diabetic subjects since destruction of the islet β-cells in type 1 diabetes removes the source of IAPP.

Type 2 diabetes is associated with a decrease in insulin secretion and increasing hyperglycemia as a result of β-cell failure. A correlation between β-cell failure in type 2 diabetes and the formation of pancreatic islet amyloid deposits is established. IAPP (amylin), the major component of islet amyloid, is co-secreted with insulin from β-cell and aggregates to form amyloid fibrils that are toxic to β-cells.

Conversion from soluble monomer IAPP to β-sheet fibrils involves changes in the molecular conformation, cellular biochemistry and diabetes-related factors. In humans, the level of production of IAPP is important but is not the main factor in islet amyloidosis. Animal models of islet amyloidosis suggest that diabetes is induced by the deposits whereas in man, fibril formation appears to result from diabetes-associated islet dysfunction. Islet secretory failure results from progressive amyloidosis which provides a target for new therapeutic interventions.

Human IAPP protein is expressed from IAPP gene and is processed from an 89-residue coding sequence (SEQ ID NO: 81). Proislet amyloid polypeptide (proIAPP, proamylin, proislet protein) is produced in the pancreatic beta cells (β-cells) as a 67 amino acid, 7404 Dalton pro-peptide and undergoes post-translational modifications including protease cleavage to produce amylin.

SEQ ID NO.: 81
MGILKLQVFLIVLSVALNHLKATPIESHQVEKRKCNTATCATQRLANFLV

HSSNNFGAILSSTNVGSNTYGKRNAVEVLKREPLNYLPL

In various embodiments, the present antibodies are directed to/or raised against a peptide comprising part of wild type or mutant IAPP, including stretches of amino acids of SEQ ID NO: 81.

In various embodiments, the present agents of conformation-sensitive antibodies target mutated IAPP protein, optionally in the context of a protein aggregate. In various embodiments, the present agents of conformation-sensitive antibodies target the following peptide sequences of IAPP protein, including but not limited to SEQ ID NO: 82.

SEQ ID NO.: 82 (34-70)
KCNTATCATQRLANFLVHSSNNFGAILSSTNVGSNTY

In various embodiments, the present antibodies are directed to/or raised against a peptide comprising part or all of amino acids of SEQ ID NO: 82.

In some embodiments, the present invention relates to an anti-amyloid therapeutic vaccine and solubilizing monoclonal antibody. The present invention also includes antigenic peptide fragments modified so as to increase their antigenicity. For example, antigenic moieties and adjuvants may be attached to or admixed with the peptide. Examples of antigenic moieties and adjuvants include, but are not limited to, lipophilic muramyl dipeptide derivatives, nonionic block polymers, aluminum hydroxide or aluminum phosphate adjuvant, and mixtures thereof. It is also to be understood that the supramolecular antigenic construct compositions of the present invention can further comprise additional adjuvants including, but not limited to, keyhole limpet hemocyanin (KLH), bovine serum albumin (BSA) and other adjuvants such as, for example, lipid A, alum, calcium phosphate, interleukin 1, and/or microcapsules of polysaccharides and proteins, but particularly a detoxified lipid A, such as monophosphoryl or diphosphoryl lipid A, or alum, further preservatives, diluents, emulsifiers, stabilizers, and other components that are known and used in vaccines of the prior art. Moreover, any adjuvant system known in the art can be used in the composition of the present invention. Such adjuvants include, but are not limited to, Freund's incomplete adjuvant, Freund's complete adjuvant, polydispersed β-(1,4) linked acetylated mannan ("Acemannan"), TITERMAX® (polyoxyethylene-polyoxypropylene copolymer adjuvants from CytRx Corporation), modified lipid adjuvants from Chiron Corporation, saponin derivative adjuvants from Cambridge Biotech, killed *Bordetella pertussis*, the lipopolysaccharide (LPS) of gram-negative bacteria, large polymeric anions such as dextran sulfate, and inorganic gels such as alum, aluminum hydroxide, or aluminum phosphate.

In various embodiments, the agents of the invention, e.g. transfected cells comprising conformation-sensitive antibodies, are capable of substantially solubilzing aggregates that are linked to disease, e.g. ALS. In some embodiments, the solubilization is in vivo. In some embodiments, the solubilization is in vitro. In various embodiments, the agents cause about 90% solubilization, or about 80% solubilization, or about 70% solubilization, or about 60% solubilization, or about 50% solubilization, or about 40% solubilization, or about 30% solubilization, or about 25% solubilization.

Further, in some embodiments, the agents of the invention target the toxic form of the aggregate conformation. Since alone the β-sheet conformation of Aβ is cytotoxic, the antigenic construct elicits antibodies displaying a higher affinity for Aβ in that conformation, as compared to the affinity for the alpha-helix or random coil conformation of the amyloid target. Synthetic peptide, immunogens that mimic the conformation of a target epitope of pathological relevance offer the possibility to precisely control the immune response specificity.

In some embodiments of the present invention, the peptide of interest is added to phospholipids to give a peptide/phospholipid ratio of about 1:100. In other aspects, the peptide/phospholipid ratio is about 1:50, about 1:150, about 1:200, about 1:250, or about 1:300.

The term "antibody," as used herein, is intended to refer to immunoglobulin molecules comprised of four polypeptide chains, two heavy (H) chains and two light (L) chains inter-connected by disulfide bonds capable of binding one or more antigens (e.g. bi-specific or multi-specific antibodies). Each heavy chain is comprised of a heavy chain variable region (abbreviated herein as HCVR or $V_H$) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, CL. The $V_H$ and $V_L$ regions can be further subdivided into regions of hypervariability, termed complementarity determining regions (CDRs), interspersed with regions that are more conserved, termed framework regions (FR). Each variable region ($V_H$ or $V_L$) contains 3 CDRs, designated CDR1, CDR2 and CDR3. Each variable region also contains 4 framework sub-regions, designated FR1, FR2, FR3 and FR4. The term antibody includes all types of antibodies, including, for example, IgA, IgG, IgD, IgE and IgM, and their respective subclasses (isotypes), e.g., IgG-1, IgG-2, IgG-3, and IgG-4; IgA-1 and IgA-2. The term "antibody" as used herein is also intended to refer to antibody fragments and antigen-binding fragments.

In certain embodiments, the agent is an antibody. The antibody may be polyclonal or monoclonal; intact or truncated (e.g., F(ab')$_2$, Fab, Fv); bispecific or multispecific; xenogeneic, allogeneic, syngeneic, or modified forms thereof (e.g., a chimeric antibody or a humanized antibody). In an embodiment, the agent is a monoclonal antibody. The monoclonal antibody may be a non-human mammal-derived monoclonal antibody, a recombinant chimeric monoclonal antibody, a recombinant humanized monoclonal antibody, or a human monoclonal antibody. In certain embodiments, the antibody further comprises an Fc region of an immunoglobulin (e.g. IgA, IgG, IgE, IgD or IgM) which may interact with Fc receptors and activate an immune response.

A variety of suitable antibody formats are known in the art, such as, bispecific IgG-like formats (e.g., chimeric antibodies, humanized antibodies, human antibodies, single chain antibodies, heterodimers of antibody heavy chains and/or light chains, antigen-binding fragments of any of the foregoing (e.g., a Fv fragment (e.g., single chain Fv (scFv), a disulfide bonded Fv), a Fab fragment, a Fab' fragment, a F(ab')$_2$ fragment), a single variable domain (e.g., $V_H$, $V_L$, $V_{HH}$, a dAb, and modified versions of any of the foregoing (e.g., modified by the covalent attachment of polyalkylene glycol (e.g., polyethylene glycol, polypropylene glycol, polybutylene glycol) or other suitable polymer).

Further, smaller immunoglobulin molecules have been constructed and are possible formats for the present agents.

A single-chain variable antibody fragment (scFv) comprises an antibody heavy chain variable domain joined via a short peptide to an antibody light chain variable domain (Huston et al., Proc. Natl. Acad. Sci. USA, 1988, 85: 5879-83). Because of the small size of scFv molecules, they exhibit more effective penetration into tissues than whole immunoglobulin. Alternatively, it has been proposed that fusion of a scFv to another molecule, such as a toxin, could take advantage of the specific antigen-binding activity and the small size of a scFv to deliver the toxin to a target tissue. See Chaudary et al., Nature 1989, 339:394; Batra et al., Mol. Cell. Biol. 1991, 11:2200. Conjugation or fusion of toxins to scFvs has thus been offered as an alternative strategy to provide potent, antigen-specific molecules.

Antibodies that are agents of the present invention and/or suitable for practicing the methods described herein can be, for example, monoclonal, polyclonal, bispecific, multispecific, and can include, but are not limited to, human, humanized or chimeric antibodies, comprising single chain antibodies, Fab fragments, F(ab') fragments, fragments produced by a Fab expression library, and/or binding fragments of any of the above. Antibodies also refer to immunoglobulin molecules and immunologically active portions of immunoglobulin molecules, i.e., molecules that contain at least two antigen or target binding sites against at least two targets described herein. The immunoglobulin molecules described herein can be of any type (e.g., IgG, IgE, IgM, IgD, IgA and IgY), class (e.g., IgG1, IgG2, IgG3, IgG4, IgA1 and IgA2) or subclass of immunoglobulin molecule, as is understood by one of skill in the art. In addition, antibodies (e.g. mono-specific, bi-specific, and/or mutli-specific) suitable for practicing the methods of the invention described herein can be, for example, Probodies (e.g. capped or masked prodrug antibodies (e.g. Cytomix)); Diabodies; "BITEs"; TandAbs; Flexibodies; Camelid Antibodies; dAbs; Immunobodies; Triomabs; Troybodies; Pepbodies; Vaccibodies; SigA plAntibodies; SMIPs; NARs; IgNARs; XmABs; syn-humanisation antibodies; minibodies; RabMAbs; Fcabs; mAb2 antibodies; Sympress antibodies; UniBodies; DuoBodies; or Vascular Targeting antibodies, as described in US Patent Nos. or Patent Publication Nos. U.S. Pat. No. 7,150,872, US 2007/004909, U.S. Pat. Nos. 5,837, 242, 7,235,641, US 2005/089519, US 2005/079170, U.S. Pat. No. 6,838,254, US 2003/088074, US 2006/280734, US 2004/146505, U.S. Pat. Nos. 5,273,743, 6,551,592, 6,294, 654, US 2004/101905, US 2004/253238, U.S. Pat. No. 6,303,341, US 2008/227958, US 2005/043519, US 2009/148438, US 2008/0181890, US 2008/095767, U.S. Pat. No. 5,837,821, WO 2009/117531, US 2005/033031, US 2009/298195, US 2009/298195, European Patent Publication EP 2152872, WO 2010/063785, US 2010/105874, U.S. Pat. No. 7,087,411 and/or US 2010/316602. See also, Storz Mabs. 2011 May-June; 3(3): 310-317.

In some embodiments of the invention described herein, the antibody is an antibody fragment. As used herein, the term "antibody fragment" or "antigen-binding fragment" refers to a protein fragment that comprises only a portion of an intact antibody, generally including an antigen binding site of the intact antibody and thus retaining the ability to bind antigen. Examples of antibody fragments include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CHI domain; (v) the Fv fragment having the $V_L$ and $V_H$ domains of a single arm of an antibody; (vi) the dAb fragment (Ward et al., Nature 341, 544-546 (1989)) which consists of a $V_H$ domain; (vii) isolated CDR regions; (viii) F(ab')$_2$ fragments, a bivalent fragment including two Fab' fragments linked by a disulphide bridge at the hinge region; (ix) single chain antibody molecules (e.g. single chain Fv; scFv) (Bird et al., Science 242:423-426 (1988); and Huston et al, PNAS (USA) 85:5879-5883 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments ($V_H$-$C_h$1-$V_H$-$C_h$1) which, together with complementary light chain polypeptides, form a pair of antigen binding regions (Zapata et al., Protein Eng. 8(10): 1057-1062 (1995); and U.S. Pat. No. 5,641,870).

Repair

The main obstacle to brain delivery of drugs, proteins, oligonucleotides, etc. is constituted by the blood brain barrier. The BBB is practically impermeable. In some embodiments, the present invention can be used to repair the BBB, e.g., in diseases like Alzheimer Disease (AD) and Amyotrophic Lateral Sclerosis (ALS). In other embodiments, the present invention allows for the repair of BBB as well as release of antibodies or antibody fragments by the BBB without damaging the BBB and its functions.

In some embodiments, the present invention relates to the repair of cellular damage in tumors, diabetes II, heart attack, myocardial infarction, stroke, respiratory insufficiency, etc. The cellular vehicles described herein (e.g., EPCs) are therapeutic tools when they are modified by transfection with genes encoding therapeutic proteins, peptides, antibodies, antibody fragments, etc.

In some embodiments, the present invention can be used for repair of angiogenesis in retina, repair of wounds caused by a deficient blood supply (diabetes foot), repair of myocardial tissue after heart attack, vessel normalization in case of pathological tumor angiogenesis, skin diseases, etc.

Vectors

This invention also provides nucleic acid constructs that encode one or more antibodies or portions thereof and, optionally, allow for expression of the antibodies or portions thereof in prokaryotic and eukaryotic cells. For example, this invention provides vectors (e.g., DNA- or RNA-based vectors, including replication vectors or expression vectors) containing nucleotide sequences that encode one or more antibodies directed against (or antibody that specifically binds to) TDP43, beta-amyloid (Aβ), SOD-1, FUS/TLS, α-synuclein, Tau protein, and IAPP. In other embodiments, this invention provides vectors containing nucleotide sequences that encode a portion of one or more antibodies directed against (or antibody that specifically binds to) TDP43, beta-amyloid (Aβ), SOD-1, FUS/TLS, α-synuclein, Tau protein, and IAPP. For example, in one embodiment, one vector encodes a heavy chain or portions thereof and another vector encodes the light chain of the antibody or portions thereof.

In one embodiment, the vector includes the whole antibody or Fab portion of the antibody and is transfected into a host cell to express the whole antibody or the Fab portion of the antibody. In another embodiment, two or more vectors are transfected in to the host cell where a first vector encodes for a first portion of the antibody (e.g., the heavy chain) and a second vector encodes for a second portion of the antibody (e.g., the light chain). Such two or more vectors may be, in one example, cotransfected into the host cell.

Figure 3:
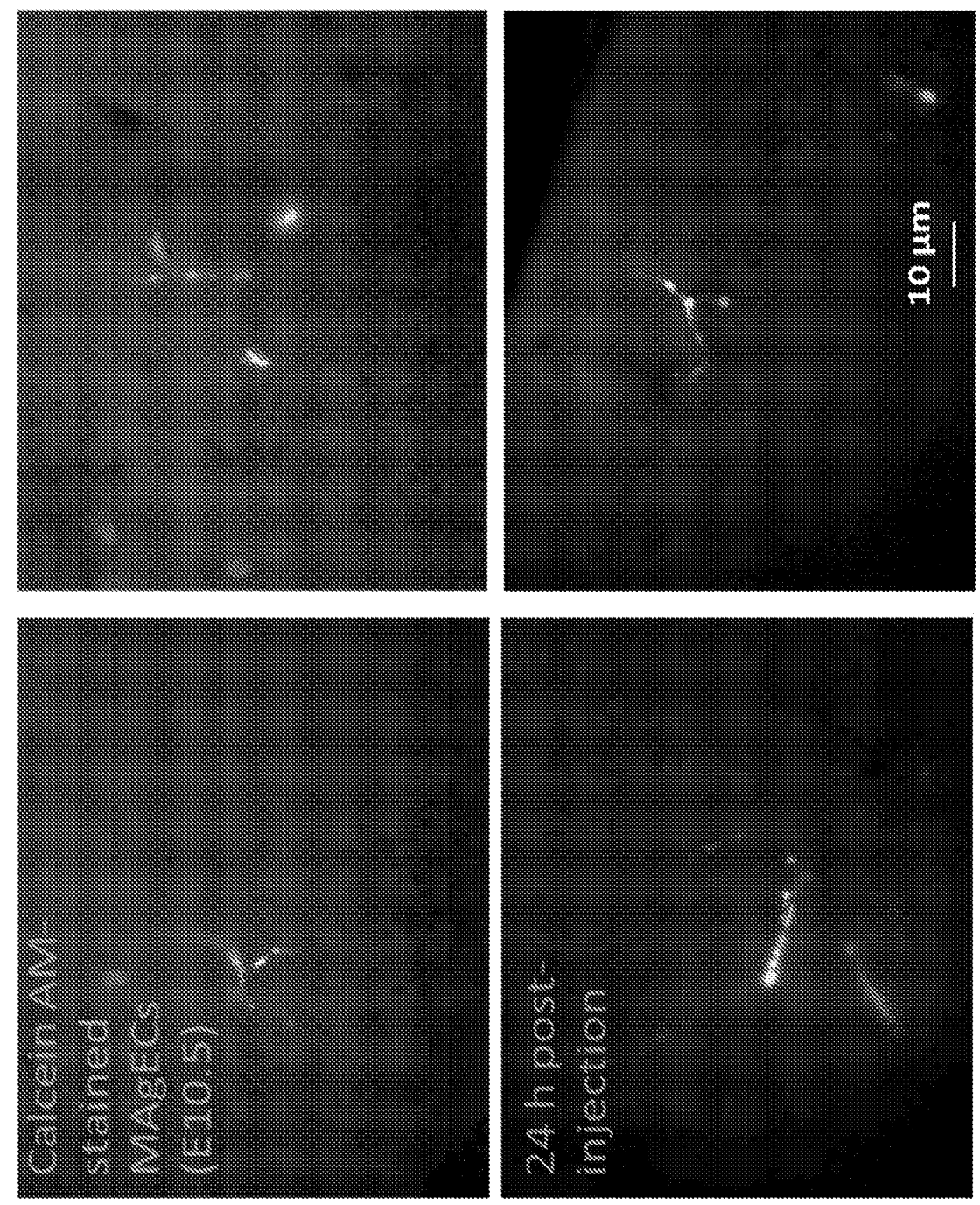
FIG. 3 depicts the fluorescence microscopy detection of GFP-MAgEC 10.5 in the mouse brain microvasculature.
Figure 4:
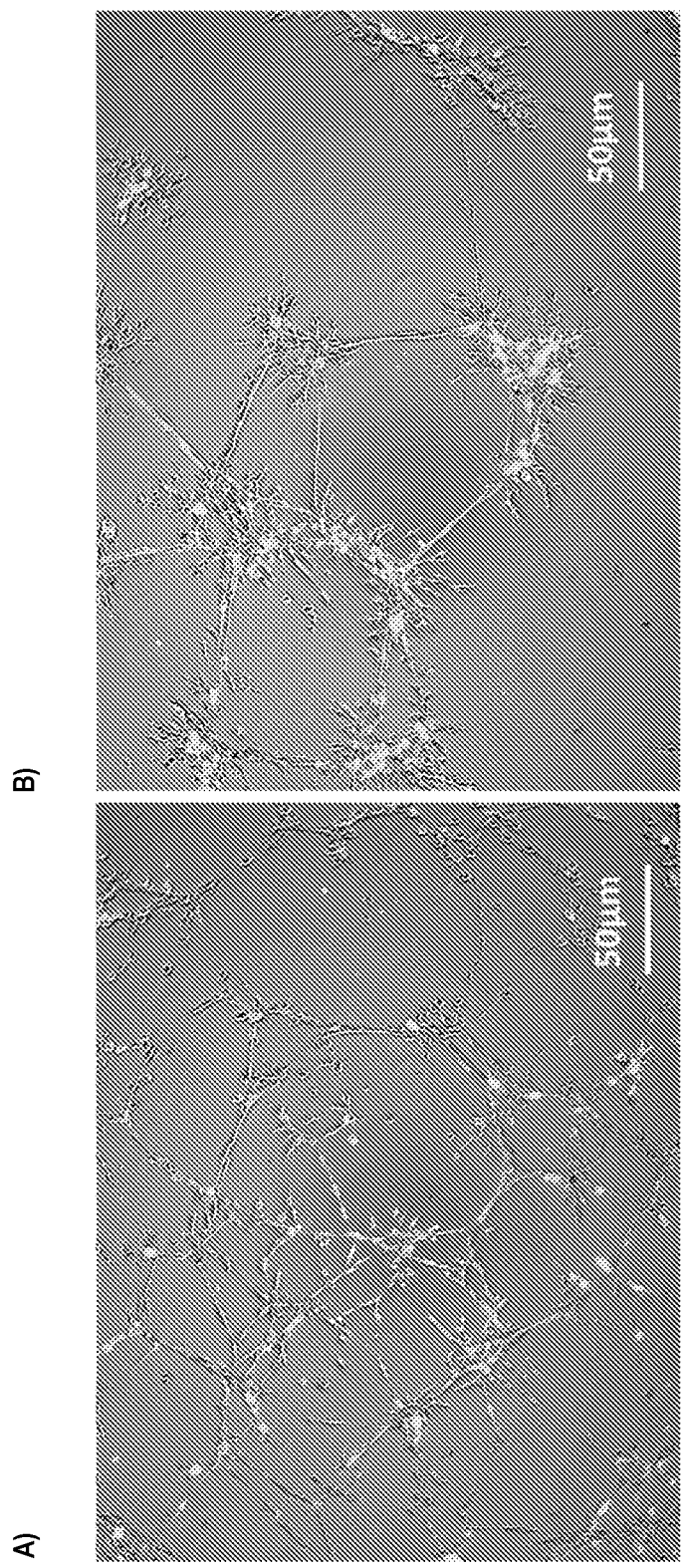
FIG. 4A-B shows cooperation in the angiogenesis process between the co-cultivated BBB (MBrMEC Hoescht-labelled) and the EPCs (GFP-MAgEC 10.5 cells) via co-localization of fluorescence signals.
Figure 5:
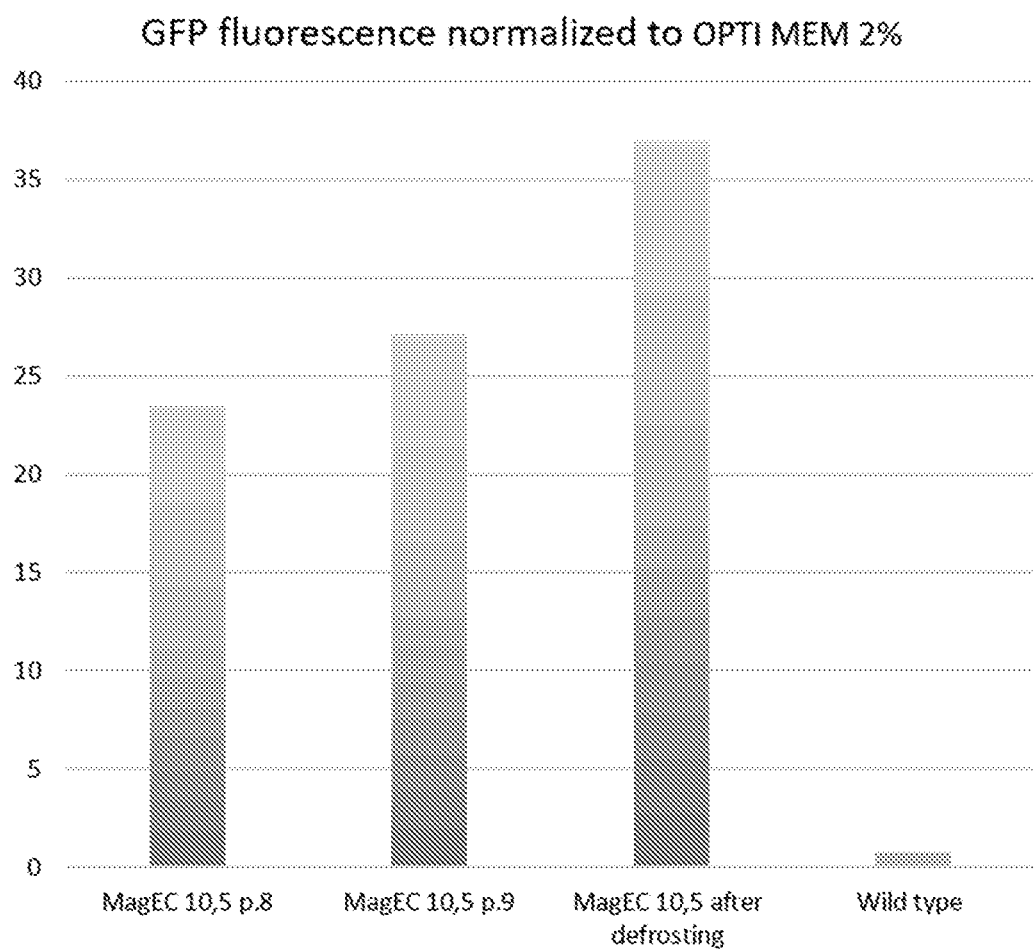
FIG. 5A-C depicts the results of using flow cytometry to measure GFP expression by EPCs transfected with a vector over time, where MAgEC 10.5 p.8 is synonymous with MAgEC 10.5 cells after 8 passages and MAgEC 10.5 p.9 is synonymous with MAgEC 10.5 cells after 9 passages. A wild-type control where cells were not transfected with a vector showed little to no GFP expression.
Figure 5:
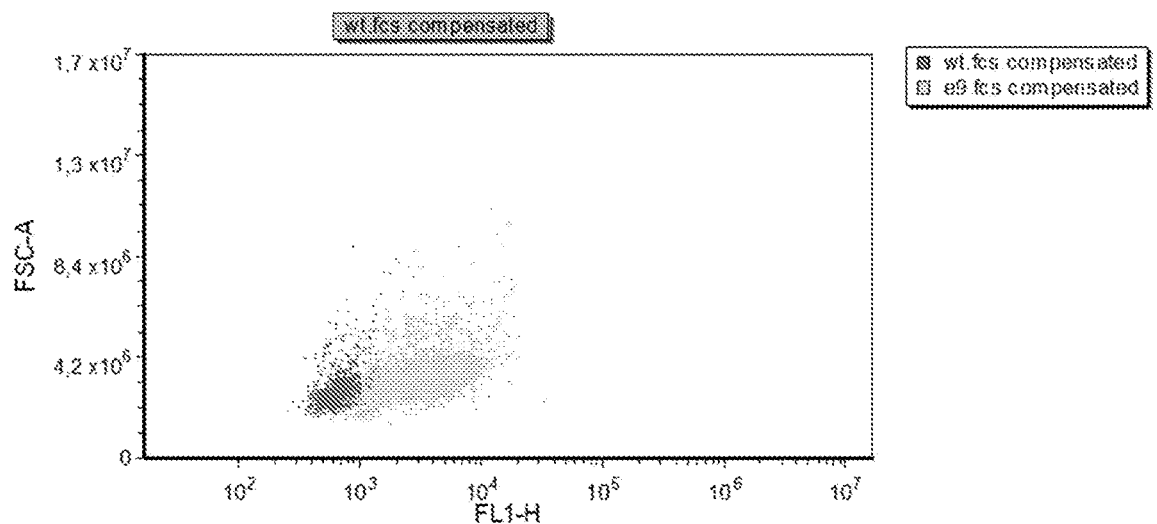
Figure 5:
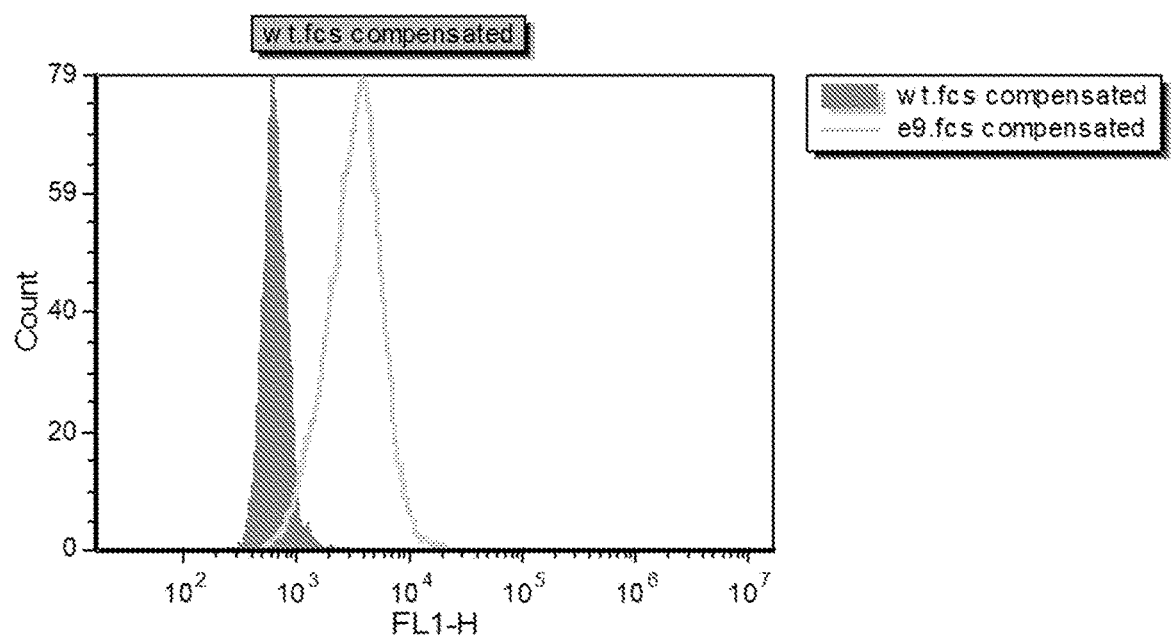
Figure 6:
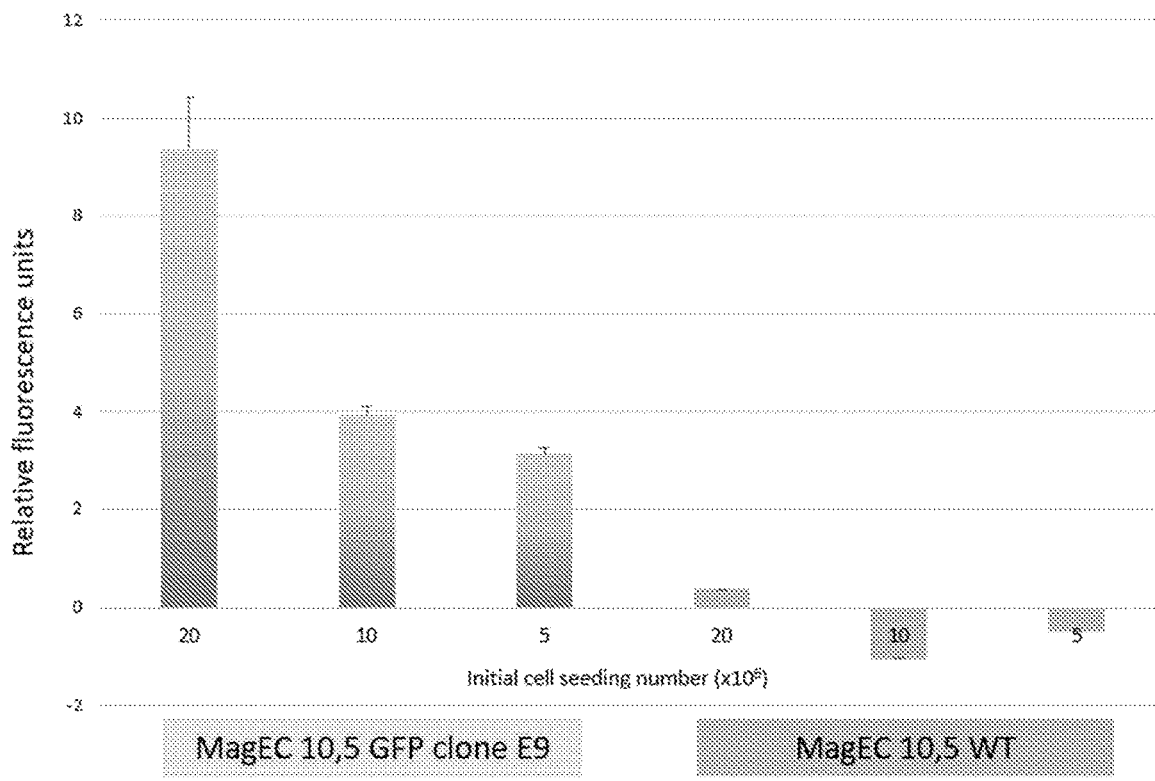
FIG. 6 depicts GFP secretion as a function of cell number.
Figure 7:
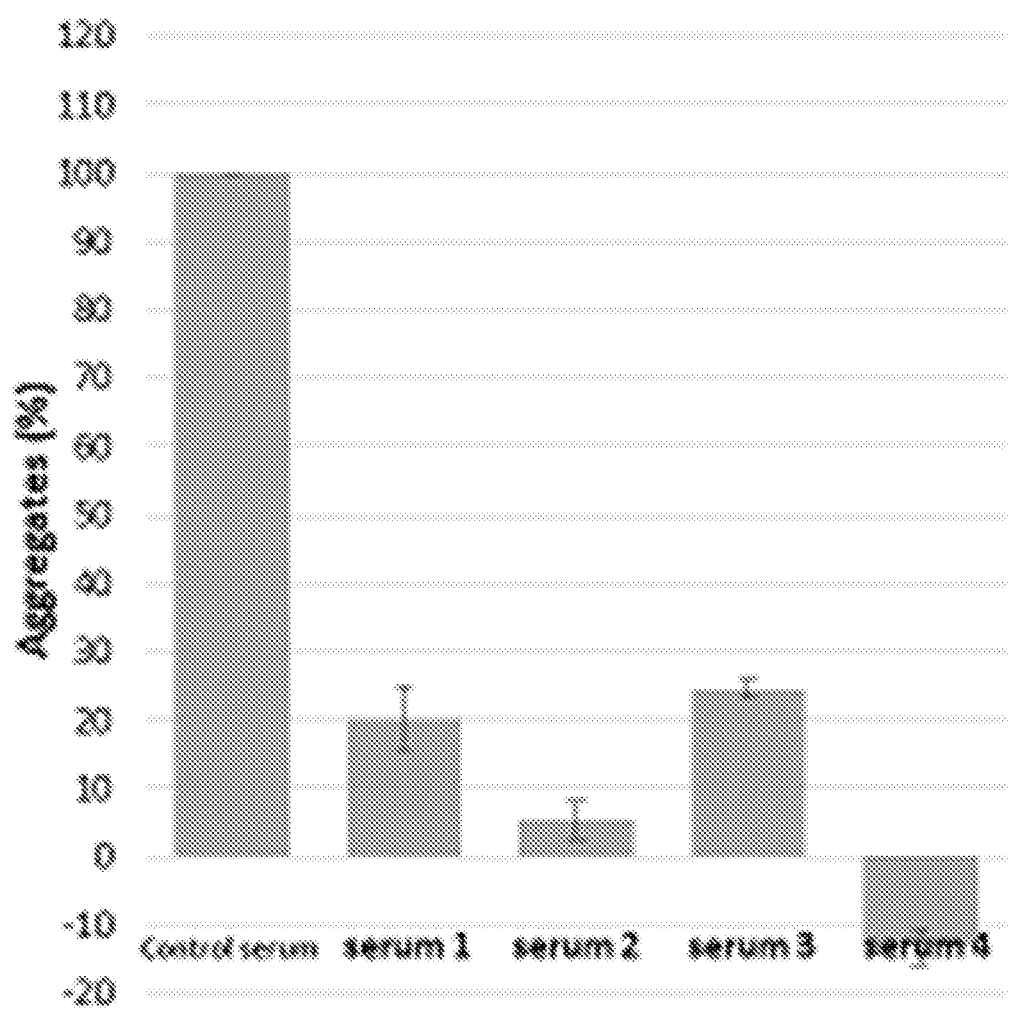
FIG. 7A-B depicts the percentage of aggregated protein in the presence of anti-sera of immunized C57BL/6 mice compared to sera of non-immunized mouse (control) measuring the ThT fluorescence emission.
Figure 7:
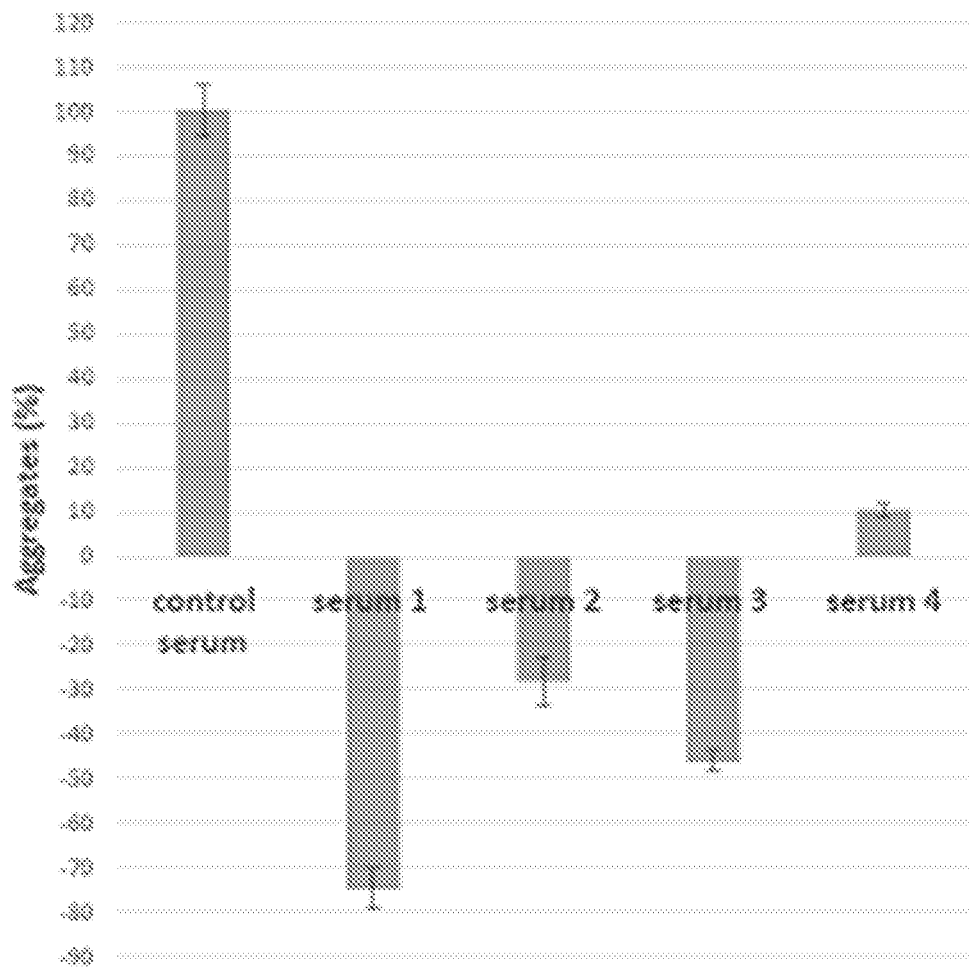
Figure 8:
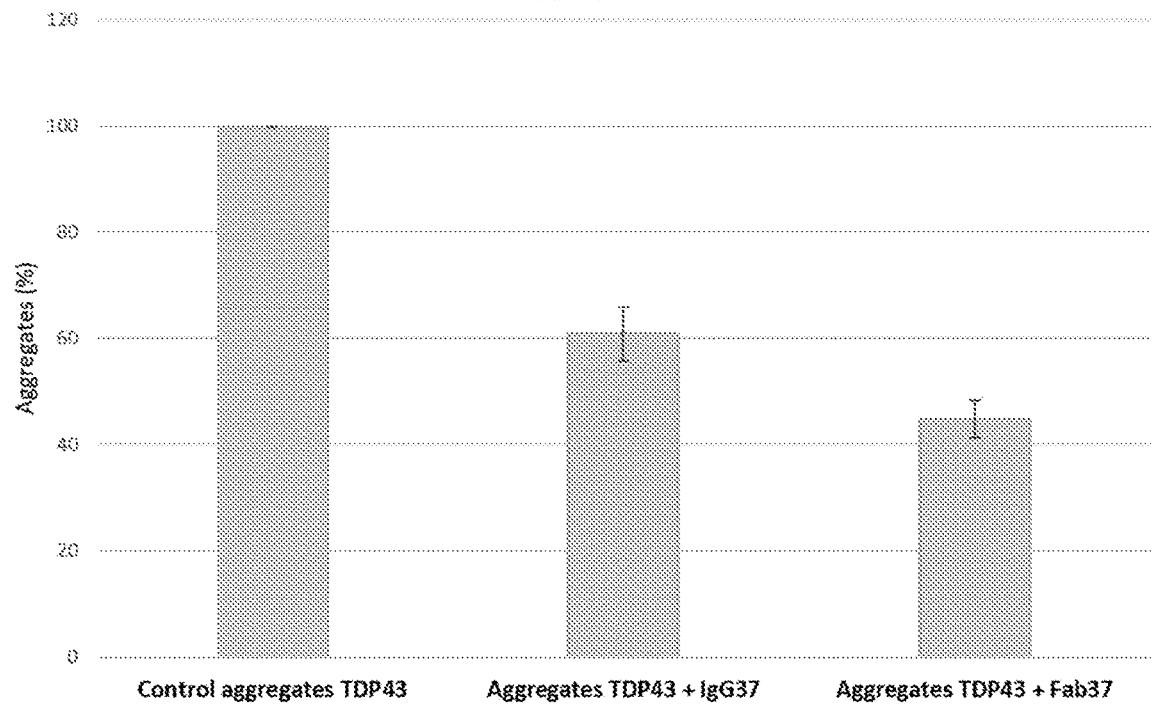
FIG. 8 shows the solubilization of TDP-43 aggregates with purified anti-TDP-43 antibodies (both IgG and Fab) in mice.
Figure 9:
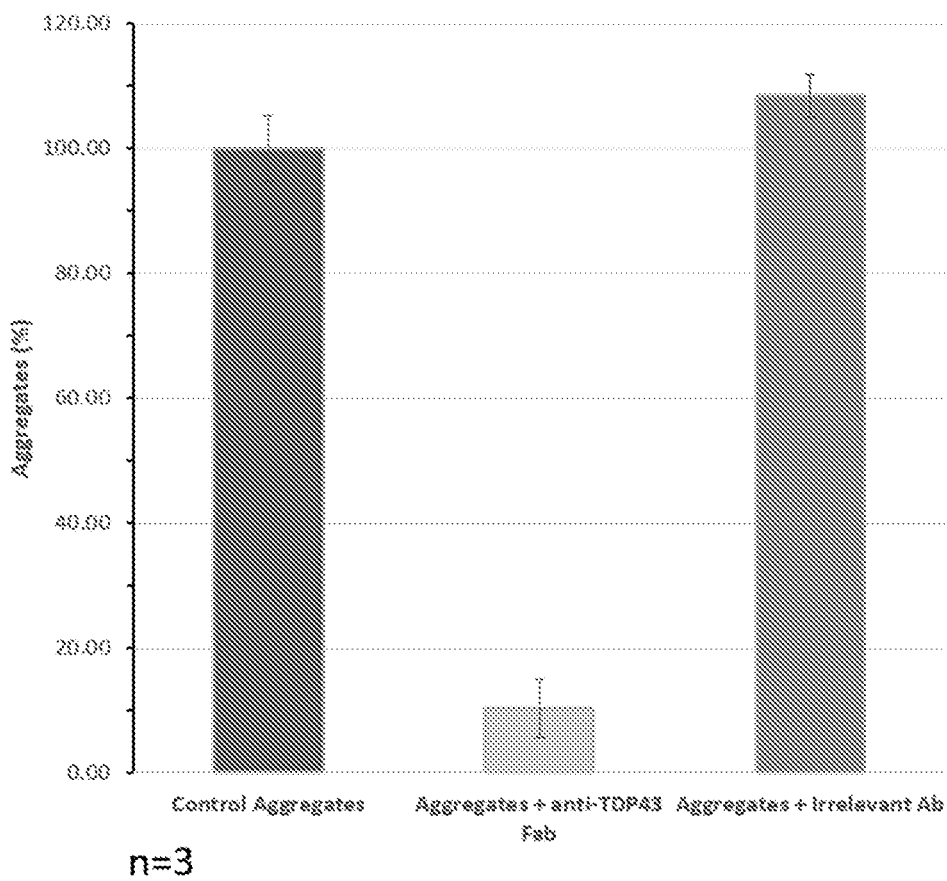
FIG. 9A-B shows the solubilization of TDP-43 and β-Amyloid aggregates.
Figure 9:
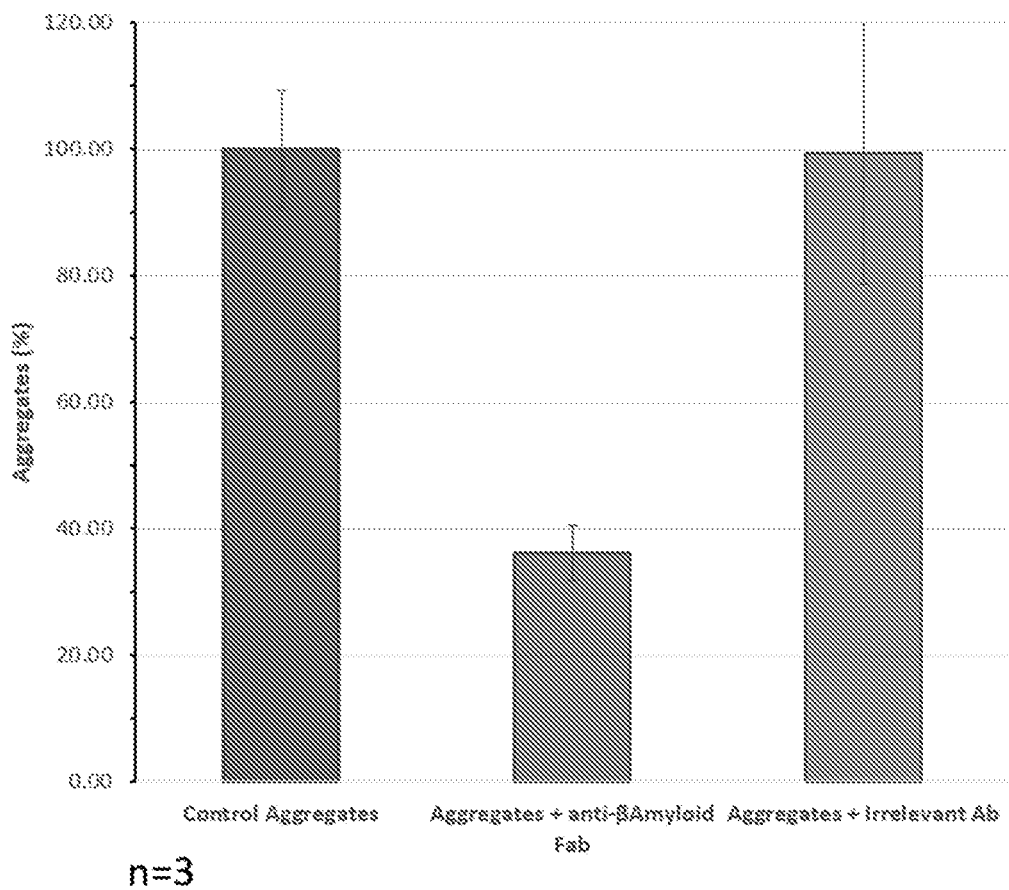
Figure 10:
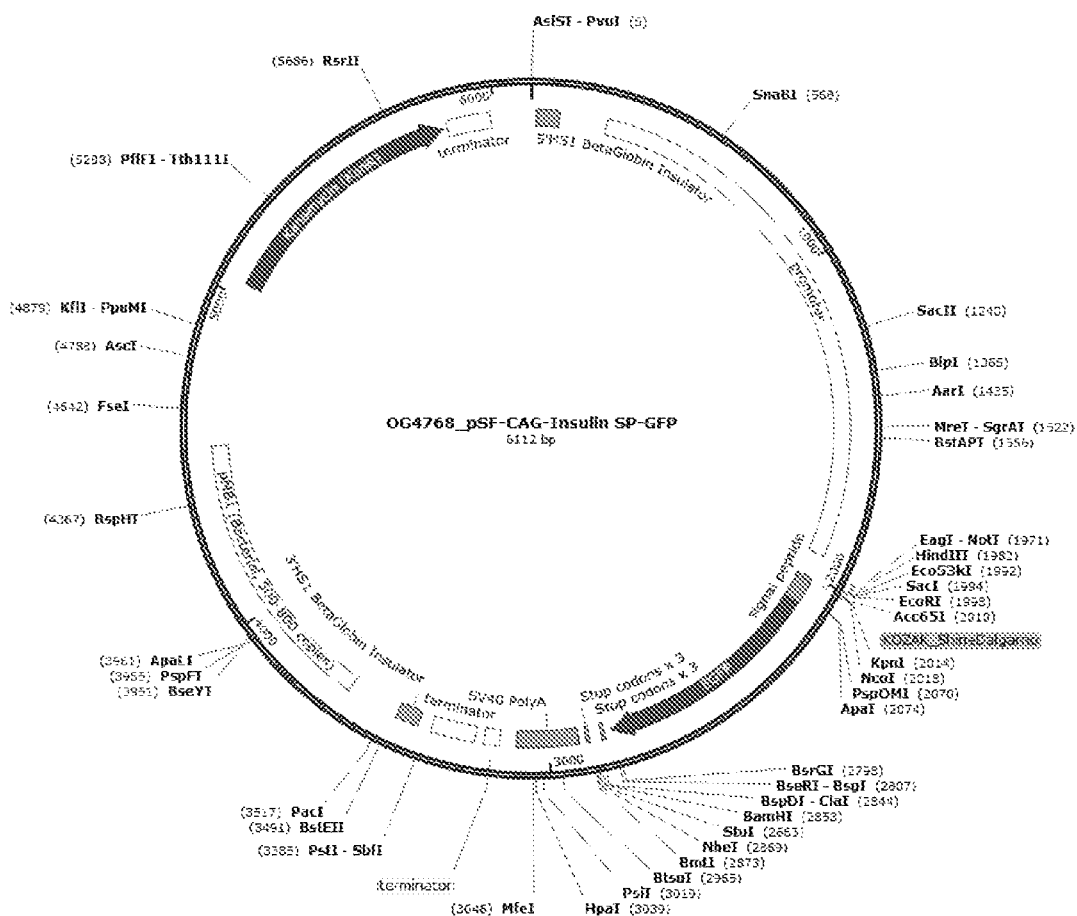
FIG. 10 depicts a map of the OG4768_pSF-CAG-Insulin SP-GFP vector.
Figure 11:
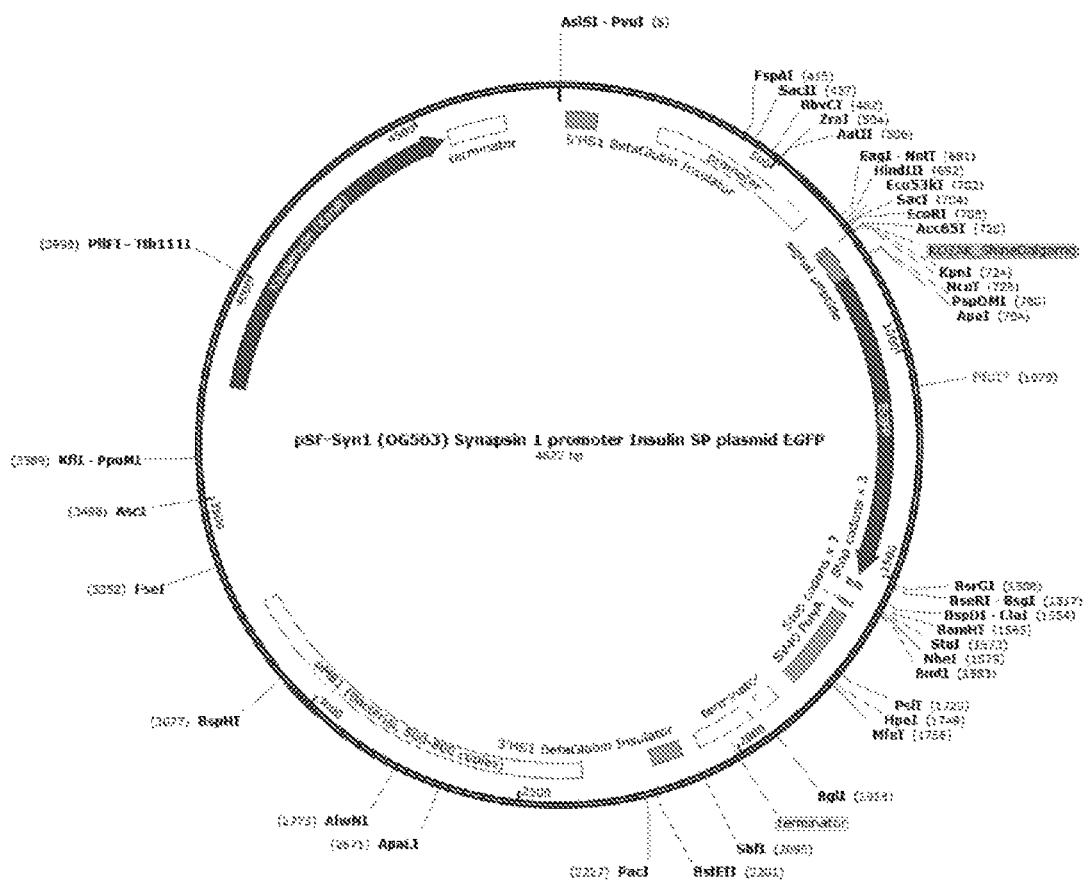
FIG. 11 depicts a map of the OG503_pSF-Synapsin-Insulin SP-GFP vector.
Figure 12:
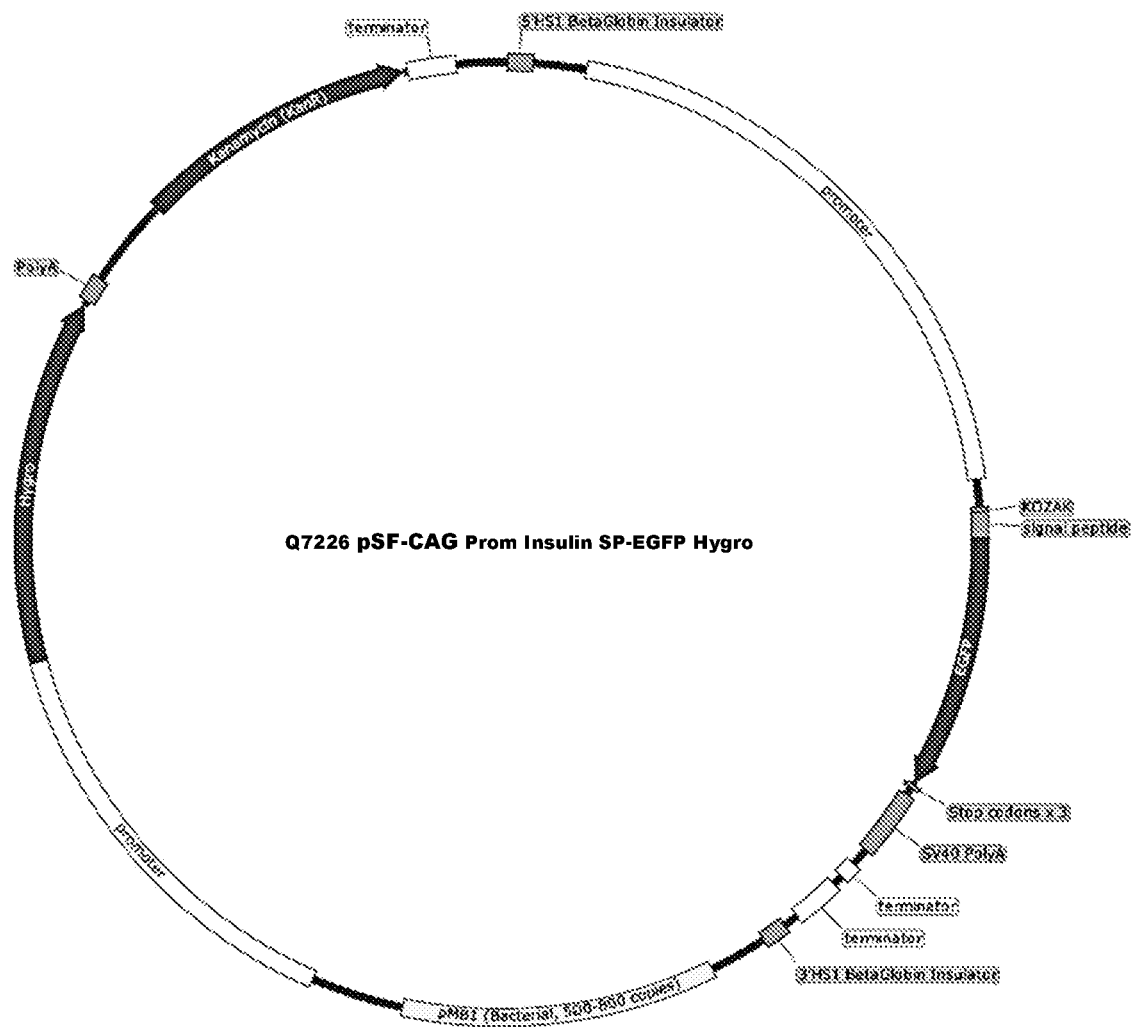
FIG. 12 depicts a map of the Q7226 pSF-CAG Prom Insulin SP-EGFP Hygro vector.
Figure 13:
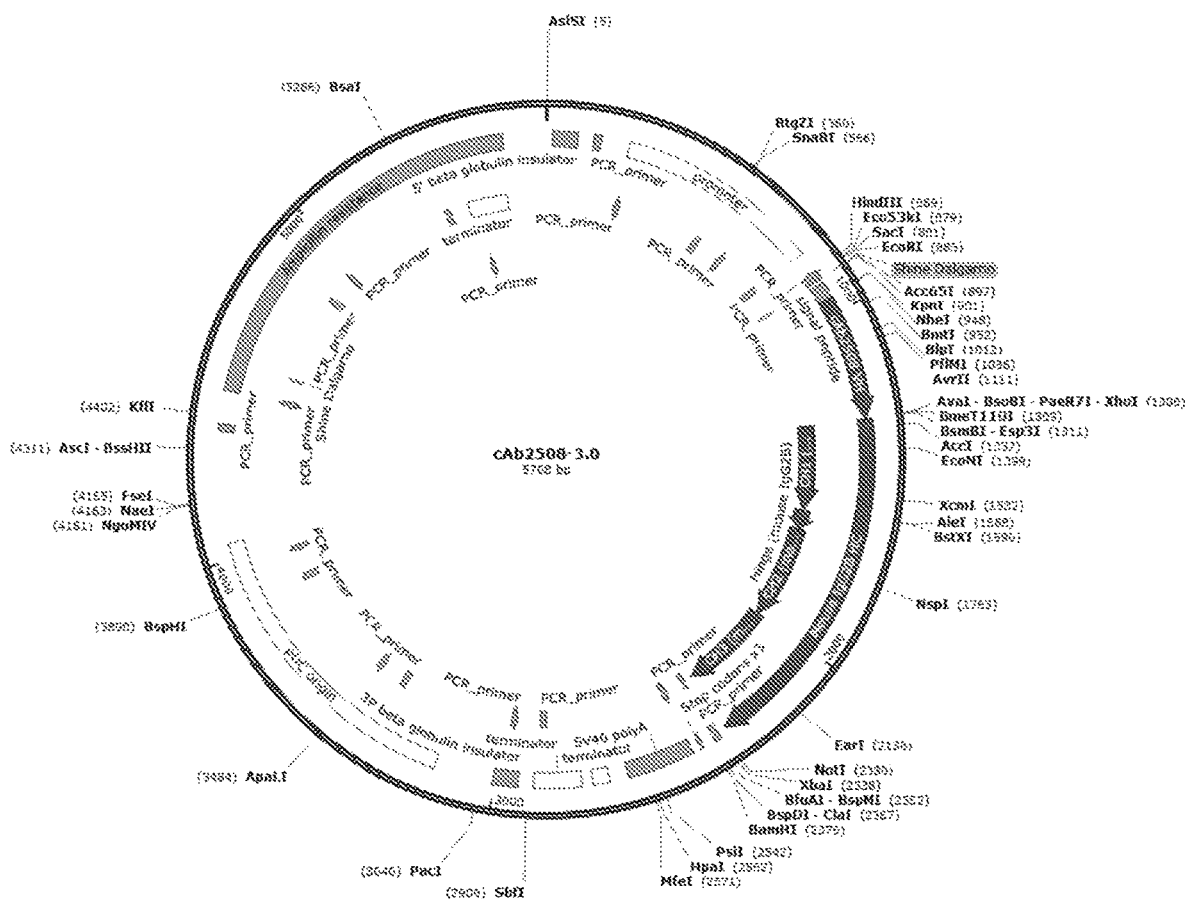
FIG. 13 depicts a map of the cAb2508-3.0 vector (SEQ ID NO: 84) expressing antiTDP43 Fab antibody fragment having a nucleotide sequence encoding the heavy chain and the light chain.
Figure 14:
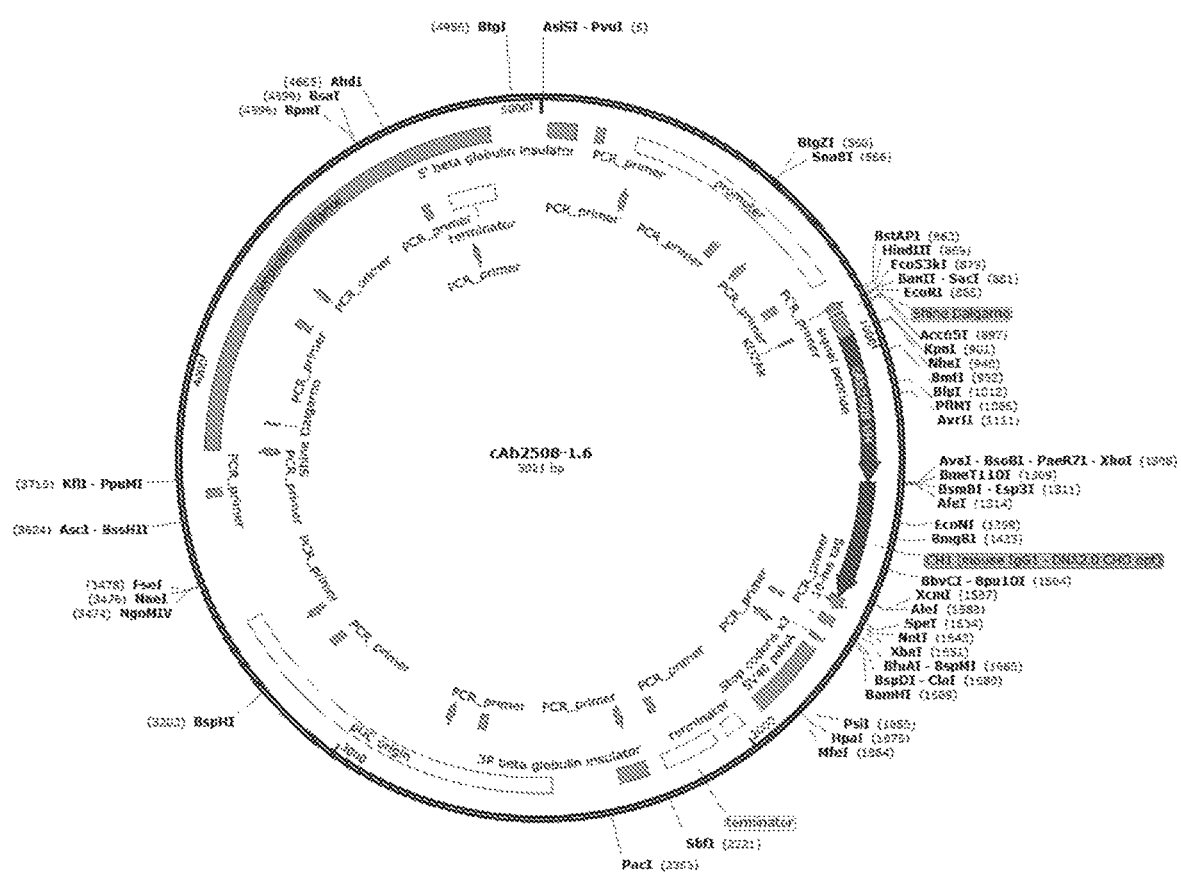
FIG. 14 depicts a map of the cAb2508-1.6 vector (SEQ ID NO: 83) expressing portions of antiTDP43 Fab antibody fragment having a nucleotide sequence encoding the heavy chain.
Figure 15:
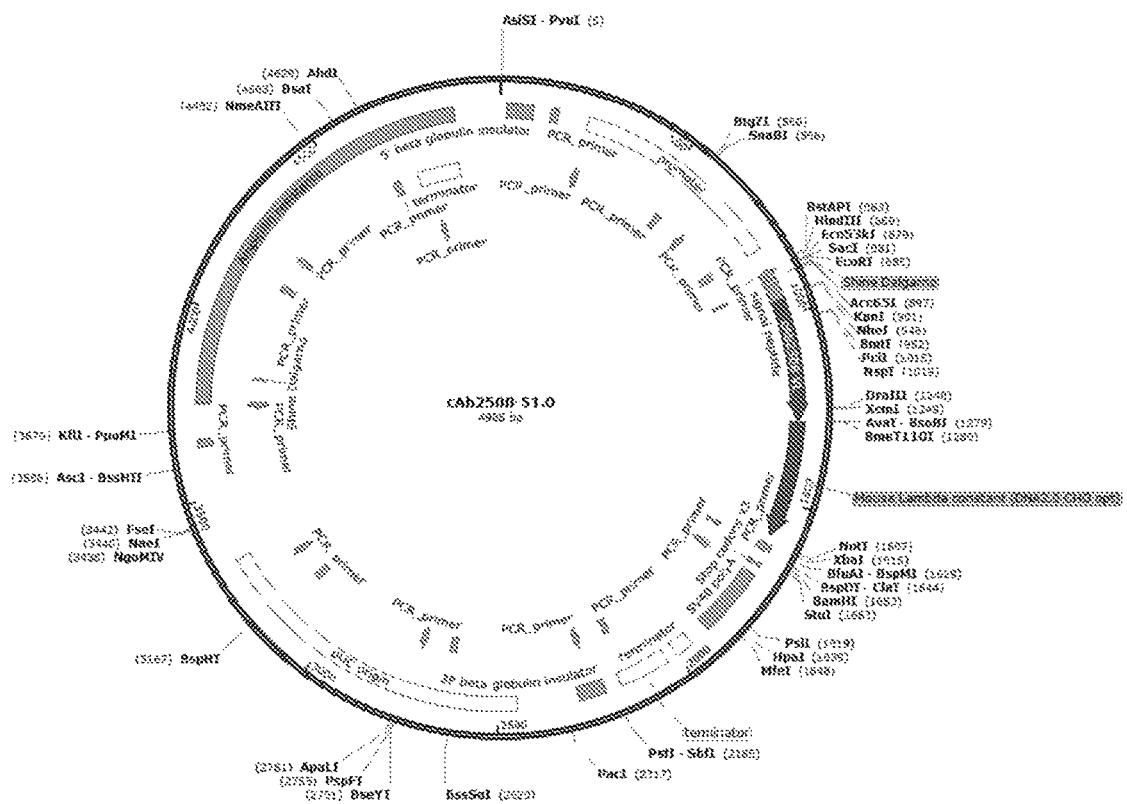
FIG. 15 depicts a map of the cAb2508-51.0 vector (SEQ ID NO: 85) expressing portions of antiTDP43 Fab antibody fragment having a nucleotide sequence encoding the light chain.
Figure 16:
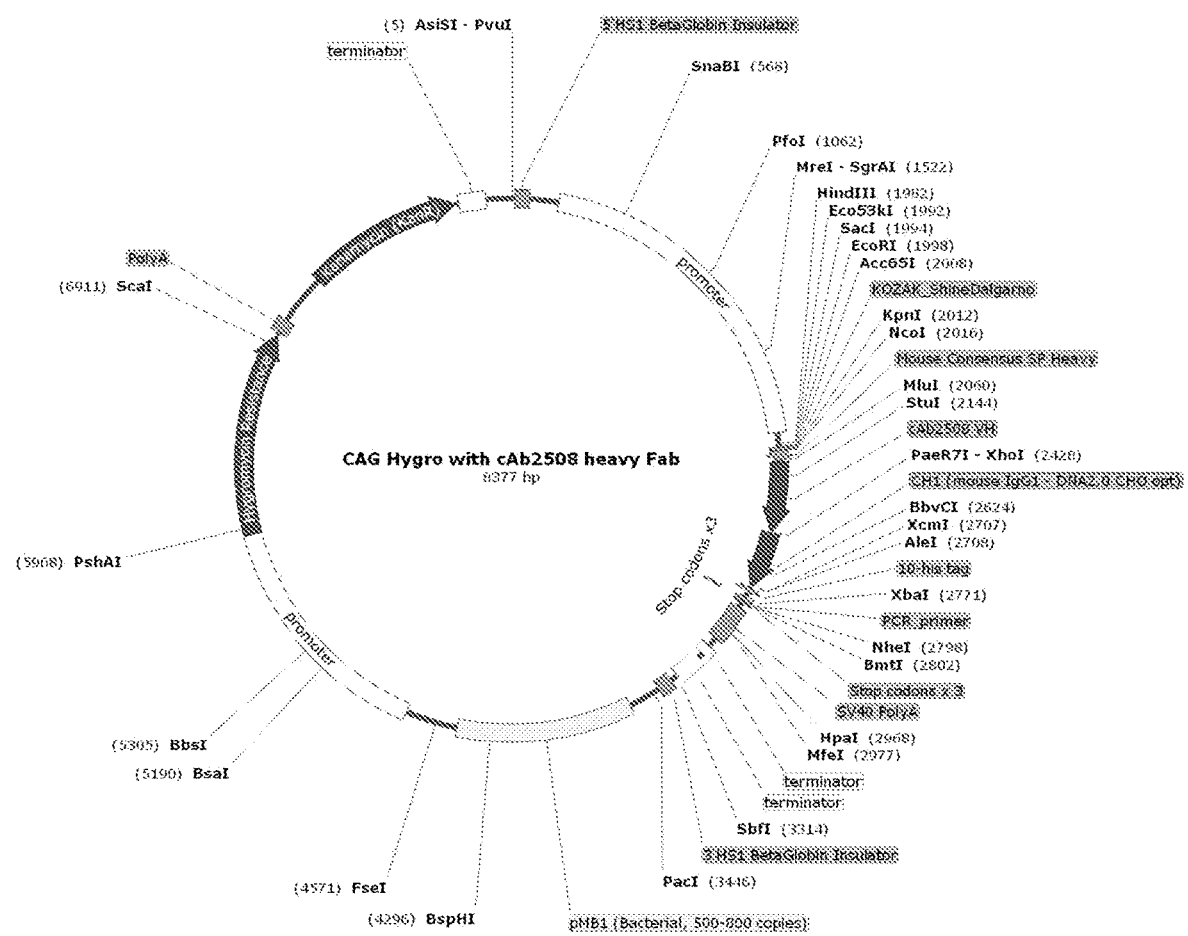
FIG. 16 depicts a map of the CAG Hygro with cAb2508 Heavy Fab vector (SEQ ID NO: 86) expressing portions of antiTDP43 Fab antibody fragment having a nucleotide sequence encoding the heavy chain.
Figure 17:
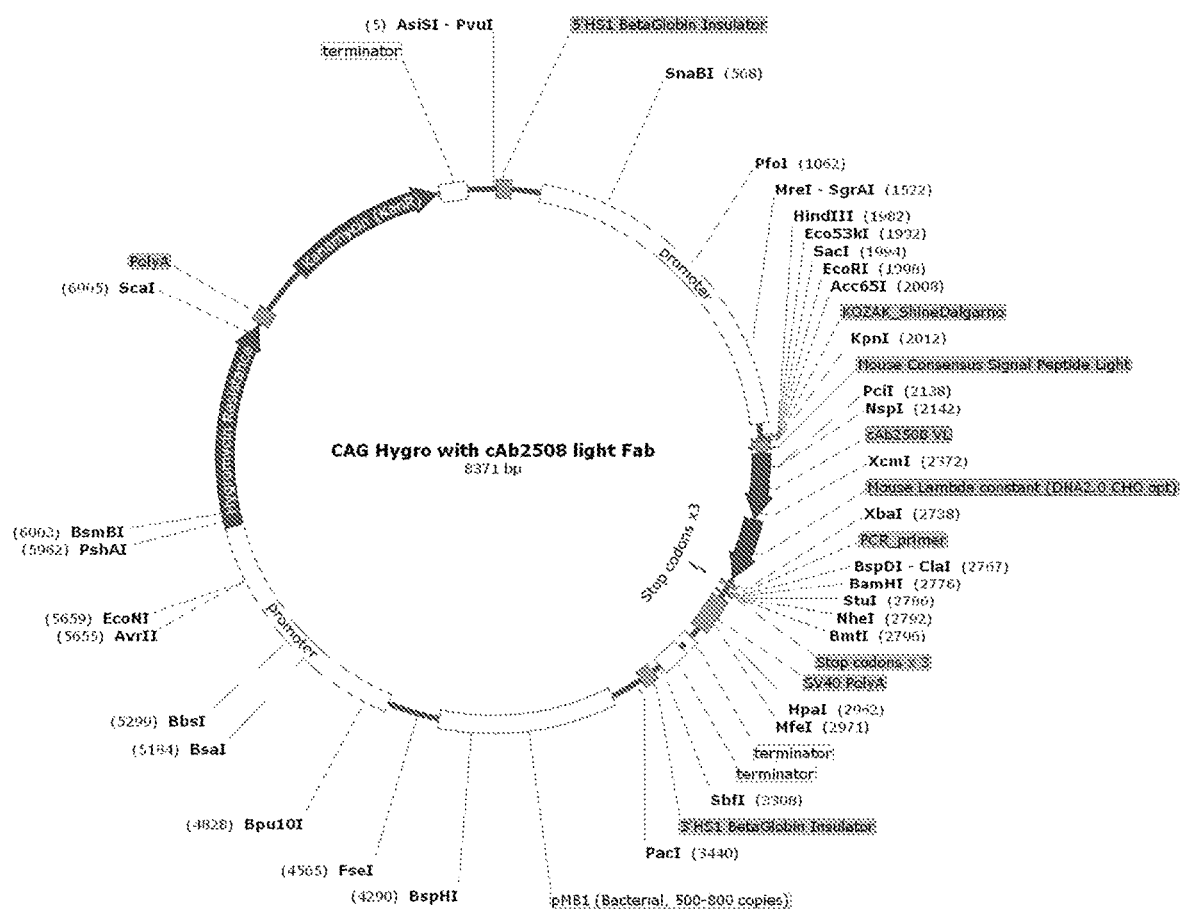
FIG. 17 depicts a map of the CAG hygro with cAb2508 Light Fab vector (SEQ ID NO: 87) expressing portions of antiTDP43 Fab antibody fragment having a nucleotide sequence encoding the light chain.
Figure 18:
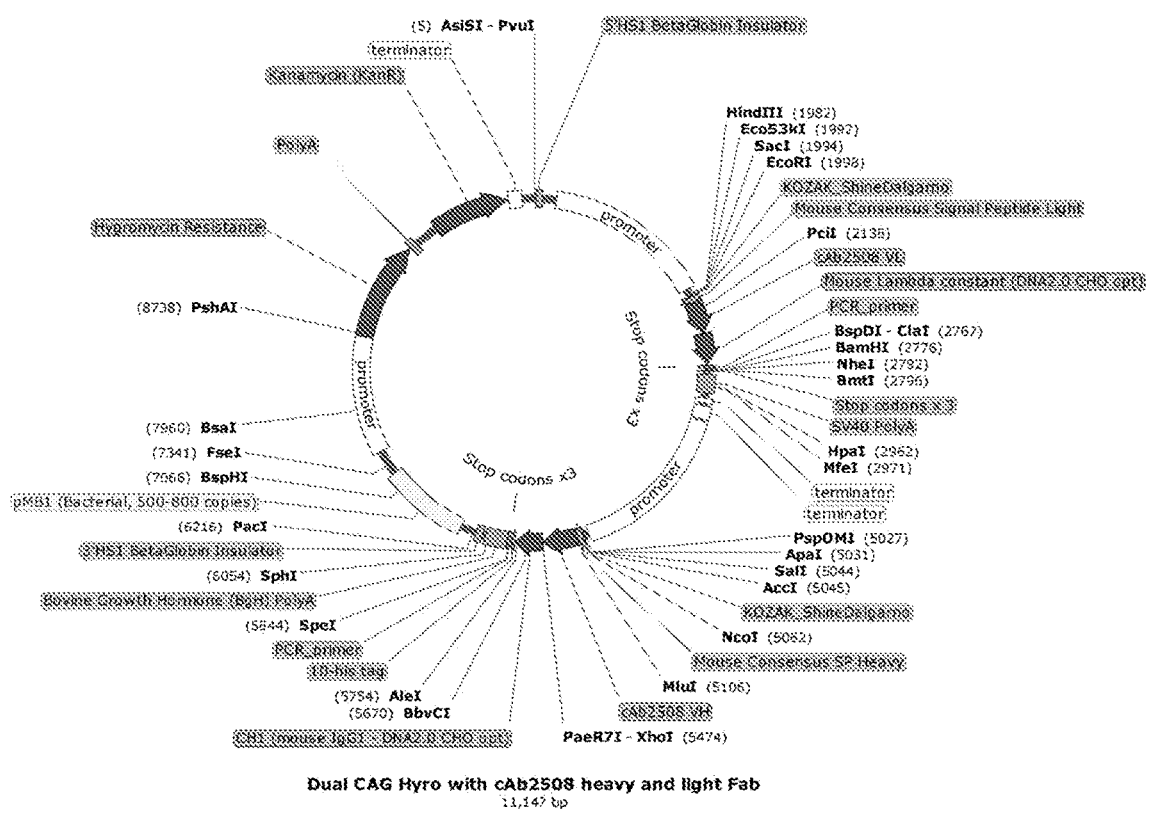
FIG. 18 depicts a map of the Dual CAG Hygro cAb2508 heavy and light Fab vector (SEQ ID NO: 88) expressing antiTDP43 Fab antibody fragment having a nucleotide sequences encoding the heavy chain and the light chain.
Figure 19:
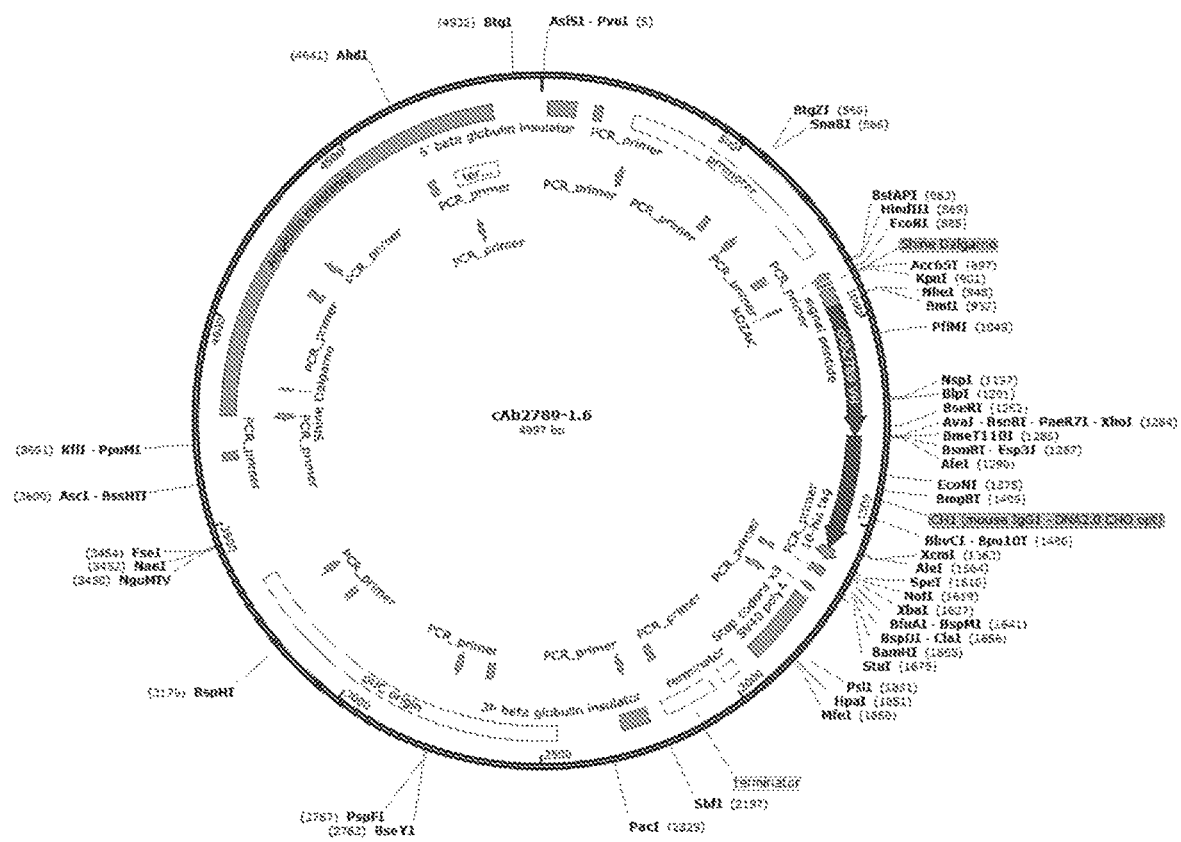
FIG. 19 depicts a map of the cAb2789-1.6 vector (SEQ ID NO: 89) expressing portion of anti-β Amyloid Fab antibody fragment having a nucleotide sequence encoding the heavy chain.
Figure 20:
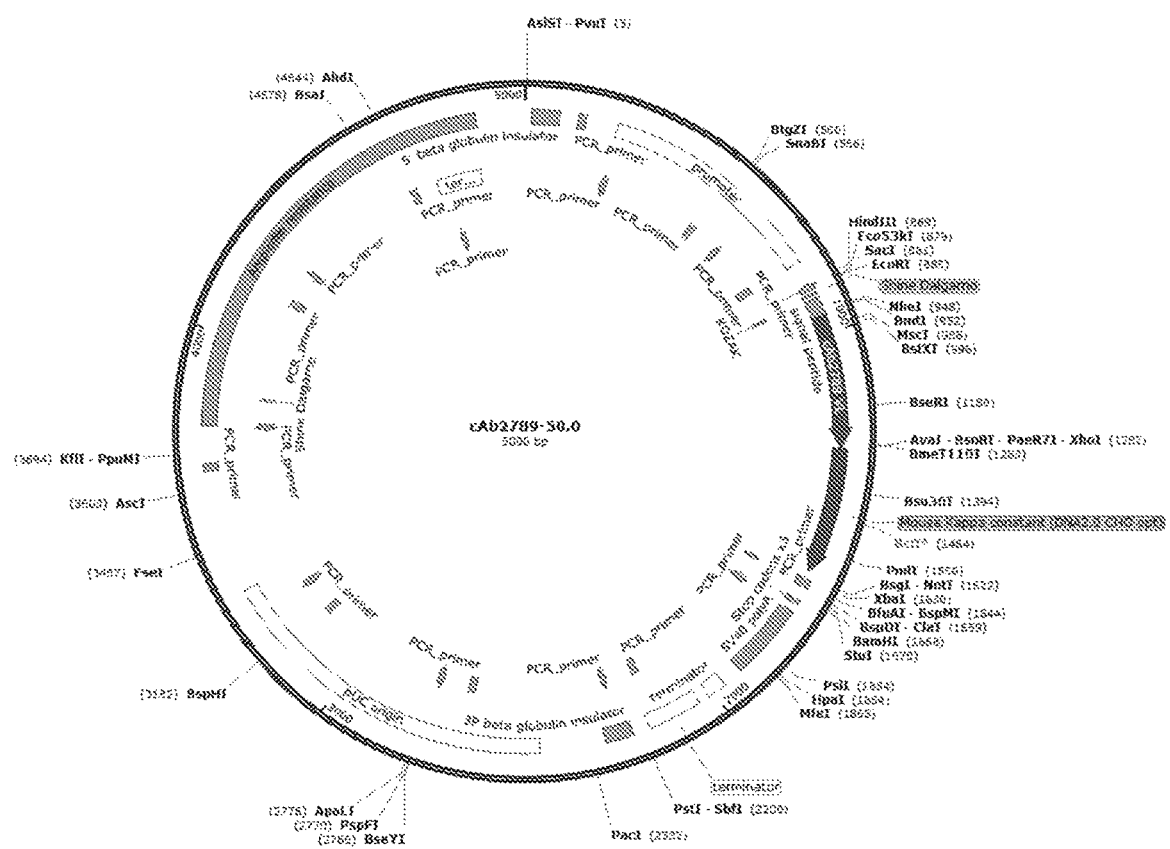
FIG. 20 depicts a map of the cAb2789-50.0 vector (SEQ ID NO: 90) expressing portion of anti-β Amyloid Fab antibody fragment having a nucleotide sequence encoding the light chain.
Figure 21:
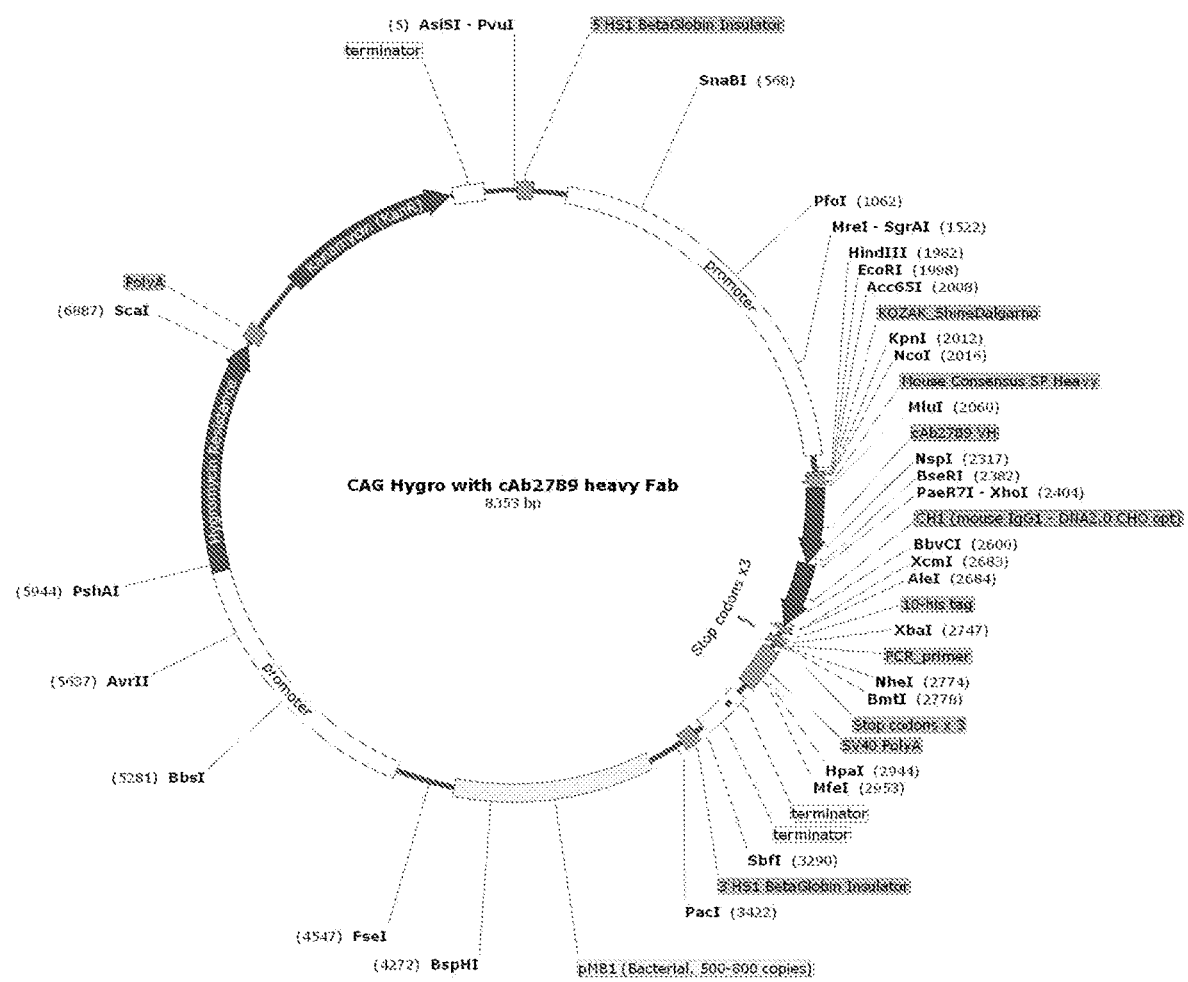
FIG. 21 depicts a map of the CAG Hygro cAb2789 Heavy Fab vector (SEQ ID NO: 91) expressing portion of anti-β Amyloid Fab antibody fragment having a nucleotide sequence encoding the heavy chain.
Figure 22:
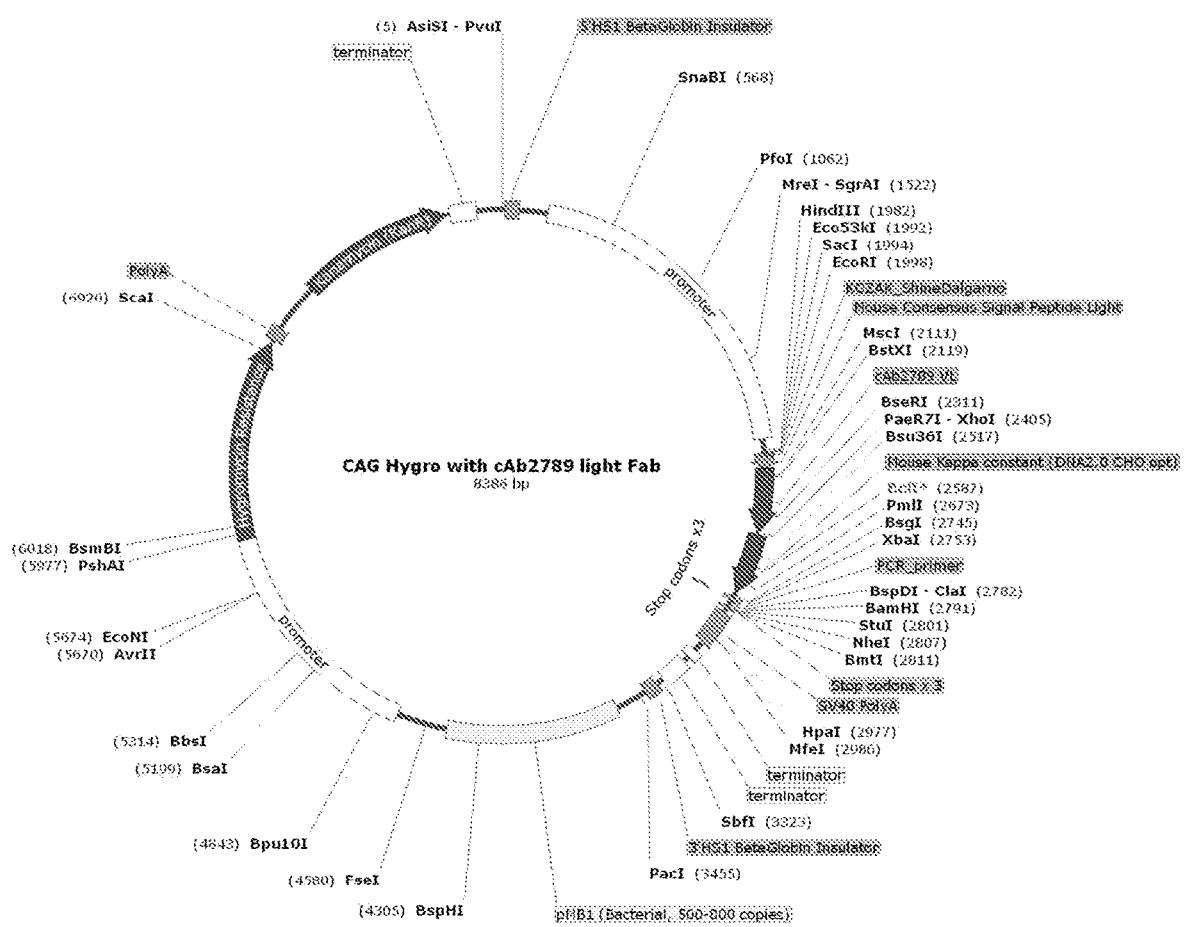
FIG. 22 depicts a map of the CAG Hygro cAb2789 Light Fab vector (SEQ ID NO: 92) expressing portion of anti-β Amyloid Fab antibody fragment having a nucleotide sequence encoding the light chain.
Figure 23:
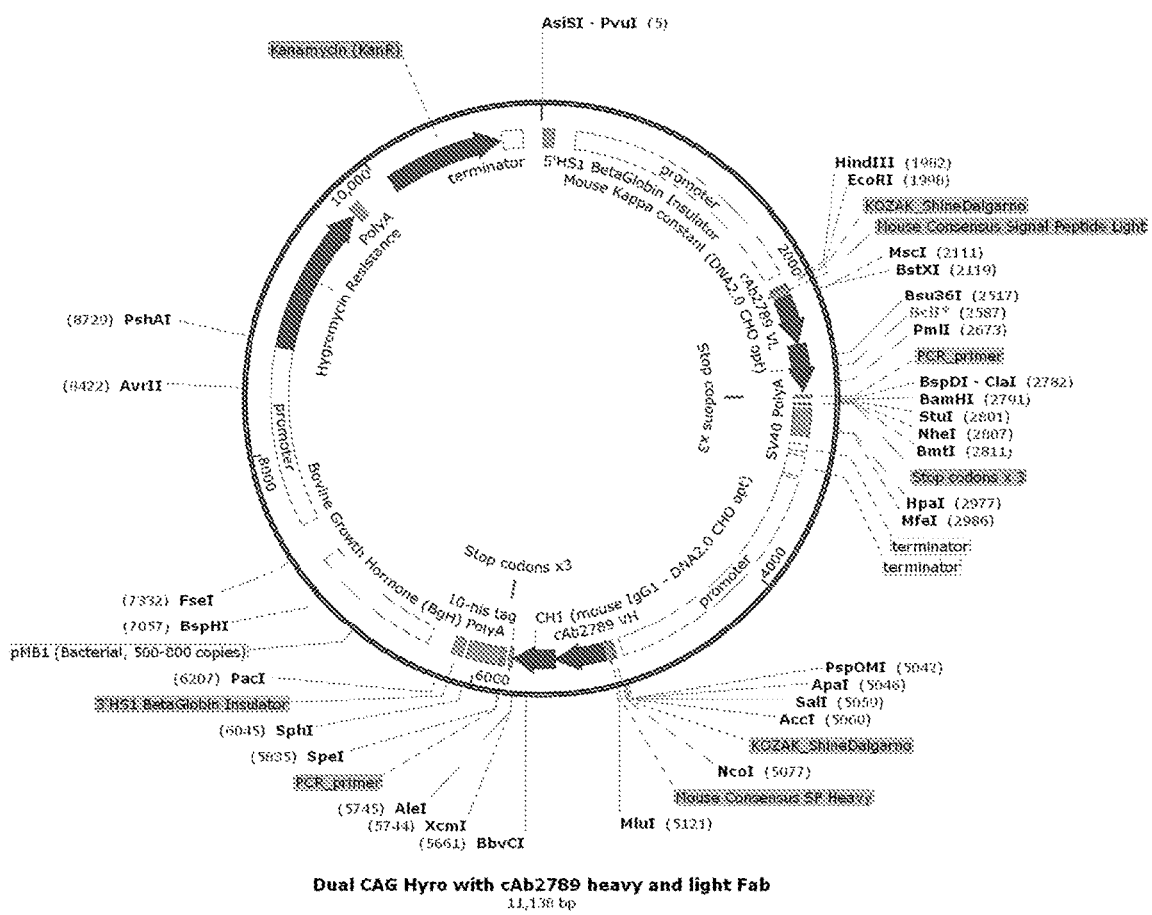
FIG. 23 depicts a map of the CAG Hygro cAb2789 Heavy and Light Fab vector (SEQ ID NO: 93) expressing anti-β Amyloid Fab antibody fragment having a nucleotide sequence encoding the heavy and the light chains.

The vectors provided herein contain a nucleotide sequence that encodes an antibody or a portion thereof. Examples of vectors of the invention are described in FIGS. 2 to 14 which show the map of the vector. In addition, sequences of exemplary vectors are provided in SEQ ID NOs: 83-93. FIGS. 4-6 show first generation vectors expressing anti-TDP43 antibody or a portion thereof. FIGS. 7-9 show second generation vectors expressing anti-TDP43 antibody or a portion thereof. FIGS. 10 and 11 show first generation vectors expressing anti-beta amyloid antibody or a portion thereof. FIGS. 12-14 show second generation vectors expressing anti-beta amyloid antibody or a portion thereof.

In addition, this invention provides methods for making the vectors described herein, as well as methods for introducing the vectors into appropriate host cells for expression of the encoded antibodies. In general, the methods provided herein include constructing nucleic acid sequences encoding an antibody, cloning the sequences encoding the antibody into an expression vector. The expression vector can be introduced into host cells or incorporated into virus particles, either of which can be administered to a subject.

cDNA or DNA sequences encoding antibodies disclosed herein can be obtained (and, if desired, modified) using conventional DNA cloning and mutagenesis methods, DNA amplification methods, and/or synthetic methods. In general, a sequence encoding an antibody can be inserted into a cloning vector for genetic modification and replication purposes prior to expression. Each coding sequence can be operably linked to a regulatory element, such as a promoter, for purposes of expressing the encoded protein in suitable host cells in vitro and in vivo.

Expression vectors can be introduced into host cells for producing antibodies disclosed herein. There are a variety of techniques available for introducing nucleic acids into viable cells. Techniques suitable for the transfer of nucleic acid into mammalian cells in vitro include the use of liposomes, electroporation, microinjection, cell fusion, polymer-based systems, DEAE-dextran, viral transduction, the calcium phosphate precipitation method, etc. For in vivo gene transfer, a number of techniques and reagents may also be used, including liposomes; natural polymer-based delivery vehicles, such as chitosan and gelatin; viral vectors are also suitable for in vivo transduction. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429-4432 (1987); and Wagner et al., Proc. Natl. Acad. Sci. USA 87, 3410-3414 (1990).

Where appropriate, gene delivery agents such as, e.g., integration sequences can also be employed. Numerous integration sequences are known in the art (see, e.g., Nunes-Duby et al., Nucleic Acids Res. 26:391-406, 1998; Sadwoski, J. Bacteriol., 165:341-357, 1986; Bestor, Cell, 122 (3):322-325, 2005; Plasterk et al., TIG 15:326-332, 1999; Kootstra et al., Ann. Rev. Pharm. Toxicol., 43:413-439, 2003). These include recombinases and transposases. Examples include Cre (Sternberg and Hamilton, J. Mol. Biol., 150:467-486, 1981), lambda (Nash, Nature, 247, 543-545, 1974), Fip (Broach, et al., Cell, 29:227-234, 1982), R (Matsuzaki, et al., J. Bacteriology, 172:610-618, 1990), cpC31 (see, e.g., Groth et al., J. Mol. Biol. 335:667-678, 2004), sleeping beauty, transposases of the mariner family (Plasterk et al., supra), and components for integrating viruses such as AAV, retroviruses, and antiviruses having components that provide for virus integration such as the LTR sequences of retroviruses or lentivirus and the ITR sequences of AAV (Kootstra et al., Ann. Rev. Pharm. Toxicol., 43:413-439, 2003).

Both prokaryotic and eukaryotic vectors can be used for expression of antibodies disclosed herein. Prokaryotic vectors include constructs based on E. coli sequences (see, e.g., Makrides, *Microbiol Rev* 1996, 60:512-538). Non-limiting examples of regulatory regions that can be used for expression in E. coli include lac, trp, lpp, phoA, recA, tac, T3, T7 and $\lambda P_L$. Non-limiting examples of prokaryotic expression vectors may include the λgt vector series such as λgt11 (Huynh et al., in "DNA Cloning Techniques, Vol. I: A Practical Approach," 1984, (D. Glover, ed.), pp. 49-78, IRL Press, Oxford), and the pET vector series (Studier et al., *Methods Enzymol* 1990, 185:60-89). Prokaryotic host-vector systems cannot perform much of the post-translational processing of mammalian cells, however. Thus, eukaryotic host-vector systems may be particularly useful.

A variety of regulatory regions can be used for expression of the antibodies disclosed herein in mammalian host cells. For example, the SV40 early and late promoters, the cytomegalovirus (CMV) immediate early promoter, and the Rous sarcoma virus long terminal repeat (RSV-LTR) promoter can be used. Inducible promoters that may be useful in mammalian cells include, without limitation, promoters associated with the metallothionein II gene, mouse mammary tumor virus glucocorticoid responsive long terminal repeats (MMTV-LTR), the β-interferon gene, and the hsp70 gene (see, Williams et al., *Cancer Res* 1989, 49:2735-42; and Taylor et al., *Mol Cell Biol* 1990, 10:165-75).

In an embodiment, the present invention contemplates the use of inducible promoters capable of effecting high level of expression transiently in response to a cue. Illustrative inducible expression control regions include those comprising an inducible promoter that is stimulated with a cue such as a small molecule chemical compound. Particular examples can be found, for example, in U.S. Pat. Nos. 5,989,910, 5,935,934, 6,015,709, and 6,004,941, each of which is incorporated herein by reference in its entirety.

An expression vector can also include transcription enhancer elements, such as those found in SV40 virus, Hepatitis B virus, cytomegalovirus, immunoglobulin genes, metallothionein, and 3-actin (see, Bittner et al., *Meth Enzymol* 1987, 153:516-544; and Gorman, *Curr Op Biotechnol* 1990, 1:36-47). In addition, an expression vector can contain sequences that permit maintenance and replication of the vector in more than one type of host cell, or integration of the vector into the host chromosome. Such sequences include, without limitation, to replication origins, autonomously replicating sequences (ARS), centromere DNA, and telomere DNA.

In addition, an expression vector can contain one or more selectable or screenable marker genes for initially isolating, identifying, or tracking host cells that contain DNA encoding antibodies as described herein. For long term, stable expression in mammalian cells can be useful. A number of selection systems can be used for mammalian cells. For example, the Herpes simplex virus thymidine kinase (Wigler et al., Cell 1977, 11:223), hypoxanthine-guanine phosphoribosyltransferase (Szybalski and Szybalski, *Proc Natl Acad Sci USA* 1962, 48:2026), and adenine phosphoribosyltransferase (Lowy et al., *Cell* 1980, 22:817) genes can be employed in tk-, hgprt-, or aprt-cells, respectively. In addition, antimetabolite resistance can be used as the basis of selection for dihydrofolate reductase (dhfr), which confers resistance to methotrexate (Wigler et al., Proc Natl Acad Sci USA 1980, 77:3567; O'Hare et al., *Proc Natl Acad Sci USA* 1981, 78:1527); gpt, which confers resistance to mycophenolic acid (Mulligan and Berg, *Proc Natl Acad Sci USA* 1981, 78:2072); neomycin phosphotransferase (neo), which confers resistance to the aminoglycoside G-418 (Colberre-Garapin et al., *J Mol Biol* 1981, 150:1); and hygromycin phosphotransferase (hyg), which confers resistance to hygromycin (Santerre et al., Gene 1984, 30:147). Other selectable markers known in the art, such as, Kanamycin resistance, ampicillin resistance, histidinol and ZEOCIN™ (phleormin D1) also can be used.

A number of viral-based expression systems also can be used with mammalian cells to produce the antibody disclosed herein. Vectors using DNA virus backbones have been derived from simian virus 40 (SV40) (Hamer et al., *Cell* 1979, 17:725), adenovirus (Van Doren et al., *Mol Cell Biol* 1984, 4:1653), adeno-associated virus (McLaughlin et al., *J Virol* 1988, 62:1963), and bovine papillomas virus (Zinn et al., *Proc Natl Accd Sci USA* 1982, 79:4897). When an adenovirus is used as an expression vector, the donor DNA sequence may be ligated to an adenovirus transcription/translation control complex, e.g., the late promoter and tripartite leader sequence. Nucleotide sequence encoding the antibodies disclosed herein may then be inserted in the adenovirus genome by in vitro or in vivo recombination. Insertion in a non-essential region of the viral genome (e.g., region E1 or E3) can result in a recombinant virus that is viable and capable of expressing heterologous products in infected hosts. (See, e.g., Logan and Shenk, *Proc Natl Acad Sci USA* 1984, 81:3655-3659).

Bovine papillomavirus (BPV) can infect many higher vertebrates, including man, and its DNA replicates as an episome. A number of shuttle vectors have been developed for recombinant gene expression which exist as stable, multicopy (20-300 copies/cell) extrachromosomal elements in mammalian cells. Typically, these vectors contain a segment of BPV DNA (the entire genome or a 69% transforming fragment), a promoter with a broad host range, a polyadenylation signal, splice signals, a selectable marker, and "poisonless" plasmid sequences that allow the vector to be propagated in *E. coli*. Following construction and amplification in bacteria, the expression gene constructs are transfected into cultured mammalian cells by, for example, calcium phosphate coprecipitation. For those host cells that do not manifest a transformed phenotype, selection of transformants is achieved by use of a dominant selectable marker, such as histidinol and G418 resistance.

Alternatively, the vaccinia 7.5K promoter can be used. (See, e.g., Mackett et al., *Proc Natl Acad Sci USA* 1982, 79:7415-7419; Mackett et al., *J Virol* 1984, 49:857-864; and Panicali et al., *Proc Natl Acad Sci USA* 1982, 79:4927-4931.) In cases where a human host cell is used, vectors based on the Epstein-Barr virus (EBV) origin (OriP) and EBV nuclear antigen 1 (EBNA-1; a trans-acting replication factor) can be used. Such vectors can be used with a broad range of human host cells, e.g., EBO-pCD (Spickofsky et al., *DNA Prot Eng Tech* 1990, 2:14-18); pDR2 and λDR2 (available from Clontech Laboratories).

Retroviruses, such as Moloney murine leukemia virus, can be used since most of the viral gene sequence can be removed and replaced with exogenous coding sequence while the missing viral functions can be supplied in trans. In contrast to transfection, retroviruses can efficiently infect and transfer genes to a wide range of cell types including, for example, primary hematopoietic cells. Moreover, the host range for infection by a retroviral vector can be manipulated by the choice of envelope used for vector packaging.

For example, a retroviral vector can comprise a 5' long terminal repeat (LTR), a 3' LTR, a packaging signal, a bacterial origin of replication, and a selectable marker. The antibody coding sequence, for example, can be inserted into a position between the 5' LTR and 3' LTR, such that transcription from the 5' LTR promoter transcribes the cloned DNA. The 5' LTR contains a promoter (e.g., an LTR promoter), an R region, a U5 region, and a primer binding site, in that order. Nucleotide sequences of these LTR elements are well known in the art. A heterologous promoter as well as multiple drug selection markers also can be included in the expression vector to facilitate selection of infected cells. See, McLauchlin et al., *Prog Nucleic Acid Res Mol Biol* 1990, 38:91-135; Morgenstern et al., *Nucleic Acid Res* 1990, 18:3587-3596; Choulika et al., *J Virol* 1996, 70:1792-1798; Boesen et al., *Biotherapy* 1994, 6:291-302; Salmons and Gunzberg, *Human Gene Ther* 1993, 4:129-141; and Grossman and Wilson, *Curr Opin Genet Devel* 1993, 3:110-114.

Any of the cloning and expression vectors described herein may be synthesized and assembled from known DNA sequences using techniques that are known in the art. The regulatory regions and enhancer elements can be of a variety of origins, both natural and synthetic. Some vectors and host cells may be obtained commercially. Non-limiting examples of useful vectors are described in Appendix 5 of *Current Protocols in Molecular Biology,* 1988, ed. Ausubel et al., Greene Publish. Assoc. & Wiley Interscience, which is incorporated herein by reference; and the catalogs of commercial suppliers such as Clontech Laboratories, Stratagene Inc., and Invitrogen, Inc.

In some embodiments, the nucleotide sequences in the vectors that express an antibody may be codon optimized, for example the codons may be optimized for human use. In some embodiments the nucleotide sequences may be mutated to abrogate the normal in vivo function of the encoded proteins or codon optimized for human use.

As regards codon optimization, the nucleic acid molecules have a nucleotide sequence that encodes the antibodies of the invention and can be designed to employ codons that are used in the genes of the subject in which the antibody is to be produced. Many viruses, including HIV and other lentiviruses, use a large number of rare codons and, by altering these codons to correspond to codons commonly used in the desired subject, enhanced expression of the antibodies can be achieved. The codons used are "humanized" codons, i.e., the codons are those that appear frequently in highly expressed human genes (Andre et al., J. Virol. 72:1497-1503, 1998). Such codon usage provides for efficient expression of the transgenic antibodies in human cells. Any suitable method of codon optimization may be used. Such methods, and the selection of such methods, are well known to those of skill in the art.

Administration

The invention is based, in part, on the finding that the peripheral administration of the present cells allows for effective delivery of therapeutic agents (inclusive of, without limitation, the Fabs described herein) across the BBB. The invention is based, in part, on the finding that the peripheral administration of the present cells allows for effective delivery of therapeutic agents (inclusive of, without limitation, the Fabs described herein) to and/or past the BBB. Such peripheral administration includes, in some embodiments, any administration route which does not imply direct injection into the brain. More particularly, in some embodiments, peripheral administration comprises systemic injections, such as intramuscular (i.m.), intravenous (i.v.), intraperitoneal (i.p.), intra-arterial, sub-cutaneous or transdermic injections. Peripheral administration also includes oral administration, delivery using implants, or administration by instillation through the respiratory system, e.g., using sprays, aerosols or any other appropriate formulations.

Pharmaceutical Compositions and Formulation

The present invention further provides pharmaceutical compositions of the contemplated therapeutic agents, and a pharmaceutically acceptable carrier or excipient. As one skilled in the art will recognize, the agents described herein may be made up, together or separately, in any suitable form appropriate for the desired use and route of administration. As used herein the term "pharmaceutically acceptable" means approved by a regulatory agency of the Federal or a state government or listed in the U.S. Pharmacopeia or other generally recognized pharmacopeia for use in animals, and more particularly in humans. Examples of suitable dosage forms include, for example, oral, parenteral, and intravenous dosage forms.

Suitable dosage forms for oral use include, for example, solid dosage forms such as tablets, dispersible powders, granules, and capsules. In such dosage forms, the active agent is mixed with at least one inert, pharmaceutically acceptable excipient or carrier such as sodium citrate, dicalcium phosphate, etc., and/or a) fillers or extenders such as starches, lactose, sucrose, glucose, mannitol, silicic acid, microcrystalline cellulose, etc.; b) binders such as, for example, carboxymethylcellulose, alginates, gelatin, polyvinylpyrrolidone, sucrose, acacia, etc.; c) humectants such as glycerol, etc.; d) disintegrating agents such as agar-agar, calcium carbonate, potato or tapioca starch, alginic acid, certain silicates, sodium carbonate, cross-linked polymers such as crospovidone (cross-linked polyvinylpyrrolidone), croscarmellose sodium (cross-linked sodium carboxymethylcellulose), sodium starch glycolate, etc.; e) solution retarding agents such as paraffin, etc.; f) absorption accelerators such as quaternary ammonium compounds, etc.; g) wetting agents such as, for example, cetyl alcohol and glycerol monostearate, etc.; h) absorbents such as kaolin and bentonite clay, etc.; and i) lubricants such as talc, calcium stearate, magnesium stearate, solid polyethylene glycols, sodium lauryl sulfate, glyceryl behenate, etc., and mixtures of such excipients. One of skill in the art will recognize that particular excipients may have two or more functions in the oral dosage form. In the case of an oral dosage form, for example, a capsule or a tablet, the dosage form may also comprise buffering agents.

The solid oral dosage forms can be prepared by any conventional method known in the art, for example granulation (e.g., wet or dry granulation) of the active agent with one or more suitable excipients. Alternatively, the active agent can be layered onto an inert core (e.g., a nonpareil/sugar sphere or silica sphere) using conventional methods such as fluidized bed or pan coating, or extruded and spheronized using methods known in the art, into active agent-containing beads. Such beads can then be incorporated into tablets or capsules using conventional methods.

The solid dosage forms of capsules, tablets, granules, active agent-containing beads can be prepared with coatings, such as enteric coatings, reverse enteric coatings, extended release coatings, pulsatile release coatings, etc. and other coatings, or combinations of coatings, well known in the art. Optionally, the dosage forms may release the active ingredient(s) only, or preferentially, in a certain part of the intestinal tract, for example, in a delayed manner.

Liquid dosage forms for oral administration include pharmaceutically acceptable emulsions, solutions, suspensions, syrups and elixirs. In addition to the active agents, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, etc., and mixtures thereof.

Besides inert diluents, the oral compositions can also include adjuvants such as sweetening, flavoring, and perfuming agents.

Suspensions, in addition to the active agents, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art.

The formulations comprising the therapeutic agents of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

It will be appreciated that the actual dose of the therapeutic agents to be administered according to the present invention will vary according to the particular agent, the particular dosage form, and the mode of administration. Many factors that may modify the action of the agents described herein (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

The desired dose of the therapeutic agents may be presented as one dose or two or more sub-doses administered at appropriate intervals throughout the dosing period (e.g., about one hour, about one day, about one week, etc).

In accordance with certain embodiments of the invention, the therapeutic agents may be administered, for example, more than once daily, about once per day, about every other day, about every third day, or about once a week.

The agents of the present invention may be administered by any appropriate route, for example, parenterally or non-parenterally. In an embodiment, the present agent may be administered parenterally, including for example, intravenous, intramuscular, intraperitoneal, subcutaneous and intra-articular injection and infusion, among others.

Additional Agents and Administration

In some embodiments, the present agents may be used alone or in combination with one or more additional agent(s) for simultaneous, separate or sequential use.

For instance, when used in the context of ALS, an additional agent may be Riluzole (e.g. RILUTEK, see, e.g., U.S. Pat. Nos. 5,527,814 and 6,432,992, the contents of which are hereby incorporated by reference). In some embodiments, the additional agent is one or more of an anti-Nogo-A antibody, GM604 (GENERVON), fingolimod (e.g. GILENYA), Dexpramipexole (BIOGEN), ceftriaxone, CK2017357 (TIRASEMTIV, CYTOKINETICS), NP001 (NEURALTUS PHARMACEUTICALS), lithium, selegiline hydrochloride (ELDEPRYL), GF-1 (rhIGF-1, or IGF-1), or derivatives thereof. In some embodiments, the additional agent is one that targets one or more neurotrophic factors, e.g. NGF, BDNF, CNTF, and MNTF.

Further, in the context of type 2 diabetes, an additional agent may be insulin and/or any non-insulin diabetes agents (e.g. selected from metformin (e.g. GLUCOPHAGE, GLUMETZA); sulfonylureas (e.g. glyburide (e.g. DIABETA, GLYNASE), glipizide (e.g. GLUCOTROL) and glimepiride (e.g. AMARYL)); thiazolidinediones (e.g. rosiglitazone (e.g. AVANDIA) and pioglitazone (e.g. ACTOS)); DPP-4 inhibitors (e.g. sitagliptin (e.g. JANUVIA), saxagliptin (e.g. ONGLYZA) and linagliptin (e.g. TRADJENTA)); GLP-1 receptor agonists (e.g. exenatide (e.g. BYETTA) and liraglutide (e.g. VICTOZA)); and SGLT2 inhibitors (e.g. canagliflozin (e.g. NVOKANA) and dapagliflozin (e.g. FARXIGA))) and/or insulin may be used in treatment. For example, certain patients may be able to manage diabetes with diet and exercise alone (e.g. along with glucose monitoring). However, often this is not the case and therapeutic agents are needed. A first line of treatment may be a non-insulin diabetes agent (e.g. selected from metformin (e.g. GLUCOPHAGE, GLUMETZA); sulfonylureas (e.g. glyburide (e.g. DIABETA, GLYNASE), glipizide (e.g. GLUCOTROL) and glimepiride (e.g. AMARYL)); thiazolidinediones (e.g. rosiglitazone (e.g. AVANDIA) and pioglitazone (e.g. ACTOS)); DPP-4 inhibitors (e.g. sitagliptin (e.g. JANUVIA), saxagliptin (e.g. ONGLYZA) and linagliptin (e.g. TRADJENTA)); GLP-1 receptor agonists (e.g. exenatide (e.g. BYETTA) and liraglutide (e.g. VICTOZA)); and SGLT2 inhibitors (e.g. canagliflozin (e.g. NVOKANA) and dapagliflozin (e.g. FARXIGA)).

Co-administration of the agents described herein with an additional agent can be simultaneous or sequential. Further, the present invention contemplates co-formulation of one or more agents of the invention with one or more additional agent(s).

In some embodiments, the agents described herein and an additional agent is administered to a subject simultaneously. The term "simultaneously" as used herein, means that agents described herein and an additional agent are administered with a time separation of no more than about 60 minutes, such as no more than about 30 minutes, no more than about 20 minutes, no more than about 10 minutes, no more than about 5 minutes, or no more than about 1 minute. Administration of the agents described herein and an additional agent can be by simultaneous administration of a single formulation (e.g., a formulation comprising the agents described herein and an additional agent) or of separate formulations (e.g., a first formulation including the agents described herein and a second formulation including an additional agent).

Co-administration does not require the therapeutic agents to be administered simultaneously, if the timing of their administration is such that the pharmacological activities of the agents described herein and an additional agent overlap in time, thereby exerting a combined therapeutic effect. For example, the agents described herein and an additional agent can be administered sequentially. The term "sequentially" as used herein means that the agents described herein and an additional agent are administered with a time separation of more than about 60 minutes. For example, the time between the sequential administration of the agents described herein and an additional agent can be more than about 60 minutes, more than about 2 hours, more than about 4 hours, more than about 8 hours, more than about 10 hours, more than about 12 hours, more than about 24 hours, more than about 36 hours, more than about 48 hours, more than about 72 hours, more than about 96 hours, or more than about 1 week apart. The optimal administration times will depend on the rates of metabolism, excretion, and/or the pharmacodynamic activity or toxicity of the agents described herein and an additional agent being administered. Either the agents described herein or an additional agent can be administered first.

Methods of measuring or monitoring the immune effect induced by the present agents are well known in the art. These methods include, but are not limited to, flow cytometry (including, for example, fluorescent activating cell sorting (FACS)), solid phase enzyme-linked immunosorbent assay (ELISA), western blotting (including in cell western), immunofluorescent staining, microengraving (see Han Q et al. Lab Chip. 2010; 10(11):1391-1400), immunofluorescent staining of incorporated bromodeoxyuridine (BrdU) or 7-aminoactinomycin D (7-MD); ELISPOT Assays; mRNA analysis; quantitative RT-PCR; TaqMan Q-PCR; histology; laser capture microdissection; and bioluminescent imaging.

In accordance with certain embodiments of the invention, the agent agents described herein and an additional agent may each be administered, for example, more than once daily, about once per day, about every other day, about every third day, or about once a week, or once every 2 or 3 weeks.

Co-administration also does not require the therapeutic agents to be administered to the subject by the same route of administration. Rather, each therapeutic agent can be administered by any appropriate route, for example, parenterally or non-parenterally.

Methods of Treatment/Patient Selection

In some embodiments, the neurodegenerative disease that is treated by the present agents is selected from MS (including without limitation the subtypes described herein), Alzheimer's. disease (including, without limitation, Early-onset Alzheimer's, Late-onset Alzheimer's, and Familial Alzheimer's disease (FAD), Parkinson's disease and parkinsonism (including, without limitation, Idiopathic Parkinson's disease, Vascular parkinsonism, Drug-induced parkinsonism, Dementia with Lewy bodies, Inherited Parkinson's, Juvenile Parkinson's), Huntington's disease, Amyotrophic lateral sclerosis (ALS, including, without limitation, Sporadic ALS, Familial ALS, Western Pacific ALS, Juvenile ALS, Hiramaya Disease).

In some embodiments, the disease is one characterized by amyloid plaque formation including secondary amyloidosis and age-related amyloidosis including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guarn Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration, but particularly a disease or condition In a specific embodiment, the disease being treated by the present agents is ALS, including, without limitation, Sporadic ALS, Familial ALS, Western Pacific ALS, Juvenile ALS, Hiramaya Disease.

In a specific embodiment, the disease being treated by the present agents is one or more of familial ALS, Motor neuropathy with pyramidal features, Finkel type SMA or SMA IV, TARDBP-related amyotrophic lateral sclerosis, C9orf72-related FTD/ALS, and CHCHD10-related ALS/FTD.

In various embodiments, the present agents find use in a method of treatment in which neurodegeneration is halted or slowed relative to an untreated state. In various embodiments, the present agents reduce or eliminate the spreading of aggregates described herein. In various embodiments, the present agents reduce or eliminate the progression of the neurodegenerative disease.

In various embodiments, the present agents reduce or eliminate the progression of ALS. In some embodiments, the present agents extend one or more of: survival, time to tracheostomy and time to mechanical ventilation. In various embodiments, the present agents improve or reduce the severity of various symptoms of ALS, including without limitation: Early symptoms of ALS often include increasing muscle weakness, especially involving the arms and legs, speech, swallowing or breathing. In some embodiments, the present agents find use in a method that delays onset of ALS or ALS symptom(s) in a patient at risk for ALS. In some embodiments, the present agents find use in a method that slows progression of ALS or ALS symptom(s) in a patient having ALS. In some embodiments, the present agents find use in a method that causes regression of ALS. In some embodiments, the present agents increase swallowing volume in a patient having ALS.

In various embodiments, the present agents improve a patient's ALS as measured via the Amyotrophic Lateral Sclerosis Functional Rating Scale (ALSFRS, see, e.g., *Arch Neurol.* 1996 February; 53(2):141-7, the entire contents of which are hereby incorporated by reference). In various embodiments, the present agents cause an increase in scoring in any of the following parameters in the ALSFRS: (1) speech, (2) salivation, (3) swallowing, (4) handwriting, (5) cutting food and handling utensils (with or without gastrostomy), (6) dressing and hygiene, (7) turning in bed and adjusting bed clothes, (8) walking, (9) climbing stairs, and (10) breathing. In various embodiments, each parameter, which is scored between 0 (worst) and 4 (best) is improved. For instance, the agents might increase the scoring of any parameter to a score of 4, or 3, or 2, or 1, relative to untreated measures.

In some embodiments, the present agents increase forced vital capacity (FVC) as described in, for example, J Neurol Neurosurg Psychiatry. 2006 March; 77(3): 390-392, the entire contents of which are hereby incorporated by reference).

In some embodiments, the present agents increase FVC above about 75% to, e.g. to about 80%, or about 85%, or about 90%, or about 95%, or about 100%.

In some embodiments, the present agents increase Appel ALS (AALS) score. The Appel ALS Scale consists of 5 subscales (Bulbar Function, Respiratory Function, Overall Muscle Strength, Upper Extremity, and Lower Extremity Function) with scores ranging from 30 (Normal) to 164 (Maximal Dysfunction). Patients with a baseline AALS score of between 40 and 80 may be patients of the present invention.

In some embodiments, the present invention relates to the treatment of tumors, heart attack, myocardial infarction, stroke, respiratory insufficiency, etc.

In some embodiments, the present invention relates to the treatment of angiogenesis in retina, repair of wounds caused by a deficient blood supply (diabetes foot), repair of myocardial tissue after heart attack, vessel normalization in case of pathological tumor angiogenesis, skin diseases, etc.

In some embodiments, the present invention relates to the treatment of type 2 diabetes (or "type 2 diabetes mellitus" or "noninsulin-dependent diabetes mellitus (NIDDM)" or "adult-onset diabetes"). In some embodiments, the present invention relates to the treatment of an inappropriate increase in blood glucose levels, which generates chronic complications as it affects large and small vessels and nerves. In some embodiments, the present invention relates to the treatment of insulin resistance.

As used herein, the terms "subject" and "patient" refer to any animal, such as a mammal. The term "mammal" as used herein refers to any mammal classified as a mammal, including humans, non-human primates, apes, pigs, cows, goats, sheep, horses, dogs, cats and those mammals employed in scientific research commonly known in the art, for example, mice, rats, hamsters, rabbits, guinea-pigs, and ferrets. In one embodiment of the invention, the mammal is a human.

This invention is further illustrated by the following non-limiting examples.

EXAMPLES

Example 1: Insertion of Transfected Cells in an In-Vitro Model of the Human Blood Brain Barrier (BBB) and Export of GFP by the Transfected Cells The purpose of this experiment was to assess the ability of the EPCs to integrate into the BBB.

Specifically, the BBB was set up by coating cell culture inserts with 1:20 collagen for 1 hour at 37° C., followed by seeding with $2\times10^5$ hCMEC/D3 cells in OptiMEM. 500 µl of Optimem was pipetted into a receiver well (i.e., the basolateral side), and the BBB was then incubated for 72 hours at 37° C./5% $CO_2$ in order to allow for monolayer formation. On Day 4, the medium was removed and replaced with HEPC.CB1 pI.CAG.GFP cells. The experimental groups were split into (1) a positive control (n=3) of HEPC.CB1 pI.CAG.GFP only (GFP-EPCs); and (2) a BBB experimental group (n=3) of hCMEC/D3 (BBB)+HEPC.CB1 pI.CAG.GFP cells. Specifically, the HEPC.CB1 cells were suspended in OptiMEM to $1.2\times10^7$/ml, and finally a 200 µl cell suspension was combined with 1800 µl OptiMEM to $10^6$ cells/ml ($2\times10^5$ cells/200 µl). Medium was then removed from upper and lower wells, and 200 µl of the cell suspension as transferred to the upper well. 500 µl of Optimem was added to the lower well and the BBB was allowed to incubated for 48 hours @ 37° C./5% $CO_2$. On Day 6, 300 µl of medium was pipetted from the receiver well (i.e., the basolateral side) into a black 96-well plate. GFP was then quantified using Lumistar (BMG Biotech).

The results showed that when the GFP-EPCs were added to BBB (hCMEC/D3), they insert into the apical and basolateral side, and 37% to 73% of the GFP is found on the basolateral side, suggesting than the GFP-EPCs can integrate into the BBB and release the GFP (the native permeability of this BBB model for 20 kDa protein (similar to GFP) is less than 5%.

Human endotheial precursor cells (HEPC.CB1, the equivalent of murine MAgEC 10.5 cells) were isolated and electroporated. A model of the human blood brain barrier (BBB) was constructed based upon work of Weksler B., Ignacio A Romero and Pierre-Olivier Couraud (2013) Fluids and Barriers of the CNS 2013, 10:16, using a human CMEC/D3 cell line. Injection of $4.5\times10^9$ transfected cells (where the overall cells produced at least 4.5 mg Fab/day) were added to the constituted BBB, incubated overnight with it then washed 3 times and the fluorescence emission of the BBB was assayed. The fluorescence of GFP expressed by the transfected cells, which was detected in the washed BBB, indicated insertion of these cells in the barrier. A schematic of the overall experiment is depicted in FIG. 1.

The electroporated cells (or those treated with cationic lipids) were cultured in cell culture inserts (Millicell®). At 6 hours, 24 hours, 48 hours after electroporation the cells were washed and the GFP fluorescence was measured. The supernatants in the medium on both sides of the BBB were measured as well and the intensity of fluorescence was quantitated after 48 hours. The fluorescence results indicated substantial export of the expressed GFP by the cells transfected.

Figure 2:
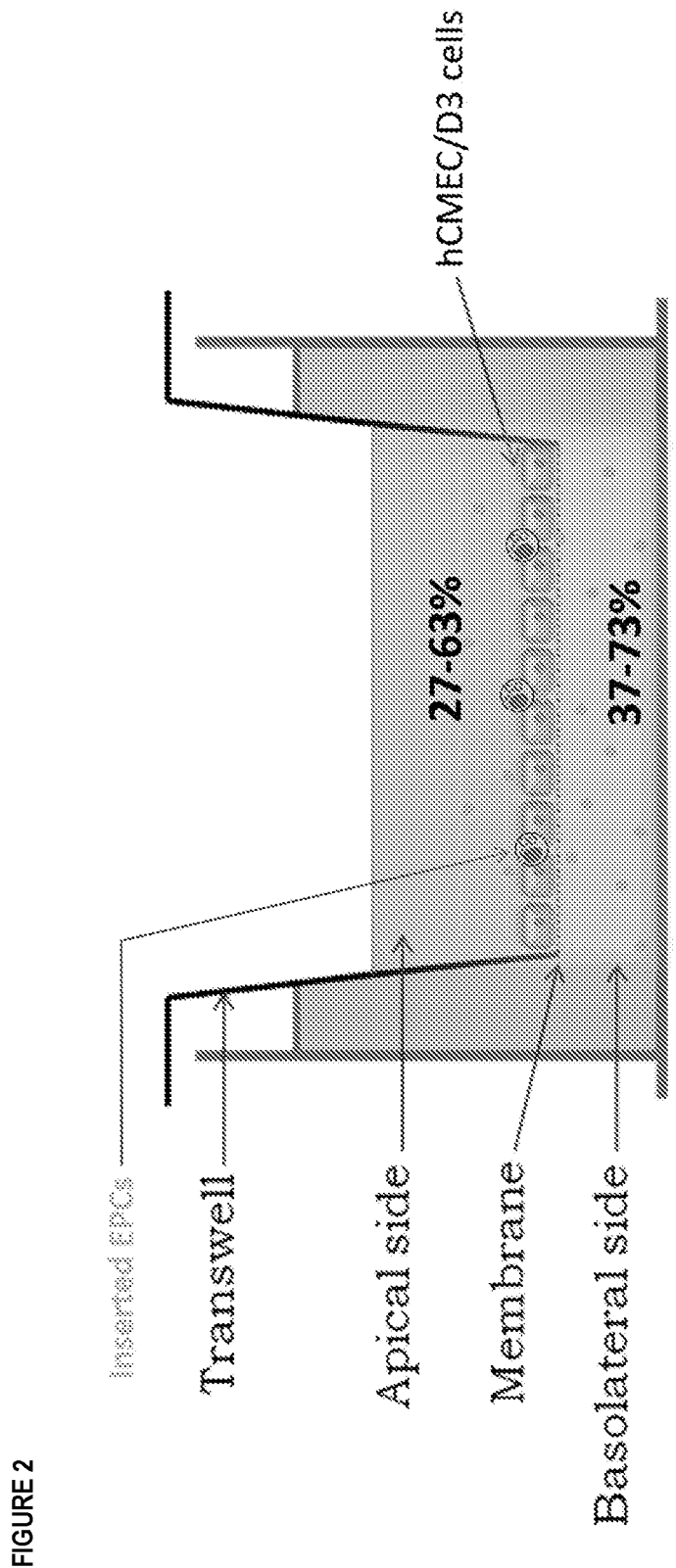
FIG. 2 shows that from 37% to 73% of the GFP expressed by the EPCs was expressed in the basolateral side of the BBB, while from 27%-63% GFP expression was found on the apical side of the BBB.

FIG. 2 shows that from 37% to 73% of the GFP expressed by the EPCs was expressed in the basolateral side of the BBB, while from 27%-63% GFP expression was found on the apical side of the BBB. Taking into account that 37% to 73% of expressed proteins were released from the EPCs inserted into the BBB compared to 0.21% upon systemic IV inoculation of intact antibodies, this experiment showed that a significant amount of antibodies and/or protein end up in the brain parenchyma and microvasculature using the EPCs as targeted carriers and producers of antibodies.

Example 2: Homing of the Transfected Cells to the Brain Microvasculature

Early precursors of brain microvascular endothelial cells and mature cells were transfected with vectors described in Example 5. The two types of transfected cells were inserted in the blood brain barrier in-vitro and GFP fluorescence was measured. Results showed that the insertion of precursor cells in BBB was significantly higher than that of mature cells, which was very weak.

To test whether MAgEC cells (E10.5) would adhere to vessel walls in vivo in the mouse brain and stay there for a prolonged period of time, $10^6$ MAgEC cells were injected into the right common carotid artery of the BALB/c× DSRed⁻ mouse. 24 hours later, the brain was processed for sectioning and imaging. FIG. 3 depicts the fluorescence microscopy detection of GFP-MAgEC 10.5 in the mouse brain microvasculature. The results show that when the EPCs are co-cultured with mature endothelial cells (MBrMEC), it is observed that insertion of the EPCs into the BBB cooperates to create vessels.

Example 3: Homing of Transfected EPCs to the Blood Brain Barrier

The purpose of this experiment was to determine whether inserted transfected EPCs were incorporated in the angiogenesis network formed by the BBB cells (MBrMEC cells used as surrogate for BBB). In particular, the cells used were the MBrMEC, Hoescht-labelled beforehand, to create the BBB and the GFP transfected MAgEC10.5 as EPCs. To evaluate the angiogenesis and the interaction between EPCs and BBB, both cell types were seeded on Matrigel-coated wells or slides. The Matrigel matrix was diluted by two thirds in optiMEM (without FBS) at 4° C. Matrigel was allowed to polymerize at room temperature, and then the cells ($2.5 \times 10^4$ cells per milliliter) were seeded. Endothelial cell rearrangement and vessel formation was observed regularly under an inverted light contrast microscope at specific time points. Cooperation in the angiogenesis process between the co-cultivated BBB (MBrMEC Hoescht-labelled) and the EPCs (GFP-MAgEC 10.5 cells) was shown via co-localization of fluorescence signals, as depicted in FIG. 4A-B. FIG. 4A depicts fluorescence imaging at 5 hours, and FIG. 4B depicts fluorescence imaging at 12 hours. The imaging shows that while the MBrMEC are making tubes, the MAgEC 10.5 cells co-localize with the MBrMEC at the nodes. Indeed, the in vivo experiment on aged WT mice confirmed that the GFP-EPCs migrate to the brain (Homing) as shown on the fluorescence imaging.

Expression vectors were constructed for anti-TDP43 and anti-βamyloid, which are abundantly expressed even in non-specialized human cells and which retain their affinity for the antigens against which they were raised.

When injected in the carotid artery of mice, the homing of the transfected EPCs to the BBB was demonstrated, as well as their association with the BBB. Moreover, it was shown that, in an in vitro BBB model, greater than 70% of the produced proteins by the transfected EPCs are released in the basolateral compartment and only about 22% are left in the apical compartment. Compared with the very low BBB crossing of the intact IgG (0.21%) of the injected mAbs, they represent a potential significant advantage.

Example 4: Solubilization of TDP43 and Aβ Aggregates In Vitro

Antibodies were raised against Aβ and TDP43 in order to determine solubilization of the associated aggregated proteins. To determine the capacity of these antibodies to solubilize preformed TDP43 and Aβ aggregates, a disaggregation assay test of TDP43 and Aβ aggregates was performed. FIG. 7A shows that the antibodies were able to dissolve in-vitro aggregates of the TDP43 proteins. FIG. 7B shows that the antibodies were able to dissolve in-vitro aggregates of the Aβ proteins.

Specifically, reaction tubes containing 30 μg of TDP43$_{311-344}$/10 μl of PBS and 30 μg of Aβ$_{1-16}$/10 μl of PBS, pH 7.3, were incubated for 1 week at 37° C. Aggregation was measured by thioflavin T (ThT)-binding assay in which the dye's fluorescence emission intensity reflects the degree of TDP43 fibrillar aggregation. Disaggregation was followed after addition of various undiluted sera of immunized mice or purified antibodies to the preformed fibers (10 μl each). The reaction mixtures were incubated for 2 days at 37° C. An irrelevant control antibody (mouse IgG) was used at a final concentration of 1 mg/ml. Fluorescence (excitation: 450 nm; emission: 482 nm) was measured on Fluoromax3 (Horiba Fluoromax 4C fluorometer, Japan) after addition of 1 ml of ThT (3 μM in 50 mM sodium phosphate buffer, pH 6.0). Sera with ThT was used as controls to substract the emission of the sera themselves from the emission of the reaction mixtures (aggregates+ThT+sera), so as to follow the emission of the aggregates only.

Maximum solubilization obtained with both proteins and with the corresponding anti-sera was 100%. FIG. 7A-B depicts the percentage of aggregated protein in the presence of anti-sera of immunized C57BL/6 mice compared to sera of non-immunized mouse (control) measuring the ThT fluorescence emission. FIG. 7A: TDP43 and FIG. 7B: Aβ.

FIG. 8 shows the solubilization of TDP-43 aggregates with purified anti-TDP-43 antibodies (both IgG and Fab) in mice. Specifically, the percentage of TDP-43 aggregates was reduced when anti-TDP-43 antibodies were administered as compared to the control group that was not administered anti-TDP-43 antibodies. The group that was administered the Fab anti-TDP-43 antibody exhibited the greater reduction in TDP-43 aggregates as compared to the control group.

FIG. 9A shows shows the solubilization of TDP-43 aggregates with the inventive anti-TDP-43 antigen-binding fragments (Fab) expressed by vector in human cells (HEK293 cell line), as compared to a control group where no Fab was administered and a control group where an irrelevant antibody was administered. FIG. 9A depicts a reduction in the percentage of TDP-43 aggregates where anti-TDP-43 Fab was administered, as compared to the control groups. Accordingly, the data shows that the inventive anti-TDP-43 Fab, which was successfully expressed in human HEK cells, produced active Fab and the capacity of the anti-TDP-43 Fab to solubilize aggregates was about 90% of the aggregates. FIG. 9B shows the solubilization of β-Amyloid aggregates with the inventive anti-β-Amyloid antigen-binding fragments (Fab) expressed by vector in human cells (HEK293 cell line), as compared to a control group where no Fab was administered and a control group where an irrelevant antibody was administered.

FIG. 9B depicts a reduction in the percentage of β-Amyloid aggregates where anti-β-Amyloid Fab was administered, as compared to the control groups. Accordingly, the data shows that the inventive anti-β-Amyloid Fab, which was successfully expressed in human HEK cells, produced active Fab and the capacity of the anti-β-Amyloid Fab to solubilize aggregates was about 64% of the aggregates.

Example 5: Preparation of Expression Vectors

Vectors were created express secreted GFP, anti-β-Amyloid fragment antibody (Fab) and anti-TDP43 Fab. The backbone is the same for all, e.g., a CAG promoter to have a strong expression in Endothelial Progenitor Cells (EPCs); the Kanamycin for bacteria selection; and the Hygromycin for mammal cells selection. The GFP vector includes an insulin peptide signal to allow the secretion of the GFP from the EPCs. There are three vectors for the "anti-protein" vectors, one expressing the light chain of the Fab, one the heavy chain (including a 10-His tag) and one "Dual" expressing both chains (with His tag) with a dual CAG promoter.

The vectors used were based on the pUC high copy derived from pBR322. A Synapsin promoter is included to promote expression in neurons or a CAG promoter is included for their expression in endothelial cells. The protein expressed is the eGFP and a peptide signal from the insulin gene. In this way, the GFP expressed in neurons or endothelial cells was secreted, favored by the peptide signal. In the case of neuron targeting, a 14 aa peptide sequence X will be used. FIG. 10 depicts a map of the OG4768_pSF-CAG-Insulin SP-GFP vector. FIG. 11 depicts a map of the OG503_pSF-Synapsin-Insulin SP-GFP vector. FIG. 12 depicts a map of the Q7226 pSF-CAG Prom Insulin SP-EGFP Hygro vector.

GFP expression was measured over time using the plasmid GFP (i.e., Q7226 pSF-CAG Prom Insulin SP-EGFP Hygro) of FIG. 12. As depicted in FIG. 5A-C, flow cytometry was used to measure GFP expression by EPCs transfected with the vector over time, where MAgEC 10.5 p.8 is synonymous with MAgEC 10.5 cells after 8 passages and MAgEC 10.5 p.9 is synonymous with MAgEC 10.5 cells after 9 passages. A wild-type control where cells were not transfected with a vector showed little to no GFP expression. FIG. 6 depicts GFP secretion as a function of cell number. The GFP-EPCs clones created by stable lipotransfection that were characterized for long-term expression displayed strong GFP expression even after 9 passages.

Example 6: Transfection of Microvascular Endothelial Cells

Brain microvascular endothelial cells (and/or their precursors) collected from WT mice and transgenic mice for human Alzheimer 5XFAD are transfected with the vectors described in Example 5 either by electroporation or with the help of cationic lipids, e.g., lipofectine, lipofectamine. Expression is followed by measuring the fluorescence emission of GFP.

The 5XFAD transgenic mice overexpress mutant human APP (695) with four Familial Alzheimer's Disease (FAD) mutations along with human PS1 harboring two FAD mutations. Both transgenes are regulated by the mouse Thy1 promoter to drive overexpression in the brain. 5XFAD mice recapitulate major features of Alzheimer's Disease amyloid pathology and may be a useful model of intraneuronal Abeta-42 induced neurodegeneration and amyloid plaque formation.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

Those skilled in the art will recognize, or be able to ascertain, using no more than routine experimentation, numerous equivalents to the specific embodiments described specifically herein.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

REFERENCES

All of the following documents are incorporated by reference in their entireties.

1. Polymenidou, M. and D. W. Cleveland (2011) Cell 147, 498-508
2. Polymenidou, M. and D. W. Cleveland (2012) J. Exp. Med 209, 889-893
3. Lagier-Tourenne, C., Polymenidou, M. and Cleveland, D. W. (2010) Hum Mol Genet 19 (R1), R46-R64
4. Nicolau, C., Greferath, R, Balaban T. S. Lazarte J. E. and Hopkins R. L. (2002) Proc. Natl. Acad. Sci. USA 99, 2332-2337
5. Muhs, A., Hickman, D. T., Pihlgren, M., Chouard, N., Giriens, V., Meershman, C., Van de Auwera, I., Leuven, F. V., Sugawara, M., Weingartner, M.-C., Bechinger Greferath, R., Kolonko, N., Nagel-Steger, L., Riesner, D., Brady R. O., Pfeifer, A. and Nicolau, C. (2007) Proc. Natl. Acad. Sci. USA 104, 9810-9815
6. Hickman, D. T., Lopez-Deber, M. P., Ndao, D. M., Silva, A. B., Nand, D., Pihlgren, M., Giriens, V., Madani, R., St-Pierre, A., Karastaneva, H., Nagel-Steger, L., Willbold, D., Riesner, D., Nicolau, C., Baldus, M., Pfeifer, A. and Muhs, A. (2011) J. Biol. Hem. 286, 13966-13976
7. Rosen, D. R., Siddique, T., Patterson, D., Figlewicz D., et al (1993) Nature 362, 59-62
8. Ilieva, H., Polymenidou, M., Cleveland, D. W. (2009) J. Cell Biol. 187, 761-772
9. Kerman, A., Liu, H. N., Croul, S., Bilbao, J. et al. (2010) Acta Neuropathol. 119, 335-344
10. Bosco, D. A., Morfini, G., Karabaca, Song, Y., et al (2010) Nature Neurosci 13, 1396-1403
11. Arai, T., Hasegawa, M., Akiyama, H., Ikeda, K. et al (2006) Biochem. Biophys. Comm. 351, 602-611
12. Newman, M., Sampather, D. N., Kwong, L. K., Trux, A. C. et al (2006) Science 314, 130-133
13. Gilks, N., Kederasha, N., Agodele, M., Sen, L. et al (2004) Mol. Biol. Cell 15, 5383-5398
14. Kabashi, E., Vidmanis, P. N., Dion, P., Spiegelman, D. et al (2008) Nat. Genet 40, 572-574
15. Sredharan, J., Blair I. P., Tripethi, V. B., Hu, X. et al (2008) Science 319, 1668-1672
16. Vance, C., Rogelj, B., Hortobagyi, T., DeVoss K. J. et al (2009) Science 323, 1208-1211
17. Chia, R., Tattum, M. H., Jones, S., Collings, I. J. et al (2010) PloS One 5, e10627
18. Grad, L. I., Guest, W. C., Yanai, A., Pokrikeusky, A. et al (2011) Proc. Natl. Acad. Sci USA 108, 16398-16403
19. Munch, C., O'Brien, J. and Bertolotti, A. (2011) Proc. Natl. Acad. Sci USA 108, 3548-3553
20. Prudencio, M., Hart P. J., Borchlt, D. R. and Anderson, P. M. (2009) Hum. Mol. Genet 18, 3217-3226
21a. Tosi, P. F., Rada, D., Nicolau C. (1995) Biochem. Biophys. Res. Comm. 212, 494-500
21b. Pawlack-Robin, C., Tosi, P. F., Perrin, J., Devy, L. et al (2004) Eur. J. Cancer 40, 606-613
22. Perrin, J., Gatocrillat, G., Balasse, El, Odot, J., Nicolau, C. et al (2007) Biochem. Biophys. Res. Comm. 3, 325-330

23. Gatouillat, G., Odot, E., Balasse, E. et al (2007) Cancer Lett. 257, 165-171.
24. Lim L., Wey Y., Lu Y., Song J. (2016) PLOS Biology
25. Chandra, S., et. Al. (2003) J. Biol. Chem. 278, 15313-18.
26. Leonidas Stefanis (2012) CSH Persp. Med. 4:a009399.
27. Mandelkow, E., et. Al. (2012) CSH Persp. Med. 2:a006247.
28. Marzban, L., et. Al. (2003) Exp. Geront. 38, 347-351.
29. Jaikaran, E., et. Al. (2001) Biochem. Bioph. Acta 1537, 179-203.
30. Higham, C., et. Al. (2000) Eur. J. Biochem. 267, 4998-5004.
31. Watson, D., et. Al. (2009) Vaccine 27, 4672-83.
32. Alving, C., et. Al. (2012) Expert Rev. Vacc. 11, 733-744.
33. Deffar, K., et. Al. (2009) J. Mol. Biol. 425, 2397-411.
34. Harmsen, M. and Haard, H. (2007) App. Micro. Biotech. 77, 13-22.
35. Guilliams, T., et. Al. (2013) J. Mol. Biol. 425, 2397-411.
36. Hickman et al. (2016) U.S. Pat. No. 9,289,488 B2
37. Weksler B., Ignacio A Romero and Pierre-Olivier Couraud (2013) Fluids and Barriers of the CNS 2013, 10:16
38. Klimkiewicz et al. (2017) Cancer Letters. 396, pages 10-20.
39. Collet et al. (2015) Contemp. Oncol. (Pozn.). 19(1A): A39-A43.
40. Kieda et al. (2016) U.S. Pat. No. 9,228,173 B2
41. Kieda et al. (2017) U.S. Pat. No. 9,631,178 B2

What is claimed is:

1. A method for solubilizing TDP-43 protein aggregates in a subject having Amyotrophic Lateral Sclerosis (ALS), comprising administering to the subject a microvascular endothelial cell (MEC) comprising a nucleic acid encoding an anti-TDP-43 Fab, wherein the MEC traffics and releases the anti-TDP-43 Fab past the blood brain barrier (BBB) to a site of TDP-43 protein aggregation, wherein the anti-TDP-43 Fab comprises; a variable heavy chain domain (VH) and a variable light chain domain (VL), wherein the VH comprises heavy chain complementarity-determining regions (CDRs) comprising a CDR1 having the amino acid sequence of SEQ ID NO: 19; a CDR2 having the amino acid sequence of SEQ ID NO: 20; and a CDR3 having the amino acid sequence of SEQ ID NO: 21; and the VL comprises light chain CDRs comprising a CDR1 having the amino acid sequence of SEQ ID NO: 22; a CDR2 having the amino acid sequence of SEQ ID NO: 23; and a CDR3 having the amino acid sequence of SEQ ID NO: 24.

2. The method of claim 1, wherein the VH comprises the amino acid sequence which is at least 95% identical to the amino acid sequence of SEQ ID NO: 13.

3. The method of claim 1, wherein the VL comprises the amino acid sequence which is at least 95% identical to the amino acid sequence of SEQ ID NO: 14.

4. The method of claim 1, wherein the MEC is an autologous MEC that is derived from the subject.

5. The method of claim 4, wherein the autologous MEC is derived from bone marrow, brain, CNS, heart, liver, or pancreas of the subject.

6. The method of claim 5, wherein the method allows for homing properties of the MEC to traffic and release the anti-TDP-43 Fab in an organospecific manner.

7. The method of claim 1, wherein the nucleic acid comprises a Synapsin promoter that promotes expression in neurons.

8. The method of claim 1, wherein the nucleic acid comprises a CAG promoter that promotes expression in endothelial cells.

9. The method of claim 1, wherein the nucleic acid comprises an insulin sequence that promotes the export of anti-TDP-43 Fab.

* * * * *

SEQUENCE LISTING

```
<160> NUMBER OF SEQ ID NOS: 94

<210> SEQ ID NO 1
<211> LENGTH: 360
<212> TYPE: DNA
<213> ORGANISM: Artificial Sequence
<220> FEATURE:
<223> OTHER INFORMATION: Synthetic polymer.

<400> SEQUENCE: 1
caggttcagc tgcagcagtc tggagctgag ctggcgaggc ctggggcttc agtgaagctg      60
tcctgcaagg cttctggcta caccttcaca agctatggta taagctgggt gaggcagaga     120
actggacagg gccttgagtg gattggagag atttatccta gacgtggtaa tacttactac     180
aatgagaagt tcaagggcaa ggccacactg actgcataca aatcctccgg cacagcgtac     240
atggagctcc gcagcctgac atctgaggac tctgcggtct ttttctgtgc aagagggggt     300
atctactatg gtaacttatt tgactactgg ggccaaggca ccactctcac agtctcctca     360

<210> SEQ ID NO 2
<211> LENGTH: 57
<212> TYPE: DNA
<213> ORGANISM: Artificial Sequence
<220> FEATURE:
<223> OTHER INFORMATION: Synthetic polymer.

<400> SEQUENCE: 2
atggaatgga tctggatctt tctcttcatc ctgtcaggaa ctgcaggtgt ccaatcc          57

<210> SEQ ID NO 3
<211> LENGTH: 1008
<212> TYPE: DNA
<213> ORGANISM: Artificial Sequence
<220> FEATURE:
<223> OTHER INFORMATION: Synthetic polymer.

<400> SEQUENCE: 3
gccaaaacaa cacccccatc agtctatcca ctggcccctg ggtgtggaga tacaactggt      60
tcctctgtga ctctgggatg cctggtcaag ggctacttcc ctgagtcagt gactgtgact     120
tggaactctg gatccctgtc cagcagtgtg cacaccttcc cagctctcct gcagtctgga     180
ctctacacta tgagcagctc agtgactgtc ccctccagca cctggccaag tcagaccgtc     240
acctgcagcg ttgctcaccc agccagcagc accacggtgg acaaaaaact tgagcccagc     300
gggcccattt caacaatcaa ccctgtcct ccatgcaagg agtgtcacaa atgcccagct     360
cctaacctcg agggtggacc atccgtcttc atcttccctc caaatatcaa ggatgtactc     420
atgatctccc tgacacccaa ggtcacgtgt gtggtggtgg atgtgagcga ggatgaccca     480
```

-continued

```
gacgtccgga tcagctggtt tgtgaacaac gtggaagtac acacagctca gacacaaacc    540
catagagagg attacaacag tactatccgg gtggtcagtg ccctccccat ccagcaccag    600
gactggatga gtggcaagga gttcaaatgc aaggtcaaca acaaagacct cccatcaccc    660
atcgagagaa ccatctcaaa aattaaaggg ctagtcagag ctccacaagt atacatcttg    720
ccgccaccag cagagcagtt gtccaggaaa gatgtcagtc tcacttgcct ggtcgtgggc    780
ttcaaccctg agacatcag tgtggagtgg accagcaatg gcatacaga ggagaactac    840 aaggacaccg caccagtcct ggactctgac ggttcttact tcatatacag caagctcgat    900
ataaaaacaa gcaagtggga gaaaacagat tccttctcat gcaacgtgag acacgagggt    960
ctgaaaaatt actacctgaa gaagaccatc tcccggtctc cgggtaaa             1008
```

<210> SEQ ID NO 4
<211> LENGTH: 330
<212> TYPE: DNA
<213> ORGANISM: Artificial Sequence
<220> FEATURE:
<223> OTHER INFORMATION: Synthetic polymer.

<400> SEQUENCE: 4

```
caggctgttg tgactcagga atctgcactc accacatcac ctggtgaaac agtcacactc     60
acttgtcgct caagtactgg ggctgttaca actagtaact atgccaactg ggtccaagaa    120
aaaccagatc atttattcac tggtctaata ggtggtacca caaccgagc tccaggtgtt    180 cctgccagat tctcaggctc cctgattgga gacaaggctg ccctcaccat cacagggca    240 cagactgagg atgaggcaat atatttctgt gctctatggt tcagcaacca ctgggtgttc    300
ggtggaggaa ccaaactgac tgtcctaggc                                     330
```

<210> SEQ ID NO 5
<211> LENGTH: 57
<212> TYPE: DNA
<213> ORGANISM: Artificial Sequence
<220> FEATURE:
<223> OTHER INFORMATION: Synthetic polymer.

<400> SEQUENCE: 5

```
atggcctgga tttcacttat actctctctc ctggctctca gctcaggggc catttcc         57
```

<210> SEQ ID NO 6
<211> LENGTH: 315
<212> TYPE: DNA
<213> ORGANISM: Artificial Sequence
<220> FEATURE:
<223> OTHER INFORMATION: Synthetic polymer.

<400> SEQUENCE: 6

```
cagcccaagt cttcgccatc agtcaccctg tttccacctt cctctgaaga gctcgagact     60
aacaaggcca cactggtgtg tacgatcact gatttctacc caggtgtggt gacagtggac    120
tggaaggtag atggtacccc tgtcactcag ggtatggaga caacccagcc ttccaaacag    180
agcaacaaca agtacatggc tagcagctac ctgaccctga cagcaagagc atgggaaagg    240
catagcagtt acagctgcca ggtcactcat gaaggtcaca ctgtggagaa gagtttgtcc    300
cgtgctgact gttcc                                                     315
```

<210> SEQ ID NO 7
<211> LENGTH: 336
<212> TYPE: DNA

<213> ORGANISM: Artificial Sequence
<220> FEATURE:
<223> OTHER INFORMATION: Synthetic polymer.

<400> SEQUENCE: 7

```
caggttcagc tgcagcagtc tggggctgag ctggtgaagc ctggggcctc agtgaagatt      60
tcctgcaaag cttctggcta cgcattcagt aactactgga tgaactgggt gaagcagagg     120
cctggaaagg gtcttgagtg gattggacag atttatcctg agatggtga tactaactac      180 aacggaaagt tcaagggcaa ggccacactg actgcagaca atcctccag cacagcctac      240 atgcagctca gcagcctgac ctctgaggac tctgcggtct atttctgtgc aagaggtgac     300
tactggggcc aaggcaccac tctcacagtc tcctca                                336
```

<210> SEQ ID NO 8
<211> LENGTH: 339
<212> TYPE: DNA
<213> ORGANISM: Artificial Sequence
<220> FEATURE:
<223> OTHER INFORMATION: Synthetic polymer.

<400> SEQUENCE: 8

```
gacattgtga tgacacagtc tccatcctcc ctggctatgt cagtaggaca gaaggtcact      60
atgagctgca gtccagtca gagcctttta aatagtagca atcaaaagaa ctatttggcc      120
tggtaccagc agaaaccagg acagtctcct aaacttctgg tatactttgc atccactagg     180
gaatctgggg tccctgatcg cttcataggc agtggatctg ggacagattt cactcttacc     240
atcagcagtg tgcaggctga agacctggca gattacttct gtcagcaaca ttataacact     300
ccgctcacgt tcggtgctgg gaccaagctg gagctgaaa                             339
```

<210> SEQ ID NO 9
<211> LENGTH: 1365
<212> TYPE: DNA
<213> ORGANISM: Artificial Sequence
<220> FEATURE:
<223> OTHER INFORMATION: Synthetic polymer.

<400> SEQUENCE: 9

```
gagagtcagt ccttcccaaa tgtcttcccc ctcgtctcct gcgagagccc cctgtctgat      60
aagaatctgg tggccatggg ctgcctggcc cgggacttcc tgcccagcac catttccttc     120
acctggaact accagaacaa cactgaagtc atccagggta tcagaacctt cccaacactg     180
aggacagggg gcaagtacct agccaccctcg caggtgttgc tgtctcccaa gagcatcctt     240
gaaggttcag atgaatacct ggtatgcaaa atccactacg gaggcaaaaa caaagatctg     300
catgtgccca ttccagctgt cgcagagatg aaccccaatg taaatgtgtt cgtcccacca     360
cgggatggct tctctggccc tgcaccacgc aagtctaaac tcatctgcga ggccacgaac     420
ttcactccaa aaccgatcac agtatcctgg ctaaaggatg ggaagctcgt ggaatctggc     480
ttcaccacag atccggtgac catcgagaac aaaggatcca cccccaaac ctacaaggtc     540 ataagcacac ttaccatctc tgaaatcgac tggctgaacc tgaatgtgta cacctgccgt     600
gtggatcaca gggtctcac cttcttgaag aacgtgtcct ccacatgtgc tgccagtccc     660
tccacagaca tcctaacctt caccatcccc ccctcctttg ccgacatctt cctcagcaag     720
tccgctaacc tgacctgtct ggtctcaaac ctggcaacct atgaaaccct gaatatctcc     780
tgggcttctc aaagtggtga accactggaa accaaaatta aaatcatgga aagccatccc     840
aatggcacct tcagtgctaa gggtgtggct agtgtttgtg tggaagactg gaataacagg     900
```

```
aaggaatttg tgtgtactgt gactcacagg gatctgcctt caccacagaa gaaattcatc    960
tcaaaaccca atgaggtgca caaacatcca cctgctgtgt acctgctgcc accagctcgt   1020
gagcaactga acctgaggga gtcagccaca gtcacctgcc tggtgaaggg cttctctcct   1080
gcagacatca gtgtgcagtg gcttcagaga gggcaactct gcccccaaga gaagtatgtg   1140
accagtgccc cgatgccaga gcctggggcc ccaggcttct actttaccca cagcatcctg   1200
actgtgacag aggaggaatg gaactccgga gagacctata cctgtgttgt aggccacgag   1260
gccctgccac acctggtgac cgagaggacc gtggacaagt ccactggtaa acccacactg   1320
tacaatgtct ccctgatcat gtctgacaca ggcggcacct gctat              1365

<210> SEQ ID NO 10
<211> LENGTH: 321
<212> TYPE: DNA
<213> ORGANISM: Artificial Sequence
<220> FEATURE:
<223> OTHER INFORMATION: Synthetic polymer.

<400> SEQUENCE: 10
cgggctgatg ctgcaccaac tgtatccatc ttcccaccat ccagtgagca gttaacatct    60
ggaggtgcct cagtcgtgtg cttcttgaac aacttctacc ccaaagacat caatgtcaag   120
tggaagattg atggcagtga acgacaaaat ggcgtcctga acagttggac tgatcaggac   180
agcaaagaca gcacctacag catgagcagc accctcacgt tgaccaagga cgagtatgaa   240
cgacataaca gctatacctg tgaggccact cacaagacat caacttcacc cattgtcaag   300
agcttcaaca ggaatgagtg t                                             321

<210> SEQ ID NO 11
<211> LENGTH: 57
<212> TYPE: DNA
<213> ORGANISM: Artificial Sequence
<220> FEATURE:
<223> OTHER INFORMATION: Synthetic polymer.

<400> SEQUENCE: 11
atggaatggc ctttgatctt tctcttcctc ctgtcaggaa ctgcaggtgt ccaatcc       57

<210> SEQ ID NO 12
<211> LENGTH: 60
<212> TYPE: DNA
<213> ORGANISM: Artificial Sequence
<220> FEATURE:
<223> OTHER INFORMATION: Synthetic polymer.

<400> SEQUENCE: 12
atggaatcac agacccaggt cctcatgttt cttctgctct gggtatctgg tgcctgtgca    60

<210> SEQ ID NO 13
<211> LENGTH: 120
<212> TYPE: PRT
<213> ORGANISM: Artificial Sequence
<220> FEATURE:
<223> OTHER INFORMATION: Synthetic polymer.

<400> SEQUENCE: 13

Gln Val Gln Leu Gln Gln Ser Gly Ala Glu Leu Ala Arg Pro Gly Ala
 1               5                  10                  15

Ser Val Lys Leu Ser Cys Lys Ala Ser Gly Tyr Thr Phe Thr Ser Tyr
            20                  25                  30
```

Gly Ile Ser Trp Val Arg Gln Arg Thr Gly Gln Gly Leu Glu Trp Ile
            35                  40                  45

Gly Glu Ile Tyr Pro Arg Arg Gly Asn Thr Tyr Tyr Asn Glu Lys Phe
 50                  55                  60

Lys Gly Lys Ala Thr Leu Thr Ala Tyr Lys Ser Ser Gly Thr Ala Tyr
65                  70                  75                  80

Met Glu Leu Arg Ser Leu Thr Ser Glu Asp Ser Ala Val Phe Phe Cys
                85                  90                  95

Ala Arg Gly Gly Ile Tyr Tyr Gly Asn Leu Phe Asp Tyr Trp Gly Gln
            100                 105                 110

Gly Thr Thr Leu Thr Val Ser Ser
            115                 120

<210> SEQ ID NO 14
<211> LENGTH: 110
<212> TYPE: PRT
<213> ORGANISM: Artificial Sequence
<220> FEATURE:
<223> OTHER INFORMATION: Synthetic polymer.

<400> SEQUENCE: 14

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
 50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Phe Ser Asn
                85                  90                  95

His Trp Val Phe Gly Gly Gly Thr Lys Leu Thr Val Leu Gly
            100                 105                 110

<210> SEQ ID NO 15
<211> LENGTH: 336
<212> TYPE: PRT
<213> ORGANISM: Artificial Sequence
<220> FEATURE:
<223> OTHER INFORMATION: Synthetic polymer.

<400> SEQUENCE: 15

Ala Lys Thr Thr Pro Pro Ser Val Tyr Pro Leu Ala Pro Gly Cys Gly
1               5                   10                  15

Asp Thr Thr Gly Ser Ser Val Thr Leu Gly Cys Leu Val Lys Gly Tyr
            20                  25                  30

Phe Pro Glu Ser Val Thr Val Thr Trp Asn Ser Gly Ser Leu Ser Ser
        35                  40                  45

Ser Val His Thr Phe Pro Ala Leu Leu Gln Ser Gly Leu Tyr Thr Met
 50                  55                  60

Ser Ser Ser Val Thr Val Pro Ser Ser Thr Trp Pro Ser Gln Thr Val
65                  70                  75                  80

Thr Cys Ser Val Ala His Pro Ala Ser Ser Thr Thr Val Asp Lys Lys
                85                  90                  95

Leu Glu Pro Ser Gly Pro Ile Ser Thr Ile Asn Pro Cys Pro Pro Cys
            100                 105                 110

```
Lys Glu Cys His Lys Cys Pro Ala Pro Asn Leu Glu Gly Gly Pro Ser
            115                 120                 125

Val Phe Ile Phe Pro Pro Asn Ile Lys Asp Val Leu Met Ile Ser Leu
        130                 135                 140

Thr Pro Lys Val Thr Cys Val Val Asp Val Ser Glu Asp Pro
145                 150                 155                 160

Asp Val Arg Ile Ser Trp Phe Val Asn Asn Val Glu Val His Thr Ala
                165                 170                 175

Gln Thr Gln Thr His Arg Glu Asp Tyr Asn Ser Thr Ile Arg Val Val
            180                 185                 190

Ser Ala Leu Pro Ile Gln His Gln Asp Trp Met Ser Gly Lys Glu Phe
        195                 200                 205

Lys Cys Lys Val Asn Asn Lys Asp Leu Pro Ser Pro Ile Glu Arg Thr
210                 215                 220

Ile Ser Lys Ile Lys Gly Leu Val Arg Ala Pro Gln Val Tyr Ile Leu
225                 230                 235                 240

Pro Pro Pro Ala Glu Gln Leu Ser Arg Lys Asp Val Ser Leu Thr Cys
                245                 250                 255

Leu Val Val Gly Phe Asn Pro Gly Asp Ile Ser Val Glu Trp Thr Ser
            260                 265                 270

Asn Gly His Thr Glu Glu Asn Tyr Lys Asp Thr Ala Pro Val Leu Asp
        275                 280                 285

Ser Asp Gly Ser Tyr Phe Ile Tyr Ser Lys Leu Asp Ile Lys Thr Ser
        290                 295                 300

Lys Trp Glu Lys Thr Asp Ser Phe Ser Cys Asn Val Arg His Glu Gly
305                 310                 315                 320

Leu Lys Asn Tyr Tyr Leu Lys Lys Thr Ile Ser Arg Ser Pro Gly Lys
                325                 330                 335

<210> SEQ ID NO 16
<211> LENGTH: 105
<212> TYPE: PRT
<213> ORGANISM: Artificial Sequence
<220> FEATURE:
<223> OTHER INFORMATION: Synthetic polymer.

<400> SEQUENCE: 16

Gln Pro Lys Ser Ser Pro Ser Val Thr Leu Phe Pro Pro Ser Ser Glu
1               5                   10                  15

Glu Leu Glu Thr Asn Lys Ala Thr Leu Val Cys Thr Ile Thr Asp Phe
            20                  25                  30

Tyr Pro Gly Val Val Thr Val Asp Trp Lys Val Asp Gly Thr Pro Val
        35                  40                  45

Thr Gln Gly Met Glu Thr Thr Gln Pro Ser Lys Gln Ser Asn Asn Lys
    50                  55                  60

Tyr Met Ala Ser Ser Tyr Leu Thr Leu Thr Ala Arg Ala Trp Glu Arg
65                  70                  75                  80

His Ser Ser Tyr Ser Cys Gln Val Thr His Glu Gly His Thr Val Glu
                85                  90                  95

Lys Ser Leu Ser Arg Ala Asp Cys Ser
            100                 105

<210> SEQ ID NO 17
<211> LENGTH: 19
<212> TYPE: PRT
<213> ORGANISM: Artificial Sequence
```

```
<220> FEATURE:
<223> OTHER INFORMATION: Synthetic polymer.

<400> SEQUENCE: 17

Met Glu Trp Ile Trp Ile Phe Leu Phe Ile Leu Ser Gly Thr Ala Gly
1               5                   10                  15

Val Gln Ser

<210> SEQ ID NO 18
<211> LENGTH: 19
<212> TYPE: PRT
<213> ORGANISM: Artificial Sequence
<220> FEATURE:
<223> OTHER INFORMATION: Synthetic polymer.

<400> SEQUENCE: 18

Met Ala Trp Ile Ser Leu Ile Leu Ser Leu Leu Ala Leu Ser Ser Gly
1               5                   10                  15

Ala Ile Ser

<210> SEQ ID NO 19
<211> LENGTH: 5
<212> TYPE: PRT
<213> ORGANISM: Artificial Sequence
<220> FEATURE:
<223> OTHER INFORMATION: Synthetic polymer.

<400> SEQUENCE: 19

Ser Tyr Gly Ile Ser
1               5

<210> SEQ ID NO 20
<211> LENGTH: 17
<212> TYPE: PRT
<213> ORGANISM: Artificial Sequence
<220> FEATURE:
<223> OTHER INFORMATION: Synthetic polymer.

<400> SEQUENCE: 20

Glu Ile Tyr Pro Arg Arg Gly Asn Thr Tyr Tyr Asn Glu Lys Phe Lys
1               5                   10                  15

Gly

<210> SEQ ID NO 21
<211> LENGTH: 11
<212> TYPE: PRT
<213> ORGANISM: Artificial Sequence
<220> FEATURE:
<223> OTHER INFORMATION: Synthetic polymer.

<400> SEQUENCE: 21

Gly Gly Ile Tyr Tyr Gly Asn Leu Phe Asp Tyr
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Synthetic polymer.

<400> SEQUENCE: 22

Arg Ser Ser Thr Gly Ala Val Thr Thr Ser Asn Tyr Ala Asn
1               5                   10
```

```
<210> SEQ ID NO 23
<211> LENGTH: 7
<212> TYPE: PRT
<213> ORGANISM: Artificial Sequence
<220> FEATURE:
<223> OTHER INFORMATION: Synthetic polymer.

<400> SEQUENCE: 23

Gly Thr Asn Asn Arg Ala Pro
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic polymer.

<400> SEQUENCE: 24

Ala Leu Trp Phe Ser Asn His Trp Val
1               5

<210> SEQ ID NO 25
<211> LENGTH: 414
<212> TYPE: PRT
<213> ORGANISM: Artificial Sequence
<220> FEATURE:
<223> OTHER INFORMATION: Synthetic polymer.

<400> SEQUENCE: 25

Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
            20                  25                  30

Ala Gln Phe Pro Gly Ala Cys Gly Leu Arg Tyr Arg Asn Pro Val Ser
        35                  40                  45

Gln Cys Met Arg Gly Val Arg Leu Val Glu Gly Ile Leu His Ala Pro
    50                  55                  60

Asp Ala Gly Trp Gly Asn Leu Val Tyr Val Val Asn Tyr Pro Lys Asp
65                  70                  75                  80

Asn Lys Arg Lys Met Asp Glu Thr Asp Ala Ser Ser Ala Val Lys Val
                85                  90                  95

Lys Arg Ala Val Gln Lys Thr Ser Asp Leu Ile Val Leu Gly Leu Pro
            100                 105                 110

Trp Lys Thr Thr Glu Gln Asp Leu Lys Glu Tyr Phe Ser Thr Phe Gly
        115                 120                 125

Glu Val Leu Met Val Gln Val Lys Lys Asp Leu Lys Thr Gly His Ser
    130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
            180                 185                 190

Val Phe Val Gly Arg Cys Thr Glu Asp Met Thr Glu Asp Glu Leu Arg
        195                 200                 205

Glu Phe Phe Ser Gln Tyr Gly Asp Val Met Asp Val Phe Ile Pro Lys
    210                 215                 220

Pro Phe Arg Ala Phe Ala Phe Val Thr Phe Ala Asp Asp Gln Ile Ala
```

```
                225                 230                 235                 240

Gln Ser Leu Cys Gly Glu Asp Leu Ile Ile Lys Gly Ile Ser Val His
                        245                 250                 255

Ile Ser Asn Ala Glu Pro Lys His Asn Ser Asn Arg Gln Leu Glu Arg
                    260                 265                 270

Ser Gly Arg Phe Gly Gly Asn Pro Gly Gly Phe Gly Asn Gln Gly Gly
                275                 280                 285

Phe Gly Asn Ser Arg Gly Gly Ala Gly Leu Gly Asn Asn Gln Gly
            290                 295                 300

Ser Asn Met Gly Gly Gly Met Asn Phe Gly Ala Phe Ser Ile Asn Pro
        305                 310                 315                 320

Ala Met Met Ala Ala Ala Gln Ala Ala Leu Gln Ser Ser Trp Gly Met
                        325                 330                 335

Met Gly Met Leu Ala Ser Gln Gln Asn Gln Ser Gly Pro Ser Gly Asn
                    340                 345                 350

Asn Gln Asn Gln Gly Asn Met Gln Arg Glu Pro Asn Gln Ala Phe Gly
                355                 360                 365

Ser Gly Asn Asn Ser Tyr Ser Gly Ser Asn Ser Gly Ala Ala Ile Gly
            370                 375                 380

Trp Gly Ser Ala Ser Asn Ala Gly Ser Gly Ser Gly Phe Asn Gly Gly
        385                 390                 395                 400

Phe Gly Ser Ser Met Asp Ser Lys Ser Ser Gly Trp Gly Met
                        405                 410

<210> SEQ ID NO 26
<211> LENGTH: 34
<212> TYPE: PRT
<213> ORGANISM: Artificial Sequence
<220> FEATURE:
<223> OTHER INFORMATION: Synthetic polymer.

<400> SEQUENCE: 26

Met Asn Phe Gly Ala Phe Ser Ile Asn Pro Ala Met Met Ala Ala Ala
1               5                   10                  15

Gln Ala Ala Leu Gln Ser Ser Trp Gly Met Met Gly Met Leu Ala Ser
            20                  25                  30

Gln Gln

<210> SEQ ID NO 27
<211> LENGTH: 10
<212> TYPE: PRT
<213> ORGANISM: Artificial Sequence
<220> FEATURE:
<223> OTHER INFORMATION: Synthetic polymer.

<400> SEQUENCE: 27

Met Asn Phe Gly Ala Phe Ser Ile Asn Pro
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic polymer.

<400> SEQUENCE: 28

Glu Asp Leu Ile Ile Lys Gly Ile Ser Val
1               5                   10
```

```
<210> SEQ ID NO 29
<211> LENGTH: 42
<212> TYPE: PRT
<213> ORGANISM: Artificial Sequence
<220> FEATURE:
<223> OTHER INFORMATION: Synthetic polymer.

<400> SEQUENCE: 29

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 30
<211> LENGTH: 16
<212> TYPE: PRT
<213> ORGANISM: Artificial Sequence
<220> FEATURE:
<223> OTHER INFORMATION: Synthetic polymer.

<400> SEQUENCE: 30

Asp Ala Glu Phe Arg His Asp Ser Gly Tyr Glu Val His His Gln Lys
1               5                   10                  15

<210> SEQ ID NO 31
<211> LENGTH: 113
<212> TYPE: PRT
<213> ORGANISM: Artificial Sequence
<220> FEATURE:
<223> OTHER INFORMATION: Synthetic polymer.

<400> SEQUENCE: 31

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Asn Thr Pro Leu Thr Phe Gly Ala Gly Thr Lys Leu Glu Leu
            100                 105                 110

Lys

<210> SEQ ID NO 32
<211> LENGTH: 455
<212> TYPE: PRT
<213> ORGANISM: Artificial Sequence
<220> FEATURE:
<223> OTHER INFORMATION: Synthetic polymer.

<400> SEQUENCE: 32

Glu Ser Gln Ser Phe Pro Asn Val Phe Pro Leu Val Ser Cys Glu Ser
1               5                   10                  15

Pro Leu Ser Asp Lys Asn Leu Val Ala Met Gly Cys Leu Ala Arg Asp
```

```
                    20                  25                  30
Phe Leu Pro Ser Thr Ile Ser Phe Thr Trp Asn Tyr Gln Asn Asn Thr
                35                  40                  45
Glu Val Ile Gln Gly Ile Arg Thr Phe Pro Thr Leu Arg Thr Gly Gly
     50                  55                  60
Lys Tyr Leu Ala Thr Ser Gln Val Leu Leu Ser Pro Lys Ser Ile Leu
 65                  70                  75                  80
Glu Gly Ser Asp Glu Tyr Leu Val Cys Lys Ile His Tyr Gly Gly Lys
                 85                  90                  95
Asn Lys Asp Leu His Val Pro Ile Pro Ala Val Ala Glu Met Asn Pro
                100                 105                 110
Asn Val Asn Val Phe Val Pro Arg Asp Gly Phe Ser Gly Pro Ala
            115                 120                 125
Pro Arg Lys Ser Lys Leu Ile Cys Glu Ala Thr Asn Phe Thr Pro Lys
            130                 135                 140
Pro Ile Thr Val Ser Trp Leu Lys Asp Gly Lys Leu Val Glu Ser Gly
145                 150                 155                 160
Phe Thr Thr Asp Pro Val Thr Ile Glu Asn Lys Gly Ser Thr Pro Gln
                165                 170                 175
Thr Tyr Lys Val Ile Ser Thr Leu Thr Ile Ser Glu Ile Asp Trp Leu
                180                 185                 190
Asn Leu Asn Val Tyr Thr Cys Arg Val Asp His Arg Gly Leu Thr Phe
            195                 200                 205
Leu Lys Asn Val Ser Ser Thr Cys Ala Ala Ser Pro Ser Thr Asp Ile
            210                 215                 220
Leu Thr Phe Thr Ile Pro Pro Ser Phe Ala Asp Ile Phe Leu Ser Lys
225                 230                 235                 240
Ser Ala Asn Leu Thr Cys Leu Val Ser Asn Leu Ala Thr Tyr Glu Thr
                245                 250                 255
Leu Asn Ile Ser Trp Ala Ser Gln Ser Gly Glu Pro Leu Glu Thr Lys
                260                 265                 270
Ile Lys Ile Met Glu Ser His Pro Asn Gly Thr Phe Ser Ala Lys Gly
            275                 280                 285
Val Ala Ser Val Cys Val Glu Asp Trp Asn Asn Arg Lys Glu Phe Val
            290                 295                 300
Cys Thr Val Thr His Arg Asp Leu Pro Ser Pro Gln Lys Lys Phe Ile
305                 310                 315                 320
Ser Lys Pro Asn Glu Val His Lys His Pro Pro Ala Val Tyr Leu Leu
                325                 330                 335
Pro Pro Ala Arg Glu Gln Leu Asn Leu Arg Glu Ser Ala Thr Val Thr
                340                 345                 350
Cys Leu Val Lys Gly Phe Ser Pro Ala Asp Ile Ser Val Gln Trp Leu
            355                 360                 365
Gln Arg Gly Gln Leu Leu Pro Gln Glu Lys Tyr Val Thr Ser Ala Pro
            370                 375                 380
Met Pro Glu Pro Gly Ala Pro Gly Phe Tyr Phe Thr His Ser Ile Leu
385                 390                 395                 400
Thr Val Thr Glu Glu Trp Asn Ser Gly Glu Thr Tyr Thr Cys Val
                405                 410                 415
Val Gly His Glu Ala Leu Pro His Leu Val Thr Glu Arg Thr Val Asp
                420                 425                 430
Lys Ser Thr Gly Lys Pro Thr Leu Tyr Asn Val Ser Leu Ile Met Ser
            435                 440                 445
```

```
Asp Thr Gly Gly Thr Cys Tyr
    450                 455

<210> SEQ ID NO 33
<211> LENGTH: 107
<212> TYPE: PRT
<213> ORGANISM: Artificial Sequence
<220> FEATURE:
<223> OTHER INFORMATION: Synthetic polymer.

<400> SEQUENCE: 33

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 34
<211> LENGTH: 19
<212> TYPE: PRT
<213> ORGANISM: Artificial Sequence
<220> FEATURE:
<223> OTHER INFORMATION: Synthetic polymer.

<400> SEQUENCE: 34

Met Glu Trp Pro Leu Ile Phe Leu Phe Leu Leu Ser Gly Thr Ala Gly
1               5                   10                  15

Val Gln Ser

<210> SEQ ID NO 35
<211> LENGTH: 20
<212> TYPE: PRT
<213> ORGANISM: Artificial Sequence
<220> FEATURE:
<223> OTHER INFORMATION: Synthetic polymer.

<400> SEQUENCE: 35

Met Glu Ser Gln Thr Gln Val Leu Met Phe Leu Leu Leu Trp Val Ser
1               5                   10                  15

Gly Ala Cys Ala
            20

<210> SEQ ID NO 36
<211> LENGTH: 5
<212> TYPE: PRT
<213> ORGANISM: Artificial Sequence
<220> FEATURE:
<223> OTHER INFORMATION: Synthetic polymer.

<400> SEQUENCE: 36

Asn Tyr Trp Met Asn
1               5
```

```
<210> SEQ ID NO 37
<211> LENGTH: 17
<212> TYPE: PRT
<213> ORGANISM: Artificial Sequence
<220> FEATURE:
<223> OTHER INFORMATION: Synthetic polymer.

<400> SEQUENCE: 37

Gln Ile Tyr Pro Gly Asp Gly Asp Thr Asn Tyr Asn Gly Lys Phe Lys
1               5                   10                  15

Gly

<210> SEQ ID NO 38
<211> LENGTH: 3
<212> TYPE: PRT
<213> ORGANISM: Artificial Sequence
<220> FEATURE:
<223> OTHER INFORMATION: Synthetic polymer.

<400> SEQUENCE: 38

Gly Asp Tyr
1

<210> SEQ ID NO 39
<211> LENGTH: 17
<212> TYPE: PRT
<213> ORGANISM: Artificial Sequence
<220> FEATURE:
<223> OTHER INFORMATION: Synthetic polymer.

<400> SEQUENCE: 39

Lys Ser Ser Gln Ser Leu Leu Asn Ser Asn Gln Lys Asn Tyr Leu
1               5                   10                  15

Ala

<210> SEQ ID NO 40
<211> LENGTH: 7
<212> TYPE: PRT
<213> ORGANISM: Artificial Sequence
<220> FEATURE:
<223> OTHER INFORMATION: Synthetic polymer.

<400> SEQUENCE: 40

Phe Ala Ser Thr Arg Glu Ser
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic polymer.

<400> SEQUENCE: 41

Gln Gln His Tyr Asn Thr Pro Leu Thr
1               5

<210> SEQ ID NO 42
<211> LENGTH: 121
<212> TYPE: PRT
<213> ORGANISM: Artificial Sequence
<220> FEATURE:
<223> OTHER INFORMATION: Synthetic polymer.
<220> FEATURE:
<221> NAME/KEY: misc_feature
<222> LOCATION: (52)..(52)
```

<223> OTHER INFORMATION: Xaa can be any naturally occurring amino acid

<400> SEQUENCE: 42

Gln Val Gln Leu Gln Gln Ser Gly Ala Glu Leu Ala Arg Pro Gly Ala
1               5                   10                  15
Ser Val Lys Leu Ser Cys Lys Ala Ser Gly Tyr Thr Phe Thr Ser Tyr
            20                  25                  30
Gly Ile Arg Trp Val Lys Gln Arg Thr Gly Gln Gly Leu Glu Trp Ile
        35                  40                  45
Gly Glu Ile Xaa Pro Arg Ser Gly Asn Thr Tyr Tyr Asn Glu Lys Phe
    50                  55                  60
Lys Gly Lys Ala Thr Val Thr Ala Asp Lys Ser Ser Thr Ala Tyr
65                  70                  75                  80
Met Glu Leu Arg Ser Leu Thr Ser Glu Asp Ser Ala Val Tyr Phe Cys
                85                  90                  95
Ala Arg Ser Ile Tyr Tyr Gly Arg Pro Tyr Tyr Phe Asp Tyr Trp Gly
            100                 105                 110
Gln Gly Thr Thr Leu Thr Val Ser Ser
        115                 120

<210> SEQ ID NO 43
<211> LENGTH: 107
<212> TYPE: PRT
<213> ORGANISM: Artificial Sequence
<220> FEATURE:
<223> OTHER INFORMATION: Synthetic polymer.

<400> SEQUENCE: 43

Asp Ile Val Met Thr Gln Ser Gln Leu Phe Met Ser Thr Ser Asp Arg
1               5                   10                  15
Val Ser Val Thr Cys Lys Ala Ser Gln Asn Val Ala Val Gly Thr Asn
            20                  25                  30
Val Ala Trp Tyr Gln Gln Lys Pro Gly Gln Ser Pro Lys Ala Leu Ile
        35                  40                  45
Tyr Ser Ala Ser Tyr Arg Tyr Ser Gly Val Pro Asp Arg Phe Thr Gly
    50                  55                  60
Ser Gly Ser Gly Thr Asp Phe Thr Leu Thr Ile Ser Asn Val Gln Ser
65                  70                  75                  80
Glu Asp Leu Ala Glu Tyr Phe Cys Gln Gln Tyr Asn Ser Tyr Pro Leu
                85                  90                  95
Thr Phe Gly Ala Gly Thr Lys Leu Glu Leu Lys
            100                 105

<210> SEQ ID NO 44
<211> LENGTH: 10
<212> TYPE: PRT
<213> ORGANISM: Artificial Sequence
<220> FEATURE:
<223> OTHER INFORMATION: Synthetic polymer.

<400> SEQUENCE: 44

Gly Tyr Thr Phe Thr Ser Tyr Gly Ile Arg
1               5                   10

<210> SEQ ID NO 45
<211> LENGTH: 16
<212> TYPE: PRT
<213> ORGANISM: Artificial Sequence
<220> FEATURE:
<223> OTHER INFORMATION: Synthetic polymer.

```
<220> FEATURE:
<221> NAME/KEY: misc_feature
<222> LOCATION: (3)..(3)
<223> OTHER INFORMATION: Xaa can be any naturally occurring amino acid

<400> SEQUENCE: 45

Glu Ile Xaa Pro Arg Ser Gly Asn Thr Tyr Tyr Asn Glu Lys Phe Lys
1               5                   10                  15

<210> SEQ ID NO 46
<211> LENGTH: 12
<212> TYPE: PRT
<213> ORGANISM: Artificial Sequence
<220> FEATURE:
<223> OTHER INFORMATION: Synthetic polymer.

<400> SEQUENCE: 46

Ser Ile Tyr Tyr Gly Arg Pro Tyr Tyr Phe Asp Tyr
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Synthetic polymer.

<400> SEQUENCE: 47

Lys Ala Ser Gln Asn Val Ala Thr Asn Val Ala
1               5                   10

<210> SEQ ID NO 48
<211> LENGTH: 7
<212> TYPE: PRT
<213> ORGANISM: Artificial Sequence
<220> FEATURE:
<223> OTHER INFORMATION: Synthetic polymer.

<400> SEQUENCE: 48

Ser Ala Ser Tyr Arg Tyr Ser
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic polymer.

<400> SEQUENCE: 49

Gln Gln Tyr Asn Ser Tyr Pro Leu Thr
1               5

<210> SEQ ID NO 50
<211> LENGTH: 117
<212> TYPE: PRT
<213> ORGANISM: Artificial Sequence
<220> FEATURE:
<223> OTHER INFORMATION: Synthetic polymer.

<400> SEQUENCE: 50

Gln Val Gln Leu Gln Gln Ser Asp Ala Glu Leu Val Lys Pro Gly Ala
1               5                   10                  15

Ser Val Lys Ile Ser Cys Lys Val Ser Gly Tyr Thr Phe Thr Asp His
            20                  25                  30

Thr Ile His Trp Met Lys Gln Arg Pro Glu Gln Gly Leu Glu Trp Ile
```

```
            35                  40                  45
Gly Tyr Ile Tyr Pro Arg Asp Gly Ser Thr Lys Tyr Asn Glu Lys Phe
        50                  55                  60

Lys Gly Lys Ala Thr Leu Thr Ala Asp Lys Ser Ser Ser Thr Ala Tyr
 65                  70                  75                  80

Met Gln Leu Asn Ser Leu Thr Ser Glu Asp Ser Ala Val Tyr Phe Cys
                 85                  90                  95

Ala Arg Asp Tyr Gly Tyr Ala Phe Asp Tyr Trp Gly Gln Gly Thr Thr
            100                 105                 110

Leu Thr Val Ser Ser
        115

<210> SEQ ID NO 51
<211> LENGTH: 117
<212> TYPE: PRT
<213> ORGANISM: Artificial Sequence
<220> FEATURE:
<223> OTHER INFORMATION: Synthetic polymer.

<400> SEQUENCE: 51

Gln Val Gln Leu Gln Gln Ser Asp Ala Glu Leu Val Lys Pro Gly Ala
 1               5                  10                  15

Ser Val Lys Ile Ser Cys Lys Val Ser Gly Tyr Thr Phe Thr Asp His
                20                  25                  30

Thr Ile His Trp Met Lys Gln Arg Pro Glu Gln Gly Leu Glu Trp Ile
            35                  40                  45

Gly Tyr Ile Tyr Pro Arg Asp Gly Ser Thr Lys Tyr Asn Glu Lys Phe
        50                  55                  60

Lys Gly Lys Ala Thr Leu Thr Ala Asp Lys Ser Ser Ser Thr Ala Tyr
 65                  70                  75                  80

Met Gln Leu Asn Ser Leu Thr Ser Glu Asp Ser Ala Val Tyr Phe Cys
                 85                  90                  95

Ala Arg Asp Tyr Gly Tyr Ala Phe Asp Tyr Trp Gly Gln Gly Thr Thr
            100                 105                 110

Leu Thr Val Ser Ser
        115

<210> SEQ ID NO 52
<211> LENGTH: 109
<212> TYPE: PRT
<213> ORGANISM: Artificial Sequence
<220> FEATURE:
<223> OTHER INFORMATION: Synthetic polymer.

<400> SEQUENCE: 52

Gln Ala Val Val Thr Gln Glu Ser Ala Leu Thr Thr Ser Pro Gly Gly
 1               5                  10                  15

Thr Val Ile Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
            35                  40                  45

Leu Ile Gly Gly Thr Ser Asn Arg Ala Pro Gly Val Pro Val Arg Phe
        50                  55                  60

Ser Gly Ser Leu Ile Gly Asp Lys Ala Ala Leu Thr Ile Thr Gly Ala
 65                  70                  75                  80

Gln Thr Glu Asp Asp Ala Met Tyr Phe Cys Ala Leu Trp Tyr Ser Thr
                 85                  90                  95
```

His Tyr Val Phe Gly Gly Gly Thr Lys Val Thr Val Leu
            100                 105

<210> SEQ ID NO 53
<211> LENGTH: 109
<212> TYPE: PRT
<213> ORGANISM: Artificial Sequence
<220> FEATURE:
<223> OTHER INFORMATION: Synthetic polymer.

<400> SEQUENCE: 53

Gln Ala Val Val Thr Gln Glu Ser Ala Leu Thr Thr Ser Pro Gly Gly
1               5                   10                  15

Thr Val Ile Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Ser Asn Arg Ala Pro Gly Val Pro Val Arg Phe
    50                  55                  60

Ser Gly Ser Leu Ile Gly Asp Lys Ala Ala Leu Thr Ile Thr Gly Ala
65                  70                  75                  80

Gln Thr Glu Asp Asp Ala Met Tyr Phe Cys Ala Leu Trp Tyr Ser Thr
                85                  90                  95

His Tyr Val Phe Gly Gly Gly Thr Lys Val Thr Val Leu
            100                 105

<210> SEQ ID NO 54
<211> LENGTH: 10
<212> TYPE: PRT
<213> ORGANISM: Artificial Sequence
<220> FEATURE:
<223> OTHER INFORMATION: Synthetic polymer.

<400> SEQUENCE: 54

Gly Tyr Thr Phe Thr Asp His Thr Ile His
1               5                   10

<210> SEQ ID NO 55
<211> LENGTH: 16
<212> TYPE: PRT
<213> ORGANISM: Artificial Sequence
<220> FEATURE:
<223> OTHER INFORMATION: Synthetic polymer.

<400> SEQUENCE: 55

Tyr Ile Tyr Pro Arg Asp Gly Ser Thr Lys Tyr Asn Glu Lys Phe Lys
1               5                   10                  15

<210> SEQ ID NO 56
<211> LENGTH: 8
<212> TYPE: PRT
<213> ORGANISM: Artificial Sequence
<220> FEATURE:
<223> OTHER INFORMATION: Synthetic polymer.

<400> SEQUENCE: 56

Asp Tyr Gly Tyr Ala Phe Asp Tyr
1               5

<210> SEQ ID NO 57
<211> LENGTH: 14
<212> TYPE: PRT
<213> ORGANISM: Artificial Sequence
<220> FEATURE:

<223> OTHER INFORMATION: Synthetic polymer.

<400> SEQUENCE: 57

Arg Ser Ser Thr Gly Ala Val Thr Thr Ser Asn Tyr Ala Asn
1               5                   10

<210> SEQ ID NO 58
<211> LENGTH: 7
<212> TYPE: PRT
<213> ORGANISM: Artificial Sequence
<220> FEATURE:
<223> OTHER INFORMATION: Synthetic polymer.

<400> SEQUENCE: 58

Gly Thr Ser Asn Arg Ala Pro
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic polymer.

<400> SEQUENCE: 59

Ala Leu Trp Tyr Ser Thr His Tyr Val
1               5

<210> SEQ ID NO 60
<211> LENGTH: 121
<212> TYPE: PRT
<213> ORGANISM: Artificial Sequence
<220> FEATURE:
<223> OTHER INFORMATION: Synthetic polymer.
<220> FEATURE:
<221> NAME/KEY: misc_feature
<222> LOCATION: (52)..(52)
<223> OTHER INFORMATION: Xaa can be any naturally occurring amino acid

<400> SEQUENCE: 60

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
                20                  25                  30

Gly Ile Arg Trp Val Lys Gln Arg Thr Gly Gln Gly Leu Glu Trp Ile
            35                  40                  45

Gly Glu Ile Xaa Pro Arg Ser Gly Asn Thr Tyr Tyr Asn Glu Lys Phe
        50                  55                  60

Lys Gly Lys Ala Thr Val Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Ser Ile Tyr Tyr Gly Arg Pro Tyr Tyr Phe Asp Tyr Trp Gly
            100                 105                 110

Gln Gly Thr Thr Leu Thr Val Ser Ser
        115                 120

<210> SEQ ID NO 61
<211> LENGTH: 107
<212> TYPE: PRT
<213> ORGANISM: Artificial Sequence
<220> FEATURE:
<223> OTHER INFORMATION: Synthetic polymer.

<400> SEQUENCE: 61

Asp Ile Val Met Thr Gln Ser Gln Leu Phe Met Ser Thr Ser Val Gly
1               5                   10                  15

Asp Arg Val Ser Val Thr Cys Lys Ala Ser Gln Asn Val Ala Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Leu Lys
            100                 105

<210> SEQ ID NO 62
<211> LENGTH: 116
<212> TYPE: PRT
<213> ORGANISM: Artificial Sequence
<220> FEATURE:
<223> OTHER INFORMATION: Synthetic polymer.

<400> SEQUENCE: 62

Gln Val Gln Leu Gln Gln Ser Asp Ala Glu Leu Val Lys Pro Gly Ala
1               5                   10                  15

Ser Val Lys Ile Ser Cys Lys Val Ser Gly Tyr Thr Phe Thr Asp His
            20                  25                  30

Thr Ile His Trp Met Lys Gln Arg Pro Glu Gln Gly Leu Glu Trp Ile
        35                  40                  45

Gly Tyr Ile Tyr Pro Arg Asp Gly Ser Thr Lys Tyr Asn Glu Lys Phe
    50                  55                  60

Lys Gly Lys Ala Thr Leu Thr Ala Asp Lys Ser Ser Thr Ala Tyr
65                  70                  75                  80

Met Gln Leu Asn Ser Leu Thr Ser Glu Asp Ser Ala Val Tyr Phe Cys
                85                  90                  95

Ala Arg Asp Tyr Gly Tyr Ala Phe Asp Tyr Trp Gly Gln Gly Thr Thr
            100                 105                 110

Thr Val Ser Ser
        115

<210> SEQ ID NO 63
<211> LENGTH: 109
<212> TYPE: PRT
<213> ORGANISM: Artificial Sequence
<220> FEATURE:
<223> OTHER INFORMATION: Synthetic polymer.

<400> SEQUENCE: 63

Gln Ala Val Val Thr Gln Glu Ser Ala Leu Thr Thr Ser Pro Gly Gly
1               5                   10                  15

Thr Val Ile Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Ser Asn Arg Ala Pro Gly Val Pro Val Arg Phe
    50                  55                  60

```
Ser Gly Ser Leu Ile Gly Asp Lys Ala Ala Leu Thr Ile Thr Gly Ala
 65                  70                  75                  80

Gln Thr Glu Asp Asp Ala Met Tyr Phe Cys Ala Leu Trp Tyr Ser Thr
                 85                  90                  95

His Tyr Val Phe Gly Gly Gly Thr Lys Val Thr Val Leu
            100                 105
```

<210> SEQ ID NO 64
<211> LENGTH: 117
<212> TYPE: PRT
<213> ORGANISM: Artificial Sequence
<220> FEATURE:
<223> OTHER INFORMATION: Synthetic polymer.

<400> SEQUENCE: 64

```
Gln Val Gln Leu Gln Gln Ser Asp Ala Glu Leu Val Lys Pro Gly Ala
 1               5                   10                  15

Ser Val Lys Ile Ser Cys Lys Val Ser Gly Tyr Thr Phe Thr Asp His
             20                  25                  30

Thr Ile His Trp Met Lys Gln Arg Pro Glu Gln Gly Leu Glu Trp Ile
         35                  40                  45

Gly Tyr Ile Tyr Pro Arg Asp Gly Ser Thr Lys Tyr Asn Glu Lys Phe
 50                  55                  60

Lys Gly Lys Ala Thr Leu Thr Ala Asp Lys Ser Ser Ser Thr Ala Tyr
 65                  70                  75                  80

Met Gln Leu Asn Ser Leu Thr Ser Glu Asp Ser Ala Val Tyr Phe Cys
                 85                  90                  95

Ala Arg Asp Tyr Gly Tyr Ala Phe Asp Tyr Trp Gly Gln Gly Thr Thr
            100                 105                 110

Leu Thr Val Ser Ser
        115
```

<210> SEQ ID NO 65
<211> LENGTH: 109
<212> TYPE: PRT
<213> ORGANISM: Artificial Sequence
<220> FEATURE:
<223> OTHER INFORMATION: Synthetic polymer.

<400> SEQUENCE: 65

```
Gln Ala Val Val Thr Gln Glu Ser Ala Leu Thr Thr Ser Pro Gly Gly
 1               5                   10                  15

Thr Val Ile Leu Thr Cys Arg Ser Ser Thr Gly Ala Val Thr Thr Ser
             20                  25                  30

Asn Tyr Ala Asn Trp Val Gln Glu Lys Pro Asp His Leu Phe Thr Gly
         35                  40                  45

Leu Ile Gly Gly Thr Ser Asn Arg Ala Pro Gly Val Pro Val Arg Phe
 50                  55                  60

Ser Gly Ser Leu Ile Gly Asp Lys Ala Ala Leu Thr Ile Thr Gly Ala
 65                  70                  75                  80

Gln Thr Glu Asp Asp Ala Met Tyr Phe Cys Ala Leu Trp Tyr Ser Thr
                 85                  90                  95

His Tyr Val Phe Gly Gly Gly Thr Lys Val Thr Val Leu
            100                 105
```

<210> SEQ ID NO 66
<211> LENGTH: 112
<212> TYPE: PRT
<213> ORGANISM: Artificial Sequence
<220> FEATURE:
<223> OTHER INFORMATION: Synthetic polymer.

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45

Ala Ser Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Thr Val Thr Val Ser Ser
            100                 105                 110

<210> SEQ ID NO 67
<211> LENGTH: 112
<212> TYPE: PRT
<213> ORGANISM: Artificial Sequence
<220> FEATURE:
<223> OTHER INFORMATION: Synthetic polymer.

<400> SEQUENCE: 67

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

<210> SEQ ID NO 68
<211> LENGTH: 10
<212> TYPE: PRT
<213> ORGANISM: Artificial Sequence
<220> FEATURE:
<223> OTHER INFORMATION: Synthetic polymer.

<400> SEQUENCE: 68

Gly Phe Thr Phe Ser Ser Tyr Gly Met Ser
1               5                   10

<210> SEQ ID NO 69
<211> LENGTH: 16
<212> TYPE: PRT
<213> ORGANISM: Artificial Sequence
<220> FEATURE:
<223> OTHER INFORMATION: Synthetic polymer.

<400> SEQUENCE: 69

```
Ser Ile Asn Ser Asn Gly Gly Ser Thr Tyr Tyr Pro Asp Ser Val Lys
1               5                   10                  15
```

<210> SEQ ID NO 70
<211> LENGTH: 3
<212> TYPE: PRT
<213> ORGANISM: Artificial Sequence
<220> FEATURE:
<223> OTHER INFORMATION: Synthetic polymer.

<400> SEQUENCE: 70

```
Gly Asp Tyr
1
```

<210> SEQ ID NO 71
<211> LENGTH: 16
<212> TYPE: PRT
<213> ORGANISM: Artificial Sequence
<220> FEATURE:
<223> OTHER INFORMATION: Synthetic polymer.

<400> SEQUENCE: 71

```
Arg Ser Ser Gln Ser Leu Val Tyr Ser Asn Gly Asp Thr Tyr Leu His
1               5                   10                  15
```

<210> SEQ ID NO 72
<211> LENGTH: 7
<212> TYPE: PRT
<213> ORGANISM: Artificial Sequence
<220> FEATURE:
<223> OTHER INFORMATION: Synthetic polymer.

<400> SEQUENCE: 72

```
Lys Val Ser Asn Arg Phe Ser
1               5
```

<210> SEQ ID NO 73
<211> LENGTH: 9
<212> TYPE: PRT
<213> ORGANISM: Artificial Sequence
<220> FEATURE:
<223> OTHER INFORMATION: Synthetic polymer.

<400> SEQUENCE: 73

```
Ser Gln Ser Thr His Val Pro Trp Thr
1               5
```

<210> SEQ ID NO 74
<211> LENGTH: 7
<212> TYPE: PRT
<213> ORGANISM: Artificial Sequence
<220> FEATURE:
<223> OTHER INFORMATION: Synthetic polymer.

<400> SEQUENCE: 74

```
Arg Val Ser Asn Arg Phe Ser
1               5
```

<210> SEQ ID NO 75
<211> LENGTH: 7
<212> TYPE: PRT
<213> ORGANISM: Artificial Sequence
<220> FEATURE:
<223> OTHER INFORMATION: Synthetic polymer.

<400> SEQUENCE: 75

Lys Val Ser Ser Arg Phe Ser
1               5

<210> SEQ ID NO 76
<211> LENGTH: 116
<212> TYPE: PRT
<213> ORGANISM: Artificial Sequence
<220> FEATURE:
<223> OTHER INFORMATION: Synthetic polymer.

<400> SEQUENCE: 76

Ser Asn Cys Ala Met Asp Val Phe Met Lys Gly Leu Ser Lys Ala Lys
1               5                   10                  15

Glu Gly Val Val Ala Ala Ala Glu Lys Thr Lys Gln Gly Val Ala Glu
            20                  25                  30

Ala Ala Gly Lys Thr Lys Glu Gly Val Leu Tyr Val Gly Ser Lys Thr
        35                  40                  45

Lys Glu Gly Val Val His Gly Val Ala Thr Val Ala Glu Lys Thr Lys
    50                  55                  60

Glu Gln Val Thr Asn Val Gly Gly Ala Val Val Thr Gly Val Thr Ala
65                  70                  75                  80

Val Ala Gln Lys Thr Val Glu Gly Ala Gly Ser Ile Ala Ala Ala Thr
                85                  90                  95

Gly Phe Val Lys Lys Asp Gln Leu Gly Lys Glu Gly Tyr Gln Asp Tyr
            100                 105                 110

Glu Pro Glu Ala
        115

<210> SEQ ID NO 77
<211> LENGTH: 36
<212> TYPE: PRT
<213> ORGANISM: Artificial Sequence
<220> FEATURE:
<223> OTHER INFORMATION: Synthetic polymer.

<400> SEQUENCE: 77

Lys Glu Gln Val Thr Asn Val Gly Gly Ala Val Val Thr Gly Val Thr
1               5                   10                  15

Ala Val Ala Gln Lys Thr Val Glu Gly Ala Gly Ser Ile Ala Ala Ala
            20                  25                  30

Thr Gly Phe Val
        35

<210> SEQ ID NO 78
<211> LENGTH: 758
<212> TYPE: PRT
<213> ORGANISM: Artificial Sequence
<220> FEATURE:
<223> OTHER INFORMATION: Synthetic polymer.

<400> SEQUENCE: 78

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ser Pro Leu
        35                  40                  45

Gln Thr Pro Thr Glu Asp Gly Ser Glu Pro Gly Ser Glu Thr Ser
    50                  55                  60

Asp Ala Lys Ser Thr Pro Thr Ala Glu Asp Val Thr Ala Pro Leu Val

-continued

```
            65                  70                  75                  80
Asp Glu Gly Ala Pro Gly Lys Gln Ala Ala Gln Pro His Thr Glu
                    85                  90                  95
Ile Pro Glu Gly Thr Thr Ala Glu Glu Ala Gly Ile Gly Asp Thr Pro
                    100                 105                 110
Ser Leu Glu Asp Glu Ala Ala Gly His Val Thr Gln Glu Pro Glu Ser
                    115                 120                 125
Gly Lys Val Val Gln Glu Gly Phe Leu Arg Glu Pro Gly Pro Pro Gly
                    130                 135                 140
Leu Ser His Gln Leu Met Ser Gly Met Pro Gly Ala Pro Leu Leu Pro
145                 150                 155                 160
Glu Gly Pro Arg Glu Ala Thr Arg Gln Pro Ser Gly Thr Gly Pro Glu
                    165                 170                 175
Asp Thr Glu Gly Gly Arg His Ala Pro Glu Leu Leu Lys His Gln Leu
                    180                 185                 190
Leu Gly Asp Leu His Gln Glu Gly Pro Pro Leu Lys Gly Ala Gly Gly
                    195                 200                 205
Lys Glu Arg Pro Gly Ser Lys Glu Val Asp Glu Arg Asp Val
210                 215                 220
Asp Glu Ser Ser Pro Gln Asp Ser Pro Ser Lys Ala Ser Pro Ala
225                 230                 235                 240
Gln Asp Gly Arg Pro Pro Gln Thr Ala Ala Arg Glu Ala Thr Ser Ile
                    245                 250                 255
Pro Gly Phe Pro Ala Glu Gly Ala Ile Pro Leu Pro Val Asp Phe Leu
                    260                 265                 270
Ser Lys Val Ser Thr Glu Ile Pro Ala Ser Glu Pro Asp Gly Pro Ser
                    275                 280                 285
Val Gly Arg Ala Lys Gly Gln Asp Ala Pro Leu Glu Phe Thr Phe His
                    290                 295                 300
Val Glu Ile Thr Pro Asn Val Gln Lys Glu Gln Ala His Ser Glu Glu
305                 310                 315                 320
His Leu Gly Arg Ala Ala Phe Pro Gly Ala Pro Gly Glu Gly Pro Glu
                    325                 330                 335
Ala Arg Gly Pro Ser Leu Gly Glu Asp Thr Lys Glu Ala Asp Leu Pro
                    340                 345                 350
Glu Pro Ser Glu Lys Gln Pro Ala Ala Ala Pro Arg Gly Lys Pro Val
                    355                 360                 365
Ser Arg Val Pro Gln Leu Lys Ala Arg Met Val Ser Lys Ser Lys Asp
                    370                 375                 380
Gly Thr Gly Ser Asp Asp Lys Lys Ala Lys Thr Ser Thr Arg Ser Ser
385                 390                 395                 400
Ala Lys Thr Leu Lys Asn Arg Pro Cys Leu Ser Pro Lys His Pro Thr
                    405                 410                 415
Pro Gly Ser Ser Asp Pro Leu Ile Gln Pro Ser Ser Pro Ala Val Cys
                    420                 425                 430
Pro Glu Pro Pro Ser Ser Pro Lys Tyr Val Ser Ser Val Thr Ser Arg
                    435                 440                 445
Thr Gly Ser Ser Gly Ala Lys Glu Met Lys Leu Lys Gly Ala Asp Gly
                    450                 455                 460
Lys Thr Lys Ile Ala Thr Pro Arg Gly Ala Ala Pro Pro Gly Gln Lys
465                 470                 475                 480
Gly Gln Ala Asn Ala Thr Arg Ile Pro Ala Lys Thr Pro Pro Ala Pro
                    485                 490                 495
```

Lys Thr Pro Pro Ser Ser Gly Glu Pro Pro Lys Ser Gly Asp Arg Ser
                500                 505                 510

Gly Tyr Ser Ser Pro Gly Ser Pro Gly Thr Pro Gly Ser Arg Ser Arg
            515                 520                 525

Thr Pro Ser Leu Pro Thr Pro Pro Thr Arg Glu Pro Lys Lys Val Ala
530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590

Gln Ile Ile Asn Lys Lys Leu Asp Leu Ser Asn Val Gln Ser Lys Cys
        595                 600                 605

Gly Ser Lys Asp Asn Ile Lys His Val Pro Gly Gly Gly Ser Val Gln
    610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gly Gln Val Glu Val
                645                 650                 655

Lys Ser Glu Lys Leu Asp Phe Lys Asp Arg Val Gln Ser Lys Ile Gly
            660                 665                 670

Ser Leu Asp Asn Ile Thr His Val Pro Gly Gly Gly Asn Lys Lys Ile
        675                 680                 685

Glu Thr His Lys Leu Thr Phe Arg Glu Asn Ala Lys Ala Lys Thr Asp
    690                 695                 700

His Gly Ala Glu Ile Val Tyr Lys Ser Pro Val Val Ser Gly Asp Thr
705                 710                 715                 720

Ser Pro Arg His Leu Ser Asn Val Ser Ser Thr Gly Ser Ile Asp Met
                725                 730                 735

Val Asp Ser Pro Gln Leu Ala Thr Leu Ala Asp Glu Val Ser Ala Ser
            740                 745                 750

Leu Ala Lys Gln Gly Leu
        755

<210> SEQ ID NO 79
<211> LENGTH: 31
<212> TYPE: PRT
<213> ORGANISM: Artificial Sequence
<220> FEATURE:
<223> OTHER INFORMATION: Synthetic polymer.

<400> SEQUENCE: 79

Val Ser Thr Glu Ile Pro Ala Ser Glu Pro Asp Gly Pro Ser Val Gly
1               5                   10                  15

Arg Ala Lys Gly Gln Asp Ala Pro Leu Glu Phe Thr Phe His Val
            20                  25                  30

<210> SEQ ID NO 80
<211> LENGTH: 31
<212> TYPE: PRT
<213> ORGANISM: Artificial Sequence
<220> FEATURE:
<223> OTHER INFORMATION: Synthetic polymer.

<400> SEQUENCE: 80

Glu Ile Thr Pro Asn Val Gln Lys Glu Gln Ala His Ser Glu Glu His

```
1               5                  10                 15
Leu Gly Arg Ala Ala Phe Pro Gly Ala Pro Gly Glu Gly Pro Glu
            20                 25                 30

<210> SEQ ID NO 81
<211> LENGTH: 89
<212> TYPE: PRT
<213> ORGANISM: Artificial Sequence
<220> FEATURE:
<223> OTHER INFORMATION: Synthetic polymer.

<400> SEQUENCE: 81

Met Gly Ile Leu Lys Leu Gln Val Phe Leu Ile Val Leu Ser Val Ala
1               5                   10                  15

Leu Asn His Leu Lys Ala Thr Pro Ile Glu Ser His Gln Val Glu Lys
            20                  25                  30

Arg Lys Cys Asn Thr Ala Thr Cys Ala Thr Gln Arg Leu Ala Asn Phe
        35                  40                  45

Leu Val His Ser Ser Asn Asn Phe Gly Ala Ile Leu Ser Ser Thr Asn
    50                  55                  60

Val Gly Ser Asn Thr Tyr Gly Lys Arg Asn Ala Val Glu Val Leu Lys
65                  70                  75                  80

Arg Glu Pro Leu Asn Tyr Leu Pro Leu
                85

<210> SEQ ID NO 82
<211> LENGTH: 37
<212> TYPE: PRT
<213> ORGANISM: Artificial Sequence
<220> FEATURE:
<223> OTHER INFORMATION: Synthetic polymer.

<400> SEQUENCE: 82

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 83
<211> LENGTH: 5021
<212> TYPE: DNA
<213> ORGANISM: Artificial Sequence
<220> FEATURE:
<223> OTHER INFORMATION: Synthetic polymer.

<400> SEQUENCE: 83
gcgatcgcgg ctcccgacat cttggaccat tagctccaca ggtatcttct tccctctagt      60
ggtcataaca gcagcttcag ctacctctca attcaaaaaa cccctcaaga cccgtttaga     120
ggccccaagg ggttatgcta tcaatcgttg cgttacacac acaaaaaacc aacacacatc     180
catcttcgat ggatagcgat tttattatct aactgctgat cgagtgtagc cagatctagt     240
aatcaattac ggggtcatta gttcatagcc catatatgga gttccgcgtt acataactta     300
cggtaaatgg cccgcctggc tgaccgccca acgacccccg cccattgacg tcaataatga     360
cgtatgttcc catagtaacg ccaataggga ctttccattg acgtcaatgg gtggagtatt     420
tacggtaaac tgcccacttg gcagtacatc aagtgtatca tatgccaagt acgcccccta     480
ttgacgtcaa tgacggtaaa tggcccgcct ggcattatgc ccagtacatg accttatggg     540
```

```
actttcctac ttggcagtac atctacgtat tagtcatcgc tattaccatg ctgatgcggt    600
tttggcagta catcaatggg cgtggatagc ggtttgactc acggggattt ccaagtctcc    660
accccattga cgtcaatggg agtttgtttt ggcaccaaaa tcaacgggac tttccaaaat    720
gtcgtaacaa ctccgcccca ttgacgcaaa tgggcggtag gcgtgtacgg tgggaggtct    780
atataagcag agctggttta gtgaaccgtc agatcagatc tttgtcgatc ctaccatcca    840
ctcgacacac ccgccagcag ccgctgccaa gcttccgagc tctcgaattc aaaggaggta    900
cccaccatgc cgctgctgct actgctgccc ctgctgtggg caggggcgct agctcaagtg    960
cagctgcaga gagcggagc cgaactggct agacccggag cctccgtgaa gctgagctgt   1020
aaggcctccg gctacacctt caccagctac ggcatcagct gggtgaggca aggaccggc   1080 caaggactgg aatggatcgg cgagatctac cctaggaggg gcaacaccta ctacaacgag   1140
aagttcaagg gcaaggccac actgacagcc tacaagtcca gcggcacagc ctacatggag   1200
ctgagatctc tgaccagcga ggatagcgcc gtgttctttt gcgccagagg cggcatctac   1260
tacggcaatc tgttcgacta ctggggccaa ggcaccacac tgaccgtctc gagcgctaag   1320
acgactccac cgtccgtgta cccgctcgcg ccaggttcgg ccgctcagac gaacagcatg   1380
gtgaccctcg gctgcctcgt gaagggttat ttcccagagc cggtgaccgt gacgtggaac   1440
tccggctcac tgtcatcggg cgtgcacact tttccagcag tgctgcagtc ggacctttac   1500
accctcagct cgtccgtcac cgtcccttca tcaacttggc ctagccagac cgtgacttgc   1560
aatgtcgccc accggcgtc cagcactaag gtggacaaga agatccacca ccatcaccat   1620
caccatcacc atcactagtg agcggccgcg tctagacctg cactgactga ctgatacaat   1680
cgatttctgg atccgcaggc ctctcctagc ttgactgact gagatacagc gtaccttcag   1740
ctcacagaca tgataagata cattgatgag tttggacaaa ccacaactag aatgcagtga   1800
aaaaaatgct ttatttgtga aatttgtgat gctattgctt tatttgtaac cattataagc   1860
tgcaataaac aagttaacaa caacaattgc attcatttta tgtttcaggt tcaggggagag   1920 gtgtgggagg ttttttaaag caagtaaaac ctctacaaat gtggtattgg cccatctcta   1980
tcggtatcgt agcataaccc cttggggcct ctaaacgggt cttgaggggt ttttgtgcc    2040 cctccggccg gattgctatc taccggcatt ggcgcagaaa aaaatgcctg atgcgacgct   2100
gcgcgtctta ctcccacata tgccagat tcagcaacgg atacggcttc cccaacttgc    2160
ccacttccat acgtgtcctc cttaccagaa atttatcctt aaggtcgtca gctatcctgc   2220
aggcgatctc tcgatttcga tcaagacatt ccttaatgg tcttttctgg acaccactag    2280
gggtcagaag tagttcatca aactttcttc cctccctaat ctcattggtt accttgggct   2340
atcgaaactt aattaaccag tcaagtcagc tacttggcga atcgacttg tctgggtttc    2400 gactacgctc agaattgcgt cagtcaagtt cgatctggtc cttgctattg cacccgttct   2460
ccgattacga gtttcattta aatcatgtga gcaaaaggcc agcaaaggc caggaaccgt    2520 aaaaaggccg cgttgctggc gttttccat aggctccgcc ccctgacga gcatcacaaa    2580 aatcgacgct caagtcagag gtggcgaaac ccgacaggac tataaagata ccaggcgttt   2640
ccccctggaa gctccctcgt gcgctctcct gttccgaccc tgccgcttac cggatacctg   2700
tccgcctttc tcccttcggg aagcgtggcg ctttctcata gctcacgctg taggtatctc   2760
agttcggtgt aggtcgttcg ctccaagctg ggctgtgtgc acgaaccccc cgttcagccc   2820
gaccgctgcg ccttatccgg taactatcgt cttgagtcca acccggtaag acacgactta   2880
```

| | |
|---|---|
| tcgccactgg cagcagccac tggtaacagg attagcagag cgaggtatgt aggcggtgct | 2940 |
| acagagttct tgaagtggtg gcctaactac ggctacacta aagaacagt atttggtatc | 3000 |
| tgcgctctgc tgaagccagt taccttcgga aaaagagttg gtagctcttg atccggcaaa | 3060 |
| caaaccaccg ctggtagcgg tggtttttt gtttgcaagc agcagattac gcgcagaaaa | 3120 |
| aaaggatctc aagaagatcc tttgatcttt tctacggggt ctgacgctca gtggaacgaa | 3180 |
| aactcacgtt aagggatttt ggtcatgaga ttatcaaaaa ggatcttcac ctagatcctt | 3240 |
| ttaaattaaa aatgaagttt taaatcaatc taaagtatat atgagtaaac ttggtctgac | 3300 |
| agttaccaat gcttaatcag tgaggcacct atctcagcga tctgtctatt tcgttcatcc | 3360 |
| atagttgcat ttaaatttcc gaactctcca aggccctcgt cggaaaatct tcaaaccttt | 3420 |
| cgtccgatcc atcttgcagg ctacctctcg aacgaactat cgcaagtctc ttggccggcc | 3480 |
| ttgcgccttg gctattgctt ggcagcgcct atcgccaggt attactccaa tcccgaatat | 3540 |
| ccgagatcgg gatcacccca gagaagttca acctacatcc tcaatcccga tctatccgag | 3600 |
| atccgaggaa tatcgaaatc ggggcgcgcc tggtgtaccg agaacgatcc tctcagtgcg | 3660 |
| agtctcgacg atccatatcg ttgcttggca gtcagccagt cggaatccag cttgggaccc | 3720 |
| aggaagtcca atcgtcagat attgtactca agcctggtca cggcagcgta ccgatctgtt | 3780 |
| taaacctaga tattgatagt ctgatcggtc aacgtataat cgagtcctag cttttgcaaa | 3840 |
| catctatcaa gagacaggat cagcaggagg ctttcgcatg agtattcaac atttccgtgt | 3900 |
| cgcccttatt ccctttttg cggcattttg ccttcctgtt tttgctcacc cagaaacgct | 3960 |
| ggtgaaagta aaagatgctg aagatcagtt gggtgcgcga gtgggttaca tcgaactgga | 4020 |
| tctcaacagc ggtaagatcc ttgagagttt tcgccccgaa gaacgctttc caatgatgag | 4080 |
| cacttttaaa gttctgctat gtggcgcggt attatcccgt attgacgccg ggcaagagca | 4140 |
| actcggtcgc cgcatacact attctcagaa tgacttggtt gagtattcac cagtcacaga | 4200 |
| aaagcatctt acggatggca tgacagtaag agaattatgc agtgctgcca taaccatgag | 4260 |
| tgataacact gcggccaact tacttctgac aacgattgga ggaccgaagg agctaaccgc | 4320 |
| ttttttgcac aacatggggg atcatgtaac tcgccttgat cgttgggaac cggagctgaa | 4380 |
| tgaagccata ccaaacgacg agcgtgacac cacgatgcct gtagcaatgg caacaacctt | 4440 |
| gcgtaaacta ttaactggcg aactacttac tctagcttcc cggcaacagt tgatagactg | 4500 |
| gatggaggcg gataaagttg caggaccact tctgcgctcg gcccttccgg ctggctggtt | 4560 |
| tattgctgat aaatctggag ccggtgagcg tgggtctcgc ggtatcattg cagcactggg | 4620 |
| gccagatggt aagccctccc gtatcgtagt tatctacacg acggggagtc aggcaactat | 4680 |
| ggatgaacga aatagacaga tcgctgagat aggtgcctca ctgattaagc attggtaacc | 4740 |
| gattctaggt gcattggcgc agaaaaaaat gcctgatgcg acgctgcgcg tcttatactc | 4800 |
| ccacatatgc cagattcagc aacggatacg gcttccccaa cttgcccact tccatacgtg | 4860 |
| tcctccttac cagaaattta tccttaagat cccgaatcgt ttaaactcga ctctggctct | 4920 |
| atcgaatctc cgtcgtttcg agcttacgcg aacagccgtg gcgctcattt gctcgtcggg | 4980 |
| catcgaatct cgtcagctat cgtcagctta ccttttttggc a | 5021 |

```
<210> SEQ ID NO 84
<211> LENGTH: 5708
<212> TYPE: DNA
<213> ORGANISM: Artificial Sequence
<220> FEATURE:
<223> OTHER INFORMATION: Synthetic polymer.
```

<400> SEQUENCE: 84

```
gcgatcgcgg ctcccgacat cttggaccat tagctccaca ggtatcttct tccctctagt      60
ggtcataaca gcagcttcag ctacctctca attcaaaaaa cccctcaaga cccgtttaga     120
ggccccaagg ggttatgcta tcaatcgttg cgttacacac acaaaaaacc aacacacatc     180
catcttcgat ggatagcgat tttattatct aactgctgat cgagtgtagc cagatctagt     240
aatcaattac ggggtcatta gttcatagcc catatatgga gttccgcgtt acataactta     300
cggtaaatgg cccgcctggc tgaccgccca acgaccccg cccattgacg tcaataatga      360
cgtatgttcc catagtaacg ccaataggga ctttccattg acgtcaatgg gtggagtatt     420
tacggtaaac tgcccacttg gcagtacatc aagtgtatca tatgccaagt acgcccccta     480
ttgacgtcaa tgacggtaaa tggcccgcct ggcattatgc ccagtacatg accttatggg     540
actttcctac ttggcagtac atctacgtat tagtcatcgc tattaccatg ctgatgcggt     600
tttggcagta catcaatggg cgtggatagc ggtttgactc acggggattt ccaagtctcc     660
accccattga cgtcaatggg agtttgtttt ggcaccaaaa tcaacgggac tttccaaaat     720
gtcgtaacaa ctccgcccca ttgacgcaaa tgggcggtag gcgtgtacgg tgggaggtct     780
atataagcag agctggttta gtgaaccgtc agatcagatc tttgtcgatc ctaccatcca     840
ctcgacacac cgccagcag ccgctgccaa gcttccgagc tctcgaattc aaaggaggta      900
cccaccatgc cgctgctgct actgctgccc ctgctgtggg caggggcgct agctcaagtg     960
cagctgcagc agagcggagc cgaactggct agacccggag cctccgtgaa gctgagctgt    1020
aaggcctccg gctacacctt caccagctac ggcatcagct gggtgaggca aaggaccggc    1080
caaggactgg aatggatcgg cgagatctac cctaggaggg gcaacaccta ctacaacgag    1140
aagttcaagg gcaaggccac actgacagcc tacaagtcca gcggcacagc ctacatggag    1200
ctgagatctc tgaccagcga ggatagcgcc gtgttctttt gcgccagagg cggcatctac    1260
tacggcaatc tgttcgacta ctggggccaa ggcaccacac tgaccgtctc gagcgccaaa    1320
accaccctc catccgtcta ccctctcgcc ccggctgcg gcgacaccac tggatcatcc      1380
gtgacttccg gatgcctggt caagggatac ttccgggagc cggtcactgt gacctggaac    1440
tccggttcac tgtcatcatc cgtccacacc tttccggccc tgctgcagtc gggcttgtac    1500
accatgagca gcagcgtgac cgtgccatcc tcgacctggc ctagccaaac cgtgacttgc    1560
tccgtggcac accctgcgtc gtccactact gtggacaaga agctggagcc gtccggacct    1620
atctccacca ttaacccctg cccgccctgc aaggaatgtc acaagtgtcc cgctcccaat    1680
cttgagggag ggcccagcgt gttcattttc cctcctaaca ttaaggatgt gctgatgatc    1740
tccctgactc ccaaagtgac atgcgtggtg gtggacgtgt cagaagatga cccggacgtc    1800
cagatcagct ggttcgtgaa caacgtggaa gtgcatacgg cgcagaccca gactcaccgc    1860
gaggactata acagcaccat cagggtcgtg tccaccctgc cgattcagca ccaggactgg    1920
atgtccggga aggagttcaa gtgcaaggtc aacaacaagg acctcccatc cccgatcgaa    1980
cggaccatct cgaagatcaa gggcctcgtg cgggcccctc aagtgtacac gctgccgcca    2040
ccggccgagc agctgtcgcg gaaggacgtg tcccttacct gtctcgtcgt gggttttaac    2100
cccggagata tttcggtgga gtggaccagc aacggccaca ccgaagagaa ctacaaggat    2160
accgcccgg tgctggactc cgacgggtcc tacttcatct actccaagct gaatatgaaa    2220
acctctaagt gggaaaagac tgatagcttc tcgtgcaacg tcagacatga aggcttgaag    2280
```

```
aactactacc tgaaaaagac tatctcccgc tcgcccggaa agtagtgagc ggccgcgtct    2340
agacctgcac tgactgactg atacaatcga tttctggatc cgcaggcctc tcctagcttg    2400
actgactgag atacagcgta ccttcagctc acagacatga taagatacat tgatgagttt    2460
ggacaaacca caactagaat gcagtgaaaa aaatgcttta tttgtgaaat tgtgatgct     2520 attgctttat ttgtaaccat tataagctgc aataaacaag ttaacaacaa caattgcatt    2580
cattttatgt ttcaggttca gggggaggtg tgggaggttt tttaaagcaa gtaaaacctc    2640
tacaaatgtg gtattggccc atctctatcg gtatcgtagc ataacccctt ggggcctcta    2700
aacgggtctt gaggggtttt ttgtgcccct ccggccggat tgctatctac cggcattggc    2760
gcagaaaaaa atgcctgatg cgacgctgcg cgtcttatac tcccacatat gccagattca    2820
gcaacggata cggcttcccc aacttgccca cttccatacg tgtcctcctt accagaaatt    2880
tatccttaag gtcgtcagct atcctgcagg cgatctctcg atttcgatca agacattcct    2940
ttaatggtct tttctggaca ccactagggg tcagaagtag ttcatcaaac tttcttccct    3000
ccctaatctc attggttacc ttgggctatc gaaacttaat taaccagtca agtcagctac    3060
ttggcgagat cgacttgtct gggtttcgac tacgctcaga attgcgtcag tcaagttcga    3120
tctggtcctt gctattgcac ccgttctccg attacgagtt tcatttaaat catgtgagca    3180
aaaggccagc aaaaggccag gaaccgtaaa aaggccgcgt tgctggcgtt tttccatagg    3240
ctccgccccc ctgacgagca tcacaaaaat cgacgctcaa gtcagaggtg gcgaaacccg    3300
acaggactat aaagatacca ggcgtttccc cctggaagct ccctcgtgcg ctctcctgtt    3360
ccgaccctgc cgcttaccgg atacctgtcc gcctttctcc cttcgggaag cgtggcgctt    3420
tctcatagct cacgctgtag gtatctcagt tcggtgtagg tcgttcgctc caagctgggc    3480
tgtgtgcacg aaccccccgt tcagcccgac cgctgcgcct tatccggtaa ctatcgtctt    3540
gagtccaacc cggtaagaca cgacttatcg ccactggcag cagccactgg taacaggatt    3600
agcagagcga ggtatgtagg cggtgctaca gagttcttga agtggtggcc taactacggc    3660
tacactagaa gaacagtatt tggtatctgc gctctgctga gccagttacc ttcggaaaa    3720 agagttggta gctcttgatc cggcaaacaa accaccgctg gtagcggtgg ttttttgtt    3780 tgcaagcagc agattacgcg cagaaaaaaa ggatctcaag aagatccttt gatcttttct    3840
acggggtctg acgctcagtg gaacgaaaac tcacgttaag ggattttggt catgagatta    3900
tcaaaaagga tcttcaccta gatccttta aattaaaaat gaagttttaa atcaatctaa    3960
agtatatatg agtaaacttg gtctgacagt taccaatgct taatcagtga ggcacctatc    4020
tcagcgatct gtctatttcg ttcatccata gttgcattta aatttccgaa ctctccaagg    4080
ccctcgtcgg aaaatcttca aacctttcgt ccgatccatc ttgcaggcta cctctcgaac    4140
gaactatcgc aagtctcttg gccggccttg cgccttggct attgcttggc agcgcctatc    4200
gccaggtatt actccaatcc cgaatatccg agatcgggat caccccagag aagttcaacc    4260
tacatcctca atcccgatct atccgagatc cgaggaatat cgaaatcggg gcgcgcctgg    4320
tgtaccgaga acgatcctct cagtgcgagt ctcgacgatc catatcgttg cttggcagtc    4380
agccagtcga atccagcttt gggacccagg aagtccaatc gtcagatatt gtactcaagc    4440
ctggtcacgg cagcgtaccg atctgtttaa acctagatat tgatagtctg atcggtcaac    4500
gtataatcga gtcctagctt ttgcaaacat ctatcaagag acaggatcag caggaggctt    4560
tcgcatgagt attcaacatt tccgtgtcgc ccttattccc ttttttgcgg cattttgcct    4620
tcctgttttt gctcacccag aaacgctggt gaaagtaaaa gatgctgaag atcagttggg    4680
```

```
tgcgcgagtg ggttacatcg aactggatct caacagcggt aagatccttg agagttttcg   4740
ccccgaagaa cgctttccaa tgatgagcac ttttaaagtt ctgctatgtg gcgcggtatt   4800
atcccgtatt gacgccgggc aagagcaact cggtcgccgc atacactatt ctcagaatga   4860
cttggttgag tattcaccag tcacagaaaa gcatcttacg gatggcatga cagtaagaga   4920
attatgcagt gctgccataa ccatgagtga taacactgcg gccaacttac ttctgacaac   4980
gattggagga ccgaaggagc taaccgcttt tttgcacaac atgggggatc atgtaactcg   5040
ccttgatcgt tgggaaccgg agctgaatga agccatacca aacgacgagc gtgacaccac   5100
gatgcctgta gcaatggcaa caaccttgcg taaactatta actggcgaac tacttactct   5160
agcttcccgg caacagttga tagactggat ggaggcggat aaagttgcag gaccacttct   5220
gcgctcggcc cttccggctg ctggtttat tgctgataaa tctggagccg tgagcgtgg    5280 gtctcgcggt atcattgcag cactggggcc agatggtaag ccctcccgta tcgtagttat   5340
ctacacgacg gggagtcagg caactatgga tgaacgaaat agacagatcg ctgagatagg   5400
tgcctcactg attaagcatt ggtaaccgat tctaggtgca ttggcgcaga aaaaaatgcc   5460
tgatgcgacg ctgcgcgtct tatactccca catatgccag attcagcaac ggatacggct   5520
tccccaactt gcccacttcc atacgtgtcc tccttaccag aaatttatcc ttaagatccc   5580
gaatcgttta aactcgactc tggctctatc gaatctccgt cgtttcgagc ttacgcgaac   5640
agccgtggcg ctcatttgct cgtcgggcat cgaatctcgt cagctatcgt cagcttacct   5700
ttttggca                                                            5708
```

<210> SEQ ID NO 85
<211> LENGTH: 4985
<212> TYPE: DNA
<213> ORGANISM: Artificial Sequence
<220> FEATURE:
<223> OTHER INFORMATION: Synthetic polymer.

<400> SEQUENCE: 85

```
gcgatcgcgg ctcccgacat cttggaccat tagctccaca ggtatcttct tccctctagt     60
ggtcataaca gcagcttcag ctacctctca attcaaaaaa cccctcaaga cccgtttaga    120
ggccccaagg ggttatgcta tcaatcgttg cgttacacac acaaaaaacc aacacacatc    180
catcttcgat ggatagcgat tttattatct aactgctgat cgagtgtagc cagatctagt    240
aatcaattac ggggtcatta gttcatagcc catatatgga gttccgcgtt acataactta    300
cggtaaatgg cccgcctggc tgaccgccca acgaccccg cccattgacg tcaataatga    360
cgtatgttcc catagtaacg ccaatagggac ctttccattg acgtcaatgg gtggagtatt    420
tacggtaaac tgcccacttg gcagtacatc aagtgtatca tatgccaagt acgcccccta    480
ttgacgtcaa tgacggtaaa tggcccgcct ggcattatgc ccagtacatg accttatggg    540
actttcctac ttggcagtac atctacgtat tagtcatcgc tattaccatg ctgatgcggt    600
tttggcagta catcaatggg cgtggatagc ggtttgactc acggggattt ccaagtctcc    660
accccattga cgtcaatggg agtttgtttt ggcaccaaaa tcaacgggac tttccaaaat    720
gtcgtaacaa ctccgcccca ttgacgcaaa tgggcggtag gcgtgtacgg tgggaggtct    780
atataagcag agctggttta gtgaaccgtc agatcagatc tttgtcgatc ctaccatcca    840
ctcgacacac cgccagcag ccgctgccaa gcttccgagc tctcgaattc aaaggaggta    900
cccaccatgc cgctgctgct actgctgccc ctgctgtggg cagggcgct agctcaagcc    960
```

-continued

```
gtggtgaccc aagagtccgc tctgacaaca agccccggcg agacagtgac actgacatgt    1020
agaagcagca ccggagccgt gaccaccagc aactacgcca actgggtgca agagaagccc    1080
gaccatctgt ttaccggact gatcggaggc accaataaca gagcccccgg cgtgcccgcc    1140
agatttagcg gctctctgat tggcgacaag gctgctctga ccatcaccgg agcccagacc    1200
gaggacgagg ccatctactt ctgcgctctg tggttcagca accactgggt gtttggcggc    1260
ggcaccaaac tgaccgtgct cgggcagcct aaaagctcgc cgtccgtgac cctctttcca    1320
ccatcatcgg aagagctgga aaccaacaag gctactctcg tctgcaccat cacggatttc    1380
taccccggag tggtcaccgt ggactggaaa gtggacggga ctccggtgac tcagggaatg    1440
gaaacgaccc aaccgtcaaa gcagtcgaac aataagtaca tggcctccag ctacctgacc    1500
ttgaccgcca gagcgtggga gcggcacagc tcctactcat gtcaagtcac tcacgaaggc    1560
catactgtgg agaagagcct gtcccgcgca gattgctcgt agtgagcggc cgcgtctaga    1620
cctgcactga ctgactgata caatcgattt ctggatccgc aggcctctcc tagcttgact    1680
gactgagata cagcgtacct tcagctcaca gacatgataa gatacattga tgagtttgga    1740
caaaccacaa ctagaatgca gtgaaaaaaa tgctttattt gtgaaatttg tgatgctatt    1800
gctttatttg taaccattat aagctgcaat aaacaagtta acaacaacaa ttgcattcat    1860
tttatgtttc aggttcaggg ggaggtgtgg gaggttttt aaagcaagta aaacctctac    1920
aaatgtggta ttggcccatc tctatcggta tcgtagcata ccccttgggg cctctaaac    1980
gggtcttgag gggttttttg tgcccctccg ccggattgc tatctaccgg cattggcgca    2040
gaaaaaatg cctgatgcga cgctgcgcgt cttatactcc cacatatgcc agattcagca    2100
acggatacgg cttccccaac ttgcccactt ccatcgtgt cctccttacc agaaatttat    2160
ccttaaggtc gtcagctatc ctgcaggcga tctctcgatt tcgatcaaga cattcccttta    2220
atggtctttt ctggacacca ctaggggtca gaagtagttc atcaaacttt cttccctccc    2280
taatctcatt ggttaccttg ggctatcgaa acttaattaa ccagtcaagt cagctacttg    2340
gcgagatcga cttgtctggg tttcgactac gctcagaatt gcgtcagtca agttcgatct    2400
ggtccttgct attgcacccg ttctccgatt acgagtttca tttaaatcat gtgagcaaaa    2460
ggccagcaaa aggccaggaa ccgtaaaaag gccgcgttgc tggcgttttt ccataggctc    2520
cgcccccctg acgagcatca caaaaatcga cgctcaagtc agaggtggcg aaacccgaca    2580
ggactataaa gataccaggc gtttccccct ggaagctccc tcgtgcgctc tcctgttccg    2640
accctgccgc ttaccggata cctgtccgcc tttctccctt cgggaagcgt ggcgctttct    2700
catagctcac gctgtaggta tctcagttcg gtgtaggtcg ttcgctccaa gctgggctgt    2760
gtgcacgaac cccccgttca gcccgaccgc tgcgccttat ccggtaacta tcgtcttgag    2820
tccaacccgg taagacacga cttatcgcca ctggcagcag ccactggtaa caggattagc    2880
agagcgaggt atgtaggcgg tgctacagag ttcttgaagt ggtggcctaa ctacggctac    2940
actagaagaa cagtatttgg tatctgcgct ctgctgaagc cagttacctt cggaaaaaga    3000
gttggtagct cttgatccgg caaacaaacc accgctggta gcggtggttt ttttgtttgc    3060
aagcagcaga ttacgcgcag aaaaaaagga tctcaagaag atcctttgat cttttctacg    3120
gggtctgacg ctcagtggaa cgaaaactca cgttaaggga ttttggtcat gagattatca    3180
aaaaggatct tcacctagat ccttttaaat taaaaatgaa gttttaaatc aatctaaagt    3240
atatatgagt aaacttggtc tgacagttac caatgcttaa tcagtgaggc acctatctca    3300
gcgatctgtc tatttcgttc atccatagtt gcatttaaat ttccgaactc tccaaggccc    3360
```

```
tcgtcggaaa atcttcaaac ctttcgtccg atccatcttg caggctacct ctcgaacgaa    3420
ctatcgcaag tctcttggcc ggccttgcgc cttggctatt gcttggcagc gcctatcgcc    3480
aggtattact ccaatcccga atatccgaga tcgggatcac cccagagaag ttcaacctac    3540
atcctcaatc ccgatctatc cgagatccga ggaatatcga atcggggcg cgcctggtgt     3600 accgagaacg atcctctcag tgcgagtctc gacgatccat atcgttgctt ggcagtcagc    3660
cagtcggaat ccagcttggg acccaggaag tccaatcgtc agatattgta ctcaagcctg    3720
gtcacggcag cgtaccgatc tgtttaaacc tagatattga tagtctgatc ggtcaacgta    3780
taatcgagtc ctagcttttg caaacatcta tcaagagaca ggatcagcag gaggctttcg    3840
catgagtatt caacatttcc gtgtcgccct tattcccttt tttgcggcat tttgccttcc    3900 tgttttgct cacccagaaa cgctggtgaa agtaaaagat gctgaagatc agttgggtgc     3960
gcgagtgggt tacatcgaac tggatctcaa cagcggtaag atccttgaga gttttcgccc    4020
cgaagaacgc tttccaatga tgagcacttt taaagttctg ctatgtggcg cggtattatc    4080
ccgtattgac gccgggcaag agcaactcgg tcgccgcata cactattctc agaatgactt    4140
ggttgagtat tcaccagtca cagaaaagca tcttacggat ggcatgacag taagagaatt    4200
atgcagtgct gccataacca tgagtgataa cactgcggcc aacttacttc tgacaacgat    4260
tggaggaccg aaggagctaa ccgcttttttt gcacaacatg ggggatcatg taactcgcct    4320
tgatcgttgg gaaccggagc tgaatgaagc cataccaaac gacgagcgtg acaccacgat    4380
gcctgtagca atggcaacaa ccttgcgtaa actattaact ggcgaactac ttactctagc    4440
ttcccggcaa cagttgatag actggatgga ggcggataaa gttgcaggac cacttctgcg    4500
ctcggccctt ccggctggct ggtttattgc tgataaatct ggagccggtg agcgtgggtc    4560
tcgcggtatc attgcagcac tggggccaga tggtaagccc tcccgtatcg tagttatcta    4620
cacgacgggg agtcaggcaa ctatggatga acgaaataga cagatcgctg agataggtgc    4680
ctcactgatt aagcattggt aaccgattct aggtgcattg gcgcagaaaa aaatgcctga    4740
tgcgacgctg cgcgtcttat actcccacat atgccagatt cagcaacgga tacggcttcc    4800
ccaacttgcc cacttccata cgtgtcctcc ttaccagaaa tttatcctta agatcccgaa    4860
tcgtttaaac tcgactctgg ctctatcgaa tctccgtcgt ttcgagctta cgcgaacagc    4920
cgtggcgctc atttgctcgt cgggcatcga atctcgtcag ctatcgtcag cttacctttt    4980
tggca                                                                4985
```

<210> SEQ ID NO 86
<211> LENGTH: 8377
<212> TYPE: DNA
<213> ORGANISM: Artificial Sequence
<220> FEATURE:
<223> OTHER INFORMATION: Synthetic polymer.

<400> SEQUENCE: 86

```
gcgatcgcgg ctcccgacat cttggaccat tagctccaca ggtatcttct tccctctagt      60
ggtcataaca gcagcttcag ctacctctca attcaaaaaa cccctcaaga cccgtttaga     120
ggccccaagg ggttatgcta tcaatcgttg cgttacacac acaaaaaacc aacacacatc     180
catcttcgat ggatagcgat tttattatct aactgctgat cgagtgtagc cagatctata     240
gtaatcaatt acgggtcat tagttcatag cccatatatg gagttccgcg ttacataact      300
tacggtaaat ggcccgcctg gctgaccgcc caacgacccc cgcccattga cgtcaataat     360
```

```
gacgtatgtt cccatagtaa cgccaatagg gactttccat tgacgtcaat gggtggacta    420
tttacggtaa actgcccact tggcagtaca tcaagtgtat catatgccaa gtacgccccc    480
tattgacgtc aatgacggta aatggcccgc ctggcattat gcccagtaca tgaccttatg    540
ggactttcct acttggcagt acatctacgt attagtcatc gctattacca tcgtcgaggt    600
tgagccccac gttctgcttc actctcccca tctccccccc ctccccaccc caattttgt     660 atttatttat tttttaatta ttttatgcag cgatggggc ggggggggg gggcgcgcg       720 ccaggcgggg cggggcgggg cgaggggcgg ggcggggcga ggcggagagg tgcggcggca    780
gccaatcaga gcggcgcgct ccgaaagttt cctttatgg cgaggcggcg gcggcggcgg    840
ccctataaaa agcgaagcgc gcggcgggcg ggagtcgctg cgttgccttc gccccgtgcc    900
ccgctccgcg ccgcctcgcg ccgcccgccc cggctctgac tgaccgcgtt actcccacag    960
gtgagcgggc gggacggccc ttctccctcc gggctgtaat tagcgcttgg tttaatgacg   1020
gctcgtttct tttctgtggc tgcgtgaaag ccttaaaggg ctccggagg gcctttgtgc    1080 ggggggggagc ggctcggggg gtgcgtgcgt gtgtgtgtgc gtggggagcg ccgcgtgcgg   1140
cccgcgctgc ccggcggctg tgagcgctgc gggcgcggcg cggggctttg tgcgctccgc   1200
gtgtgcgcga ggggagcgcg ggccggggc ggtgccccgc ggtgcggggg ggctgcgagg    1260
ggaacaaagg ctgcgtgcgg ggtgtgtgcg tgggggggtg agcaggggt gtgggcgcgg    1320 cggtcgggct gtaaccccc cctggcaccc ccctccccga gttgctgagc acggcccggc    1380
ttcgggtgcg gggctccgtg cggggcgtgg cgcggggctc gccgtgccgg gcggggggtg    1440
gcggcaggtg ggggtgccgg gcggggcggg gccgcctcgg gccggggagg gctcggggga   1500
ggggcgcggc ggccccggag cgccggcggc tgtcgaggcg cggcgagccg cagccattgc    1560
cttttatggt aatcgtgcga gagggcgcag ggacttcctt tgtcccaaat ctggcggagc   1620
cgaaatctgg gaggcgccgc cgcaccccct ctagcgggcg cgggcgaagc ggtgcggcgc    1680
cggcaggaag gaaatgggcg gggagggcct tcgtgcgtcg ccgcgccgcc gtccccttct    1740
ccatctccag cctcggggct gccgcagggg gacggctgcc ttcgggggg acgggcagg    1800 gcggggttcg gcttctggcg tgtgaccggc ggctttagag cctctgctaa ccatgttcat    1860
gccttcttct ttttcctaca gctcctgggc aacgtgctgg ttgttgtgct gtctcatcat    1920
tttggcaaag atctttgtcg atcctaccat ccactcgaca cacccgccag cggccgctgc    1980
caagcttccg agctctcgaa ttcaggaggt acccaccatg ggttggagcc tcatcttgct    2040
cttccttgtc gctgttgcta cgcgtgtcca ctcccaagtg cagctgcagc agagcggagc    2100
cgaactggct agacccggag cctccgtgaa gctgagctgt aaggcctccg gctacacctt    2160
caccagctac ggcatcagct gggtgaggca aggaccggc caaggactgg aatggatcgg    2220
cgagatctac cctaggaggg gcaacaccta ctacaacgag aagttcaagg gcaaggccac    2280
actgacagcc tacaagtcca gcggcacagc ctacatggag ctgagatctc tgaccagcga    2340
ggatagcgcc gtgttcttt gcgccagagg cggcatctac tacggcaatc tgttcgacta    2400
ctggggccaa ggcaccacac tgaccgtctc gagcgctaag acgactccac cgtccgtgta    2460
cccgctcgcg ccaggttcgg ccgctcagac gaacagcatg gtgaccctcg gctgcctcgt    2520
gaagggttat tcccagagc cggtgaccgt gacgtggaac tccggctcac tgtcatcggg    2580
cgtgcacact tttccagcag tgctgcagtc ggacctttac accctcagct cgtccgtcac    2640
cgtcccttca tcaacttggc ctagccagac cgtgacttgc aatgtcgccc acccggcgtc    2700
cagcactaag gtggacaaga agatccacca ccatcaccat caccatcacc atcactagag    2760
```

```
agcggccgcg tctagacctg cactgactga ctgatacgct agcttgactg actgagatac    2820
agcgtacctt cagctcacag acatgataag atacattgat gagtttggac aaaccacaac    2880
tagaatgcag tgaaaaaaat gctttatttg tgaaatttgt gatgctattg ctttatttgt    2940
aaccattata agctgcaata aacaagttaa caacaacaat tgcattcatt ttatgtttca    3000
ggttcagggg gaggtgtggg aggtttttta aagcaagtaa aacctctaca aatgtggtat    3060
tggcccatct ctatcggtat cgtagcataa ccccttgggg cctctaaacg ggtcttgagg    3120
ggttttttgt gcccctcggg ccggattgct atctaccggc attggcgcag aaaaaaatgc    3180
ctgatgcgac gctgcgcgtc ttatactccc acatatgcca gattcagcaa cggatacggc    3240
ttccccaact tgcccacttc catacgtgtc ctccttacca gaaatttatc cttaaggtcg    3300
tcagctatcc tgcaggcgat ctctcgattt cgatcaagac attcctttaa tggtcttttc    3360
tggacaccac taggggtcag aagtagttca tcaaactttc ttccctccct aatctcattg    3420
gttaccttgg gctatcgaaa cttaattaac cagtcaagtc agctacttgg cgagatcgac    3480
ttgtctgggt ttcgactacg ctcagaattg cgtcagtcaa gttcgatctg gtccttgcta    3540
ttgcacccgt tctccgatta cgagtttcat ttaaatcatg tgagcaaaag gccagcaaaa    3600
ggccaggaac cgtaaaaagg ccgcgttgct ggcgttttc cataggctcc gcccccctga    3660
cgagcatcac aaaaatcgac gctcaagtca gaggtggcga aacccgacag gactataaag    3720
ataccaggcg tttccccctg gaagctccct cgtgcgctct cctgttccga ccctgccgct    3780
taccggatac ctgtccgcct ttctcccttc gggaagcgtg cgctttctc atagctcacg    3840
ctgtaggtat ctcagttcgg tgtaggtcgt tcgctccaag ctgggctgtg tgcacgaacc    3900
ccccgttcag cccgaccgct gcgccttatc cggtaactat cgtcttgagt ccaacccggt    3960
aagacacgac ttatcgccac tggcagcagc cactggtaac aggattagca gagcgaggta    4020
tgtaggcggt gctacagagt tcttgaagtg gtggcctaac tacggctaca ctagaagaac    4080
agtatttggt atctgcgctc tgctgaagcc agttaccttc ggaaaaagag ttggtagctc    4140
ttgatccggc aaacaaacca ccgctggtag cggtggtttt tttgtttgca agcagcagat    4200
tacgcgcaga aaaaaaggat ctcaagaaga tcctttgatc ttttctacgg ggtctgacgc    4260
tcagtggaac gaaaactcac gttaagggat tttggtcatg agattatcaa aaaggatctt    4320
cacctagatc cttttaaatt aaaaatgaag ttttaaatca atctaaagta tatatgagta    4380
aacttggtct gacagttacc aatgcttaat cagtgaggca cctatctcag cgatctgtct    4440
atttcgttca tccatagttg catttaaatt tccgaactct ccaaggccct cgtcggaaaa    4500
tcttcaaacc tttcgtccga tccatcttgc aggctacctc tcgaacgaac tatcgcaagt    4560
ctcttggccg gccttgcgcc ttggctattg cttggcagcg cctatcgcca ggtattactc    4620
caatcccgaa tatccgagat cgggatcacc cgagagaagt tcaacctaca tcctcaatcc    4680
cgatctatcc gagatccgag gaatatcgaa atcgggcgc gcctggcctc cgcgccgggt    4740
tttggcgcct cccgcgggcg ccccctcgt cacggcgagc gctgccacgt cagacgaagg    4800
gcgcaggagc gtcctgatcc ttccgcccgg acgctcagga cagcggcccg ctgctcataa    4860
gactcggcct tagaacccca gtatcagcag aaggacattt taggacggga cttgggtgac    4920
tctagggcac tggttttctt tccagagagc ggaacaggcg aggaaaagta gtcccttctc    4980
ggcgattctg cggagggatc tccgtggggc ggtgaacgcc gatgattata taaggacgcg    5040
ccgggtgtgg cacagctagt tccgtcgcag ccgggatttg ggtcgcggtt cttgtttgtg    5100
```

```
gatcgctgtg atcgtcactt ggtgagtagc gggctgctgg gctggccggg gctttcgtgg    5160
ccgccgggcc gctcggtggg acggaagcgt gtggagagac cgccaagggc tgtagtctgg    5220
gtccgcgagc aaggttgccc tgaactgggg gttgggggga gcgcagcaaa atggcggctg    5280
ttcccgagtc ttgaatggaa acgcttgtg aggcgggctg tgaggtcgtt gaaacaaggt     5340 gggggcatg gtgggcggca agaacccaag gtcttgagcc cttcgctaat gcgggaaagc     5400
tcttattcgg gtgagatggg ctgggcacca tctggggacc ctgacgtgaa gtttgtcact    5460
gactggagaa ctcggtttgt cgtctgttgc ggggcggca gttatggcgg tgccgttggg     5520
cagtgcaccc gtacctttgg gagcgcgcgc cctcgtcgtg tcgtgacgtc acccgttctg    5580
ttggcttata atgcagggtg gggccacctg ccggtaggtg tgcggtaggc ttttctccgt    5640
cgcaggacgc agggttcggg cctagggtag gctctcctga atcgacaggc gccggacctc    5700
tggtgagggg agggataagt gaggcgtcag tttctttggt cggttttatg tacctatctt    5760
cttaagtagc tgaagctccg gttttgaact atgcgctcgg ggttggcgag tgtgttttgt    5820 gaagttttt aggcaccttt tgaaatgtaa tcatttgggt caatatgtaa ttttcagtgt     5880
tagacttgta aattgtccgc taaattctgg ccgttttggg cttttttgtt agacaacatg    5940
ggtaaaaagc ctgaactcac cgcgacgtct gtcgagaagt ttctgatcga aaagttcgac    6000
agcgtctccg acctgatgca gctctcggag ggcgaagaat ctcgtgcttt cagcttcgat    6060
gtaggagggc gtggatatgt cctgcgggta aatagctgcg ccgatggttt ctacaaagat    6120
cgttatgttt atcggcactt tgcatccgcc gcgctcccga ttccggaagt gcttgacatt    6180
ggggagttca gcgagagcct gacctattgc atctcccgcc gtgcacaggg tgtcacgttg    6240
caagacctgc ctgaaaccga actgcccgct gttctgcagc cggtcgcgga ggcaatggat    6300
gccatcgctg ccgccgatct tagccagacg agcgggttcg gcccattcgg accgcaagga    6360
atcggtcaat acactacatg gcgtgatttc atatgcgcga ttgctgatcc ccatgtgtat    6420
cactggcaaa ctgtgatgga cgacaccgtc agtgcgtccg tcgcgcaggc tctcgatgag    6480
ctgatgcttt gggccgagga ctgccccgaa gtccggcacc tcgtgcacgc ggatttcggc    6540
tccaacaatg tcctgacgga caatggccgc ataacagcgg tcattgactg agcgaggcg    6600 atgttcgggg attcccaata cgaggtcgcc aacatcttct tctggaggcc gtggttggct    6660
tgtatggagc agcagacgcg ctacttcgag cggaggcatc cggagcttgc aggatcgccc    6720
cggctccggg cgtatatgct ccgcattggt cttgaccaac tctatcagag cttggttgac    6780
ggcaatttcg atgatgcagc ttgggcgcag ggtcgatgcg acgcaatcgt ccgatccgga    6840
gccgggactg tcgggcgtac acaaatcgcc cgcagaagcg ccgccgtctg gaccgatggc    6900
tgtgtagaag tactcgccga tagtggaaac cgacgcccca gcactcgtcc gagggcaaag    6960
gaataagcta gtatgtaagc ctagtcttag ataataaaat cgctatccat cgaagatgga    7020
tgtgtgttgg tttttttgtgt gtgtaacgct aggcgcgcct ggtgtaccga gaacgatcct    7080
ctcagtgcga gtctcgacga tccatatcgt tgcttggcag tcagccagtc ggaatccagc    7140
ttgggaccca ggaagtccaa tcgtcagata ttgtactcaa gcctggtcac ggcagcgtac    7200
cgatctgttt aaacctagat attgatagtc tgatcggtca acgtataatc gagtcctagc    7260
ttttgcaaac atctatcaag agacaggatc agcaggaggc tttcgcatga ttgaacaaga    7320
tggattgcac gcaggttctc cggccggctt ggtggagagg ctattcggct atgactgggc    7380
acaacagaca atcggctgct ctgatgccgc cgtgttccgg ctgtcagcgc aggggcgtcc    7440
ggttcttttt gtcaagaccg acctgtccgg tgccctgaat gaactgcaag acgaggcagc    7500
```

```
gcggctatcg tggctggcga cgacgggcgt tccttgcgcg gctgtgctcg acgttgtcac    7560
tgaagcggga agggactggc tgctattggg cgaagtgccg gggcaggatc tcctgtcatc    7620
tcaccttgct cctgccgaga agtatccat catggctgat gcaatgcggc ggctgcatac     7680
gcttgatccg gctacctgcc cattcgacca ccaagcgaaa catcgcatcg agcgagcacg    7740
tactcggatg gaagccggtc ttgtcgatca ggatgatctg gacgaagagc atcaggggct    7800
cgcgccagcc gaactgttcg ccaggctcaa ggcgtctatg cccgacggcg aggatctcgt    7860
cgtgacccac ggcgatgcct gcttgccgaa tatcatggtg gaaaatggcc gcttttctgg    7920
attcatcgac tgtggccgtc tgggtgtggc ggaccgctat caggacatag cgttggctac    7980
ccgtgatatt gctgaagagc ttggcggcga atgggctgac cgcttccttg tgctttacgg    8040
tatcgccgcg cccgattcgc agcgcatcgc cttctatcgc cttcttgacg agttcttctg    8100
accgattcta ggtgcattgg cgcagaaaaa aatgcctgat gcgacgctgc gcgtcttata    8160
ctcccacata tgccagattc agcaacggat acggcttccc caacttgccc acttccatac    8220
gtgtcctcct taccagaaat ttatccttaa ggtcgtttaa actcgactct ggctctatcg    8280
aatctccgtc gtttcgagct tacgcgaaca gccgtggcgc tcatttgctc gtcgggcatc    8340
gaatctcgtc agctatcgtc agcttacctt tttggca                             8377

<210> SEQ ID NO 87
<211> LENGTH: 8371
<212> TYPE: DNA
<213> ORGANISM: Artificial Sequence
<220> FEATURE:
<223> OTHER INFORMATION: Synthetic polymer.

<400> SEQUENCE: 87
gcgatcgcgg ctcccgacat cttggaccat tagctccaca ggtatcttct tccctctagt      60
ggtcataaca gcagcttcag ctacctctca attcaaaaaa cccctcaaga cccgtttaga     120 gccccaagg ggttatgcta tcaatcgttg cgttacacac acaaaaaacc aacacacatc      180
catcttcgat ggatagcgat tttattatct aactgctgat cgagtgtagc cagatctata     240
gtaatcaatt acggggtcat tagttcatag cccatatatg gagttccgcg ttacataact     300
tacggtaaat ggcccgcctg gctgaccgcc caacgacccc cgcccattga cgtcaataat     360
gacgtatgtt cccatagtaa cgccaatagg actttccat tgacgtcaat gggtggacta      420
tttacggtaa actgcccact tggcagtaca tcaagtgtat catatgccaa gtacgccccc     480
tattgacgtc aatgacggta aatggcccgc ctggcattat gcccagtaca tgaccttatg     540
ggactttcct acttggcagt acatctacgt attagtcatc gctattacca tgcgtcgagg     600
tgagccccac gttctgcttc actctcccca tctcccccc ctcccacccc caatttgt        660 atttatttat tttttaatta ttttatgcag cgatggggc ggggggggggg gggcgcgcg      720 ccaggcgggg cgggcgggg cgaggggcgg ggcggggcga ggcggagagg tgcggcggca      780
gccaatcaga gcggcgcgct ccgaaagttt cctttatgg cgaggcggcg gcggcggcgg      840
ccctataaaa agcgaagcgc gcggcgggcg ggagtcgctg cgttgccttc gccccgtgcc     900
ccgctccgcg ccgcctcgcg ccgcccgccc cggctctgac tgaccgcgtt actcccacag     960
gtgagcgggc gggacggccc ttctccctcc gggctgtaat tagcgcttgg tttaatgacg    1020 gctcgttttct tttctgtggc tgcgtgaaag ccttaaaggg ctccgggagg ccttttgtgc   1080 ggggggggagc ggctcggggg gtgcgtgcgt gtgtgtgtgc gtggggagcg ccgcgtgcgg   1140
```

```
cccgcgctgc ccggcggctg tgagcgctgc gggcgcggcg cggggctttg tgcgctccgc    1200
gtgtgcgcga ggggagcgcg ggccgggggc ggtgccccgc ggtgcggggg ggctgcgagg    1260
ggaacaaagg ctgcgtgcgg ggtgtgtgcg tggggggggtg agcaggggggt gtgggcgcgg    1320 cggtcgggct gtaaccccccc cctggcaccc ccctccccga gttgctgagc acggcccggc    1380
ttcgggtgcg gggctccgtg cggggcgtgg cgcgggctc gccgtgccgg gcggggggtg     1440
gcggcaggtg ggggtgccgg gcggggcggg gccgcctcgg gccggggagg gctcggggga    1500
ggggcgcggc ggccccggag cgccggcggc tgtcgaggcg cggcgagccg cagccattgc    1560
cttttatggt aatcgtgcga gagggcgcag ggacttcctt tgtcccaaat ctggcggagc    1620
cgaaatctgg gaggcgccgc cgcacccccct ctagcgggcg cgggcgaagc ggtgcggcgc    1680
cggcaggaag gaaatgggcg gggagggcct tcgtgcgtcg ccgcgccgcc gtccccttct    1740
ccatctccag cctcggggct gccgcagggg gacggctgcc ttcgggggggg acggggcagg    1800 gcggggttcg gcttctggcg tgtgaccggc ggctttagag cctctgctaa ccatgttcat    1860
gccttcttct ttttcctaca gctcctgggc aacgtgctgg ttgttgtgct gtctcatcat    1920
tttggcaaag atctttgtcg atcctaccat ccactcgaca cacccgccag cggccgctgc    1980
caagcttccg agctctcgaa ttcaggaggt acccaccatg agggtccccg ctcagctcct    2040
ggggctcctg ctgctctggc tcccaggcgc gcgatgtcaa gccgtggtga cccaagagtc    2100
cgctctgaca acaagcccg gcgagacagt gacactgaca tgtagaagca gcaccggagc    2160
cgtgaccacc agcaactacg ccaactgggt gcaagagaag cccgaccatc tgtttaccgg    2220
actgatcgga ggcaccaata acagagcccc cggcgtgccc gccagattta gcggctctct    2280
gattggcgac aaggctgctc tgaccatcac cggagcccag accgaggacg aggccatcta    2340
cttctgcgct ctgtggttca gcaaccactg ggtgtttggc ggcggcacca aactgaccgt    2400
gctcgggcag cctaaaagct cgccgtccgt gaccctcttt ccaccatcat cggaagagct    2460
ggaaaccaac aaggctactc tcgtctgcac catcacggat ttctacccccg gagtggtcac    2520 cgtggactgg aaagtggacg ggactccggt gactcaggga atggaaacga cccaaccgtc    2580
aaagcagtcg aacaataagt acatggcctc cagctacctg accttgaccg ccagagcgtg    2640
ggagcggcac agctcctact catgtcaagt cactcacgaa ggccatactg tggagaagag    2700
cctgtcccgc gcagattgct cgtagtgagc ggccgcgtct agacctgcac tgactgactg    2760
atacaatcga tttctggatc cgcaggcctc tgctagcttg actgactgag atacagcgta    2820
ccttcagctc acagacatga taagatacat tgatgagttt ggacaaacca caactagaat    2880
gcagtgaaaa aaatgcttta tttgtgaaat ttgtgatgct attgctttat tgtaaccat    2940 tataagctgc aataaacaag ttaacaacaa caattgcatt cattttatgt ttcaggttca    3000
gggggaggtg tgggaggttt tttaaagcaa gtaaaacctc tacaaatgtg gtattggccc    3060
atctctatcg gtatcgtagc ataacccctt ggggcctcta acgggtctt gagggggtttt    3120 ttgtgcccct cgggccggat tgctatctac cggcattggc gcagaaaaaa atgcctgatg    3180
cgacgctgcg cgtcttatac tcccacatat gccagattca gcaacggata cggcttcccc    3240
aacttgccca cttccatacg tgtcctcctt accagaaatt tatccttaag gtcgtcagct    3300
atcctgcagg cgatctctcg atttcgatca agacattcct ttaatggtct ttctggaca    3360 ccactagggg tcagaagtag ttcatcaaac tttcttccct ccctaatctc attggttacc    3420
ttgggctatc gaaacttaat taaccagtca agtcagctac ttggcgagat cgacttgtct    3480
gggtttcgac tacgctcaga attgcgtcag tcaagttcga tctggtcctt gctattgcac    3540
```

```
ccgttctccg attacgagtt tcatttaaat catgtgagca aaaggccagc aaaaggccag    3600
gaaccgtaaa aaggccgcgt tgctggcgtt tttccatagg ctccgccccc ctgacgagca    3660
tcacaaaaat cgacgctcaa gtcagaggtg gcgaaacccg acaggactat aaagatacca    3720
ggcgtttccc cctggaagct ccctcgtgcg ctctcctgtt ccgaccctgc cgcttaccgg    3780
atacctgtcc gcctttctcc cttcgggaag cgtggcgctt tctcatagct cacgctgtag    3840
gtatctcagt tcggtgtagg tcgttcgctc caagctgggc tgtgtgcacg aaccccccgt    3900
tcagcccgac cgctgcgcct tatccggtaa ctatcgtctt gagtccaacc cggtaagaca    3960
cgacttatcg ccactggcag cagccactgg taacaggatt agcagagcga ggtatgtagg    4020
cggtgctaca gagttcttga agtggtggcc taactacggc tacactagaa gaacagtatt    4080
tggtatctgc gctctgctga agccagttac cttcggaaaa agagttggta gctcttgatc    4140
cggcaaacaa accaccgctg gtagcggtgg tttttttgtt tgcaagcagc agattacgcg    4200
cagaaaaaaa ggatctcaag aagatccttt gatcttttct acggggtctg acgctcagtg    4260
gaacgaaaac tcacgttaag ggattttggt catgagatta tcaaaaagga tcttcaccta    4320
gatcctttta aattaaaaat gaagttttaa atcaatctaa agtatatatg agtaaacttg    4380
gtctgacagt taccaatgct taatcagtga ggcacctatc tcagcgatct gtctatttcg    4440
ttcatccata gttgcattta aatttccgaa ctctccaagg ccctcgtcgg aaaatcttca    4500
aacctttcgt ccgatccatc ttgcaggcta cctctcgaac gaactatcgc aagtctcttg    4560
gccggccttg cgccttggct attgcttggc agcgcctatc gccaggtatt actccaatcc    4620
cgaatatccg agatcgggat caccccgagag aagttcaacc tacatcctca atcccgatct    4680
atccgagatc cgaggaatat cgaaatcggg gcgcgcctgg cctccgcgcc gggttttggc    4740
gcctcccgcg ggcgcccccc tcgtcacggc gagcgctgcc acgtcagacg aagggcgcag    4800
gagcgtcctg atccttccgc ccggacgctc aggacagcgg cccgctgctc ataagactcg    4860
gccttagaac cccagtatca gcagaaggac atttttaggac gggacttggg tgactctagg    4920
gcactggttt tctttccaga gagcggaaca ggcgaggaaa agtagtccct tctcggcgat    4980
tctgcggagg gatctccgtg gggcggtgaa cgccgatgat tatataagga cgcgccgggt    5040
gtggcacagc tagttccgtc gcagccggga tttgggtcgc ggttcttgtt tgtggatcgc    5100
tgtgatcgtc acttggtgag tagcgggctg ctgggctggc cggggctttc gtggccgccg    5160
ggccgctcgg tgggacggaa gcgtgtggag agaccgccaa gggctgtagt ctgggtccgc    5220
gagcaaggtt gccctgaact gggggttggg gggagcgcag caaaatggcg gctgttcccg    5280
agtcttgaat ggaagacgct tgtgaggcgg gctgtgaggt cgttgaaaca aggtgggggg    5340
catggtgggc ggcaagaacc caaggtcttg agcccttcgc taatgcggga aagctcttat    5400
tcgggtgaga tgggctgggc accatctggg gaccctgacg tgaagtttgt cactgactgg    5460
agaactcggt ttgtcgtctg ttgcggggc ggcagttatg gcggtgccgt tgggcagtgc    5520
acccgtacct ttgggagcgc gcgccctcgt cgtgtcgtga cgtcacccgt tctgttggct    5580
tataatgcag ggtggggcca cctgccggta ggtgtgcggt aggcttttct ccgtcgcagg    5640
acgcagggtt cgggcctagg gtaggctctc ctgaatcgac aggcgccgga cctctggtga    5700
ggggagggat aagtgaggcg tcagtttctt tggtcggttt tatgtaccta tcttcttaag    5760
tagctgaagc tccggttttg aactatcgcg tcggggttgg cgagtgtgtt ttgtgaagtt    5820
ttttaggcac cttttgaaat gtaatcattt gggtcaatat gtaattttca gtgttagact    5880
```

```
tgtaaattgt ccgctaaatt ctggccgttt ttggcttttt tgttagacaa catgggtaaa    5940
aagcctgaac tcaccgcgac gtctgtcgag aagtttctga tcgaaaagtt cgacagcgtc    6000
tccgacctga tgcagctctc ggagggcgaa gaatctcgtg ctttcagctt cgatgtagga    6060
gggcgtggat atgtcctgcg ggtaaatagc tgccgcgatg gtttctacaa agatcgttat    6120
gtttatcggc actttgcatc cgccgcgctc ccgattccgg aagtgcttga cattggggag    6180
ttcagcgaga gcctgaccta ttgcatctcc cgccgtgcac agggtgtcac gttgcaagac    6240
ctgcctgaaa ccgaactgcc cgctgttctg cagccggtcg cggaggcaat ggatgccatc    6300
gctgccgccg atcttagcca gacgagcggg ttcggcccat tcggaccgca aggaatcggt    6360
caatacacta catggcgtga tttcatatgc gcgattgctg atccccatgt gtatcactgg    6420
caaactgtga tggacgacac cgtcagtgcg tccgtcgcgc aggctctcga tgagctgatg    6480
ctttgggccg aggactgccc cgaagtccgg cacctcgtgc acgcggattt cggctccaac    6540
aatgtcctga cggacaatgg ccgcataaca gcggtcattg actggagcga ggcgatgttc    6600
ggggattccc aatacgaggt cgccaacatc ttcttctgga ggccgtggtt ggcttgtatg    6660
gagcagcaga cgcgctactt cgagcggagg catccggagc ttgcaggatc gccccggctc    6720
cgggcgtata tgctccgcat tggtcttgac caactctatc agagcttggt tgacggcaat    6780
ttcgatgatg cagcttgggc gcagggtcga tgcgacgcaa tcgtccgatc cggagccggg    6840
actgtcgggc gtacacaaat cgcccgcaga agccgccgcg tctggaccga tggctgtgta    6900
gaagtactcg ccgatagtgg aaaccgacgc cccagcactc gtccgagggc aaaggaataa    6960
gctagtatgt aagcctagtc ttagataata aaatcgctat ccatcgaaga tggatgtgtg    7020
ttggtttttt gtgtgtgtaa cgctaggcgc gcctggtgta ccgagaacga tcctctcagt    7080
gcgagtctcg acgatccata tcgttgcttg gcagtcagcc agtcggaatc cagcttggga    7140
cccaggaagt ccaatcgtca gatattgtac tcaagcctgg tcacggcagc gtaccgatct    7200
gtttaaacct agatattgat agtctgatcg gtcaacgtat aatcgagtcc tagcttttgc    7260
aaacatctat caagagacag gatcagcagg aggctttcgc atgattgaac aagatggatt    7320
gcacgcaggt tctccggcgg cttgggtgga gaggctattc ggctatgact gggcacaaca    7380
gacaatcggc tgctctgatg ccgccgtgtt ccggctgtca gcgcaggggc gtccggttct    7440
ttttgtcaag accgacctgt ccggtgccct gaatgaactg caagacgagg cagcgcggct    7500
atcgtggctg gcgacgacgg gcgttccttg cgcggctgtg ctcgacgttg tcactgaagc    7560
gggaagggac tggctgctat tgggcgaagt gccggggcag gatctcctgt catctcacct    7620
tgctcctgcc gagaaagtat ccatcatggc tgatgcaatg cggcggctgc atacgcttga    7680
tccggctacc tgcccattcg accaccaagc gaaacatcgc atcgagcgag cacgtactcg    7740
gatggaagcc ggtcttgtcg atcaggatga tctggacgaa gagcatcagg ggctcgcgcc    7800
agccgaactg ttcgccaggc tcaaggcgtc tatgcccgac ggcgaggatc tcgtcgtgac    7860
ccacggcgat gcctgcttgc cgaatatcat ggtggaaaat ggccgctttt ctggattcat    7920
cgactgtggc cgtctgggtg tggcggaccg ctatcaggac atagcgttgg ctacccgtga    7980
tattgctgaa gagcttggcg gcgaatgggc tgaccgcttc cttgtgcttt acggtatcgc    8040
cgctcccgat tcgcagcgca tcgccttcta tcgccttctt gacgagttct tctgaccgat    8100
tctaggtgca ttggcgcaga aaaaaatgcc tgatgcgacg ctgcgcgtct tatactccca    8160
catatgccaa attcagcaac ggatacggct tccccaactt gcccacttcc atacgtgtcc    8220
tccttaccag aaatttatcc ttaaggtcgt ttaaactcga ctctggctct atcgaatctc    8280
```

-continued

| | |
|---|---|
| cgtcgtttcg agcttacgcg aacagccgtg gcgctcattt gctcgtcggg catcgaatct | 8340 |
| cgtcagctat cgtcagctta cctttttggc a | 8371 |

<210> SEQ ID NO 88
<211> LENGTH: 11147
<212> TYPE: DNA
<213> ORGANISM: Artificial Sequence
<220> FEATURE:
<223> OTHER INFORMATION: Synthetic polymer.

<400> SEQUENCE: 88

| | |
|---|---|
| gcgatcgcgg ctcccgacat cttggaccat tagctccaca ggtatcttct tccctctagt | 60 |
| ggtcataaca gcagcttcag ctacctctca attcaaaaaa cccctcaaga cccgtttaga | 120 |
| ggccccaagg ggttatgcta tcaatcgttg cgttacacac acaaaaaacc aacacacatc | 180 |
| catcttcgat ggatagcgat tttattatct aactgctgat cgagtgtagc cagatctata | 240 |
| gtaatcaatt acggggtcat tagttcatag cccatatatg gagttccgcg ttacataact | 300 |
| tacggtaaat ggcccgcctg gctgaccgcc caacgacccc cgcccattga cgtcaataat | 360 |
| gacgtatgtt cccatagtaa cgccaatagg gactttccat tgacgtcaat gggtggacta | 420 |
| tttacggtaa actgcccact tggcagtaca tcaagtgtat catatgccaa gtacgccccc | 480 |
| tattgacgtc aatgacggta aatggcccgc ctggcattat gcccagtaca tgaccttatg | 540 |
| ggactttcct acttggcagt acatctacgt attagtcatc gctattacca tgcgtcgagg | 600 |
| tgagccccac gttctgcttc actctcccca tctcccccc ctcccacccc caattttgt | 660 |
| atttatttat tttttaatta ttttatgcag cgatggggc gggggggggg ggggcgcgcg | 720 |
| ccaggcgggg cggggcgggg cgaggggcgg ggcggggcga ggcggagagg tgcggcggca | 780 |
| gccaatcaga gcggcgcgct ccgaaagttt ccttttatgg cgaggcggcg gcggcggcgg | 840 |
| ccctataaaa agcgaagcgc gcggcgggcg ggagtcgctg cgttgccttc gccccgtgcc | 900 |
| ccgctccgcg ccgcctcgcg ccgcccgccc cggctctgac tgaccgcgtt actcccacag | 960 |
| gtgagcgggc gggacggccc ttctccctcc gggctgtaat tagcgcttgg tttaatgacg | 1020 |
| gctcgttttct tttctgtggc tgcgtgaaag ccttaaaggg ctccgggagg cctttgtgc | 1080 |
| ggggggggagc ggctcggggg gtgcgtgcgt gtgtgtgtgc gtggggagcg ccgcgtgcgg | 1140 |
| cccgcgctgc ccggcggctg tgagcgctgc gggcgcggcg cggggctttg tgcgctccgc | 1200 |
| gtgtgcgcga ggggagcgcg ggccggggc ggtgccccgc ggtgcggggg ggctgcgagg | 1260 |
| ggaacaaagg ctgcgtgcgg ggtgtgtgcg tgggggggtg agcaggggt gtgggcgcgg | 1320 |
| cggtcgggct gtaaccccc cctggcaccc ccctccccga gttgctgagc acggcccggc | 1380 |
| ttcgggtgcg gggctccgtg cggggcgtgg cgcggggctc gccgtgccgg gcggggggtg | 1440 |
| gcggcaggtg ggggtgccgg gcggggcggg gccgcctcgg gccggggagg gctcggggga | 1500 |
| ggggcgcggc ggccccggag cgccggcggc tgtcgaggcg cggcgagccg cagccattgc | 1560 |
| ctttttatggt aatcgtgcga gagggcgcag ggacttcctt tgtcccaaat ctggcggagc | 1620 |
| cgaaatctgg gaggcgccgc cgcaccccct ctagcgggcg cgggcgaagc ggtgcggcgc | 1680 |
| cggcaggaag gaaatgggcg gggagggcct tcgtgcgtcg ccgcgccgcc gtccccttct | 1740 |
| ccatctccag cctcggggct ccgcaggggg gacggctgcc ttcgggggg acgggcagg | 1800 |
| gcggggttcg gcttctggcg tgtgaccggc ggctttagag cctctgctaa ccatgttcat | 1860 |
| gccttcttct ttttcctaca gctcctgggc aacgtgctgg ttgttgtgct gtctcatcat | 1920 |

```
tttggcaaag atctttgtcg atcctaccat ccactcgaca cacccgccag cggccgctgc   1980
caagcttccg agctctcgaa ttcaggaggt acccaccatg agggtccccg ctcagctcct   2040
ggggctcctg ctgctctggc tcccaggcgc gcgatgtcaa gccgtggtga cccaagagtc   2100
cgctctgaca acaagccccg gcgagacagt gacactgaca tgtagaagca gcaccggagc   2160
cgtgaccacc agcaactacg ccaactgggt gcaagagaag cccgaccatc tgtttaccgg   2220
actgatcgga ggcaccaata acagagcccc cggcgtgccc gccagattta gcggctctct   2280
gattggcgac aaggctgctc tgaccatcac cggagcccag accgaggacg aggccatcta   2340
cttctgcgct ctgtggttca gcaaccactg ggtgtttggc ggcggcacca aactgaccgt   2400
gctcgggcag cctaaaagct cgccgtccgt gaccctcttt ccaccatcat cggaagagct   2460
ggaaaccaac aaggctactc tcgtctgcac catcacggat ttctaccccg agtggtcac    2520 cgtggactgg aaagtggacg ggactccggt gactcaggga atggaaacga cccaaccgtc   2580
aaagcagtcg aacaataagt acatggcctc cagctacctg accttgaccg ccagagcgtg   2640
ggagcggcac agctcctact catgtcaagt cactcacgaa ggccatactg tggagaagag   2700
cctgtcccgc gcagattgct cgtagtgagc ggccgcgtct agacctgcac tgactgactg   2760
atacaatcga tttctggatc cgcaggcctc tgctagcttg actgactgag atacagcgta   2820
ccttcagctc acagacatga taagatacat tgatgagttt ggacaaacca caactagaat   2880
gcagtgaaaa aaatgcttta tttgtgaaat ttgtgatgct attgctttat ttgtaaccat   2940
tataagctgc aataaacaag ttaacaacaa caattgcatt cattttatgt ttcaggttca   3000
gggggaggtg tgggaggttt tttaaagcaa gtaaaacctc tacaaatgtg gtattggccc   3060
atctctatcg gtatcgtagc ataacccctt ggggcctcta aacgggtctt gaggggtttt   3120
ttgtgcccct cgggccggat tgctatctac cggcattggc gcagaaaaaa atgcctgatg   3180
cgacgctgcg cgtcttatac tcccacatat gccagattca gcaacggata cggcttcccc   3240
aacttgccca cttccatacg tgtcctcctt accagaaatt tatccttaag gtcgtcagct   3300
atcctgcagg atagtaatca attacggggt cattagttca tagcccatat atggagttcc   3360
gcgttacata acttacggta atggcccgc ctggctgacc gcccaacgac ccccgcccat   3420
tgacgtcaat aatgacgtat gttcccatag taacgccaat agggactttc cattgacgtc   3480
aatgggtgga ctatttacgg taaactgccc acttggcagt acatcaagtg tatcatatgc   3540
caagtacgcc ccctattgac gtcaatgacg gtaaatggcc cgcctggcat tatgcccagt   3600
acatgacctt atgggacttt cctacttggc agtacatcta cgtattagtc atcgctatta   3660
ccatgcgtcg aggtgagccc cacgttctgc ttcactctcc ccatctcccc cccctcccca   3720
cccccaattt tgtatttatt tattttttaa ttatttatg cagcgatggg ggcgggggg    3780 ggggggcgc gcgccaggcg gggcggggcg gggcgagggg cggggcgggg cgaggcggag   3840
aggtgcggcg gcagccaatc agagcggcgc gctccgaaag tttccttttta tggcgaggcg   3900 gcggcggcg cggccctata aaaagcgaag cgcgcggcgg gcgggagtcg ctgcgttgcc   3960
ttcgccccgt gccccgctcc gcgccgcctc gcgccgcccg cccggctct gactgaccgc   4020 gttactccca caggtgagcg gcgggacgg cccttctccc tccgggctgt aattagcgct   4080
tggtttaatg acggctcgtt tcttttctgt ggctgcgtga aagccttaaa gggctccggg   4140 agggccttg tgcggggggg agcggctcgg ggggtgcgtg cgtgtgtgtg tgcgtgggga   4200
gcgccgcgtg cggcccgcgc tgcccggcgg ctgtgagcgc tgcggcgcg gcgcggggct   4260 ttgtgcgctc cgcgtgtgcg cgaggggagc gcgggccggg ggcggtgccc cgcggtgcgg   4320
```

```
gggggctgcg aggggaacaa aggctgcgtg cggggtgtgt gcgtgggggg gtgagcaggg    4380
ggtgtgggcg cggcggtcgg gctgtaaccc ccccctggca ccccctccc cgagttgctg     4440 agcacggccc ggcttcgggt gcggggctcc gtgcggggcg tggcgcgggg ctcgccgtgc    4500
cgggcggggg gtggcggcag gtgggggtgc cgggcgggc ggggccgcct cgggccgggg     4560
agggctcggg ggaggggcgc ggcggccccg gagcgccggc ggctgtcgag gcgcggcgag    4620
ccgcagccat tgccttttat ggtaatcgtg cgagagggcg cagggacttc ctttgtccca    4680
aatctggcgg agccgaaatc tgggaggcgc cgccgcaccc cctctagcgg gcgcgggcga    4740
agcggtgcgg cgccggcagg aaggaaatgg gcggggaggg ccttcgtgcg tcgccgcgcc    4800
gccgtcccct tctccatctc cagcctcggg gctgccgcag ggggacggct gccttcgggg    4860
gggacggggc agggcgggt tcggcttctg cgtgtgacc ggcggcttta gagcctctgc      4920
taaccatgtt catgccttct tctttttcct acagctcctg ggcaacgtgc tggttgttgt    4980
gctgtctcat cattttggca aattcgacca accttccttc gacacggggc ccaaagtact    5040
aaagtcgaca ggaggtaccc accatgggtt ggagcctcat cttgctcttc cttgtcgctg    5100
ttgctacgcg tgtccactcc caagtgcagc tgcagcagag cggagccgaa ctggctagac    5160
ccggagcctc cgtgaagctg agctgtaagg cctccggcta caccttcacc agctacggca    5220
tcagctgggt gaggcaaagg accggccaag gactggaatg gatcggcgag atctacccta    5280 ggagggggcaa cacctactac aacgagaagt tcaagggcaa ggccacactg acagcctaca    5340
agtccagcgg cacagcctac atggagctga gatctctgac cagcgaggat agcgccgtgt    5400
tcttttgcgc cagaggcggc atctactacg gcaatctgtt cgactactgg ggccaaggca    5460
ccacactgac cgtctcgagc gctaagacga ctccaccgtc cgtgtacccg ctcgcgccag    5520
gttcggccgc tcagacgaac agcatggtga ccctcggctg cctcgtgaag ggttatttcc    5580
cagagccggt gaccgtgacg tggaactccg gctcactgtc atcgggcgtg cacacttttc    5640
cagcagtgct gcagtcggac ctttacaccc tcagctcgtc cgtcaccgtc ccttcatcaa    5700
cttggcctag ccagaccgtg acttgcaatg tcgcccaccc ggcgtccagc actaaggtgg    5760
acaagaagat ccaccaccat caccatcacc atcaccatca ctagagagcg gccgcgtcta    5820
gacctgcact gactgactga tacactagtt agcctgtgcc ttctagttgc cagccatctg    5880
ttgtttgccc ctcccccgtg ccttccttga ccctggaagg tgccactccc actgtccttt    5940
cctaataaaa tgaggaaatt gcatcgcatt gtctgagtag gtgtcattct attctggggg    6000
gtggggtggg gcaggacagc aagggggagg attgggaaga caatagcagg catgctgggg    6060
atgcggtggg ctctatggcc tgcaggcgat ctctcgattt cgatcaagac attcctttaa    6120
tggtcttttc tggacaccac taggggtcag aagtagttca tcaaactttc ttccctccct    6180
aatctcattg gttaccttgg gctatcgaaa cttaattaac cagtcaagtc agctacttgg    6240
cgagatcgac ttgtctgggt ttcgactacg ctcagaattg cgtcagtcaa gttcgatctg    6300
gtccttgcta ttgcacccgt tctccgatta cgagtttcat ttaaatcatg tgagcaaaag    6360
gccagcaaaa ggccaggaac cgtaaaaagg ccgcgttgct ggcgtttttc cataggctcc    6420 gccccctga cgagcatcac aaaaatcgac gctcaagtca gaggtggcga aacccgacag    6480
gactataaag ataccaggcg tttccccctg gaagctccct cgtgcgctct cctgttccga    6540
ccctgccgct taccggatac ctgtccgcct ttctcccttc gggaagcgtg gcgctttctc    6600
atagctcacg ctgtaggtat ctcagttcgg tgtaggtcgt tcgctccaag ctgggctgtg    6660
```

-continued

```
tgcacgaacc ccccgttcag cccgaccgct gcgccttatc cggtaactat cgtcttgagt    6720
ccaacccggt aagacacgac ttatcgccac tggcagcagc cactggtaac aggattagca    6780
gagcgaggta tgtaggcggt gctacagagt tcttgaagtg gtggcctaac tacggctaca    6840
ctagaagaac agtatttggt atctgcgctc tgctgaagcc agttaccttc ggaaaaagag    6900
ttggtagctc ttgatccggc aaacaaacca ccgctggtag cggtggtttt tttgtttgca    6960
agcagcagat tacgcgcaga aaaaaaggat ctcaagaaga tcctttgatc ttttctacgg    7020
ggtctgacgc tcagtggaac gaaaactcac gttaagggat tttggtcatg agattatcaa    7080
aaaggatctt cacctagatc cttttaaatt aaaaatgaag ttttaaatca atctaaagta    7140
tatatgagta aacttggtct gacagttacc aatgcttaat cagtgaggca cctatctcag    7200
cgatctgtct atttcgttca tccatagttg catttaaatt tccgaactct caaggccct    7260 cgtcggaaaa tcttcaaacc tttcgtccga tccatcttgc aggctacctc tcgaacgaac    7320
tatcgcaagt ctcttggccg gccttgcgcc ttggctattg cttggcagcg cctatcgcca    7380
ggtattactc caatcccgaa tatccagat cgggatcacc cgagagaagt tcaacctaca    7440
tcctcaatcc cgatctatcc gagatccgag gaatatcgaa atcggggcgc gcctggcctc    7500
cgcgccgggt tttggcgcct cccgcgggcg cccccctcgt cacggcgagc gctgccacgt    7560
cagacgaagg gcgcaggagc gtcctgatcc ttccgcccgg acgctcagga cagcggcccg    7620
ctgctcataa gactcggcct tagaaccccca gtatcagcag aaggacattt taggacggga    7680
cttgggtgac tctagggcac tggttttctt tccagagagc ggaacaggcg aggaaaagta    7740
gtcccttctc ggcgattctg cggagggatc tccgtggggc ggtgaacgcc gatgattata    7800
taaggacgcg ccgggtgtgg cacagctagt tccgtcgcag ccgggatttg ggtcgcggtt    7860
cttgtttgtg gatcgctgtg atcgtcactt ggtgagtagc gggctgctgg gctggccggg    7920
gctttcgtgg ccgccgggcc gctcggtggg acggaagcgt gtggagagac cgccaagggc    7980
tgtagtctgg gtccgcgagc aaggttgccc tgaactgggg gttgggggga gcgcagcaaa    8040
atggcggctg ttcccgagtc ttgaatggaa gacgcttgtg aggcgggctg tgaggtcgtt    8100
gaaacaaggt gggggcatg gtgggcggca agaacccaag gtcttgagcc cttcgctaat    8160
gcgggaaagc tcttattcgg gtgagatggg ctgggcacca tctggggacc ctgacgtgaa    8220
gtttgtcact gactggagaa ctcggttttg cgtctgttgc gggggcggca gttatgcgg    8280 tgccgttggg cagtgcaccc gtacctttgg gagcgcgcgc cctcgtcgtg tcgtgacgtc    8340
acccgttctg ttggcttata atgcagggtg gggccacctg ccggtaggtg tgcggtaggc    8400
ttttctccgt cgcaggacgc agggttcggg cctagggtag gctctcctga atcgacaggc    8460
gccggacctc tggtgagggg agggataagt gaggcgtcag tttctttggt cggttttatg    8520
tacctatctt cttaagtagc tgaagctccg gttttgaact atgcgctcgg ggttggcgag    8580
tgtgttttgt gaagtttttt aggcaccttt tgaaatgtaa tcatttgggt caatatgtaa    8640
ttttcagtgt tagacttgta aattgtccgc taaattctgg ccgttttggg cttttttgtt    8700
agacaacatg ggtaaaaagc ctgaactcac cgcgacgtct gtcgagaagt tctgatcga    8760 aaagttcgac agcgtctccg acctgatgca gctctcggag ggcgaagaat ctcgtgcttt    8820
cagcttcgat gtaggagggc gtggatatgt cctgcgggta aatagctgcg ccgatggttt    8880
ctacaaagat cgttatgttt atcggcactt tgcatccgcc gcgctcccga ttccggaagt    8940
gcttgacatt ggggagttca gcgagagcct gacctattgc atctcccgcc gtgcacaggg    9000
tgtcacgttg caagacctgc ctgaaaccga actgcccgct gttctgcagc cggtcgcgga    9060
```

```
ggcaatggat gccatcgctg ccgccgatct tagccagacg agcgggttcg gcccattcgg    9120
accgcaagga atcggtcaat acactacatg gcgtgatttc atatgcgcga ttgctgatcc    9180
ccatgtgtat cactggcaaa ctgtgatgga cgacaccgtc agtgcgtccg tcgcgcaggc    9240
tctcgatgag ctgatgcttt gggccgagga ctgccccgaa gtccggcacc tcgtgcacgc    9300
ggatttcggc tccaacaatg tcctgacgga caatggccgc ataacagcgg tcattgactg    9360
gagcgaggcg atgttcgggg attcccaata cgaggtcgcc aacatcttct tctgaggcc     9420 gtggttggct tgtatggagc agcagacgcg ctacttcgag cggaggcatc cggagcttgc    9480
aggatcgccc cggctccggg cgtatatgct ccgcattggt cttgaccaac tctatcagag    9540
cttggttgac ggcaatttcg atgatgcagc ttgggcgcag ggtcgatgcg acgcaatcgt    9600
ccgatccgga gccgggactg tcgggcgtac acaaatcgcc cgcagaagcg ccgccgtctg    9660
gaccgatggc tgtgtagaag tactcgccga tagtggaaac cgacgcccca gcactcgtcc    9720
gagggcaaag gaataagcta gtatgtaagc ctagtcttag ataataaaat cgctatccat    9780
cgaagatgga tgtgtgttgg ttttttgtgt gtgtaacgct aggcgcgcct ggtgtaccga    9840
gaacgatcct ctcagtgcga gtctcgacga tccatatcgt tgcttggcag tcagccagtc    9900
ggaatccagc ttgggaccca ggaagtccaa tcgtcagata ttgtactcaa gcctggtcac    9960
ggcagcgtac cgatctgttt aaacctagat attgatagtc tgatcggtca acgtataatc   10020
gagtcctagc ttttgcaaac atctatcaag agacaggatc agcaggaggc tttcgcatga   10080
ttgaacaaga tggattgcac gcaggttctc cggcggcttg ggtggagagg ctattcggct   10140
atgactgggc acaacagaca atcggctgct ctgatgccgc cgtgttccgg ctgtcagcgc   10200
aggggcgtcc ggttcttttt gtcaagaccg acctgtccgg tgccctgaat gaactgcaag   10260
acgaggcagc gcggctatcg tggctggcga cgacgggcgt tccttgcgcg ctgtgctcg    10320 acgttgtcac tgaagcggga agggactggc tgctattggg cgaagtgccg ggcaggatc    10380 tcctgtcatc tcaccttgct cctgccgaga agtatccat catggctgat gcaatgcggc     10440
ggctgcatac gcttgatccg gctacctgcc cattcgacca ccaagcgaaa catcgcatcg    10500
agcgagcacg tactcggatg gaagccggtc ttgtcgatca ggatgatctg gacgaagagc    10560
atcaggggct cgcgccagcc gaactgttcg ccaggctcaa ggcgtctatg cccgacggcg    10620
aggatctcgt cgtgacccac ggcgatgcct gcttgccgaa tatcatggtg gaaaatggcc    10680
gcttttctgg attcatcgac tgtggccgtc tgggtgtggc ggaccgctat caggacatag    10740
cgttggctac ccgtgatatt gctgaagagc ttggcggcga atgggctgac cgcttccttg    10800
tgctttacgg tatcgccgcg cccgattcgc agcgcatcgc cttctatcgc cttcttgacg    10860
agttcttctg accgattcta ggtgcattgg cgcagaaaaa aatgcctgat gcgacgctgc    10920
gcgtcttata ctcccacata tgccagattc agcaacggat acggcttccc caacttgccc    10980
acttccatac gtgtcctcct taccagaaat ttatccttaa ggtcgtttaa actcgactct    11040
ggctctatcg aatctccgtc gtttcgagct tacgcgaaca gccgtggcgc tcatttgctc    11100
gtcgggcatc gaatctcgtc agctatcgtc agcttacctt tttggca                  11147
```

<210> SEQ ID NO 89
<211> LENGTH: 4997
<212> TYPE: DNA
<213> ORGANISM: Artificial Sequence
<220> FEATURE:
<223> OTHER INFORMATION: Synthetic polymer.

```
<400> SEQUENCE: 89
gcgatcgcgg ctcccgacat cttggaccat tagctccaca ggtatcttct tccctctagt      60
ggtcataaca gcagcttcag ctacctctca attcaaaaaa cccctcaaga cccgtttaga     120
ggccccaagg ggttatgcta tcaatcgttg cgttacacac acaaaaaacc aacacacatc     180
catcttcgat ggatagcgat tttattatct aactgctgat cgagtgtagc cagatctagt     240
aatcaattac ggggtcatta gttcatagcc catatatgga gttccgcgtt acataactta     300
cggtaaatgg cccgcctggc tgaccgccca acgaccccg cccattgacg tcaataatga      360
cgtatgttcc catagtaacg ccaataggga ctttccattg acgtcaatgg gtggagtatt     420
tacggtaaac tgcccacttg gcagtacatc aagtgtatca tatgccaagt acgccccta     480
ttgacgtcaa tgacggtaaa tggcccgcct ggcattatgc ccagtacatg accttatggg     540
actttcctac ttggcagtac atctacgtat tagtcatcgc tattaccatg ctgatgcggt     600
tttggcagta catcaatggg cgtggatagc ggtttgactc acggggattt ccaagtctcc     660
accccattga cgtcaatggg agtttgtttt ggcaccaaaa tcaacgggac tttccaaaat     720
gtcgtaacaa ctccgcccca ttgacgcaaa tgggcggtag gcgtgtacgg tgggaggtct     780
atataagcag agctggttta gtgaaccgtc agatcagatc tttgtcgatc ctaccatcca     840
ctcgacacac cgccagcag ccgctgccaa gcttccgagc tctcgaattc aaaggaggta      900
cccaccatgc cgctgctgct actgctgccc ctgctgtggg caggggcgct agctcaagtg     960
cagctgcagc agagcggagc cgagctggtg aagcccggag ccagcgtgaa gatcagctgc    1020
aaggccagcg gctacgcctt ctccaactac tggatgaact gggtgaagca gagacccggc    1080
aagggactgg aatggatcgg ccagatctac cccggcgacg gagacaccaa ctacaacggc    1140
aagttcaagg gcaaagccac actgaccgcc gacaagagct ccagcaccgc ctacatgcag    1200
ctgagctctc tgaccagcga ggatagcgcc gtgtacttct gcgccagagg agactactgg    1260
ggccaaggca ccacactgac cgtctcgagc gctaagacga ctccaccgtc cgtgtacccg    1320
ctcgcgccag gttcggccgc tcagacgaac agcatggtga ccctcggctg cctcgtgaag    1380
ggttatttcc cagagccggt gaccgtgacg tggaactccg gctcactgtc atcgggcgtg    1440
cacactttc cagcagtgct gcagtcggac ctttacaccc tcagctcgtc cgtcaccgtc     1500
ccttcatcaa cttggcctag ccagaccgtg acttgcaatg tcgcccaccc ggcgtccagc    1560
actaaggtgg acaagaagat ccaccaccat caccatcacc atcaccatca ctagtgagcg    1620
gccgcgtcta gacctgcact gactgactga tacaatcgat ttctggatcc gcaggcctct    1680
cctagcttga ctgactgaga tacagcgtac cttcagctca cagacatgat aagatacatt    1740
gatgagtttg gacaaaccac aactagaatg cagtgaaaaa aatgctttat ttgtgaaatt    1800
tgtgatgcta ttgctttatt tgtaaccatt ataagctgca ataaacaagt taacaacaac    1860
aattgcattc attttatgtt tcaggttcag ggggaggtgt gggaggtttt ttaaagcaag    1920
taaaacctct acaaatgtgg tattggccca tctctatcgg tatcgtagca taaccccttg    1980
gggcctctaa acgggtcttg aggggttttt tgtgcccctc cggccggatt gctatctacc    2040
ggcattggcg cagaaaaaaa tgcctgatgc gacgctgcgc gtcttatact cccacatatg    2100
ccagattcag caacggatac ggcttcccca acttgcccac ttccatacgt gtcctcctta    2160
ccagaaattt atccttaagg tcgtcagcta tcctgcaggc gatctctcga tttcgatcaa    2220
gacattcctt aatggtcttt tctggacac cactaggggt cagaagtagt tcatcaaact    2280
ttcttccctc cctaatctca ttggttacct tgggctatcg aaacttaatt aaccagtcaa    2340
```

```
gtcagctact tggcgagatc gacttgtctg ggtttcgact acgctcagaa ttgcgtcagt    2400
caagttcgat ctggtccttg ctattgcacc cgttctccga ttacgagttt catttaaatc    2460
atgtgagcaa aaggccagca aaaggccagg aaccgtaaaa aggccgcgtt gctggcgttt    2520
ttccataggc tccgcccccc tgacgagcat cacaaaaatc gacgctcaag tcagaggtgg    2580
cgaaacccga caggactata aagataccag gcgtttcccc ctggaagctc cctcgtgcgc    2640
tctcctgttc cgaccctgcc gcttaccgga tacctgtccg cctttctccc ttcgggaagc    2700
gtggcgcttt ctcatagctc acgctgtagg tatctcagtt cggtgtaggt cgttcgctcc    2760
aagctgggct gtgtgcacga accccccgtt cagcccgacc gctgcgcctt atccggtaac    2820
tatcgtcttg agtccaaccc ggtaagacac gacttatcgc cactggcagc agccactggt    2880
aacaggatta gcagagcgag gtatgtaggc ggtgctacag agttcttgaa gtggtggcct    2940
aactacggct acactagaag aacagtattt ggtatctgcg ctctgctgaa gccagttacc    3000
ttcggaaaaa gagttggtag ctcttgatcc ggcaaacaaa ccaccgctgg tagcggtggt    3060
ttttttgttt gcaagcagca gattacgcgc agaaaaaaag gatctcaaga agatcctttg    3120
atcttttcta cggggtctga cgctcagtgg aacgaaaact cacgttaagg gattttggtc    3180
atgagattat caaaaaggat cttcacctag atccttttaa attaaaaatg aagttttaaa    3240
tcaatctaaa gtatatatga gtaaacttgg tctgacagtt accaatgctt aatcagtgag    3300
gcacctatct cagcgatctg tctatttcgt tcatccatag ttgcatttaa atttccgaac    3360
tctccaaggc cctcgtcgga aaatcttcaa acctttcgtc cgatccatct tgcaggctac    3420
ctctcgaacg aactatcgca agtctcttgg ccggccttgc gccttggcta ttgcttggca    3480
gcgcctatcg ccaggtatta ctccaatccc gaatatccga gatcgggatc accccagaga    3540
agttcaacct acatcctcaa tcccgatcta tccgagatcc gaggaatatc gaaatcgggg    3600
cgcgcctggt gtaccgagaa cgatcctctc agtgcgagtc tcgacgatcc atatcgttgc    3660
ttggcagtca gccagtcgga atccagcttg gacccaggga agtccaatcg tcagatattg    3720
tactcaagcc tggtcacggc agcgtaccga tctgttttaaa cctagatatt gatagtctga    3780
tcggtcaacg tataatcgag tcctagcttt tgcaaacatc tatcaagaga caggatcagc    3840
aggaggcttt cgcatgagta ttcaacattt ccgtgtcgcc cttattccct tttttgcggc    3900
attttgcctt cctgttttg ctcacccaga acgctggtg aaagtaaaag atgctgaaga    3960
tcagttgggt gcgcgagtgg gttacatcga actggatctc aacagcggta agatccttga    4020
gagttttcgc cccgaagaac gctttccaat gatgagcact tttaaagttc tgctatgtgg    4080
cgcggtatta tcccgtattg acgccgggca agagcaactc ggtcgccgca tacactattc    4140
tcagaatgac ttggttgagt attcaccagt cacagaaaag catcttacgg atggcatgac    4200
agtaagagaa ttatgcagtg ctgccataac catgagtgat aacactgcgg ccaacttact    4260
tctgacaacg attggaggac cgaaggagct aaccgctttt ttgcacaaca tgggggatca    4320
tgtaactcgc cttgatcgtt gggaaccgga gctgaatgaa gccataccaa acgacgagcg    4380
tgacaccacg atgcctgtag caatggcaac aaccttgcgt aaactattaa ctggcgaact    4440
acttactcta gcttcccggc aacagttgat agactggatg gaggcggata agttgcagg    4500 accacttctg cgctcggccc ttccggctgg ctggtttatt gctgataaat ctggagccgg    4560
tgagcgtggg tctcgcggta tcattgcagc actggggcca gatggtaagc cctcccgtat    4620
cgtagttatc tacacgacgg ggagtcaggc aactatggat gaacgaaata gacagatcgc    4680
```

| | | |
|---|---|---|
| tgagataggt gcctcactga ttaagcattg gtaaccgatt ctaggtgcat ggcgcagaa | 4740 | |
| aaaaatgcct gatgcgacgc tgcgcgtctt atactcccac atatgccaga ttcagcaacg | 4800 | |
| gatacggctt ccccaacttg cccacttcca tacgtgtcct ccttaccaga aatttatcct | 4860 | |
| taagatcccg aatcgtttaa actcgactct ggctctatcg aatctccgtc gtttcgagct | 4920 | |
| tacgcgaaca gccgtggcgc tcatttgctc gtcgggcatc gaatctcgtc agctatcgtc | 4980 | |
| agcttacctt tttggca | 4997 | |

```
<210> SEQ ID NO 90
<211> LENGTH: 5000
<212> TYPE: DNA
<213> ORGANISM: Artificial Sequence
<220> FEATURE:
<223> OTHER INFORMATION: Synthetic polymer.

<400> SEQUENCE: 90
```

| | | |
|---|---|---|
| gcgatcgcgg ctcccgacat cttggaccat tagctccaca ggtatcttct tccctctagt | 60 | |
| ggtcataaca gcagcttcag ctacctctca attcaaaaaa cccctcaaga cccgtttaga | 120 | |
| ggccccaagg ggttatgcta tcaatcgttg cgttacacac acaaaaaacc aacacacatc | 180 | |
| catcttcgat ggatagcgat tttattatct aactgctgat cgagtgtagc cagatctagt | 240 | |
| aatcaattac ggggtcatta gttcatagcc catatatgga gttccgcgtt acataactta | 300 | |
| cggtaaatgg cccgcctggc tgaccgccca acgaccccg cccattgacg tcaataatga | 360 | |
| cgtatgttcc catagtaacg ccaataggga ctttccattg acgtcaatgg gtggagtatt | 420 | |
| tacggtaaac tgcccacttg gcagtacatc aagtgtatca tatgccaagt acgccccta | 480 | |
| ttgacgtcaa tgacggtaaa tggcccgcct ggcattatgc ccagtacatg accttatggg | 540 | |
| actttcctac ttggcagtac atctacgtat tagtcatcgc tattaccatg ctgatgcggt | 600 | |
| tttggcagta catcaatggg cgtggatagc ggtttgactc acggggattt ccaagtctcc | 660 | |
| accccattga cgtcaatggg agtttgtttt ggcaccaaaa tcaacgggac tttccaaaat | 720 | |
| gtcgtaacaa ctccgcccca ttgacgcaaa tgggcggtag gcgtgtacgg tgggaggtct | 780 | |
| atataagcag agctggttta gtgaaccgtc agatcagatc tttgtcgatc ctaccatcca | 840 | |
| ctcgacacac ccgccagcag ccgctgccaa gcttccgagc tctcgaattc aaaggaggta | 900 | |
| cccaccatgc cgctgctgct actgctgccc ctgctgtggg cagggcgct agctgacatc | 960 | |
| gtgatgacac agagccctag ctctctggcc atgtccgtgg gccagaaggt gaccatgagc | 1020 | |
| tgcaagtcca gccagtctct gctgaactcc agcaaccaga agaactatct ggcttggtac | 1080 | |
| cagcagaagc ccggccagag ccccaagctg ctcgtgtact cgccagcac cagagagagc | 1140 | |
| ggcgtgcccg acagattcat cggcagcggc agcggaaccg acttcacact gaccatctcc | 1200 | |
| tccgtgcaag ccgaggatct ggccgactat ttctgccagc agcactacaa cacccctctg | 1260 | |
| acctttggag ccggcaccaa gctcgagatc aagcgcgcag atgctgctcc taccgtgagc | 1320 | |
| atcttcccgc cgtccagcga acaactcact agcggaggcg cgtcagtggt ctgcttcctt | 1380 | |
| aacaatttct accctaagga catcaacgtc aagtggaaga ttgacggatc ggaacgccag | 1440 | |
| aacggagtgc tgaactcatg gactgatcag gattccaaag actcgactta ctccatgtcc | 1500 | |
| agcaccctga ccctgaccaa agacgagtac gaaaggcaca ctcgtacac gtgcgaagcc | 1560 | |
| acccacaaga cttccacctc gcccatcgtg aagtccttca atcgcaatga gtgctagtga | 1620 | |
| gcggccgcgt ctagacctgc actgactgac tgatacaatc gatttctgga tccgcaggcc | 1680 | |
| tctcctagct tgactgactg agatacagcg taccttcagc tcacagacat gataagatac | 1740 | |

```
attgatgagt ttggacaaac cacaactaga atgcagtgaa aaaaatgctt tatttgtgaa    1800
atttgtgatg ctattgcttt atttgtaacc attataagct gcaataaaca agttaacaac    1860
aacaattgca ttcattttat gtttcaggtt caggggaggg tgtgggaggt tttttaaagc    1920
aagtaaaacc tctacaaatg tggtattggc ccatctctat cggtatcgta gcataacccc    1980
ttggggcctc taaacgggtc ttgaggggtt ttttgtgccc ctccggccgg attgctatct    2040
accggcattg gcgcagaaaa aaatgcctga tgcgacgctg cgcgtcttat actcccacat    2100
atgccagatt cagcaacgga tacggcttcc ccaacttgcc cacttccata cgtgtcctcc    2160
ttaccagaaa tttatcctta aggtcgtcag ctatcctgca ggcgatctct cgatttcgat    2220
caagacattc ctttaatggt cttttctgga caccactagg ggtcagaagt agttcatcaa    2280
actttcttcc ctccctaatc tcattggtta ccttgggcta tcgaaactta attaaccagt    2340
caagtcagct acttggcgag atcgacttgt ctgggtttcg actacgctca gaattgcgtc    2400
agtcaagttc gatctggtcc ttgctattgc acccgttctc cgattacgag tttcatttaa    2460
atcatgtgag caaaaggcca gcaaaaggcc aggaaccgta aaaaggccgc gttgctggcg    2520 ttttttccata ggctccgccc ccctgacgag catcacaaaa atcgacgctc aagtcagagg    2580
tggcgaaacc cgacaggact ataaagatac caggcgtttc ccctggaag ctccctcgtg    2640 cgctctcctg ttccgaccct gccgcttacc ggatacctgt ccgcctttct cccttcggga    2700
agcgtggcgc tttctcatag ctcacgctgt aggtatctca gttcggtgta ggtcgttcgc    2760
tccaagctgg gctgtgtgca cgaacccccc gttcagcccg accgctgcgc cttatccggt    2820
aactatcgtc ttgagtccaa cccggtaaga cacgacttat cgccactggc agcagccact    2880
ggtaacagga ttagcagagc gaggtatgta ggcggtgcta cagagttctt gaagtggtgg    2940
cctaactacg gctacactag aagaacagta tttggtatct gcgctctgct gaagccagtt    3000
accttcggaa aaagagttgg tagctcttga tccggcaaac aaaccaccgc tggtagcggt    3060
ggtttttttg tttgcaagca gcagattacg cgcagaaaaa aaggatctca agaagatcct    3120
ttgatctttt ctacggggtc tgacgctcag tggaacgaaa actcacgtta agggattttg    3180
gtcatgagat tatcaaaaag gatcttcacc tagatccttt taaattaaaa atgaagtttt    3240
aaatcaatct aaagtatata tgagtaaact tggtctgaca gttaccaatg cttaatcagt    3300
gaggcaccta tctcagcgat ctgtctattt cgttcatcca tagttgcatt taaatttccg    3360
aactctccaa ggccctcgtc ggaaaatctt caaacctttc gtccgatcca tcttgcaggc    3420
tacctctcga acgaactatc gcaagtctct ggccggcct tgcgccttgg ctattgcttg    3480
gcagcgccta tcgccaggta ttactccaat cccgaatatc cgagatcggg atcaccccag    3540
agaagttcaa cctacatcct caatcccgat ctatccgaga tccgaggaat atcgaaatcg    3600
gggcgcgcct ggtgtaccga gaacgatcct ctcagtgcga gtctcgacga tccatatcgt    3660
tgcttggcag tcagccagtc ggaatccagc ttgggaccca ggaagtccaa tcgtcagata    3720
ttgtactcaa gcctggtcac ggcagcgtac cgatctgttt aaacctagat attgatagtc    3780
tgatcggtca acgtataatc gagtcctagc ttttgcaaac atctatcaag agacaggatc    3840
agcaggaggc tttcgcatga gtattcaaca tttccgtgtc gcccttattc cttttttgc    3900 ggcattttgc cttcctgttt ttgctcaccc agaaacgctg gtgaaagtaa aagatgctga    3960
agatcagttg ggtgcgcgag tgggttacat cgaactggat ctcaacagcg gtaagatcct    4020
tgagagtttt cgccccgaag aacgctttcc aatgatgagc acttttaaag ttctgctatg    4080
```

| | |
|---|---|
| tggcgcggta ttatcccgta ttgacgccgg gcaagagcaa ctcggtcgcc gcatacacta | 4140 |
| ttctcagaat gacttggttg agtattcacc agtcacagaa aagcatctta cggatggcat | 4200 |
| gacagtaaga gaattatgca gtgctgccat aaccatgagt gataacactg cggccaactt | 4260 |
| acttctgaca acgattggag gaccgaagga gctaaccgct tttttgcaca acatgggcga | 4320 |
| tcatgtaact cgccttgatc gttgggaacc ggagctgaat gaagccatac caaacgacga | 4380 |
| gcgtgacacc acgatgcctg tagcaatggc aacaaccttg cgtaaactat taactggcga | 4440 |
| actacttact ctagcttccc ggcaacagtt gatagactgg atggaggcgg ataaagttgc | 4500 |
| aggaccactt ctgcgctcgg cccttccggc tggctggttt attgctgata aatctggagc | 4560 |
| cggtgagcgt gggtctcgcg gtatcattgc agcactgggg ccagatggta agccctcccg | 4620 |
| tatcgtagtt atctacacga cggggagtca ggcaactatg gatgaacgaa atagacagat | 4680 |
| cgctgagata ggtgcctcac tgattaagca ttggtaaccg attctaggtg cattggcgca | 4740 |
| gaaaaaatg cctgatgcga cgctgcgcgt cttatactcc cacatatgcc agattcagca | 4800 |
| acggatacgg cttccccaac ttgcccactt ccatacgtgt cctccttacc agaaatttat | 4860 |
| ccttaagatc ccgaatcgtt taaactcgac tctggctcta tcgaatctcc gtcgtttcga | 4920 |
| gcttacgcga acagccgtgg cgctcatttg ctcgtcgggc atcgaatctc gtcagctatc | 4980 |
| gtcagcttac cttttttggca | 5000 |

<210> SEQ ID NO 91
<211> LENGTH: 8353
<212> TYPE: DNA
<213> ORGANISM: Artificial Sequence
<220> FEATURE:
<223> OTHER INFORMATION: Synthetic polymer.

<400> SEQUENCE: 91

| | |
|---|---|
| gcgatcgcgg ctcccgacat cttggaccat tagctccaca ggtatcttct tccctctagt | 60 |
| ggtcataaca gcagcttcag ctacctctca attcaaaaaa ccccctcaaga cccgtttaga | 120 |
| ggccccaagg ggttatgcta tcaatcgttg cgttacacac acaaaaaacc aacacacatc | 180 |
| catcttcgat ggatagcgat tttattatct aactgctgat cgagtgtagc cagatctata | 240 |
| gtaatcaatt acggggtcat tagttcatag cccatatatg gagttccgcg ttacataact | 300 |
| tacggtaaat ggcccgcctg gctgaccgcc caacgacccc cgcccattga cgtcaataat | 360 |
| gacgtatgtt cccatagtaa cgccaatagg gactttccat tgacgtcaat gggtggacta | 420 |
| tttacggtaa actgcccact tggcagtaca tcaagtgtat catatgccaa gtacgccccc | 480 |
| tattgacgtc aatgacggta aatggcccgc ctggcattat gcccagtaca tgaccttatg | 540 |
| ggactttcct acttggcagt acatctacgt attagtcatc gctattacca tgcgtcgagg | 600 |
| tgagccccac gttctgcttc actctcccca tctcccccc ctcccacccc caattttgt | 660 |
| atttatttat tttttaatta ttttatgcag cgatggggc ggggggggg gggcgcgcg | 720 |
| ccaggcgggg cggggcgggg cgaggggcgg ggcggggcga ggcggagagg tgcggcggca | 780 |
| gccaatcaga gcggcgcgct ccgaaagttt cctttttatgg cgaggcggcg gcggcggcgg | 840 |
| ccctataaaa agcgaagcgc gcggcgggcg ggagtcgctg cgttgccttc gccccgtgcc | 900 |
| ccgctccgcg ccgcctcgcg ccgcccgccc cggctctgac tgaccgcgtt actcccacag | 960 |
| gtgagcgggc gggacggccc ttctccctcc gggctgtaat tagcgcttgg tttaatgacg | 1020 |
| gctcgttttct tttctgtggc tgcgtgaaag ccttaaaggg ctccgggagg gcctttgtgc | 1080 |
| ggggggagc ggctcgggg gtgcgtgcgt gtgtgtgtgc gtggggagcg ccgcgtgcgg | 1140 |

```
cccgcgctgc ccggcggctg tgagcgctgc gggcgcggcg cggggctttg tgcgctccgc    1200
gtgtgcgcga ggggagcgcg ggccgggggc ggtgccccgc ggtgcggggg ggctgcgagg    1260
ggaacaaagg ctgcgtgcgg ggtgtgtgcg tggggggtg agcagggggt gtgggcgcgg     1320
cggtcgggct gtaacccccc cctggcaccc ccctccccga gttgctgagc acggcccggc    1380
ttcgggtgcg gggctccgtg cggggcgtgg cgcggggctc gccgtgccgg gcggggggtg    1440
gcggcaggtg ggggtgccgg gcggggcggg gccgcctcgg gccggggagg gctcggggga    1500
ggggcgcggc ggccccggag cgccggcggc tgtcgaggcg cggcgagccg cagccattgc    1560
cttttatggt aatcgtgcga gagggcgcag ggacttcctt tgtcccaaat ctggcggagc    1620
cgaaatctgg gaggcgccgc cgcacccccct ctagcgggcg cgggcgaagc ggtgcggcgc   1680
cggcaggaag gaaatgggcg gggagggcct tcgtgcgtcg ccgcgccgcc gtccccttct    1740
ccatctccag cctcggggct gccgcagggg gacggctgcc ttcgggggg acggggcagg     1800 gcggggttcg gcttctggcg tgtgaccggc ggctttagag cctctgctaa ccatgttcat    1860
gccttcttct ttttcctaca gctcctgggc aacgtgctgg ttgttgtgct gtctcatcat    1920
tttggcaaag atctttgtcg atcctaccat ccactcgaca cacccgccag cggccgctgc    1980
caagcttccg agctctcgaa ttcaggaggt acccaccatg ggttggagcc tcatcttgct    2040
cttccttgtc gctgttgcta cgcgtgtcca ctcccaagtg cagctgcagc agagcggagc    2100
cgagctggtg aagcccggag ccagcgtgaa gatcagctgc aaggccagcg gctacgcctt    2160
ctccaactac tggatgaact gggtgaagca gagacccggc aagggactgg aatggatcgg    2220
ccagatctac cccggcgacg gagacaccaa ctacaacggc aagttcaagg gcaaagccac    2280
actgaccgcc gacaagagct ccagcaccgc ctacatgcag ctgagctctc tgaccagcga    2340
ggatagcgcc gtgtacttct gcgccagagg agactactgg ggccaaggca ccacactgac    2400
cgtctcgagc gctaagacga ctccaccgtc cgtgtacccg ctcgcgccag ttcggccgc    2460 tcagacgaac agcatggtga ccctcggctg cctcgtgaag ggttatttcc cagagccggt    2520
gaccgtgacg tggaactccg gctcactgtc atcgggcgtg cacacttttc cagcagtgct    2580
gcagtcggac ctttacaccc tcagctcgtc cgtcaccgtc ccttcatcaa cttggcctag    2640
ccagaccgtg acttgcaatg tcgcccaccc ggcgtccagc actaaggtgg acaagaagat    2700
ccaccaccat caccatcacc atcaccatca ctagagagcg gccgcgtcta gacctgcact    2760
gactgactga tacgctagct tgactgactg agatacagcg taccttcagc tcacagacat    2820
gataagatac attgatgagt ttggacaaac cacaactaga atgcagtgaa aaaaatgctt    2880
tatttgtgaa atttgtgatg ctattgcttt atttgtaacc attataagct gcaataaaca    2940
agttaacaac aacaattgca ttcattttat gtttcaggtt caggggagg tgtgggaggt     3000 tttttaaagc aagtaaaacc tctacaaatg tggtattggc ccatctctat cggtatcgta    3060
gcataacccc ttgggcctc taaacgggtc ttgaggggtt ttttgtgccc ctcgggccgg     3120
attgctatct accggcattg gcgcagaaaa aaatgcctga tgcgacgctg cgcgtcttat    3180
actcccacat atgccagatt cagcaacgga tacggcttcc ccaacttgcc cacttccata    3240
cgtgtcctcc ttaccagaaa tttatcctta aggtcgtcag ctatcctgca ggcgatctct    3300
cgatttcgat caagacattc ctttaatggt cttttctgga caccactagg ggtcagaagt    3360
agttcatcaa actttcttcc ctccctaatc tcattggtta ccttgggcta tcgaaactta    3420
attaaccagt caagtcagct acttggcgag atcgacttgt ctgggtttcg actacgctca    3480
```

```
gaattgcgtc agtcaagttc gatctggtcc ttgctattgc acccgttctc cgattacgag    3540
tttcatttaa atcatgtgag caaaaggcca gcaaaaggcc aggaaccgta aaaaggccgc    3600
gttgctggcg ttttccata ggctccgccc ccctgacgag catcacaaaa atcgacgctc     3660
aagtcagagg tggcgaaacc cgacaggact ataaagatac caggcgtttc ccctggaag    3720 ctccctcgtg cgctctcctg ttccgaccct gccgcttacc ggatacctgt ccgcctttct    3780
cccttcggga agcgtggcgc tttctcatag ctcacgctgt aggtatctca gttcggtgta    3840
ggtcgttcgc tccaagctgg gctgtgtgca cgaaccccc gttcagcccg accgctgcgc     3900
cttatccggt aactatcgtc ttgagtccaa cccggtaaga cacgacttat cgccactggc    3960
agcagccact ggtaacagga ttagcagagc gaggtatgta ggcggtgcta cagagttctt    4020
gaagtggtgg cctaactacg gctacactag aagaacagta tttggtatct gcgctctgct    4080
gaagccagtt accttcggaa aaagagttgg tagctcttga tccggcaaac aaaccaccgc    4140
tggtagcggt ggtttttttg tttgcaagca gcagattacg cgcagaaaaa aaggatctca    4200
agaagatcct ttgatctttt ctacgggtc tgacgctcag tggaacgaaa actcacgtta     4260
agggattttg gtcatgagat tatcaaaaag gatcttcacc tagatccttt taaattaaaa    4320
atgaagtttt aaatcaatct aaagtatata tgagtaaact tggtctgaca gttaccaatg    4380
cttaatcagt gaggcaccta tctcagcgat ctgtctattt cgttcatcca tagttgcatt    4440
taaatttccg aactctccaa ggccctcgtc ggaaaatctt caaaccttc gtccgatcca    4500 tcttgcaggc tacctctcga acgaactatc gcaagtctct tggccggcct tgcgccttgg    4560
ctattgcttg gcagcgccta tcgccaggta ttactccaat cccgaatatc cgagatcggg    4620
atcacccgag agaagttcaa cctacatcct caatcccgat ctatccgaga tccgaggaat    4680
atcgaaatcg gggcgcgcct ggcctccgcg ccggggtttttg gcgcctcccg cgggcgcccc    4740
cctcgtcacg gcgagcgctg ccacgtcaga cgaagggcgc aggagcgtcc tgatccttcc    4800
gcccggacgc tcaggacagc ggcccgctgc tcataagact cggccttaga accccagtat    4860
cagcagaagg acatttagg acgggacttg ggtgactcta gggcactggt tttctttcca    4920
gagagcggaa caggcgagga aaagtagtcc cttctcggcg attctgcgga gggatctccg    4980
tggggcggtg aacgccgatg attatataag gacgcgccgg gtgtggcaca gctagttccg    5040
tcgcagccgg gatttgggtc gcggttcttg tttgtggatc gctgtgatcg tcacttggtg    5100
agtagcgggc tgctgggctg gccgggggctt tcgtggccgc cgggccgctc ggtgggacgg    5160
aagcgtgtgg agagaccgcc aagggctgta gtctgggtcc gcgagcaagg ttgccctgaa    5220
ctgggggttg gggggagcgc agcaaaatgg cggctgttcc cgagtcttga atggaagacg    5280
cttgtgaggc gggctgtgag gtcgttgaaa caaggtgggg ggcatggtgg gcggcaagaa    5340
cccaaggtct tgagcccttc gctaatgcgg gaaagctctt attcgggtga gatgggctgg    5400
gcaccatctg gggaccctga cgtgaagttt gtcactgact ggagaactcg gtttgtcgtc    5460
tgttgcgggg gcggcagtta tggcggtgcc gttgggcagt gcacccgtac ctttgggagc    5520
gcgcgccctc gtcgtgtcgt gacgtcaccc gttctgttgg cttataatgc agggtggggc    5580
cacctgccga taggtgtgcg gtaggctttt ctccgtcgca ggacgcaggg ttcgggccta    5640
gggtaggctc tcctgaatcg acaggcgccg gacctctggt gagggagggg ataagtgagg    5700
cgtcagtttc tttggtcggt tttatgtacc tatcttctta agtagctgaa gctccggttt    5760
tgaactatgc gctcggggtt ggcgagtgtg tttttgtgaag ttttttaggc accttttgaa    5820
atgtaatcat ttgggtcaat atgtaatttt cagtgttaga cttgtaaatt gtccgctaaa    5880
```

-continued

```
ttctggccgt ttttggcttt tttgttagac aacatgggta aaaagcctga actcaccgcg    5940
acgtctgtcg agaagtttct gatcgaaaag ttcgacagcg tctccgacct gatgcagctc    6000
tcggagggcg aagaatctcg tgctttcagc ttcgatgtag agggcgtgg atatgtcctg     6060
cgggtaaata gctgcgccga tggtttctac aaagatcgtt atgtttatcg cactttgca     6120
tccgccgcgc tcccgattcc ggaagtgctt gacattgggg agttcagcga gagcctgacc    6180
tattgcatct cccgccgtgc acagggtgtc acgttgcaag acctgcctga aaccgaactg    6240
cccgctgttc tgcagccggt cgcggaggca atggatgcca tcgctgccgc cgatcttagc    6300
cagacgagcg ggttcggccc attcggaccg caaggaatcg gtcaatacac tacatggcgt    6360
gatttcatat gcgcgattgc tgatccccat gtgtatcact ggcaaactgt gatggacgac    6420
accgtcagtg cgtccgtcgc gcaggctctc gatgagctga tgctttgggc cgaggactgc    6480
cccgaagtcc ggcacctcgt gcacgcggat ttcggctcca acaatgtcct gacggacaat    6540
ggccgcataa cagcggtcat tgactggagc gaggcgatgt tcggggattc ccaatacgag    6600
gtcgccaaca tcttcttctg gaggccgtgg ttggcttgta tggagcagca gacgcgctac    6660
ttcgagcgga ggcatccgga gcttgcagga tcgccccgc tccggcgta tatgctccgc       6720
attggtcttg accaactcta tcagagcttg gttgacggca atttcgatga tgcagcttgg    6780
gcgcagggtc gatgcgacgc aatcgtccga tccggagccg ggactgtcgg gcgtacacaa    6840
atcgcccgca gaagcgccgc cgtctggacc gatggctgtg tagaagtact cgccgatagt    6900
ggaaaccgac gccccagcac tcgtccgagg gcaaaggaat aagctagtat gtaagcctag    6960
tcttagataa taaaatcgct atccatcgaa gatggatgtg tgttggtttt tgtgtgtgt     7020
aacgctaggc gcgcctggtg taccgagaac gatcctctca gtgcgagtct cgacgatcca    7080
tatcgttgct tggcagtcag ccagtcggaa tccagcttgg gacccaggaa gtccaatcgt    7140
cagatattgt actcaagcct ggtcacggca gcgtaccgat ctgtttaaac ctagatattg    7200
atagtctgat cggtcaacgt ataatcgagt cctagctttt gcaaacatct atcaagagac    7260
aggatcagca ggaggctttc gcatgattga acaagatgga ttgcacgcag gttctccggc    7320
ggcttgggtg gagaggctat tcggctatga ctgggcacaa cagacaatcg gctgctctga    7380
tgccgccgtg ttccggctgt cagcgcaggg gcgtccggtt cttttttgtca agaccgacct    7440
gtccggtgcc ctgaatgaac tgcaagacga ggcagcgcgg ctatcgtggc tggcgacgac    7500
gggcgttcct tgcgcggctg tgctcgacgt tgtcactgaa gcgggaaggg actggctgct    7560
attgggcgaa gtgccggggc aggatctcct gtcatctcac cttgctcctg ccgagaaagt    7620
atccatcatg gctgatgcaa tgcggcggct gcatacgctt gatccggcta cctgcccatt    7680
cgaccaccaa gcgaaacatc gcatcgagcg agcacgtact cggatggaag ccggtcttgt    7740
cgatcaggat gatctggacg aagagcatca ggggctcgcg ccagccgaac tgttcgccag    7800
gctcaaggcg tctatgcccg acggcgagga tctcgtcgtg acccacgcg atgcctgctt      7860
gccgaatatc atggtggaaa atggccgctt ttctggattc atcgactgtg gccgtctggg    7920
tgtggcggac cgctatcagg acatagcgtt ggctacccgt gatattgctg aagagcttgg    7980
cggcgaatgg gctgaccgct tccttgtgct ttacggtatc gccgcgccg attcgcagcg     8040
catcgccttc tatcgccttc ttgacgagtt cttctgaccg attctaggtg cattggcgca    8100
gaaaaaaatg cctgatgcga cgctgcgcgt cttatactcc cacatatgcc agattcagca    8160
acggatacgg cttccccaac ttgcccactt ccatacgtgt cctccttacc agaaatttat    8220
```

```
ccttaaggtc gtttaaactc gactctggct ctatcgaatc tccgtcgttt cgagcttacg    8280
cgaacagccg tggcgctcat ttgctcgtcg ggcatcgaat ctcgtcagct atcgtcagct    8340
tacctttttg gca                                                       8353

<210> SEQ ID NO 92
<211> LENGTH: 8386
<212> TYPE: DNA
<213> ORGANISM: Artificial Sequence
<220> FEATURE:
<223> OTHER INFORMATION: Synthetic polymer.

<400> SEQUENCE: 92
gcgatcgcgg ctcccgacat cttggaccat tagctccaca ggtatcttct tccctctagt      60
ggtcataaca gcagcttcag ctacctctca attcaaaaaa cccctcaaga cccgtttaga     120
ggccccaagg ggttatgcta tcaatcgttg cgttacacac acaaaaaacc aacacacatc     180
catcttcgat ggatagcgat tttattatct aactgctgat cgagtgtagc cagatctata     240
gtaatcaatt acggggtcat tagttcatag cccatatatg gagttccgcg ttacataact     300
tacggtaaat ggcccgcctg gctgaccgcc caacgacccc cgcccattga cgtcaataat     360
gacgtatgtt cccatagtaa cgccaatagg gactttccat tgacgtcaat gggtggacta     420
tttacggtaa actgcccact tggcagtaca tcaagtgtat catatgccaa gtacgccccc     480
tattgacgtc aatgacggta aatggcccgc ctggcattat gcccagtaca tgaccttatg     540
ggactttcct acttggcagt acatctacgt attagtcatc gctattacca tgcgtcgagg     600
tgagccccac gttctgcttc actctcccca tctcccccccc ctcccacccc caatttgt      660 atttatttat tttttaatta ttttatgcag cgatgggggc gggggggggg ggggcgcgcg     720
ccaggcgggg cggggcgggg cgaggggcgg ggcggggcga ggcggagagg tgcggcggca     780
gccaatcaga gcggcgcgct ccgaaagttt ccttttatgg cgaggcggcg gcggcggcgg     840
ccctataaaa agcgaagcgc gcggcgggcg ggagtcgctg cgttgccttc gccccgtgcc     900
ccgctccgcg ccgcctcgcg ccgcccgccc cggctctgac tgaccgcgtt actcccacag     960
gtgagcgggc gggacggccc ttctccctcc gggctgtaat tagcgcttgg tttaatgacg    1020
gctcgtttct tttctgtggc tgcgtgaaag ccttaaaggg ctccgggagg gcctttgtgc    1080 ggggggggagc ggctcggggg gtgcgtgcgt gtgtgtgtgc gtggggagcg ccgcgtgcgg    1140
cccgcgctgc ccggcggctg tgagcgctgc gggcgcggcg cggggctttg tgcgctccgc    1200
gtgtgcgcga gggagcgcg ggccggggc ggtgccccgc ggtgcggggg ggctgcgagg    1260
ggaacaaagg ctgcgtgcgg ggtgtgtgcg tgggggggtg agcagggggt gtgggcgcgg    1320
cggtcgggct gtaaccccc cctggcaccc ccctccccga gttgctgagc acggcccggc    1380
ttcgggtgcg gggctccgtg cggggcgtgg cgcgggctc gccgtgccgg gcgggggtg     1440 gcggcaggtg ggggtgccgg gcgggggcggg ccgcctcgg gccggggagg gctcggggga    1500
ggggcgcggc ggccccggag cgccggcggc tgtcgaggcg cggcgagccg cagccattgc    1560
cttttatggt aatcgtgcga gagggcgcag ggacttcctt tgtcccaaat ctggcggagc    1620
cgaaatctgg gagcgccgc cgcacccct ctagcgggcg cggcgaagc ggtgcggcgc       1680 cggcaggaag gaaatgggcg gggagggcct tcgtgcgtcg ccgcgccgcc gtccccttct    1740
ccatctccag cctcggggct gccgcagggg gacggctgcc ttcgggggg acggggcagg    1800 gcggggttcg gcttctggcg tgtgaccggc ggctttagag cctctgctaa ccatgttcat    1860
gccttcttct ttttcctaca gctcctgggc aacgtgctgg ttgttgtgct gtctcatcat    1920
```

| | |
|---|---|
| tttggcaaag atctttgtcg atcctaccat ccactcgaca cacccgccag cggccgctgc | 1980 |
| caagcttccg agctctcgaa ttcaggaggt acccaccatg agggtccccg ctcagctcct | 2040 |
| ggggctcctg ctgctctggc tcccaggcgc gcgatgtgac atcgtgatga cacagagccc | 2100 |
| tagctctctg gccatgtccg tgggccagaa ggtgaccatg agctgcaagt ccagccagtc | 2160 |
| tctgctgaac tccagcaacc agaagaacta tctggcttgg taccagcaga agcccggcca | 2220 |
| gagccccaag ctgctcgtgt acttcgccag caccagagag agcggcgtgc ccgacagatt | 2280 |
| catcggcagc ggcagcggaa ccgacttcac actgaccatc tcctccgtgc aagccgagga | 2340 |
| tctggccgac tatttctgcc agcagcacta acacccct ctgacctttg gagccggcac | 2400 |
| caagctcgag atcaagcgcg cagatgctgc tcctaccgtg agcatcttcc cgccgtccag | 2460 |
| cgaacaactc actagcggag gcgcgtcagt ggtctgcttc cttaacaatt tctaccctaa | 2520 |
| ggacatcaac gtcaagtgga agattgacgg atcggaacgc cagaacggag tgctgaactc | 2580 |
| atggactgat caggattcca agactcgac ttactccatg tccagcaccc tgaccctgac | 2640 |
| caaagacgag tacgaaaggc acaactcgta cacgtgcgaa gccacccaca agacttccac | 2700 |
| ctcgcccatc gtgaagtcct tcaatcgcaa tgagtgctag tgagcggccg cgtctagacc | 2760 |
| tgcactgact gactgataca atcgatttct ggatccgcag gcctctgcta gcttgactga | 2820 |
| ctgagataca gcgtaccttc agctcacaga catgataaga tacattgatg agtttggaca | 2880 |
| aaccacaact agaatgcagt gaaaaaaatg ctttatttgt gaaatttgtg atgctattgc | 2940 |
| tttatttgta accattataa gctgcaataa acaagttaac aacaacaatt gcattcattt | 3000 |
| tatgtttcag gttcagggg aggtgtggga ggttttttaa agcaagtaaa acctctacaa | 3060 |
| atgtggtatt ggcccatctc tatcggtatc gtagcataac cccttggggc ctctaaacgg | 3120 |
| gtcttgaggg gttttttgtg cccctcgggc cggattgcta tctaccggca ttggcgcaga | 3180 |
| aaaaaatgcc tgatgcgacg ctgcgcgtct tatactccca catatgccag attcagcaac | 3240 |
| ggatacggct tccccaactt gcccacttcc atacgtgtcc tccttaccag aaatttatcc | 3300 |
| ttaaggtcgt cagctatcct gcaggcgatc tctcgatttc gatcaagaca ttcctttaat | 3360 |
| ggtcttttct ggacaccact aggggtcaga agtagttcat caaactttct tccctcccta | 3420 |
| atctcattgg ttaccttggg ctatcgaaac ttaattaacc agtcaagtca gctacttggc | 3480 |
| gagatcgact tgtctgggtt tcgactacgc tcagaattgc gtcagtcaag ttcgatctgg | 3540 |
| tccttgctat tgcacccgtt ctccgattac gagtttcatt taaatcatgt gagcaaaagg | 3600 |
| ccagcaaaag gccaggaacc gtaaaaaggc cgcgttgctg gcgttttcc ataggctccg | 3660 |
| cccccctgac gagcatcaca aaaatcgacg ctcaagtcag aggtggcgaa acccgacagg | 3720 |
| actataaaga taccaggcgt ttccccctgg aagctccctc gtgcgctctc ctgttccgac | 3780 |
| cctgccgctt accggatacc tgtccgcctt tctcccttcg ggaagcgtgg cgctttctca | 3840 |
| tagctcacgc tgtaggtatc tcagttcggt gtaggtcgtt cgctccaagc tgggctgtgt | 3900 |
| gcacgaaccc cccgttcagc ccgaccgctg cgccttatcc ggtaactatc gtcttgagtc | 3960 |
| caacccggta agacacgact tatcgccact ggcagcagcc actggtaaca ggattagcag | 4020 |
| agcgaggtat gtaggcggtg ctacagagtt cttgaagtgg tggcctaact acggctacac | 4080 |
| tagaagaaca gtatttggta tctgcgctct gctgaagcca gttaccttcg gaaaaagagt | 4140 |
| tggtagctct tgatccggca aacaaaccac cgctggtagc ggtggttttt tgtttgcaa | 4200 |
| gcagcagatt acgcgcagaa aaaaaggatc tcaagaagat cctttgatct tttctacggg | 4260 |

```
gtctgacgct cagtggaacg aaaactcacg ttaagggatt ttggtcatga gattatcaaa    4320
aaggatcttc acctagatcc ttttaaatta aaaatgaagt tttaaatcaa tctaaagtat    4380
atatgagtaa acttggtctg acagttacca atgcttaatc agtgaggcac ctatctcagc    4440
gatctgtcta tttcgttcat ccatagttgc atttaaattt ccgaactctc caaggccctc    4500
gtcggaaaat cttcaaacct ttcgtccgat ccatcttgca ggctacctct cgaacgaact    4560
atcgcaagtc tcttggccgg ccttgcgcct tggctattgc ttggcagcgc ctatcgccag    4620
gtattactcc aatcccgaat atccgagatc gggatcaccc gagagaagtt caacctacat    4680
cctcaatccc gatctatccg agatccgagg aatatcgaaa tcggggcgcg cctggcctcc    4740
gcgccgggtt ttggcgcctc ccgcgggcgc cccctcgtc acggcgagcg ctgccacgtc     4800
agacgaaggg cgcaggagcg tcctgatcct tccgcccgga cgctcaggac agcggcccgc    4860
tgctcataag actcggcctt agaaccccag tatcagcaga aggacatttt aggacgggac    4920
ttgggtgact ctagggcact ggttttcttt ccagagagcg aacaggcga ggaaaagtag     4980 tcccttctcg gcgattctgc ggagggatct ccgtggggcg gtgaacgccg atgattatat    5040
aaggacgcgc cgggtgtggc acagctagtt ccgtcgcagc cgggatttgg gtcgcggttc    5100
ttgtttgtgg atcgctgtga tcgtcacttg gtgagtagcg ggctgctggg ctggccgggg    5160
ctttcgtggc cgccgggccg ctcggtggga cggaagcgtg tggagagacc gccaagggct    5220
gtagtctggg tccgcgagca aggttgccct gaactggggg ttgggggggag cgcagcaaaa   5280 tggcggctgt tcccgagtct tgaatggaag acgcttgtga ggcgggctgt gaggtcgttg    5340
aaacaaggtg gggggcatgg tgggcggcaa gaacccaagg tcttgagccc ttcgctaatg    5400
cgggaaagct cttattcggg tgagatgggc tgggcaccat ctggggaccc tgacgtgaag    5460
tttgtcactg actggagaac tcggtttgtc gtctgttgcg ggggcggcag ttatggcggt    5520
gccgttgggc agtgcacccg taccttttggg agcgcgcgcc ctcgtcgtgt cgtgacgtca    5580
cccgttctgt tggcttataa tgcagggtgg ggccacctgc cggtaggtgt gcggtaggct    5640
tttctccgtc gcaggacgca gggttcgggc ctagggtagg ctctcctgaa tcgacaggcg    5700
ccggacctct ggtgagggga gggataagtg aggcgtcagt ttctttggtc ggttttatgt    5760
acctatcttc ttaagtagct gaagctccgg ttttgaacta tgcgctcggg gttggcgagt    5820
gtgttttgtg aagtttttta ggcacctttt gaaatgtaat catttgggtc aatatgtaat    5880
tttcagtgtt agacttgtaa attgtccgct aaattctggc cgttttttggc tttttttgtta   5940 gacaacatgg gtaaaaagcc tgaactcacc gcgacgtctg tcgagaagtt tctgatcgaa    6000
aagttcgaca gcgtctccga cctgatgcag ctctcggagg gcgaagaatc tcgtgctttc    6060
agcttcgatg taggagggcg tggatatgtc ctgcgggtaa atagctgcgc cgatggtttc    6120
tacaaagatc gttatgttta tcggcacttt gcatccgccg cgctcccgat tccggaagtg    6180
cttgacattg gggagttcag cgagagcctg acctattgca tctcccgccg tgcacagggt    6240
gtcacgttgc aagacctgcc tgaaaccgaa ctgcccgctg ttctgcagcc ggtcgcggag    6300
gcaatggatg ccatcgctgc cgccgatctt agccagacga gcgggttcgg cccattcgga    6360
ccgcaaggaa tcggtcaata cactacatgg cgtgatttca tatgcgcgat tgctgatccc    6420
catgtgtatc actggcaaac tgtgatggac gacaccgtca gtgcgtccgt cgcgcaggct    6480
ctcgatgagc tgatgctttg gccgaggac tgccccgaag tccggcacct cgtgcacgcg     6540
gatttcggct ccaacaatgt cctgacggac aatggccgca taacagcggt cattgactgg    6600
agcgaggcga tgttcgggga ttcccaatac gaggtcgcca acatcttctt ctggaggccg    6660
```

-continued

```
tggttggctt gtatggagca gcagacgcgc tacttcgagc ggaggcatcc ggagcttgca    6720
ggatcgcccc ggctccgggc gtatatgctc cgcattggtc ttgaccaact ctatcagagc    6780
ttggttgacg gcaatttcga tgatgcagct tgggcgcagg gtcgatgcga cgcaatcgtc    6840
cgatccggag ccgggactgt cgggcgtaca caaatcgccc gcagaagcgc cgccgtctgg    6900
accgatggct gtgtagaagt actcgccgat agtggaaacc gacgcccag cactcgtccg     6960 agggcaaagg aataagctag tatgtaagcc tagtcttaga taataaaatc gctatccatc    7020
gaagatggat gtgtgttggt tttttgtgtg tgtaacgcta ggcgcgcctg gtgtaccgag    7080
aacgatcctc tcagtgcgag tctcgacgat ccatatcgtt gcttggcagt cagccagtcg    7140
gaatccagct tgggacccag gaagtccaat cgtcagatat tgtactcaag cctggtcacg    7200
gcagcgtacc gatctgttta aacctagata ttgatagtct gatcggtcaa cgtataatcg    7260
agtcctagct tttgcaaaca tctatcaaga gacaggatca gcaggaggct ttcgcatgat    7320
tgaacaagat ggattgcacg caggttctcc ggcggcttgg gtggagaggc tattcggcta    7380
tgactgggca caacagacaa tcggctgctc tgatgccgcc gtgttccggc tgtcagcgca    7440
ggggcgtccg gttcttttg tcaagaccga cctgtccggt gccctgaatg aactgcaaga     7500
cgaggcagcg cggctatcgt ggctggcgac gacgggcgtt ccttgcgcgg ctgtgctcga    7560
cgttgtcact gaagcgggaa gggactggct gctattgggc gaagtgccgg ggcaggatct    7620
cctgtcatct caccttgctc ctgccgagaa agtatccatc atggctgatg caatgcggcg    7680
gctgcatacg cttgatccgg ctacctgccc attcgaccac caagcgaaac atcgcatcga    7740
gcgagcacgt actcggatgg aagccggtct tgtcgatcag gatgatctgg acgaagagca    7800 tcagggctc gcgccagccg aactgttcgc caggctcaag gcgtctatgc ccgacggcga    7860
ggatctcgtc gtgacccacg gcgatgcctg cttgccgaat atcatggtgg aaaatggccg    7920
cttttctgga ttcatcgact gtggccgtct gggtgtggcg gaccgctatc aggacatagc    7980
gttggctacc cgtgatattg ctgaagagct tggcggcgaa tgggctgacc gcttccttgt    8040
gctttacggt atcgccgcgc ccgattcgca gcgcatcgcc ttctatcgcc ttcttgacga    8100
gttcttctga ccgattctag gtgcattggc gcagaaaaaa atgcctgatg cgacgctgcg    8160
cgtcttatac tcccacatat gccagattca gcaacggata cggcttcccc aacttgccca    8220
cttccatacg tgtcctcctt accagaaatt tatccttaag gtcgtttaaa ctcgactctg    8280
gctctatcga atctccgtcg tttcgagctt acgcgaacag ccgtggcgct catttgctcg    8340
tcgggcatcg aatctcgtca gctatcgtca gcttaccttt ttggca                   8386
```

<210> SEQ ID NO 93
<211> LENGTH: 11138
<212> TYPE: DNA
<213> ORGANISM: Artificial Sequence
<220> FEATURE:
<223> OTHER INFORMATION: Synthetic polymer.

<400> SEQUENCE: 93

```
gcgatcgcgg ctccccgacat cttggaccat tagctccaca ggtatcttct tccctctagt     60
ggtcataaca gcagcttcag ctacctctca attcaaaaaa cccctcaaga cccgtttaga    120
ggccccaagg ggttatgcta tcaatcgttg cgttacacac acaaaaaacc aacacacatc    180
catcttcgat ggatagcgat tttattatct aactgctgat cgagtgtagc cagatctata    240
gtaatcaatt acggggtcat tagttcatag cccatatatg gagttccgcg ttacataact    300
```

```
tacggtaaat ggcccgcctg gctgaccgcc caacgacccc cgcccattga cgtcaataat    360
gacgtatgtt cccatagtaa cgccaatagg gactttccat tgacgtcaat gggtggacta    420
tttacggtaa actgcccact tggcagtaca tcaagtgtat catatgccaa gtacgccccc    480
tattgacgtc aatgacggta aatggcccgc ctggcattat gcccagtaca tgaccttatg    540
ggactttcct acttggcagt acatctacgt attagtcatc gctattacca tgcgtcgagg    600
tgagccccac gttctgcttc actctcccca tctccccccc ctcccacccc caattttgt     660 atttatttat tttttaatta ttttatgcag cgatggggggc gggggggggg ggggcgcgcg    720
ccaggcgggg cggggcgggg cgaggggcgg ggcggggcga ggcggagagg tgcggcggca    780
gccaatcaga gcggcgcgct ccgaaagttt ccttttatgg cgaggcggcg gcggcggcgg    840
ccctataaaa agcgaagcgc gcggcgggcg ggagtcgctg cgttgccttc gccccgtgcc    900
ccgctccgcg ccgcctcgcg ccgcccgccc cggctctgac tgaccgcgtt actcccacag    960
gtgagcgggc gggacggccc ttctccctcc gggctgtaat tagcgcttgg tttaatgacg   1020
gctcgtttct tttctgtggc tgcgtgaaag ccttaaaggg ctccgggagg cctttgtgc    1080 gggggggagc ggctcggggg gtgcgtgcgt gtgtgtgtgc gtggggagcg ccgcgtgcgg   1140
cccgcgctgc ccggcggctg tgagcgctgc gggcgcggcg cggggcttg tgcgctccgc     1200 gtgtgcgcga ggggagcgcg ggccggggc ggtgccccgc ggtgcggggg ggctgcgagg    1260
ggaacaaagg ctgcgtgcgg ggtgtgtgcg tggggggtg agcagggggt gtgggcgcg     1320 cggtcgggct gtaaccccccc cctggcaccc ccctccccga gttgctgagc acggcccggc    1380
ttcgggtgcg gggctccgtg cggggcgtgg cgcggggctc gccgtgccgg gcgggggtg     1440 gcggcaggtg ggggtgccgg gcggggcggg gccgcctcgg gccggggagg gctcggggga   1500
ggggcgcggc ggccccggag cgccggcggc tgtcgaggcg cggcgagccg cagccattgc    1560
cttttatggt aatcgtgcga gagggcgcag ggacttcctt tgtcccaaat ctggcggagc    1620
cgaaatctgg gaggcgccgc cgcacccccct ctagcgggcg cgggcgaagc ggtgcggcgc    1680
cggcaggaag gaaatgggcg gggagggcct tcgtgcgtcg ccgcgccgcc gtccccttct    1740
ccatctccag cctcggggct gccgcagggg gacggctgcc ttcgggggg acggggcagg    1800 gcggggttcg gcttctggcg tgtgaccggc ggctttagag cctctgctaa ccatgttcat    1860
gccttcttct ttttcctaca gctcctgggc aacgtgctgg ttgttgtgct gtctcatcat    1920
tttggcaaag atctttgtcg atcctaccat ccactcgaca cacccgccag cggccgctgc    1980
caagcttccg agctctcgaa ttcaggaggt acccaccatg agggtccccg ctcagctcct    2040
ggggctcctg ctgctctggc tcccaggcgc gcgatgtgac atcgtgatga cacagagccc    2100
tagctctctg gccatgtccg tgggccagaa ggtgaccatg agctgcaagt ccagccagtc    2160
tctgctgaac tccagcaacc agaagaacta tctggcttgg taccagcaga agcccggcca    2220
gagccccaag ctgctcgtgt acttcgccag caccagagag agcggcgtgc ccgacagatt    2280
catcggcagc ggcagcggaa ccgacttcac actgaccatc cctccgtgc aagccgagga    2340 tctggccgac tatttctgcc agcagcacta caacacccct ctgacctttg gagccggcac    2400
caagctcgag atcaagcgcg cagatgctgc tcctaccgtg agcatcttcc cgccgtccag    2460
cgaacaactc actagcggag gcgcgtcagt ggtctgcttc cttaacaatt tctaccctaa    2520
ggacatcaac gtcaagtgga agattgacgg atcggaacgc cagaacggag tgctgaactc    2580
atggactgat caggattcca aagactcgac ttactccatg tccagcaccc tgaccctgac    2640
caaagacgag tacgaaaggc acaactcgta cacgtgcgaa gccacccaca agacttccac    2700
```

```
ctcgcccatc gtgaagtcct tcaatcgcaa tgagtgctag tgagcggccg cgtctagacc    2760
tgcactgact gactgataca atcgatttct ggatccgcag gcctctgcta gcttgactga    2820
ctgagataca gcgtaccttc agctcacaga catgataaga tacattgatg agtttggaca    2880
aaccacaact agaatgcagt gaaaaaaatg ctttatttgt gaaatttgtg atgctattgc    2940
tttatttgta accattataa gctgcaataa acaagttaac aacaacaatt gcattcattt    3000
tatgtttcag gttcagggg aggtgtggga ggttttttaa agcaagtaaa acctctacaa    3060
atgtggtatt ggcccatctc tatcggtatc gtagcataac cccttggggc ctctaaacgg    3120
gtcttgaggg gttttttgtg cccctcgggc cggattgcta tctaccggca ttggcgcaga    3180
aaaaaatgcc tgatgcgacg ctgcgcgtct tatactccca catatgccag attcagcaac    3240
ggatacggct tccccaactt gcccacttcc atacgtgtcc tccttaccag aaatttatcc    3300
ttaaggtcgt cagctatcct gcaggatagt aatcaattac ggggtcatta gttcatagcc    3360
catatatgga gttccgcgtt acataactta cggtaaatgg cccgcctggc tgaccgccca    3420
acgaccccg cccattgacg tcaataatga cgtatgttcc catagtaacg ccaatagga    3480
cttttccattg acgtcaatgg gtggactatt tacggtaaac tgcccacttg gcagtacatc    3540
aagtgtatca tatgccaagt acgcccccta ttgacgtcaa tgacggtaaa tggcccgcct    3600
ggcattatgc ccagtacatg accttatggg actttcctac ttggcagtac atctacgtat    3660
tagtcatcgc tattaccatg cgtcgaggtg agccccacgt tctgcttcac tctccccatc    3720
tcccccccct ccccaccccc aattttgtat ttatttattt tttaattatt ttatgcagcg    3780
atggggcgg ggggggggg ggcgcgcgcc aggcggggcg gggcggggcg aggggcgggg    3840
cggggcgagg cggagaggtg cggcggcagc caatcagagc ggcgcgctcc gaaagtttcc    3900
ttttatggcg aggcggcggc ggcggcggcc ctataaaaag cgaagcgcgc ggcgggcggg    3960
agtcgctgcg ttgccttcgc cccgtgcccc gctccgcgcc gcctcgcgcc gcccgccccg    4020
gctctgactg accgcgttac tcccacaggt gagcgggcgg gacggccctt ctccctccgg    4080
gctgtaatta gcgcttggtt taatgacggc tcgtttctttt tctgtggctg cgtgaaagcc    4140
ttaaagggct ccgggagggc ctttgtgcgg ggggagcgg ctcgggggt gcgtgcgtgt    4200
gtgtgtgcgt ggggagcgcc gcgtgcggcc cgcgctgccc ggcggctgtg agcgctgcgg    4260
gcgcggcgcg gggctttgtg cgctccgcgt gtgcgcgagg ggagcgcggg ccggggggcgg    4320
tgccccgcgg tgcgggggg ctgcgagggg aacaaaggct gcgtgcgggg tgtgtgcgtg    4380
gggggtgag caggggtgt gggcgcgcg gtcgggctgt aaccccccc tggcacccccc    4440
ctccccgagt tgctgagcac ggcccggctt cgggtgcggg gctccgtgcg gggcgtggcg    4500
cggggctcgc cgtgccgggc gggggtggc ggcaggtggg ggtgccgggc ggggcggggc    4560
cgcctcgggc cggggagggc tcgggggagg ggcgcggcgg cccggagcg ccggcggctg    4620
tcgaggcgcg gcgagccgca gccattgcct tttatggtaa tcgtgcgaga gggcgcaggg    4680
acttcctttg tcccaaatct ggcggagccg aaatctggga ggcgccgccg cacccctct    4740
agcgggcgcg gcgaagcgg tgcggcgccg gcaggaagga aatgggcggg gagggccttc    4800
gtgcgtcgcc gcgccgccgt cccctctcc atctccagcc tcggggctgc cgcaggggga    4860
cggctgcctt cggggggac ggggcagggc ggggttcggc ttctggcgtg tgaccggcgg    4920
ctttagagcc tctgctaacc atgttcatgc cttcttcttt ttcctacagc tcctgggcaa    4980
cgtgctggtt gttgtgctgt ctcatcattt tggcaaattc gaccaacctt ccttcgacac    5040
```

```
ggggcccaaa gtactaaagt cgacaggagg tacccaccat gggttggagc ctcatcttgc    5100
tcttccttgt cgctgttgct acgcgtgtcc actcccaagt gcagctgcag cagagcggag    5160
ccgagctggt gaagcccgga gccagcgtga agatcagctg caaggccagc ggctacgcct    5220
tctccaacta ctggatgaac tgggtgaagc agagacccgg caagggactg aatggatcg    5280 gccagatcta ccccggcgac ggagacacca actacaacgg caagttcaag ggcaaagcca    5340
cactgaccgc cgacaagagc tccagcaccg cctacatgca gctgagctct ctgaccagcg    5400
aggatagcgc cgtgtacttc tgcgccagag gagactactg gggccaaggc accacactga    5460
ccgtctcgag cgctaagacg actccaccgt ccgtgtaccc gctcgcgcca ggttcggccg    5520
ctcagacgaa cagcatggtg accctcggct gcctcgtgaa gggttatttc ccagagccgg    5580
tgaccgtgac gtggaactcc ggctcactgt catcgggcgt gcacactttt ccagcagtgc    5640
tgcagtcgga ccttacacc ctcagctcgt ccgtcaccgt cccttcatca acttggccta    5700
gccagaccgt gacttgcaat gtcgcccacc cggcgtccag cactaaggtg acaagaaga    5760 tccaccacca tcaccatcac catcaccatc actagagagc ggccgcgtct agacctgcac    5820
tgactgactg atacactagt tagcctgtgc cttctagttg ccagccatct gttgtttgcc    5880 cctccccgt gccttccttg accctggaag gtgccactcc cactgtcctt tcctaataaa    5940
atgaggaaat tgcatcgcat tgtctgagta ggtgtcattc tattctgggg ggtggggtgg    6000
ggcaggacag caaggggag gattgggaag acaatagcag gcatgctggg gatgcggtgg    6060
gctctatggc ctgcaggcga tctctcgatt tcgatcaaga cattcctta atggtctttt    6120 ctggacacca ctaggggtca gaagtagttc atcaaacttt cttccctccc taatctcatt    6180
ggttaccttg ggctatcgaa acttaattaa ccagtcaagt cagctacttg gcgagatcga    6240
cttgtctggg tttcgactac gctcagaatt gcgtcagtca agttcgatct ggtccttgct    6300
attgcacccg ttctccgatt acgagtttca tttaaatcat gtgagcaaaa ggccagcaaa    6360
aggccaggaa ccgtaaaaag gccgcgttgc tggcgttttt ccataggctc cgcccccctg    6420
acgagcatca caaaaatcga cgctcaagtc agaggtggcg aaacccgaca ggactataaa    6480
gataccaggc gtttccccct ggaagctccc tcgtgcgctc tcctgttccg accctgccgc    6540
ttaccggata cctgtccgcc tttctccctt cgggaagcgt ggcgctttct catagctcac    6600
gctgtaggta tctcagttcg gtgtaggtcg ttcgctccaa gctgggctgt gtgcacgaac    6660 ccccgttca gcccgaccgc tgcgccttat ccggtaacta tcgtcttgag tccaacccgg    6720
taagacacga cttatcgcca ctggcagcag ccactggtaa caggattagc agagcgaggt    6780
atgtaggcgg tgctacagag ttcttgaagt ggtggcctaa ctacggctac actagaagaa    6840
cagtatttgg tatctgcgct ctgctgaagc cagttacctt cggaaaaaga gttggtagct    6900
cttgatccgg caaacaaacc accgctggta gcggtggttt ttttgtttgc aagcagcaga    6960
ttacgcgcag aaaaaaagga tctcaagaag atcctttgat cttttctacg ggtctgacg    7020 ctcagtggaa cgaaaactca cgttaaggga ttttggtcat gagattatca aaaaggatct    7080
tcacctagat ccttttaaat taaaaatgaa gttttaaatc aatctaaagt atatatgagt    7140
aaacttggtc tgacagttac caatgcttaa tcagtgaggc acctatctca gcgatctgtc    7200
tatttcgttc atccatagtt gcatttaaat ttccgaactc tccaaggccc tcgtcggaaa    7260
atcttcaaac ctttcgtccg atccatcttg caggctacct ctcgaacgaa ctatcgcaag    7320
tctcttggcc ggccttgcgc cttggctatt gcttggcagc gcctatcgcc aggtattact    7380
ccaatcccga atatccgaga tcgggatcac ccgagagaag ttcaacctac atcctcaatc    7440
```

```
ccgatctatc cgagatccga ggaatatcga atcggggcg cgcctggcct ccgcgccggg    7500
ttttggcgcc tcccgcgggc gcccccctcg tcacggcgag cgctgccacg tcagacgaag    7560
ggcgcaggag cgtcctgatc cttccgcccg gacgctcagg acagcggccc gctgctcata    7620
agactcggcc ttagaaccc cagtatcagca gaaggacatt ttaggacggg acttgggtga    7680
ctctagggca ctggttttct ttccagagag cggaacaggc gaggaaaagt agtcccttct    7740
cggcgattct gcggagggat ctccgtgggg cggtgaacgc cgatgattat ataaggacgc    7800
gccgggtgtg gcacagctag ttccgtcgca gccgggattt gggtcgcggt tcttgtttgt    7860
ggatcgctgt gatcgtcact tggtgagtag cgggctgctg gctggccgg ggctttcgtg    7920 gccgccgggc cgctcggtgg gacggaagcg tgtggagaga ccgccaaggg ctgtagtctg    7980
ggtccgcgag caaggttgcc ctgaactggg ggttgggggg agcgcagcaa aatggcggct    8040
gttcccgagt cttgaatgga agacgcttgt gaggcgggct gtgaggtcgt tgaaacaagg    8100 tgggggcat ggtgggcggc aagaacccaa ggtcttgagc ccttcgctaa tgcgggaaag    8160
ctcttattcg ggtgagatgg gctgggcacc atctgggac cctgacgtga agtttgtcac    8220
tgactggaga actcggtttg tcgtctgttg cgggggcggc agttatggcg gtgccgttgg    8280
gcagtgcacc cgtacctttg ggagcgcgcg ccctcgtcgt gtcgtgacgt cacccgttct    8340
gttggcttat aatgcagggt ggggccacct gccggtaggt gtgcggtagg cttttctccg    8400
tcgcaggacg cagggttcgg gcctagggta ggctctcctg aatcgacagg cgccggacct    8460
ctggtgaggg gagggataag tgaggcgtca gtttctttgg tcggttttat gtacctatct    8520
tcttaagtag ctgaagctcc ggttttgaac tatgcgctcg gggttggcga gtgtgttttg    8580
tgaagttttt taggcaccTt ttgaaatgta atcatttggg tcaatatgta attttcagtg    8640
ttagacttgt aaattgtccg ctaaattctg gccgttttg gctttttgt tagacaacat    8700 gggtaaaaag cctgaactca ccgcgacgtc tgtcgagaag tttctgatcg aaaagttcga    8760
cagcgtctcc gacctgatgc agctctcgga gggcgaagaa tctcgtgctt tcagcttcga    8820
tgtaggaggg cgtggatatg tcctgcgggt aaatagctgc gccgatggtt tctacaaaga    8880
tcgttatgtt tatcggcact ttgcatccgc cgcgctcccg attccggaag tgcttgacat    8940
tggggagttc agcgagagcc tgacctattg catctcccgc cgtgcacagg gtgtcacgtt    9000
gcaagacctg cctgaaaccg aactgcccgc tgttctgcag ccggtcgcgg aggcaatgga    9060
tgccatcgct gccgccgatc ttagccagac gagcgggttc ggcccattcg gaccgcaagg    9120
aatcggtcaa tacactacat ggcgtgattt catatgcgcg attgctgatc ccatgtgta    9180 tcactggcaa actgtgatgg acgacaccgt cagtgcgtcc gtcgcgcagg ctctcgatga    9240
gctgatgctt tgggccgagg actgccccga agtccggcac ctcgtgcacg cggatttcgg    9300
ctccaacaat gtcctgacgg acaatggccg cataacagcg gtcattgact ggagcgaggc    9360
gatgttcggg gattcccaat acgaggtcgc caacatcttc ttctggaggc cgtggttggc    9420
ttgtatggag cagcagacgc gctacttcga gcggaggcat ccggagcttg caggatcgcc    9480
ccggctccgg gcgtatatgc tccgcattgg tcttgaccaa ctctatcaga gcttggttga    9540
cggcaatttc gatgatgcag cttgggcgca gggtcgatgc gacgcaatcg tccgatccgg    9600
agccgggact gtcgggcgta cacaaatcgc ccgcagaagc gcgccgtct ggaccgatgg    9660 ctgtgtagaa gtactcgccg atagtggaaa ccgacgcccc agcactcgtc cgagggcaaa    9720
ggaataagct agtatgtaag cctagtctta gataataaaa tcgctatcca tcgaagatgg    9780
```

```
atgtgtgttg gttttttgtg tgtgtaacgc taggcgcgcc tggtgtaccg agaacgatcc    9840
tctcagtgcg agtctcgacg atccatatcg ttgcttggca gtcagccagt cggaatccag    9900
cttgggaccc aggaagtcca atcgtcagat attgtactca agcctggtca cggcagcgta    9960
ccgatctgtt taaacctaga tattgatagt ctgatcggtc aacgtataat cgagtcctag   10020
cttttgcaaa catctatcaa gagacaggat cagcaggagg ctttcgcatg attgaacaag   10080
atggattgca cgcaggttct ccggcggctt gggtggagag ctattcggc tatgactggg    10140 cacaacagac aatcggctgc tctgatgccg ccgtgttccg gctgtcagcg cagggcgtc    10200 cggttctttt tgtcaagacc gacctgtccg gtgccctgaa tgaactgcaa gacgaggcag   10260
cgcggctatc gtggctggcg acgacgggcg ttccttgcgc ggctgtgctc gacgttgtca   10320
ctgaagcggg aagggactgg ctgctattgg gcgaagtgcc ggggcaggat ctcctgtcat   10380
ctcaccttgc tcctgccgag aaagtatcca tcatggctga tgcaatgcgg cggctgcata   10440
cgcttgatcc ggctacctgc ccattcgacc accaagcgaa acatcgcatc gagcgagcac   10500
gtactcggat ggaagccggt cttgtcgatc aggatgatct ggacgaagag catcaggggc   10560
tcgcgccagc cgaactgttc gccaggctca aggcgtctat gcccgacggc gaggatctcg   10620
tcgtgaccca cggcgatgcc tgcttgccga atatcatggt ggaaaatggc cgcttttctg   10680
gattcatcga ctgtggccgt ctgggtgtgg cggaccgcta tcaggacata gcgttggcta   10740
cccgtgatat tgctgaagag cttggcggcg aatgggctga ccgcttcctt gtgctttacg   10800
gtatcgccgc gcccgattcg cagcgcatcg ccttctatcg ccttcttgac gagttcttct   10860
gaccgattct aggtgcattg gcgcagaaaa aaatgcctga tgcgacgctg cgcgtcttat   10920
actcccacat atgccagatt cagcaacgga tacggcttcc ccaacttgcc cacttccata   10980
cgtgtcctcc ttaccagaaa tttatcctta aggtcgttta aactcgactc tggctctatc   11040
gaatctccgt cgtttcgagc ttacgcgaac agccgtggcg ctcatttgct cgtcgggcat   11100
cgaatctcgt cagctatcgt cagcttacct ttttggca                           11138
```

<210> SEQ ID NO 94
<211> LENGTH: 112
<212> TYPE: PRT
<213> ORGANISM: Artificial Sequence
<220> FEATURE:
<223> OTHER INFORMATION: Synthetic polymer.

<400> SEQUENCE: 94

```
Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Ala Phe Ser Asn Tyr
            20                  25                  30

Trp Met Asn Trp Val Lys Gln Arg Pro Gly Lys Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Asp Tyr Trp Gly Gln Gly Thr Thr Leu Thr Val Ser Ser
            100                 105                 110
```